(12) United States Patent
Hatakeyama et al.

(10) Patent No.: US 11,643,492 B2
(45) Date of Patent: May 9, 2023

(54) BIO-ELECTRODE COMPOSITION, BIO-ELECTRODE, AND METHOD FOR MANUFACTURING BIO-ELECTRODE

(71) Applicant: SHIN-ETSU CHEMICAL CO., LTD., Tokyo (JP)

(72) Inventors: Jun Hatakeyama, Joetsu (JP); Motoaki Iwabuchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 520 days.

(21) Appl. No.: 16/815,315

(22) Filed: Mar. 11, 2020

(65) Prior Publication Data
US 2020/0317840 A1    Oct. 8, 2020

(30) Foreign Application Priority Data

Apr. 3, 2019 (JP) .............................. JP2019-071288

(51) Int. Cl.
*C08F 230/08* (2006.01)
*B01J 41/13* (2017.01)
(Continued)

(52) U.S. Cl.
CPC .............. *C08F 230/08* (2013.01); *A61B 5/24* (2021.01); *B01J 41/02* (2013.01); *B01J 41/13* (2017.01);
(Continued)

(58) Field of Classification Search
CPC .............. C08F 230/08; C08F 220/1809; C08F 220/325; C08F 220/282; C08F 220/382;
(Continued)

(56) References Cited

U.S. PATENT DOCUMENTS

| 5,981,680 A | 11/1999 | Petroff et al. |
| 10,743,788 B2 | 8/2020 | Hatakeyama et al. |

(Continued)

FOREIGN PATENT DOCUMENTS

| JP | H05-095924 A | 4/1993 |
| JP | 2002-332305 A | 11/2002 |

(Continued)

OTHER PUBLICATIONS

U.S. Appl. No. 16/815,136, filed Mar. 11, 2020 in the name of Hatakeyama et al.

(Continued)

*Primary Examiner* — Michael M. Bernshteyn
(74) *Attorney, Agent, or Firm* — Oliff PLC

(57) ABSTRACT

A bio-electrode composition includes (A) an ionic material and (B) a lithium titanate powder. The component (A) is a polymer compound containing a repeating unit-a having a structure selected from an ammonium salt, a sodium salt, a potassium salt, and a silver salt of any of fluorosulfonic acid, fluorosulfonimide, and N-carbonyl-fluorosulfonamide. Thus, the present invention provides a bio-electrode composition capable of forming a living body contact layer for a bio-electrode that is excellent in electric conductivity and biocompatibility, is light-weight, can be manufactured at low cost, and can control significant reduction in the electric conductivity even when the bio-electrode is wetted with water or dried; a bio-electrode including a living body contact layer formed of the bio-electrode composition; and a method for manufacturing the bio-electrode.

13 Claims, 2 Drawing Sheets

(51) Int. Cl.
| | |
|---|---|
| *C08F 220/18* | (2006.01) |
| *C08F 220/32* | (2006.01) |
| *C08F 220/28* | (2006.01) |
| *C08F 220/38* | (2006.01) |
| *B01J 41/02* | (2006.01) |
| *B01J 41/14* | (2006.01) |
| *C08F 220/40* | (2006.01) |
| *C08L 33/08* | (2006.01) |
| *C08L 83/04* | (2006.01) |
| *A61B 5/24* | (2021.01) |
| *A61B 5/05* | (2021.01) |
| *A61B 5/25* | (2021.01) |
| *C08F 212/14* | (2006.01) |
| *C08G 77/00* | (2006.01) |
| *A61B 5/0531* | (2021.01) |

(52) U.S. Cl.
CPC ............ *B01J 41/14* (2013.01); *C08F 212/30* (2020.02); *C08F 220/1809* (2020.02); *C08F 220/282* (2020.02); *C08F 220/325* (2020.02); *C08F 220/382* (2020.02); *C08F 220/387* (2020.02); *C08F 220/40* (2013.01); *C08G 77/70* (2013.01); *C08L 33/08* (2013.01); *C08L 83/04* (2013.01); *A61B 5/0531* (2013.01); *A61B 5/25* (2021.01); *A61B 2562/0215* (2017.08); *A61B 2562/125* (2013.01); *C08L 2203/02* (2013.01); *C08L 2205/025* (2013.01); *C08L 2205/03* (2013.01)

(58) Field of Classification Search
CPC ............... C08F 220/287; C08F 220/40; C08F 212/30; B01J 41/02; B01J 41/14; C08L 33/08; C08L 83/04; C08L 2203/02; C08L 2205/025; C08L 2205/03; A61B 2562/0215; A61B 2562/125; A61B 5/0531; A61B 5/25
USPC ......................................................... 600/396
See application file for complete search history.

(56) References Cited

U.S. PATENT DOCUMENTS

| | | | |
|---|---|---|---|
| 10,759,938 B2 | 9/2020 | Hatakeyama et al. | |
| 10,808,148 B2* | 10/2020 | Hatakeyama | ........ A61B 5/0531 |
| 10,864,366 B2 | 12/2020 | Hatakeyama et al. | |
| 11,071,485 B2* | 7/2021 | Hatakeyama | ............ C08K 9/02 |
| 2002/0188069 A1 | 12/2002 | Sugo et al. | |
| 2008/0118860 A1 | 5/2008 | Harada et al. | |
| 2009/0061358 A1 | 3/2009 | Ohashi et al. | |
| 2009/0214606 A1 | 8/2009 | Bujard et al. | |
| 2013/0140083 A1 | 6/2013 | Izawa et al. | |
| 2015/0275060 A1 | 10/2015 | Kuroda et al. | |
| 2016/0155530 A1 | 6/2016 | Someya et al. | |
| 2016/0190641 A1 | 6/2016 | Lee et al. | |
| 2017/0275510 A1 | 9/2017 | Quan et al. | |
| 2018/0086948 A1* | 3/2018 | Hatakeyama | ............ C09J 11/06 |
| 2018/0168470 A1* | 6/2018 | Hatakeyama | ......... A61L 31/028 |
| 2018/0223133 A1 | 8/2018 | Hatakeyama et al. | |
| 2018/0229023 A1 | 8/2018 | Hatakeyama et al. | |
| 2018/0273811 A1 | 9/2018 | Cura et al. | |
| 2019/0298891 A1 | 10/2019 | Hatakeyama et al. | |

FOREIGN PATENT DOCUMENTS

| | | | | |
|---|---|---|---|---|
| JP | 2003-225217 A | | 8/2003 | |
| JP | 2004-033468 A | | 2/2004 | |
| JP | 2005-320418 A | | 11/2005 | |
| JP | 2008-111103 A | | 5/2008 | |
| JP | 2009-080474 A | | 4/2009 | |
| JP | 2011-079946 A | | 4/2011 | |
| JP | 2015-019806 A | | 2/2015 | |
| JP | 2015-100673 A | | 6/2015 | |
| JP | 2015-193803 A | | 11/2015 | |
| JP | 2016-011338 A | | 1/2016 | |
| JP | 2016-065238 A | | 4/2016 | |
| JP | 5940529 B2 | | 6/2016 | |
| JP | 5940529 B2 | * | 6/2016 | ........... C01G 23/005 |
| JP | 2018099504 A | | 6/2018 | |
| JP | 2018126496 A | | 8/2018 | |
| JP | 2018130533 A | | 8/2018 | |
| JP | 2019503406 A | | 2/2019 | |
| KR | 10-2018-0035691 A | | 4/2018 | |
| KR | 20180035691 A | * | 4/2018 | |
| WO | 2013/039151 A1 | | 3/2013 | |

OTHER PUBLICATIONS

Aug. 27, 2021 Office Action Issued in U.S. Appl. No. 16/815,136.
Jan. 12, 2021 Office Action issued in Korean Patent Application No. 10-2020-0038544.
Mar. 11, 2022 Notice of Allowance issued in U.S. Appl. No. 16/815,136.
Aug. 28, 2020 extended Search Report issued in European Patent Application No. 20166906.6.

* cited by examiner

[FIG. 1]
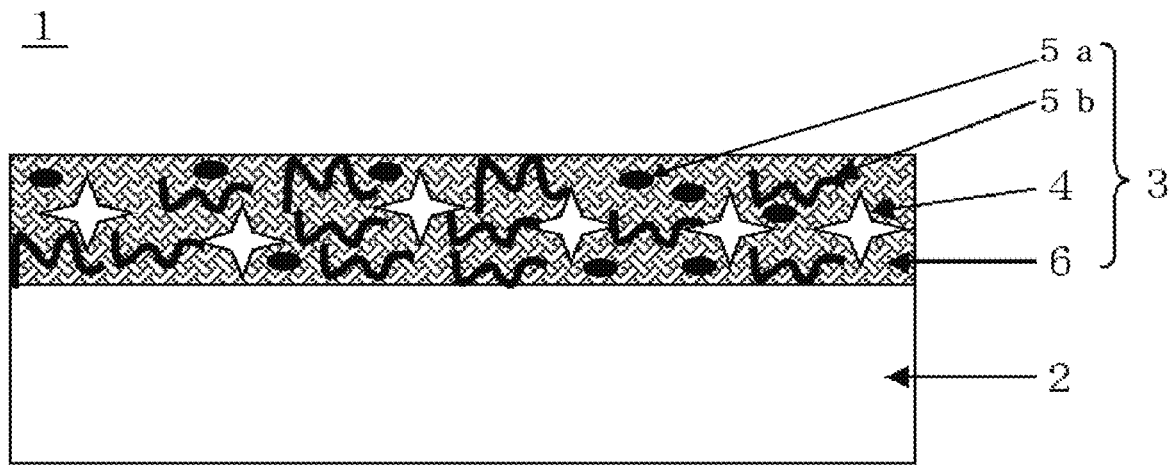
[FIG. 2]
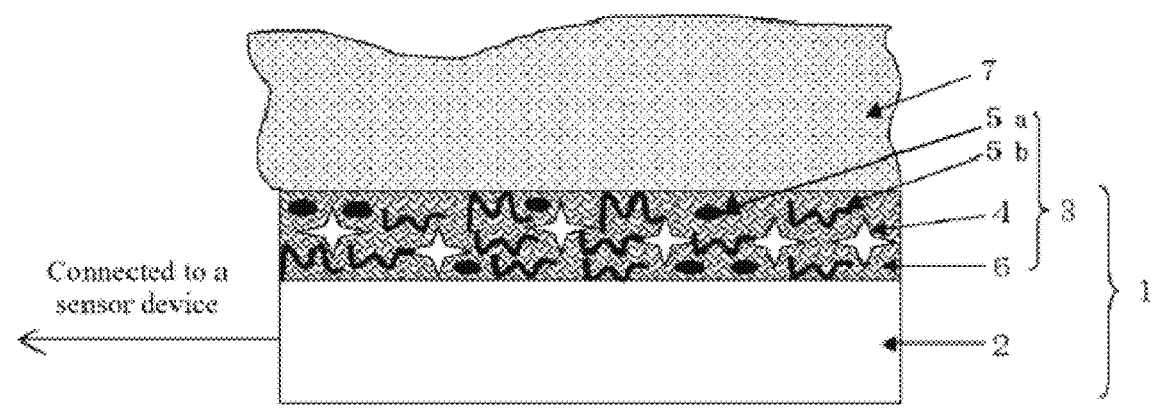
[FIG. 3A]
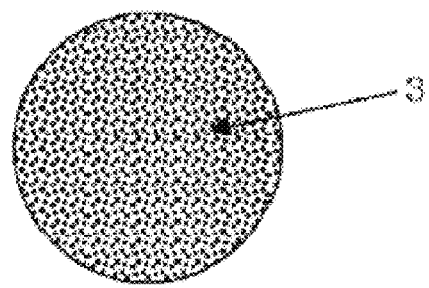

BIO-ELECTRODE COMPOSITION, BIO-ELECTRODE, AND METHOD FOR MANUFACTURING BIO-ELECTRODE

TECHNICAL FIELD

The present invention relates to a bio-electrode that is used in contact with the skin of a living body and capable of detecting physical conditions such as heart rate by an electric signal transmitted from the skin, a method for manufacturing the bio-electrode, and a bio-electrode composition desirably used for a bio-electrode.

BACKGROUND ART

A recent growing popularity of Internet of Things (IoT) has accelerated the development of such major wearable devices as watches and glasses that allow for Internet access. Even in the fields of medicine and sports, wearable devices for constantly monitoring the user's physical state are increasingly demanded, and such technological development is expected to be further encouraged.

In the field of medicine, including an electrocardiogram for detecting an electric signal to measure the motion of the heart, use of wearable devices for monitoring the state of human organs by detecting extremely weak current has been examined. The electrocardiogram measurement is conducted by attaching an electrode coated with an electro-conductive paste to a body, but this is a single (not continuous), short-time measurement. On the other hand, the above medical wearable device is aimed at continuously monitoring the state of physical conditions for a few weeks. Accordingly, a bio-electrode used in a medical wearable device is required to make no changes in electric conductivity even in long-time use and cause no skin allergy. In addition to these, bio-electrodes must be light-weight and produced at low cost.

Medical wearable devices are classified into two types: direct body attachment and clothing attachment. As one typical body attachment device, a bio-electrode is proposed which is formed of a hydrophilic gel containing water and electrolytes as ingredients of the above electro-conductive paste (Patent Document 1). The hydrophilic gel, containing sodium, potassium, and calcium electrolytes in a hydrophilic polymer for retaining water, detects changes in ion concentration from the skin to convert the data into electricity. Meanwhile, one typical clothing attachment device is proposed which is characterized by a method for using as an electrode a fabric including an electro-conductive polymer, such as PEDOT-PSS (Poly-3,4-ethylenedioxythiophene-polystyrenesulfonate), and a silver paste incorporated into the fiber (Patent Document 2).

However, the use of the hydrophilic gel containing water and electrolytes unfortunately brings about loss of electric conductivity due to water evaporation in drying process. Meanwhile, the use of a higher ionization tendency metal such as copper can cause some users to suffer from skin allergy. The use of an electro-conductive polymer such as PEDOT-PSS can also cause skin allergy due to the strong acidity of the electro-conductive polymer, as well as peeling of the electro-conductive polymer from fibers during washing.

By taking advantage of excellent electric conductivity, the use of electrode materials formed of metal nanowire, carbon black, carbon nanotube, or the like has been examined (Patent Documents 3, 4, and 5). With higher contact probability, metal nanowires can conduct electricity in small quantities of the wires to be added. Nevertheless, metal nanowires, formed of a pointed thin material, may cause skin allergy. Likewise, carbon nanotubes can stimulate (irritate) a living body. Although the carbon black is not as poisonous as carbon nanotube, it also stimulates the skin. Accordingly, even though these electrode materials themselves cause no allergic reaction, the biocompatibility can be degraded depending on the shape of a material and its inherent stimulation, thereby failing to satisfy both electric conductivity and biocompatibility.

Although metal films seem to function as an excellent bio-electrode thanks to extremely high electric conductivity, this is not always the case. Upon heartbeat, the human skin releases not only extremely weak current, but also a sodium ion, a potassium ion, or a calcium ion. It is thus necessary to convert changes in ion concentration into current, which is what less ionized precious metals unfortunately fail to do efficiently. The resulting bio-electrode using the precious metal is characterized by high impedance and high resistance to the skin during electrical conduction.

Bio-electrodes using another electro-conductive material have been proposed in each of which an ionic polymer is added (Patent Documents 6, 7, 8). A bio-electrode obtained by mixing a silicone adhesive with an ion polymer and a carbon powder added thereto has adhesion and high water repellency so that biological signals can be stably collected even when the bio-electrode is attached to the skin for a long time in a wet state by shower or sweat. Ion polymers do not permeate to the skin and hence do not stimulate the skin, and the biocompatibility is high. From these aspects, the bio-electrode enables long-time attachment.

Although silicones are inherently insulators, the ionic conductivity is improved by the combination with an ionic polymer and a carbon powder, and thus the function as a bio-electrode is obtained. Nevertheless, it has been desired to improve the performance by further improving the ionic conductivity.

CITATION LIST

Patent Literature

Patent Document 1: International Patent Laid-Open Publication No. WO2013/039151
Patent Document 2: Japanese Unexamined Patent Application Publication No. 2015-100673
Patent Document 3: Japanese Unexamined Patent Application Publication No. H5-095924
Patent Document 4: Japanese Unexamined Patent Application Publication No. 2003-225217
Patent Document 5: Japanese Unexamined Patent Application Publication No. 2015-019806
Patent Document 6: Japanese Unexamined Patent Application Publication No. 2018-99504
Patent Document 7: Japanese Unexamined Patent Application Publication No. 2018-126496
Patent Document 8: Japanese Unexamined Patent Application Publication No. 2018-130533

SUMMARY OF INVENTION

Technical Problem

The present invention has been made to solve the problems and has an object to provide: a bio-electrode composition capable of forming a living body contact layer for a bio-electrode that is excellent in electric conductivity and biocompatibility, is light-weight, can be manufactured at low cost, and can control significant reduction in the electric conductivity even when the bio-electrode is wetted with water or dried; a bio-electrode including a living body contact layer formed of the bio-electrode composition; and a method for manufacturing the bio-electrode.

Solution to Problem

To achieve the object, the present invention provides a bio-electrode composition comprising:
(A) an ionic material; and
(B) a lithium titanate powder,
wherein the component (A) is a polymer compound comprising a repeating unit-a having a structure selected from an ammonium salt, a sodium salt, a potassium salt, and a silver salt of any of fluorosulfonic acid, fluorosulfonimide, and N-carbonyl-fluorosulfonamide.

Such a bio-electrode composition is capable of forming a living body contact layer for a bio-electrode that is excellent in electric conductivity and biocompatibility, light-weight, manufacturable at low cost, and free from large lowering of the electric conductivity even when the bio-electrode is wetted with water or dried.

The repeating unit-a is preferably a repeating unit having at least one of structures shown by the following general formulae (1)-1 to (1)-4,

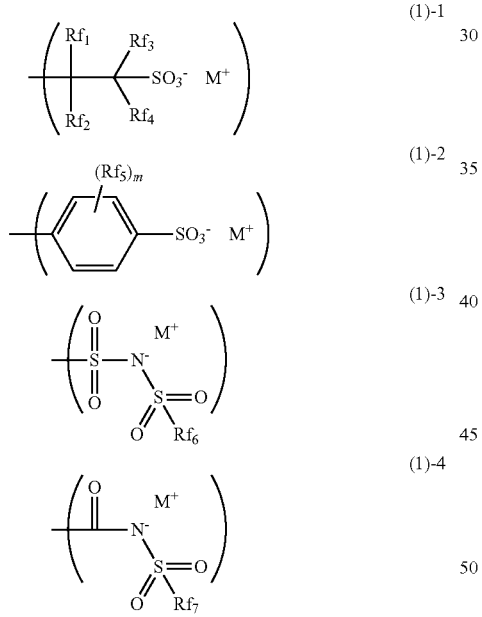

wherein $Rf_1$ and $Rf_2$ each represent a hydrogen atom, a fluorine atom, an oxygen atom, a methyl group, or a trifluoromethyl group, provided that when $Rf_1$ represents an oxygen atom, $Rf_2$ also represents the oxygen atom to form a carbonyl group together with a carbon atom bonded therewith; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms and at least one or more fluorine atoms; "m" represents an integer of 1 to 4; and $M^+$ represents an ion selected from an ammonium ion, a sodium ion, a potassium ion, and a silver ion.

The repeating unit-a having such structures enables the bio-electrode composition to form a living body contact layer for a bio-electrode that is more excellent in electric conductivity and biocompatibility, light-weight, manufacturable at low cost, and free from large lowering of the electric conductivity even when the bio-electrode is wetted with water or dried.

The repeating unit-a is preferably at least one repeating unit selected from repeating units-a1 to -a7 shown by the following general formula (2),

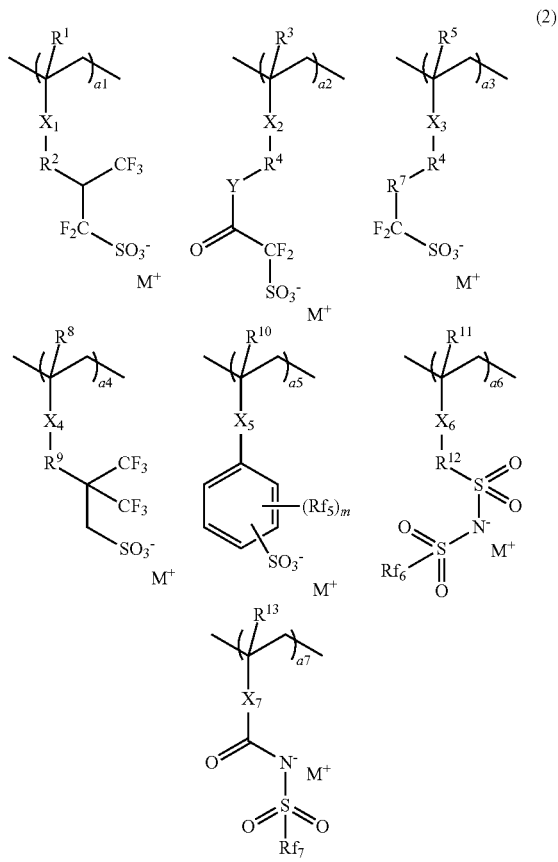

wherein $R^1$, $R^3$, $R^5$, $R^8$, $R^{10}$, $R^{11}$ and $R^{13}$ each independently represent a hydrogen atom or a methyl group; $R^2$, $R^4$, $R^6$, $R^9$, and $R^{12}$ each independently represent any of a single bond, an ester group, and a linear, branched, or cyclic hydrocarbon group having 1 to 13 carbon atoms optionally having either or both of an ether group and an ester group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$ and $X_6$ each independently represent any of a single bond, a phenylene group, a naphthylene group, an ether group, an ester group, and an amide group; $X_5$ represents any of a single bond, an ether group, and an ester group; $X_7$ represents any of a single bond, an arylene group having 6 to 12 carbon atoms, a —C(=O)—O—$R^{18}$— group, and a —C(=O)—NH—$R^{18}$— group, and $X_7$ optionally has one or more selected from an ether group, a carbonyl group, an ester group, and an amide group; $R^{18}$ represents a single bond, a linear, branched, or cyclic alkylene group having 1 to 12 carbon atoms, or a divalent aromatic hydrocarbon group having 6 to 10 carbon atoms, and the aromatic hydrocarbon group is optionally partially hydrogenated; Y represents an oxygen atom or a —NR$^{19}$— group, and Y and R$^4$ are optionally bonded to each other to form a ring; R$^{19}$ represents a hydrogen atom, or a linear or branched alkyl group having 1 to 4 carbon atoms; "m" represents an integer of 1 to 4; a1, a2, a3, a4, a5, a6 and a7 represent numbers satisfying 0≤a1≤1.0, 0≤a2≤1.0, 0≤a3≤1.0, 0≤a4≤1.0, 0≤a5≤1.0, 0≤a6≤1.0, 0≤a7≤1.0, and 0≤a1+a2+a3+a4+a5+a6+a7≤1.0; and M$^+$ represents an ion selected from an ammonium ion, a sodium ion, a potassium ion, and a silver ion.

With such a component (A), the effects of the present invention can be further improved.

The component (A) can contain the repeating unit-a having the ammonium salt structure which contains an ammonium ion shown by the following general formula (3),

(3)

wherein R$^{101d}$, R$^{101e}$, R$^{101f}$, and R$^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, and optionally have one or more selected from an ether group, a carbonyl group, an ester group, a hydroxy group, an amino group, a nitro group, a sulfonyl group, a sulfinyl group, a halogen atom, and a sulfur atom; R$^{101d}$ and R$^{101e}$, or R$^{101d}$, R$^{101e}$, and R$^{101f}$, are optionally bonded to each other together with a nitrogen atom bonded therewith to form a ring in which R$^{101d}$ and R$^{101e}$, or R$^{101d}$, R$^{101e}$, and R$^{101f}$, represent an alkylene group having 3 to 10 carbon atoms, or to form a heteroaromatic ring having the nitrogen atom in the formula within the ring.

The component (A) having such an ammonium ion allows the present invention to achieve more improved effects.

The inventive bio-electrode composition may comprise, in addition to the components (A) and (B), a component (C) containing:

a silicone resin having an SiO$_2$ unit and an R$_x$SiO$_{(4-x)/2}$ unit, wherein R represents a substituted or unsubstituted monovalent hydrocarbon group having 1 to 10 carbon atoms, and "x" is a number in a range of 2.5 to 3.5;

diorganosiloxane having an alkenyl group; and organohydrogenpolysiloxane having an SiH group.

In such a bio-electrode composition, (A) the ionic material (salt) is compatibilized, thereby making it possible to prevent elution of the salt, hold the lithium titanate powder and so forth, and achieve adhesion.

The bio-electrode composition preferably further comprises an organic solvent.

Such a bio-electrode composition has more favorable coating properties.

In the inventive bio-electrode composition, the component (B) is preferably a powder of lithium titanate having a spinel structure.

Such a component (B) makes the bio-electrode composition have excellent ion reception sensitivity and favorable ionic conductivity.

More preferably, the bio-electrode composition further comprises a carbon material in addition to the lithium titanate powder.

The electric conductivity can be further improved by adding a carbon material as described above.

In this case, the carbon material is more preferably either or both of carbon black and carbon nanotube.

In the inventive bio-electrode composition, such carbon materials are particularly suitably usable.

The present invention also provides a bio-electrode comprising an electro-conductive base material and a living body contact layer formed on the electro-conductive base material, wherein the living body contact layer is a cured material of the above-described bio-electrode composition.

The ionic material allows the inventive bio-electrode to achieve both of electric conductivity and biocompatibility. The inventive bio-electrode also has adhesion and can keep the contact area with skin constant to obtain electric signals from skin stably in high sensitivity.

In this case, the electro-conductive base material preferably comprises one or more species selected from gold, silver, silver chloride, platinum, aluminum, magnesium, tin, tungsten, iron, copper, nickel, stainless steel, chromium, titanium, and carbon.

In the inventive bio-electrode, such electro-conductive base materials are particularly suitably usable.

The present invention also provides a method for manufacturing a bio-electrode having an electro-conductive base material and a living body contact layer formed on the electro-conductive base material, comprising: applying the above-described bio-electrode composition onto the electro-conductive base material; and curing the bio-electrode composition to form the living body contact layer.

The inventive method for manufacturing a bio-electrode makes it possible to manufacture the inventive bio-electrode, which is excellent in electric conductivity and biocompatibility, light-weight, and free from large lowering of the electric conductivity even when the bio-electrode is wetted with water or dried, easily at low cost.

In this event, the electro-conductive base material preferably comprises one or more species selected from gold, silver, silver chloride, platinum, aluminum, magnesium, tin, tungsten, iron, copper, nickel, stainless steel, chromium, titanium, and carbon.

In the inventive method for manufacturing a bio-electrode, such electro-conductive base materials are particularly suitably usable.

Advantageous Effects of Invention

As described above, the inventive bio-electrode composition makes it possible to form a living body contact layer for a bio-electrode that is capable of conducting electric signals from skin efficiently to a device (i.e., excellent in electric conductivity), free from the risk of causing allergies even when the bio-electrode is worn on skin for a long time (i.e., excellent in biocompatibility), light-weight, manufacturable at low cost, and free from large lowering of the electric conductivity even when the bio-electrode is wetted with water or dried.

The inventive bio-electrode, with the living body contact layer being formed of a cured material of the inventive bio-electrode composition described above, is excellent in electric conductivity and biocompatibility, light-weight, manufacturable at low cost, and free from large lowering of the electric conductivity even when the bio-electrode is wetted with water or dried as described above.

Additionally, the inventive method for manufacturing a bio-electrode makes it possible to manufacture the inventive bio-electrode, which is excellent in electric conductivity and biocompatibility, light-weight, and free from large lowering of the electric conductivity even when the bio-electrode is wetted with water or dried, easily at low cost.

BRIEF DESCRIPTION OF DRAWINGS

FIG. 1 is a schematic sectional view showing an example of the inventive bio-electrode;

FIG. 2 is a schematic sectional view showing an example of the inventive bio-electrode worn on a living body;

FIG. 3A is a schematic view of a bio-electrode produced in Examples of the present invention viewed from the living body contact layer side;

DESCRIPTION OF EMBODIMENTS

Figure 3B:
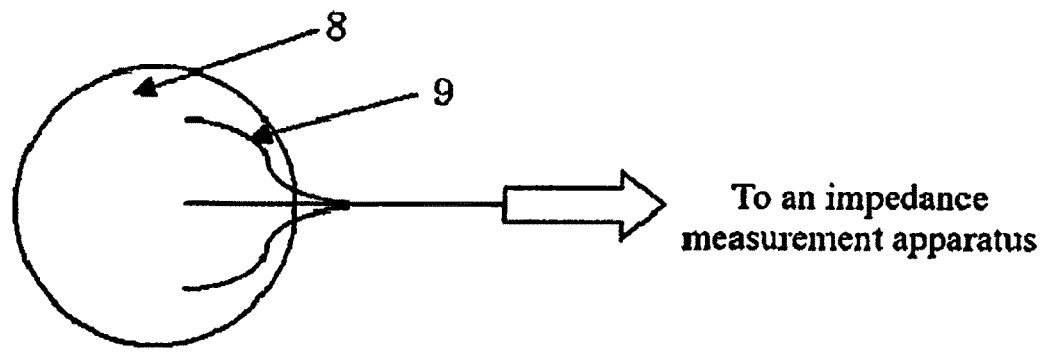
FIG. 3B is a schematic view of the bio-electrode produced in Examples of the present invention viewed from the electro-conductive base material side.

As described above, it has been desired to develop: a bio-electrode composition capable of forming a living body contact layer for a bio-electrode that is excellent in electric conductivity and biocompatibility, light-weight, manufacturable at low cost, and free from large lowering of the electric conductivity even when the bio-electrode is wetted with water or dried; a bio-electrode in which the living body contact layer is formed from the bio-electrode composition; and a method for manufacturing the bio-electrode.

The surface of skin releases ions of sodium, potassium, and calcium in accordance with heartbeat. A bio-electrode has to convert the increase and decrease of these ions released from skin to electric signals. Accordingly, the bio-electrode has to be composed of a material that is excellent in ionic conductivity to transmit the increase and decrease of ions.

The present inventors have noticed ionic liquids as a material that is highly ionic conductive. Ionic liquids are characterized by high thermal and chemical stability as well as excellent electric conductivity, thereby having been widely used for battery uses. Illustrative examples of known ionic liquids include hydrochloric acid salt, hydrobromic acid salt, hydroiodic acid salt, trifluoromethanesulfonic acid salt, nonafluorobutanesulfonic acid salt, bis(trifluoromethanesulfonyl)imide acid salt, hexafluorophosphate salt, and tetrafluoroborate salt of sulfonium, phosphonium, ammonium, morpholinium, pyridinium, pyrrolidinium, and imidazolium. However, these salts (particularly, the ones with low molecular weight) are generally liable to hydrate, thereby causing a defect such that the salt is extracted with perspiration or by washing to lower the electric conductivity of a bio-electrode in which the living body contact layer is formed from a bio-electrode composition containing these salts. In addition, the tetrafluoroborate salt is highly toxic, and the other salts are highly water-soluble to easily permeate into skin, thereby causing an issue of rough dry skin (i.e., highly irritative to skin).

In neutralized salts formed from highly acidic acids, the ions are strongly polarized to improve the ionic conductivity. This is why lithium salts of bis(trifluoromethanesulfonyl)imidic acid and tris(trifluoromethanesulfonyl)methide acid show high ionic conductivity as a lithium ion battery. On the other hand, before the formation of the neutralized salt, the higher acidity of the acid makes the salt have stronger irritation to a body. That is, ionic conductivity and irritation to a body are in relation of trade-off. In a salt applied to a bio-electrode, however, higher ionic conductivity and lower irritation to a body have to be combined.

As the molecular weight of ionic compound increases, the permeability and the stimulus to skin tend to decrease. Accordingly, the ionic compound is preferably a polymer type with higher molecular weight. Thus the present inventors have first conceived to polymerize such an ionic compound by forming it to have a polymerizable double bond.

Meanwhile, a negative electrode material of a lithium ion battery is also a material excellent in ionic conductivity. Although carbon-based materials are currently employed as a negative electrode material of a lithium ion battery, lithium titanate-based materials have been examined to further increase the batter capacity. The mechanism of receiving electricity and ions released from the skin is common between a bio-electrode and a negative electrode of an ion battery. Hence, the present invention has been devised, considering that a lithium titanate-based material examined for lithium ion battery is also applicable to a bio-electrode.

The inventors have diligently studied the above subjects and consequently found that when an ion polymer and a lithium titanate powder are combined as a bio-electrode composition, this makes it possible to form a living body contact layer for a bio-electrode that is excellent in electric conductivity and biocompatibility, light-weight, manufacturable at low cost, and free from large lowering of the electric conductivity even when the bio-electrode is wetted with water or dried; thereby bringing the present invention to completion.

That is, the present invention is a bio-electrode composition comprising:

(A) an ionic material; and
(B) a lithium titanate powder, wherein the component (A) is a polymer compound comprising a repeating unit-a having a structure selected from an ammonium salt, a sodium salt, a potassium salt, and a silver salt of any of fluorosulfonic acid, fluorosulfonimide, and N-carbonyl-fluorosulfonamide.

Hereinafter, the present invention will be described in detail, but the present invention is not limited thereto.

<Bio-Electrode Composition>

The inventive bio-electrode composition contains (A) an ionic material and (B) a lithium titanate powder. The inventive bio-electrode composition can further contain, other than the components (A) and (B), optional components such as a resin other than the component (A), an organic solvent, and a carbon material, as necessary. Hereinafter, each component will be described more specifically.

[(A) Ionic Material (Salt)]

The salt to be added to the inventive bio-electrode composition as (A) the ionic material (conductive material) is a polymer compound containing a repeating unit-a having a structure selected from the group consisting of an ammonium salt, a sodium salt, a potassium salt, and a silver salt of any of fluorosulfonic acid, fluorosulfonimide, and N-carbonyl-fluorosulfonamide.

The repeating unit-a can be a repeating unit having at least one of structures shown by the following general formulae (1)-1 to (1)-4,

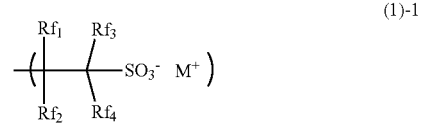

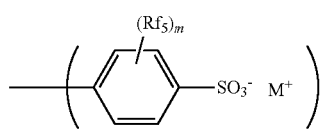
(1)-2

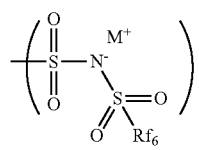
(1)-3

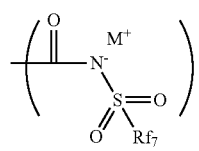
(1)-4 where $Rf_1$ and $Rf_2$ each represent a hydrogen atom, a fluorine atom, an oxygen atom, a methyl group, or a trifluoromethyl group, provided that when $Rf_1$ represents an oxygen atom, $Rf_2$ also represents the oxygen atom to form a carbonyl group together with a carbon atom bonded therewith; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms and at least one or more fluorine atoms; "m" represents an integer of 1 to 4; and $M^+$ represents an ion selected from an ammonium ion, a sodium ion, a potassium ion, and a silver ion.

The repeating unit-a is preferably at least one repeating unit selected from repeating units-a1 to -a7 shown by the following general formula (2),

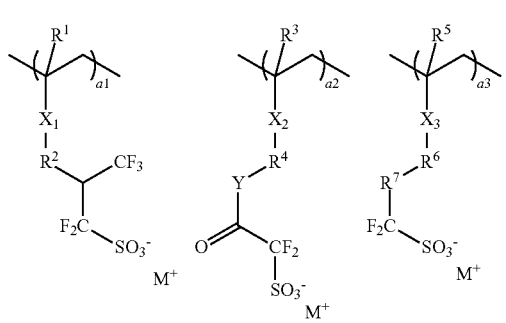
(2)

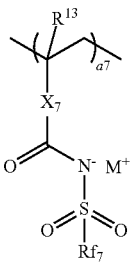

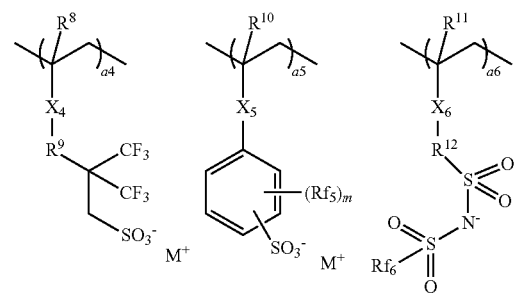

where $R^1$, $R^3$, $R^5$, $R^8$, $R^{10}$, $R^{11}$ and $R^{13}$ each independently represent a hydrogen atom or a methyl group; $R^2$, $R^4$, $R^6$, $R^9$, and $R^{12}$ each independently represent any of a single bond, an ester group, and a linear, branched, or cyclic hydrocarbon group having 1 to 13 carbon atoms optionally having either or both of an ether group and an ester group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$ and $X_6$ each independently represent any of a single bond, a phenylene group, a naphthylene group, an ether group, an ester group, and an amide group; $X_5$ represents any of a single bond, an ether group, and an ester group; $X_7$ represents any of a single bond, an arylene group having 6 to 12 carbon atoms, a —C(=O)—O—$R^{18}$— group, and a —C(=O)—NH—$R^{18}$— group, and $X_7$ optionally has one or more selected from an ether group, a carbonyl group, an ester group, and an amide group; $R^{18}$ represents a single bond, a linear, branched, or cyclic alkylene group having 1 to 12 carbon atoms, or a divalent aromatic hydrocarbon group having 6 to 10 carbon atoms, and the aromatic hydrocarbon group is optionally partially hydrogenated; Y represents an oxygen atom or a —$NR^{19}$— group, and Y and $R^4$ are optionally bonded to each other to form a ring; $R^{19}$ represents a hydrogen atom, or a linear or branched alkyl group having 1 to 4 carbon atoms; "m" represents an integer of 1 to 4; a1, a2, a3, a4, a5, a6 and a7 represent numbers satisfying $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 \leq a1+a2+a3+a4+a5+a6+a7 \leq 1.0$; and $M^+$ represents an ion selected from an ammonium ion, a sodium ion, a potassium ion, and a silver ion.

Among the repeating units-a1 to -a7 shown by the general formula (2), the repeating units-a1 to a5 can be obtained from fluorosulfonic acid salt monomers specifically exemplified below.

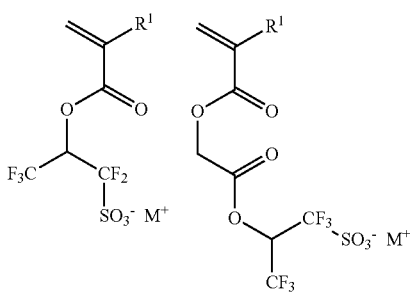

-continued
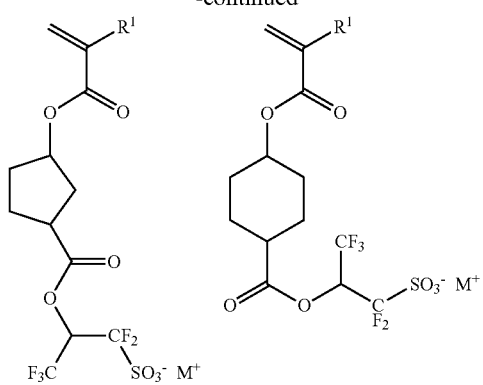
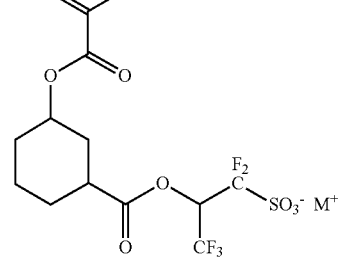
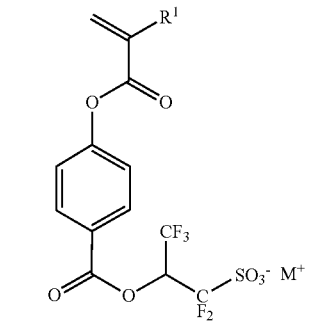
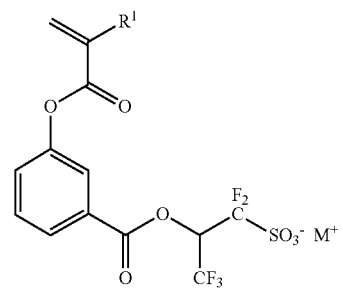
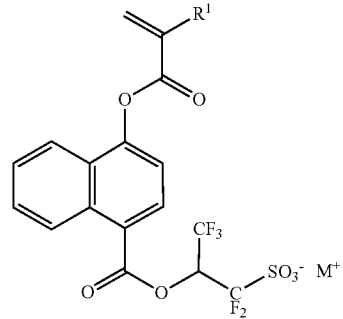
-continued
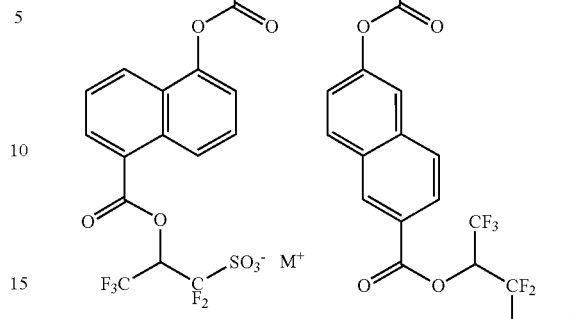
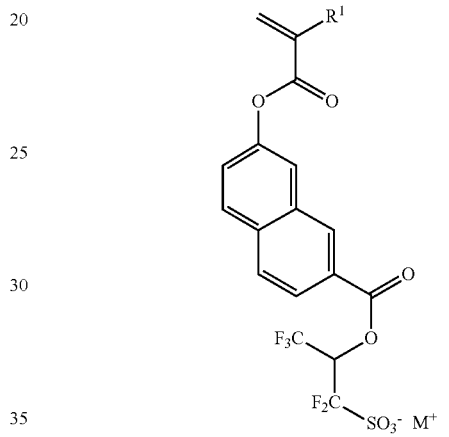
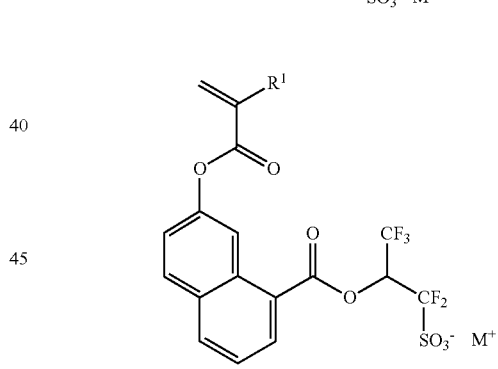
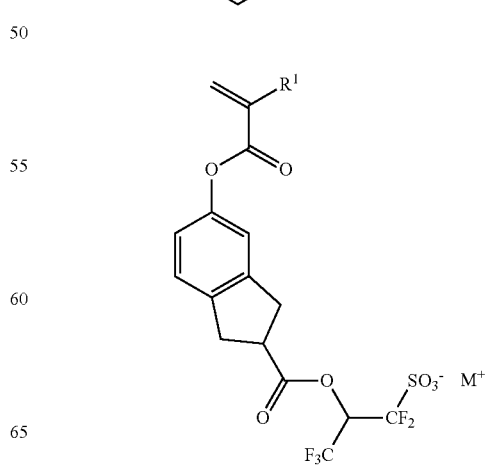

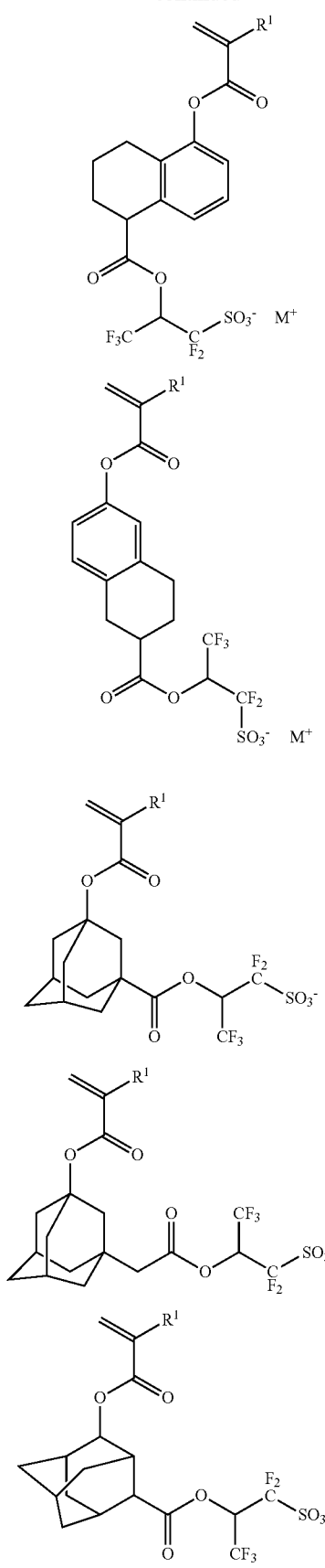
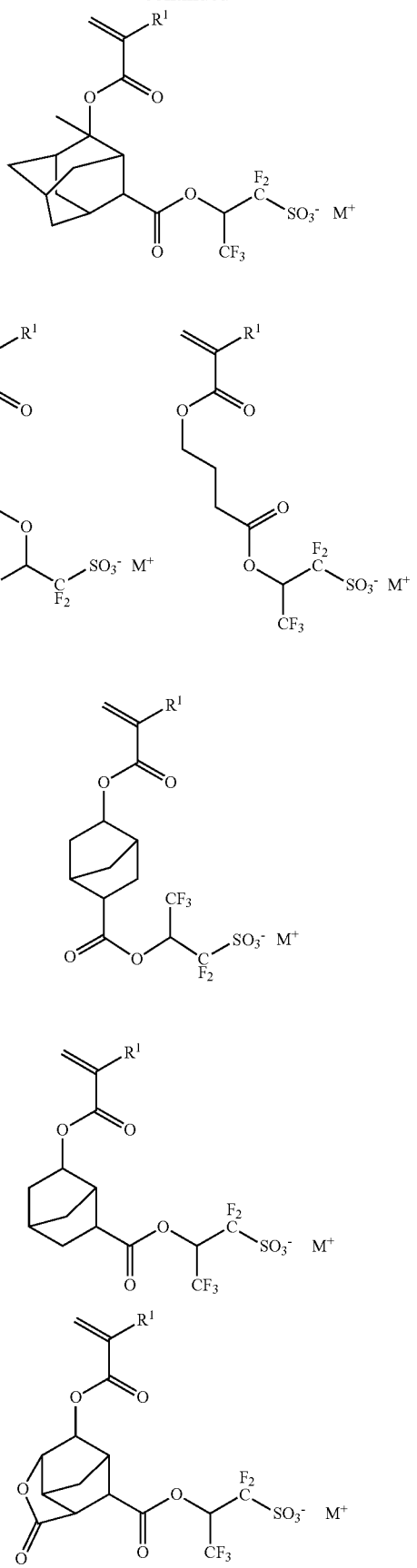

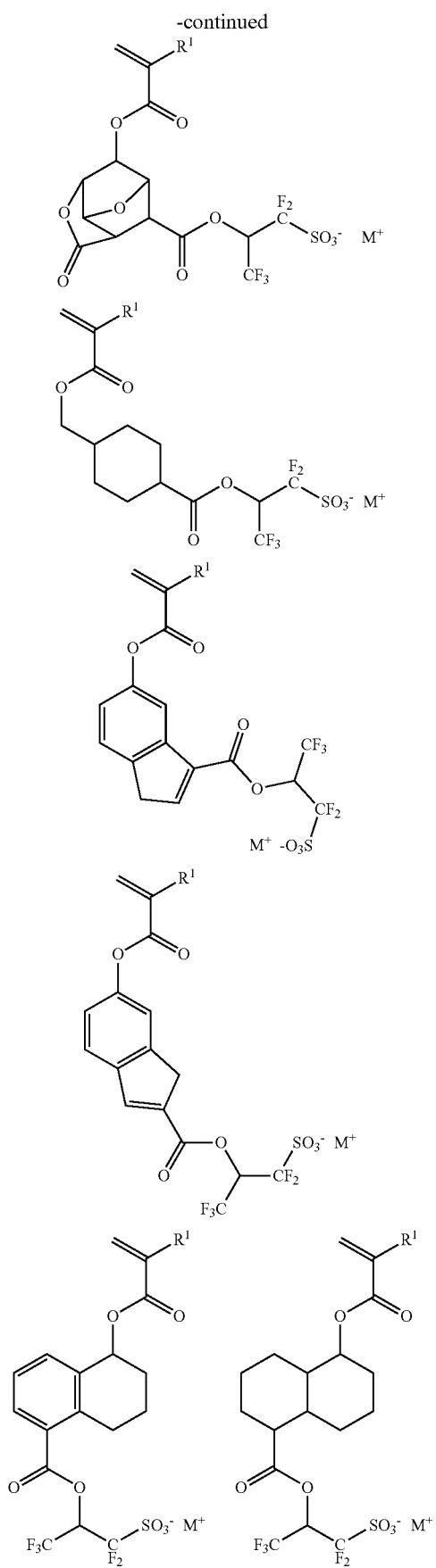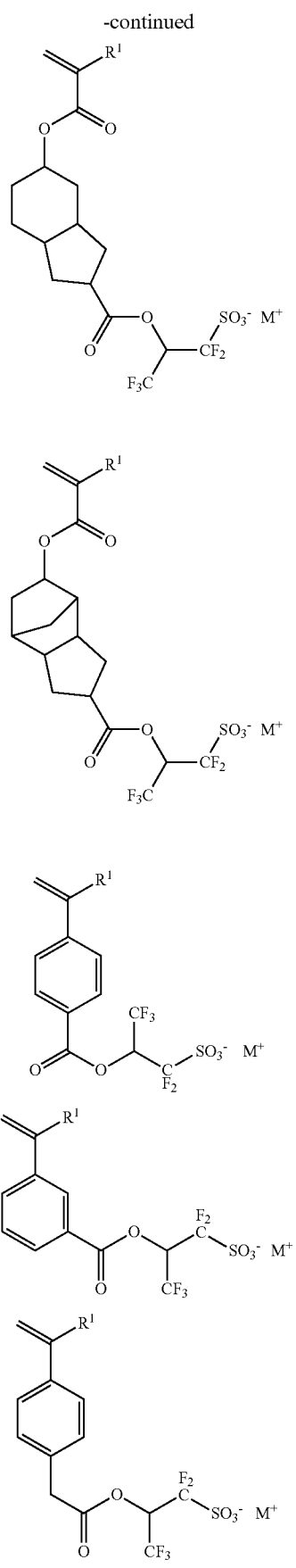

-continued

-continued
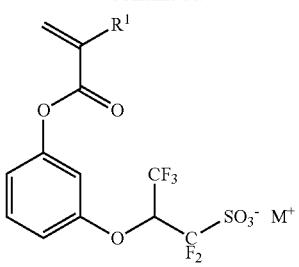
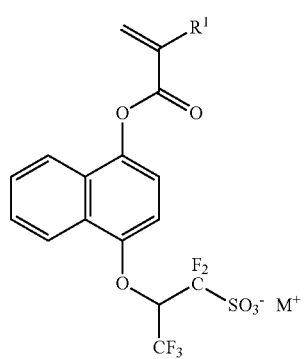
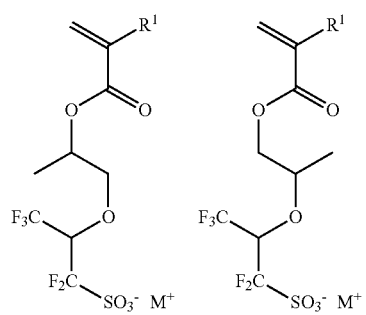
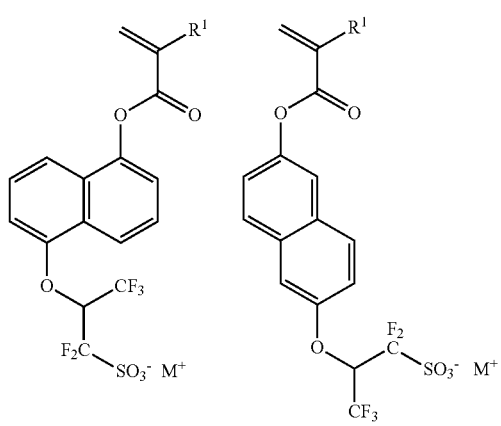
-continued
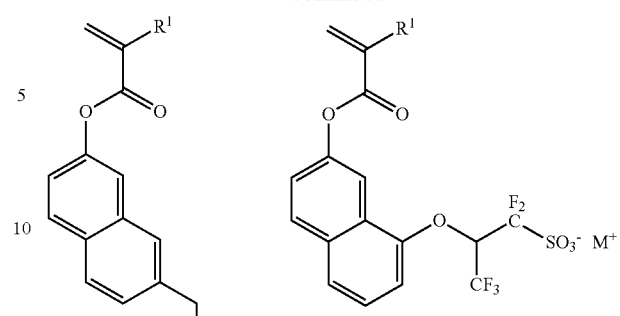
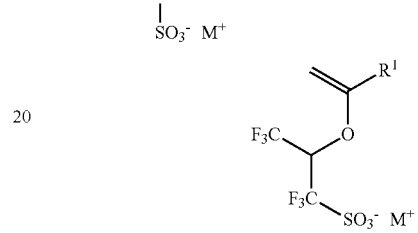
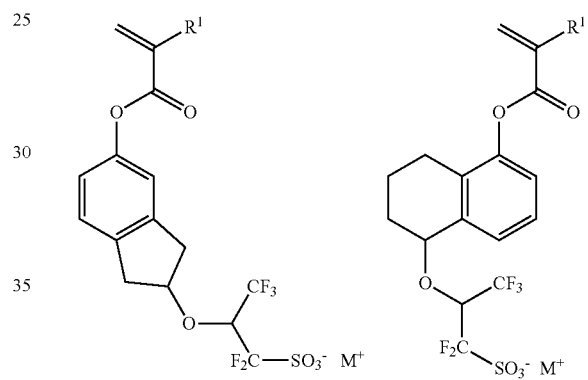
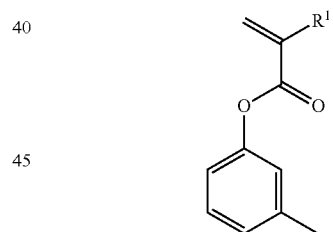
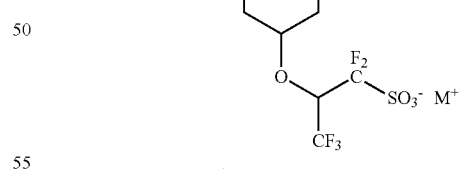
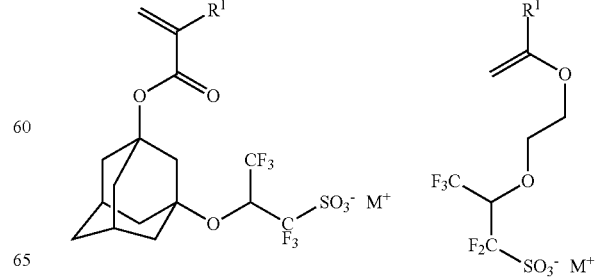

-continued
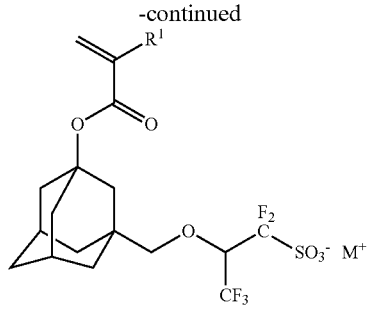
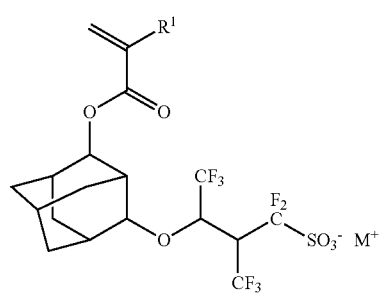
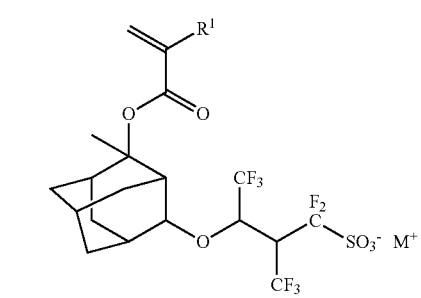
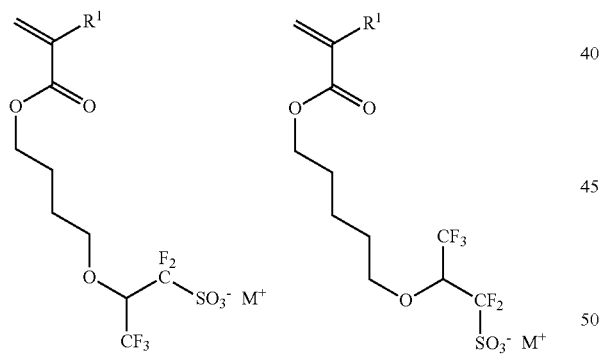
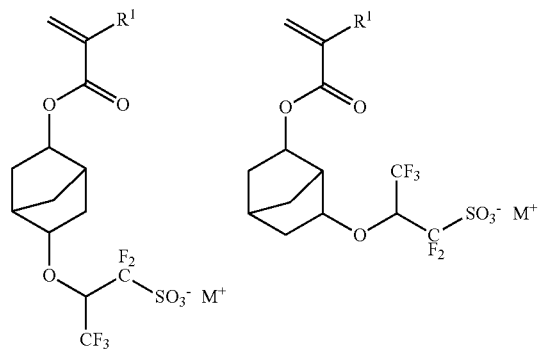
-continued
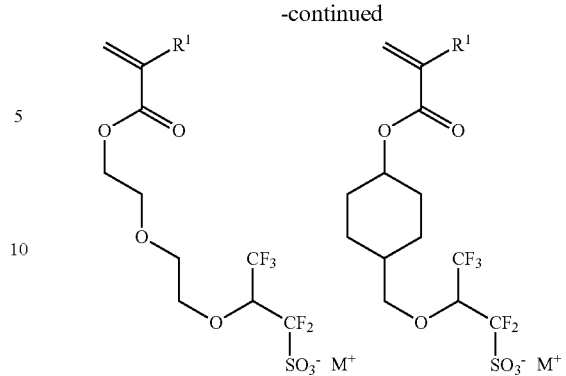
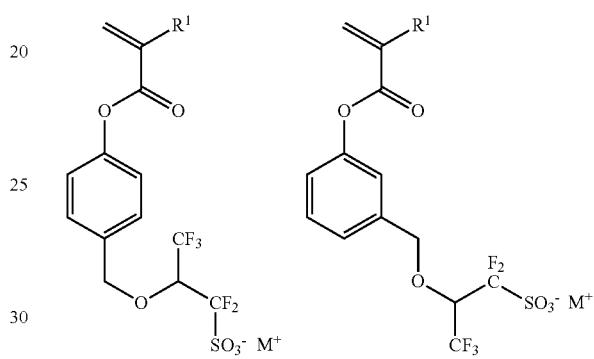
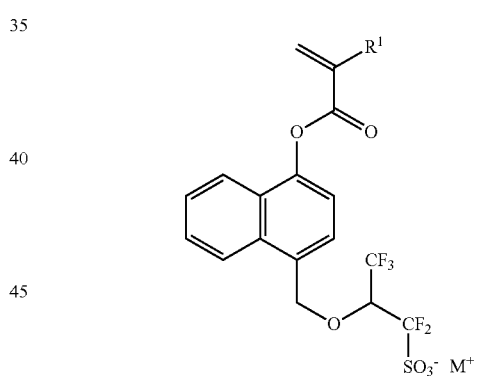
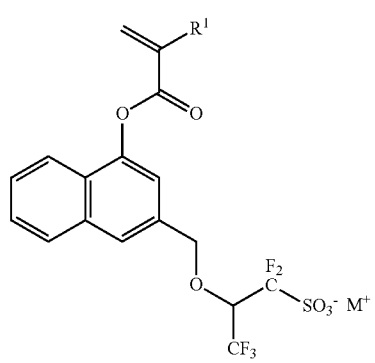

-continued
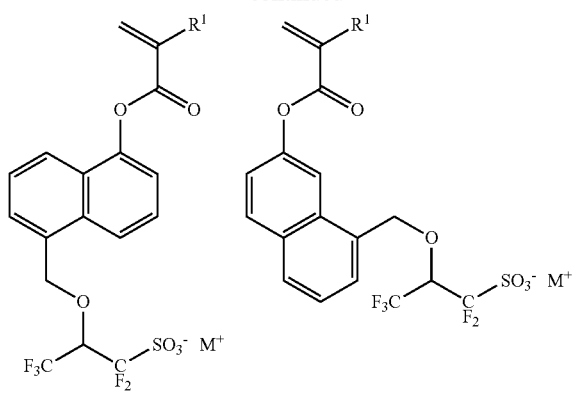
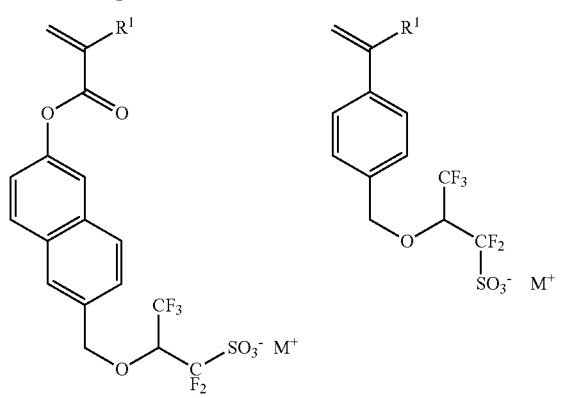
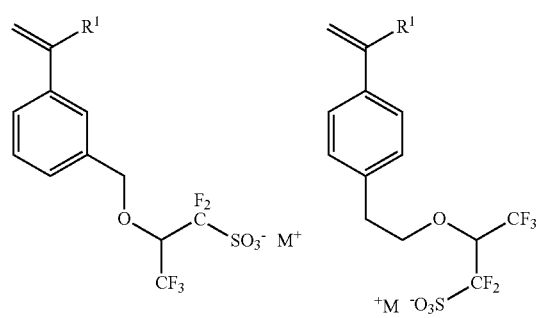
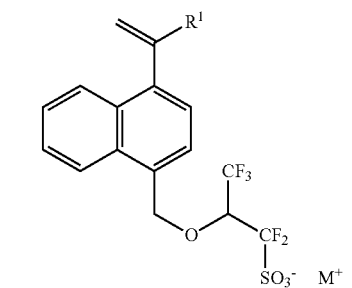
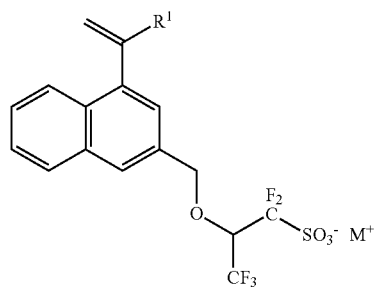
-continued
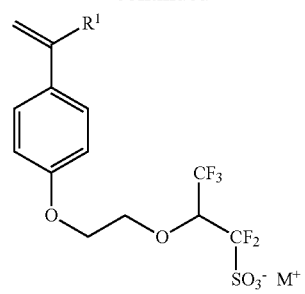
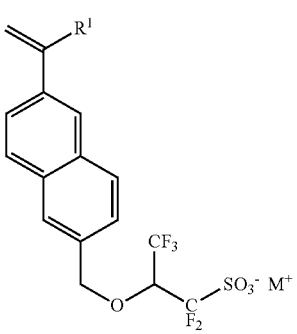
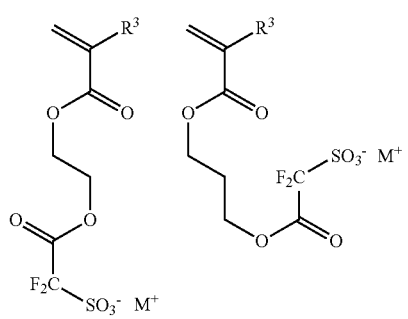
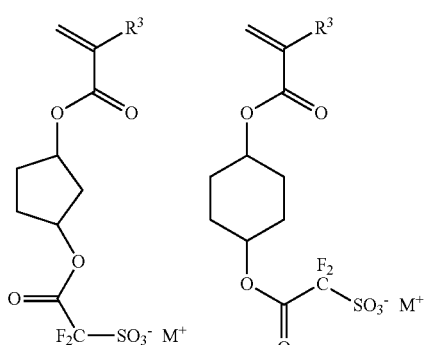
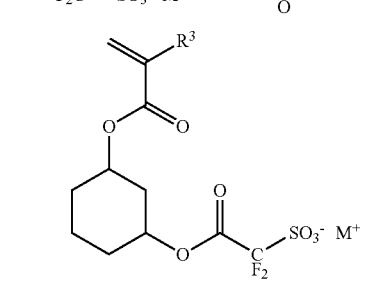

-continued
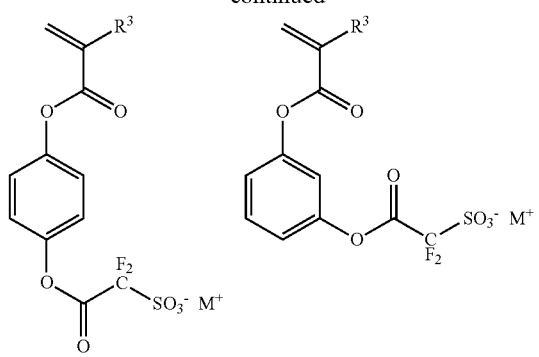
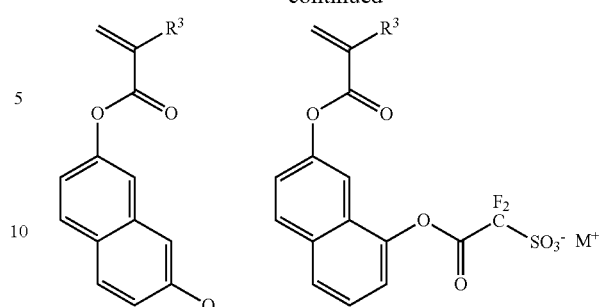
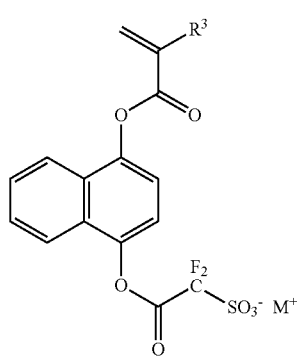
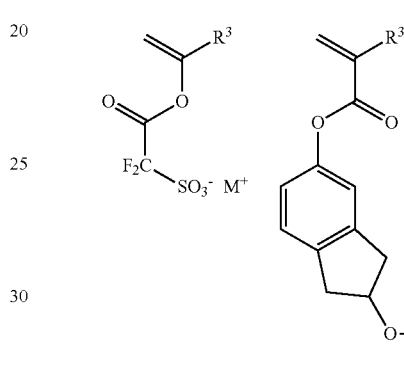
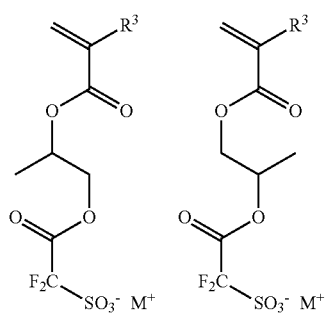
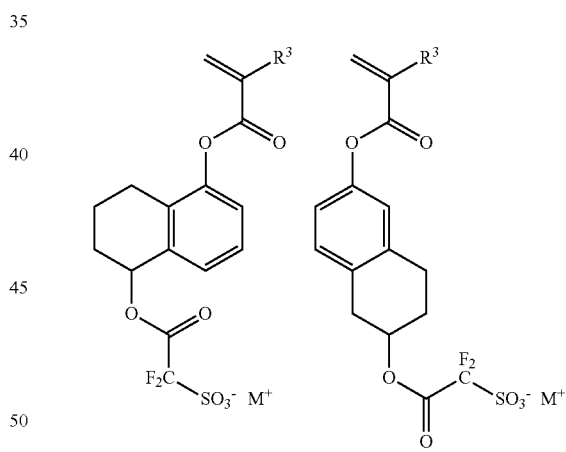
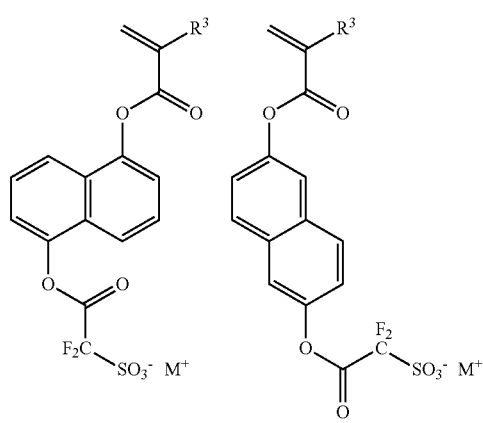
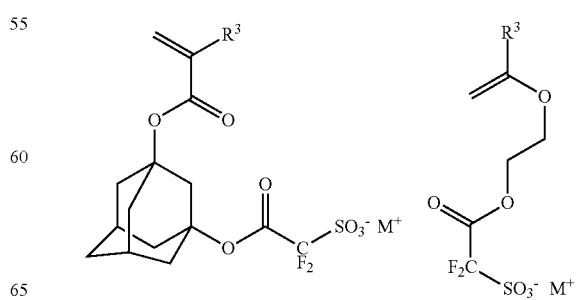

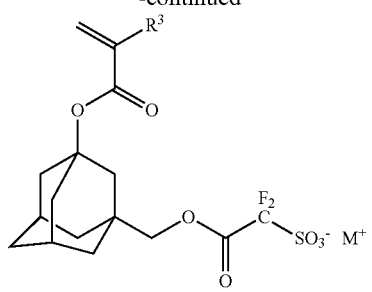
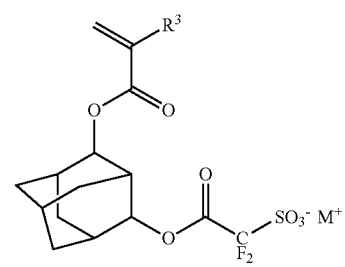
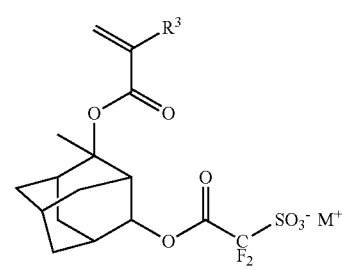
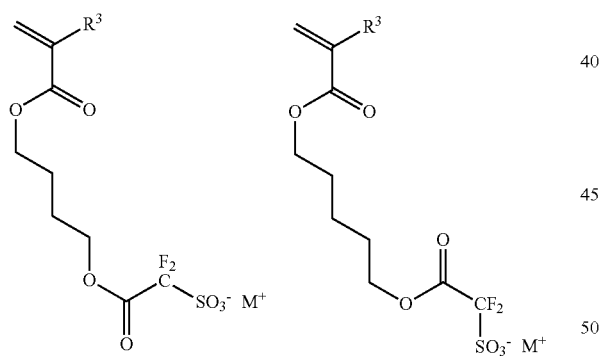
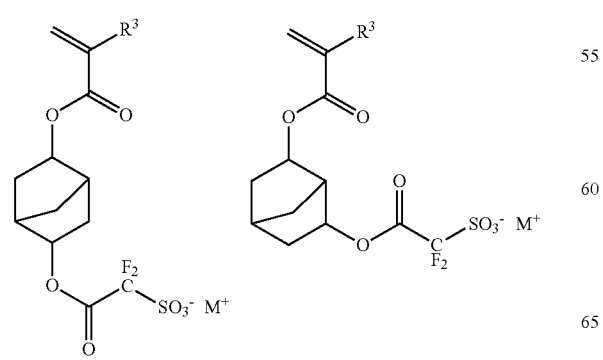
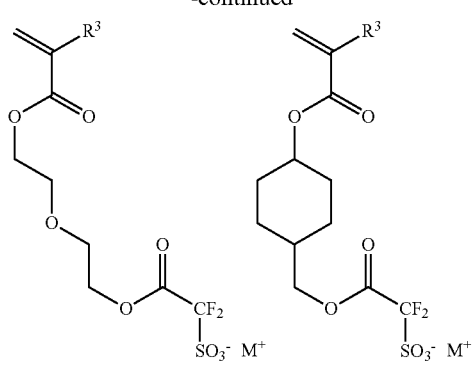
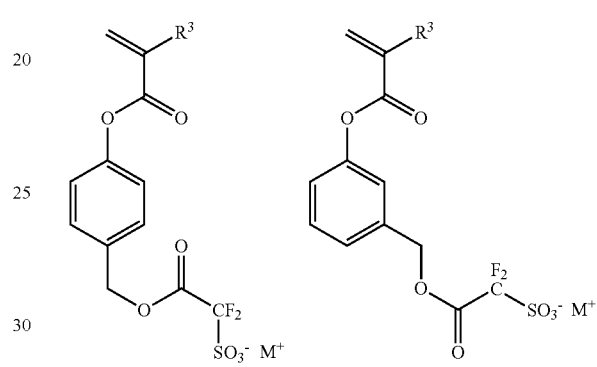
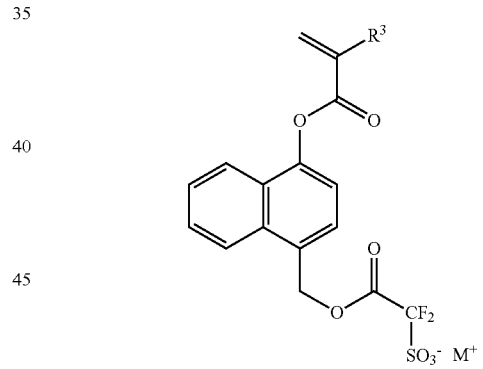
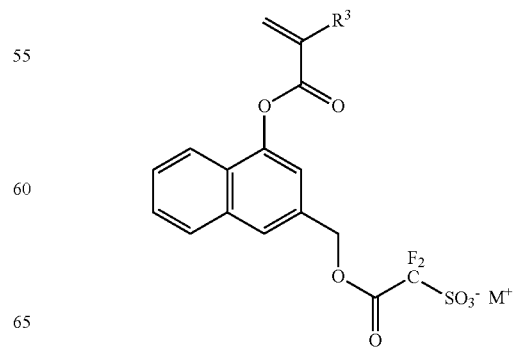

29
-continued
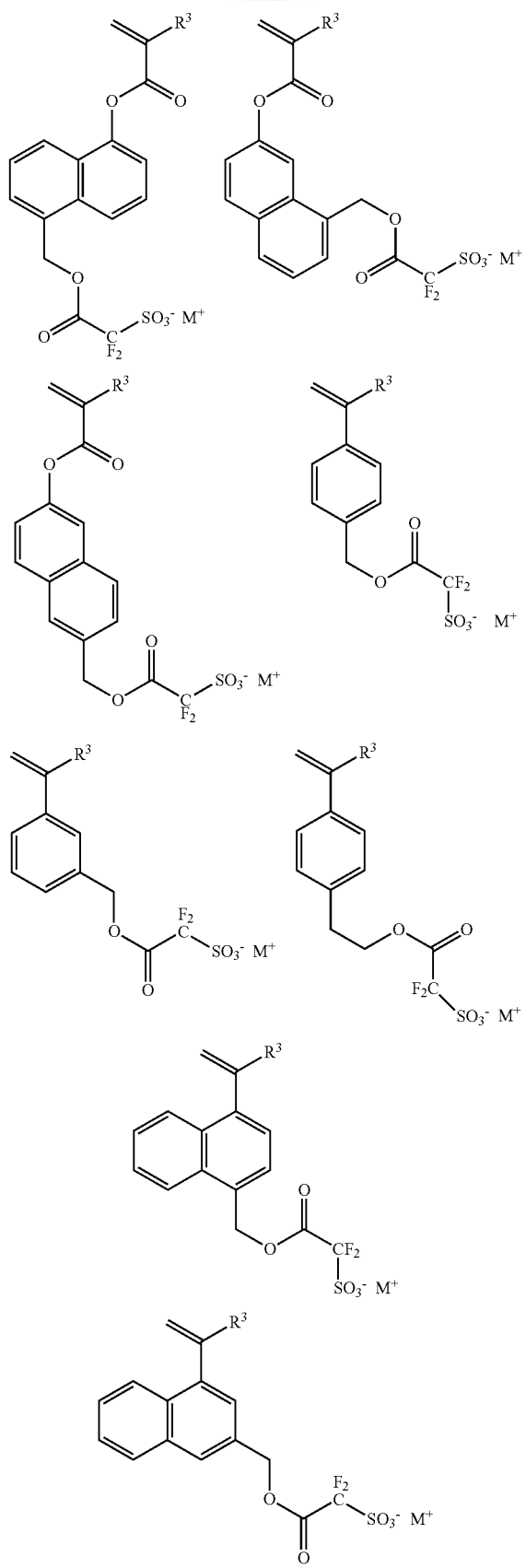
30
-continued
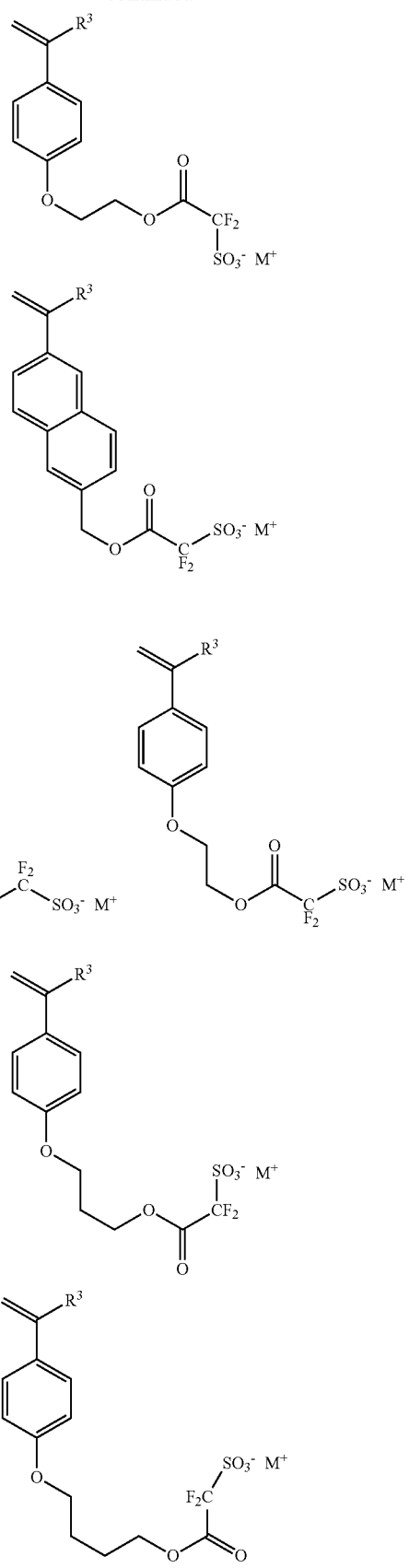

31
-continued
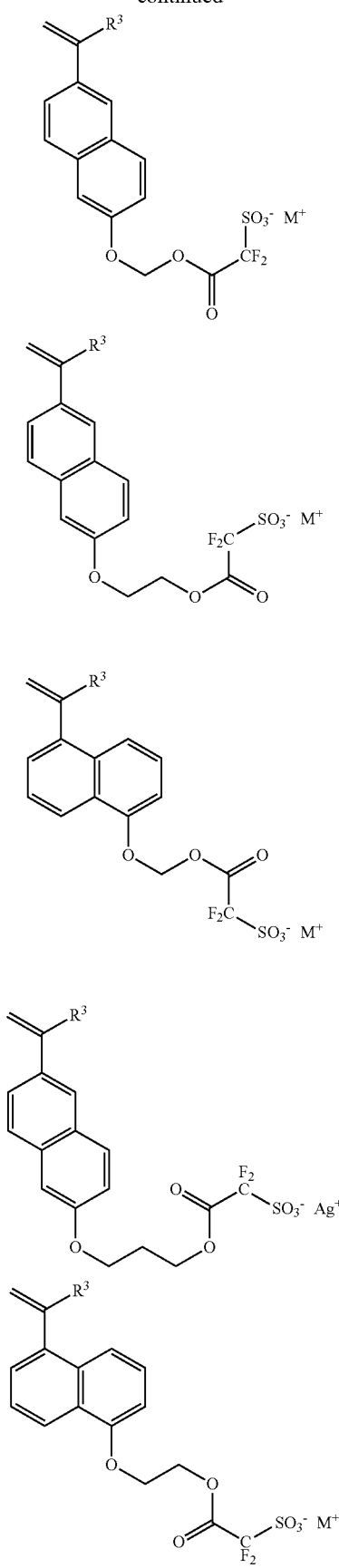
32
-continued
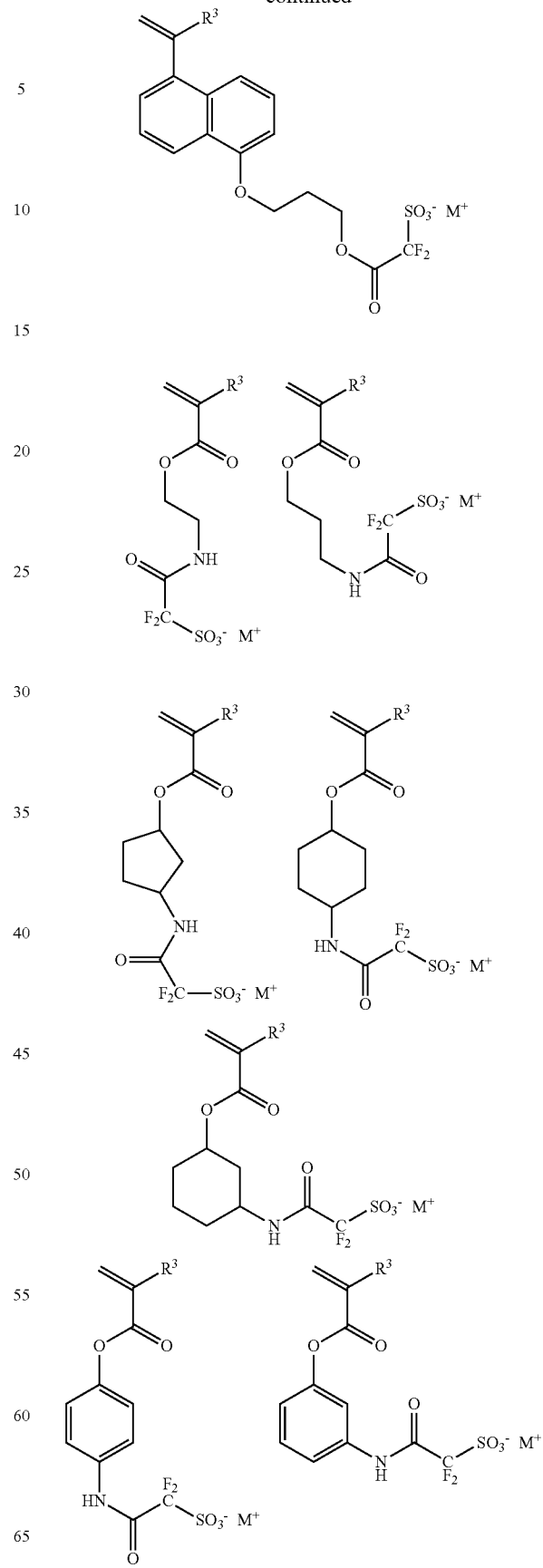

33
-continued
34
-continued
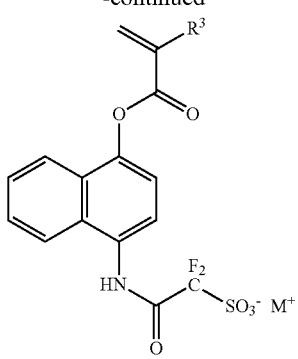
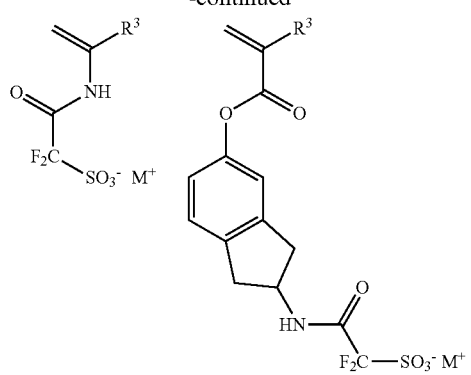
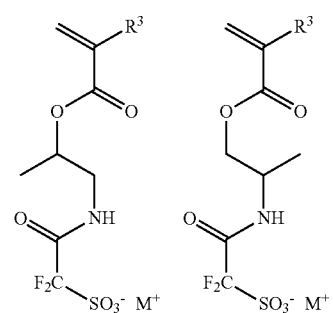
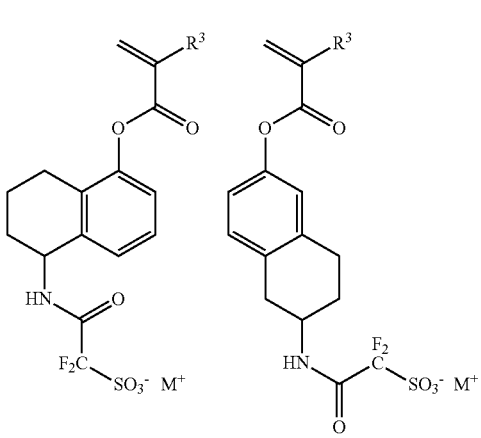
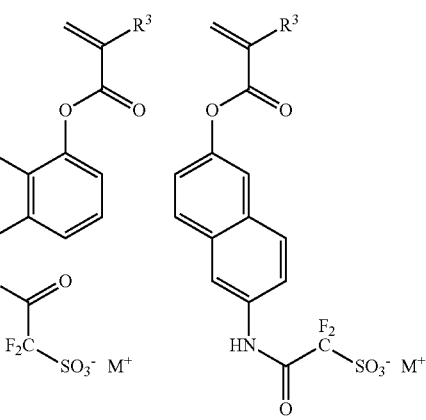
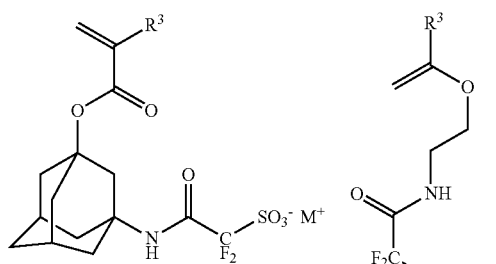
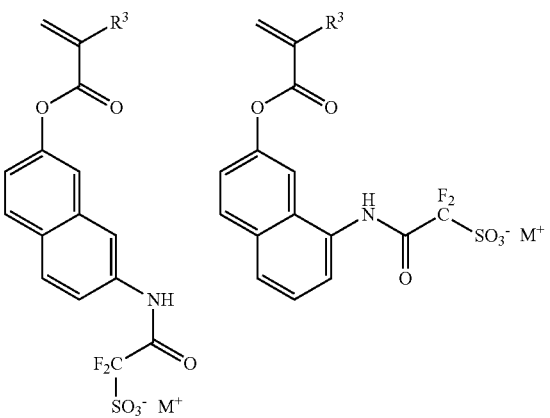
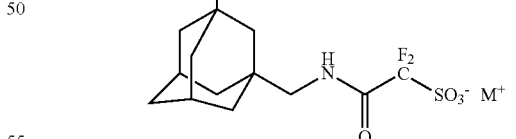
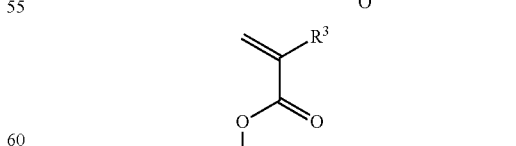

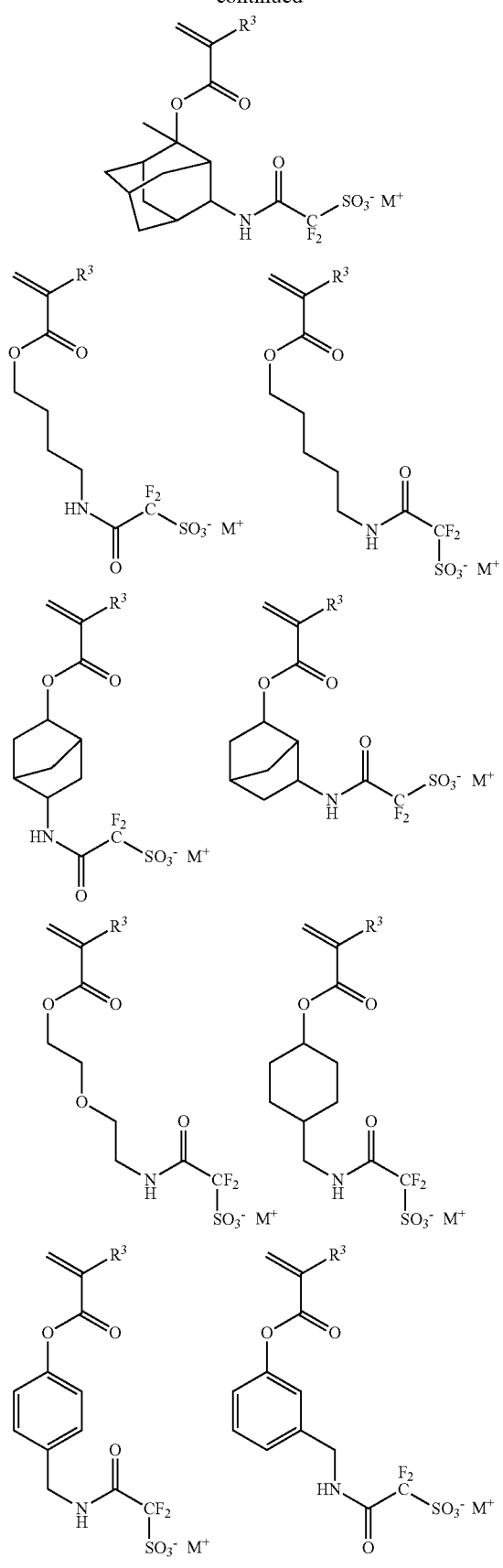
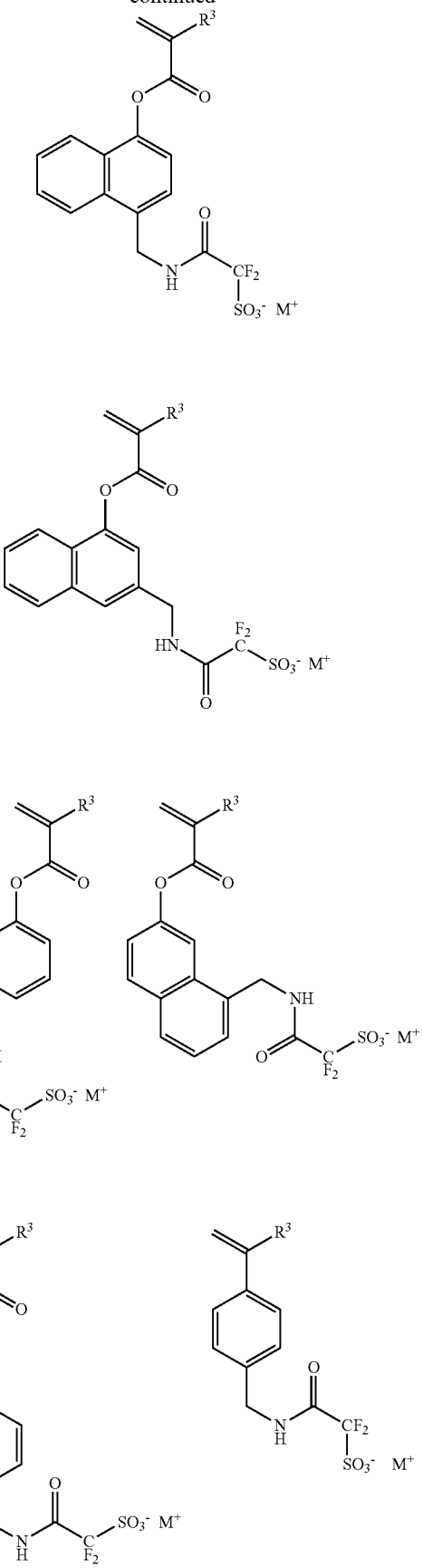

-continued
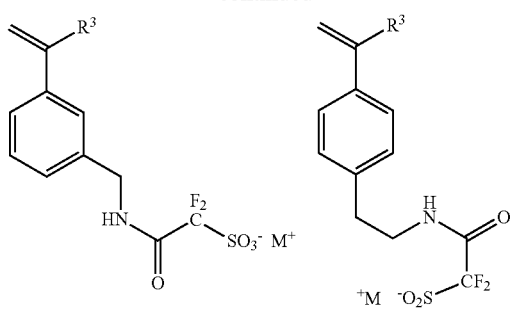
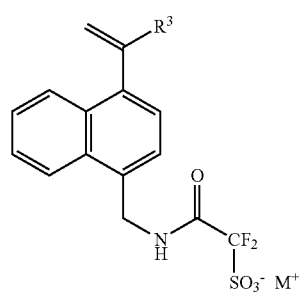
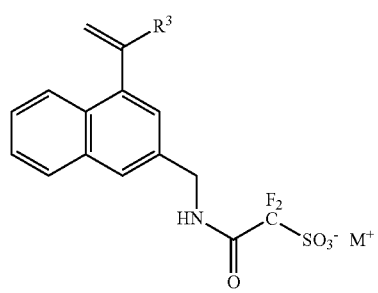
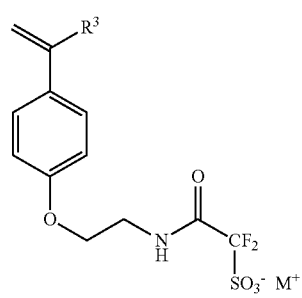
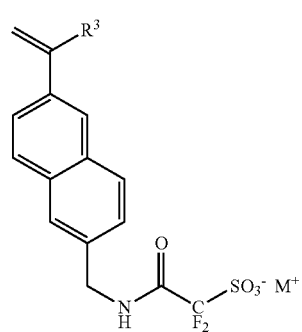
-continued
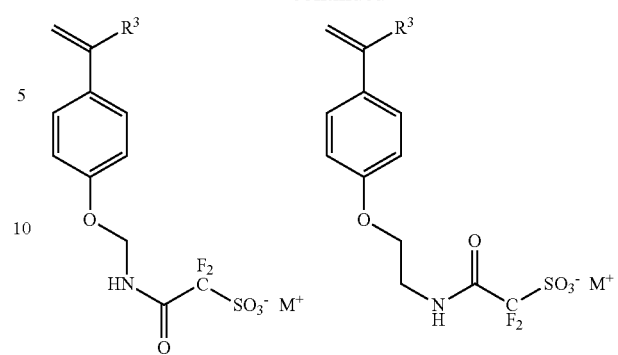
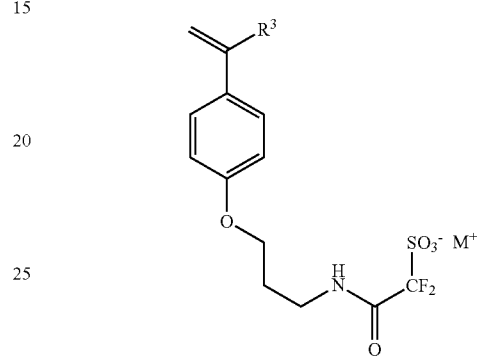
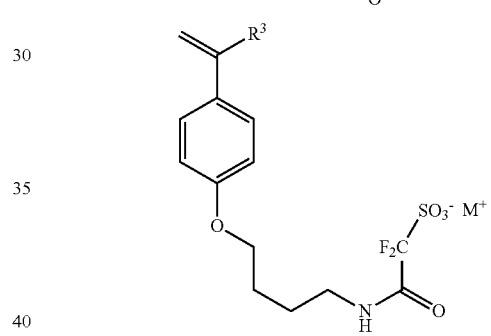
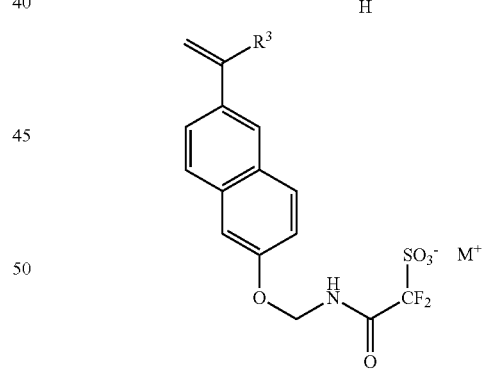
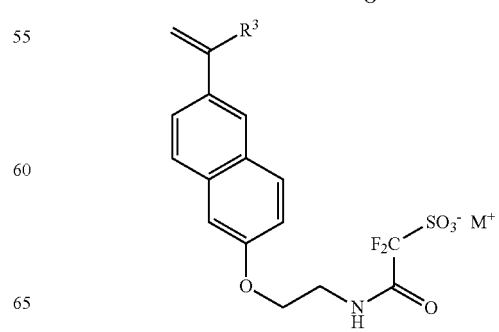

-continued
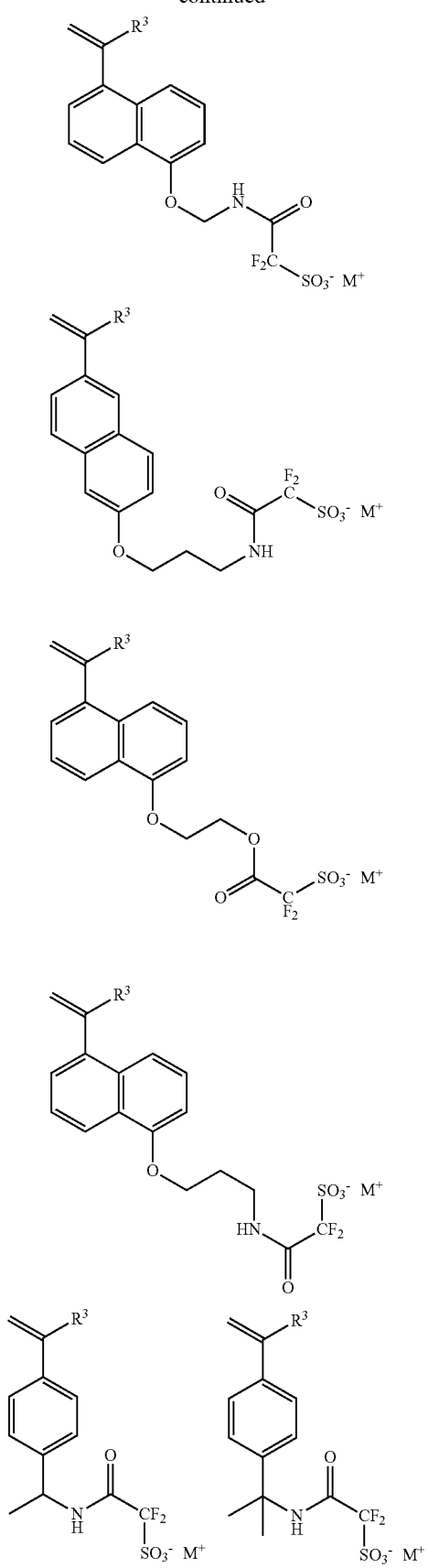
-continued
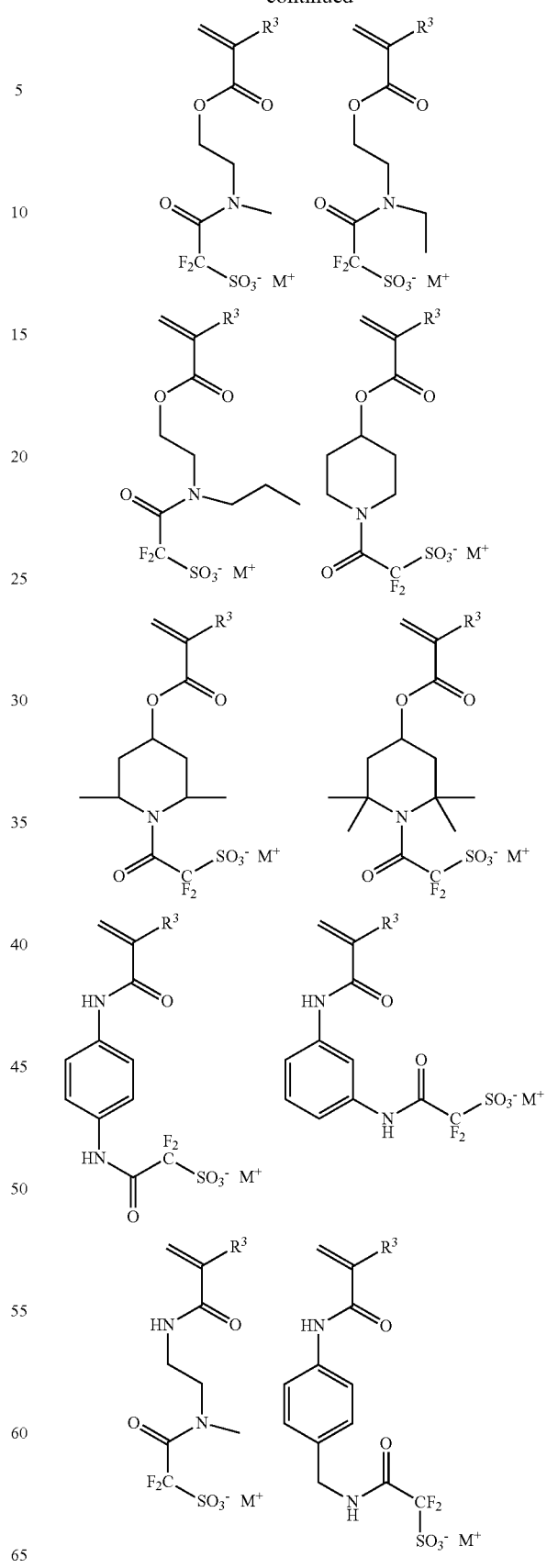

-continued
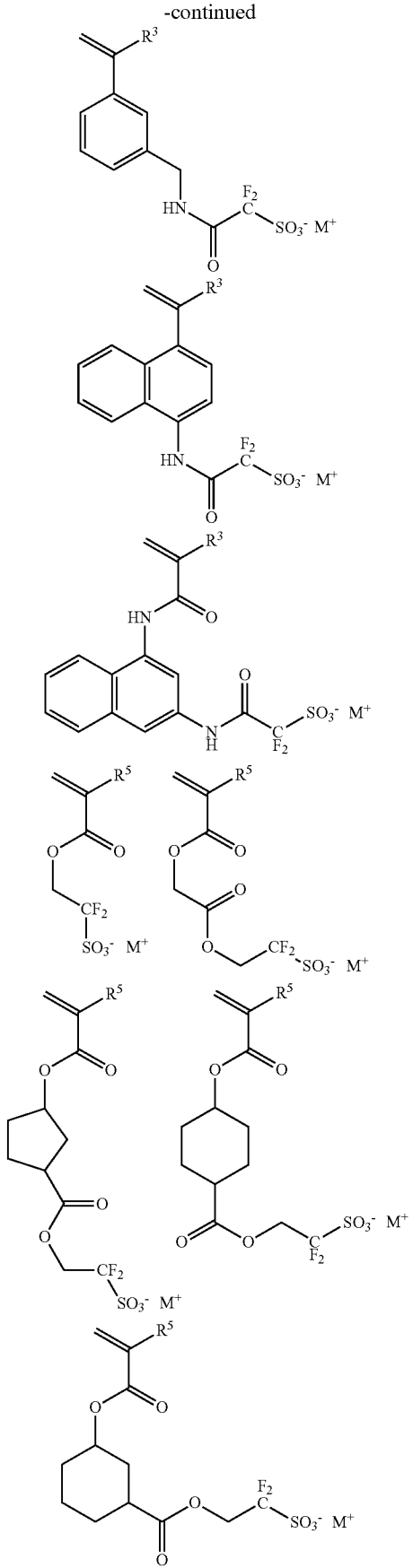
-continued
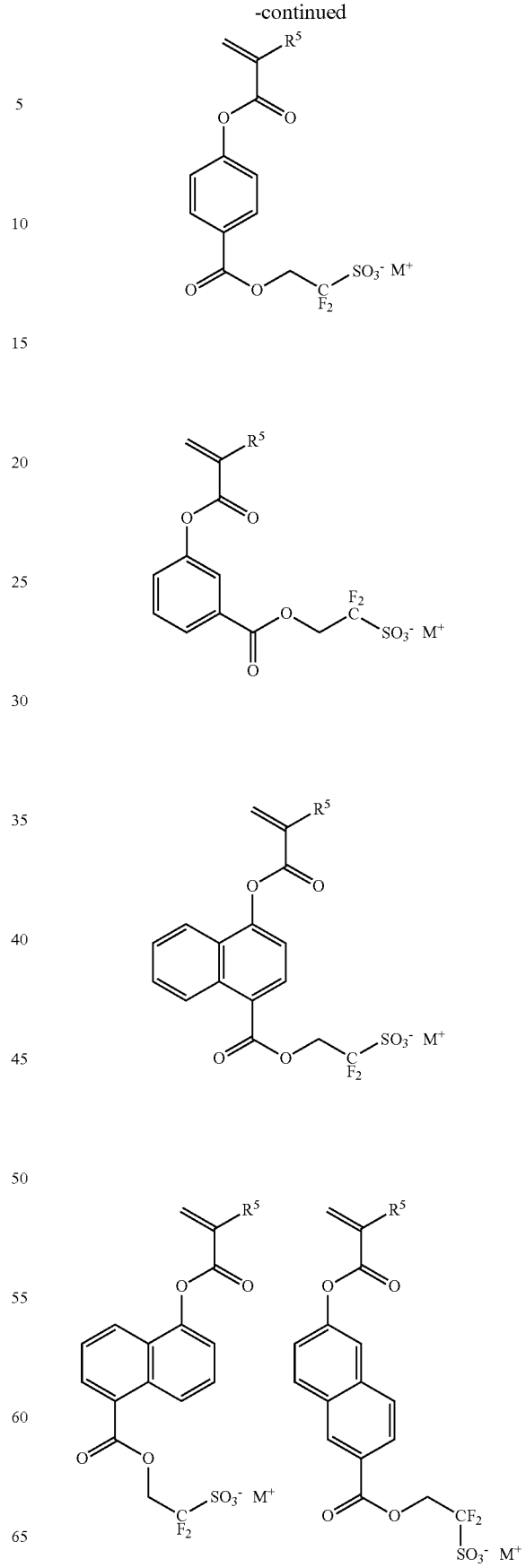

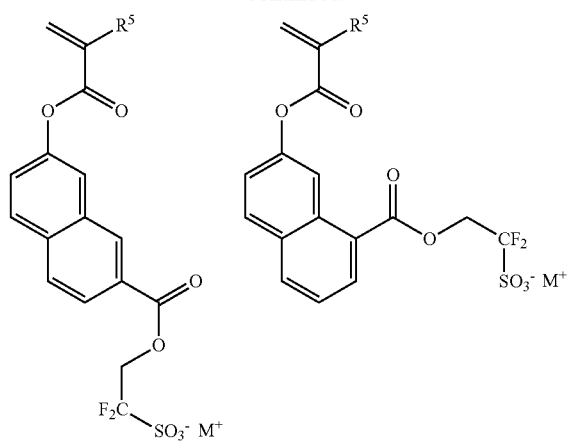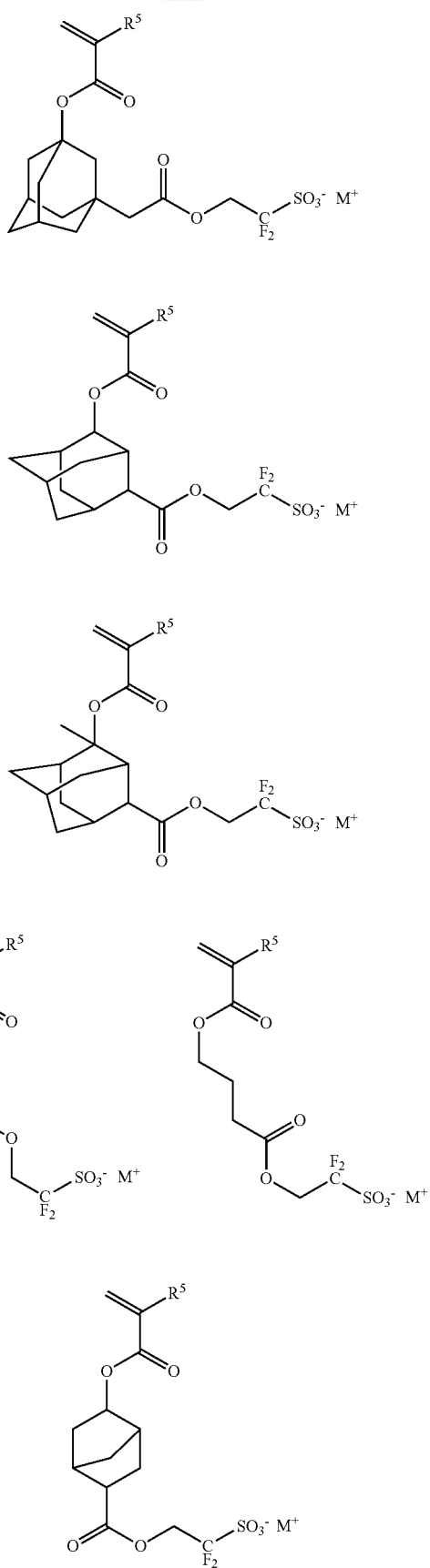

-continued
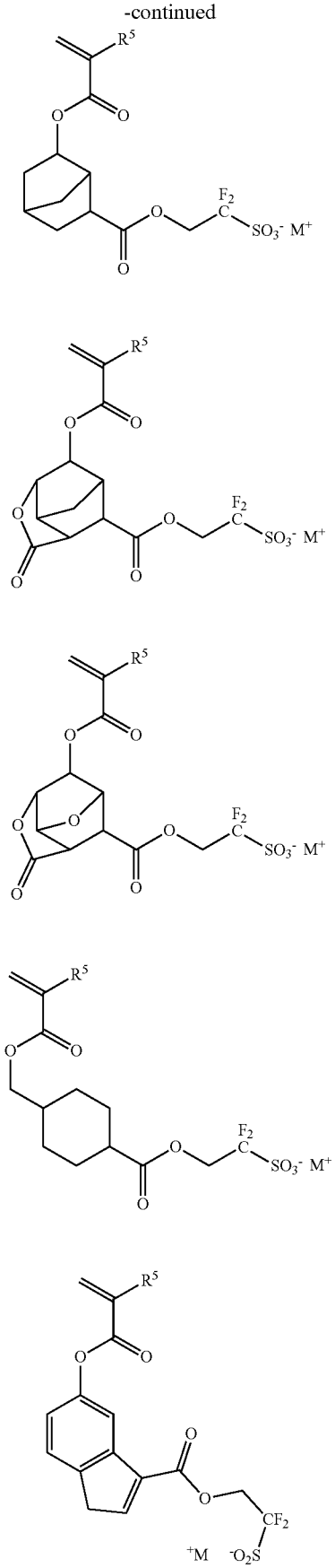
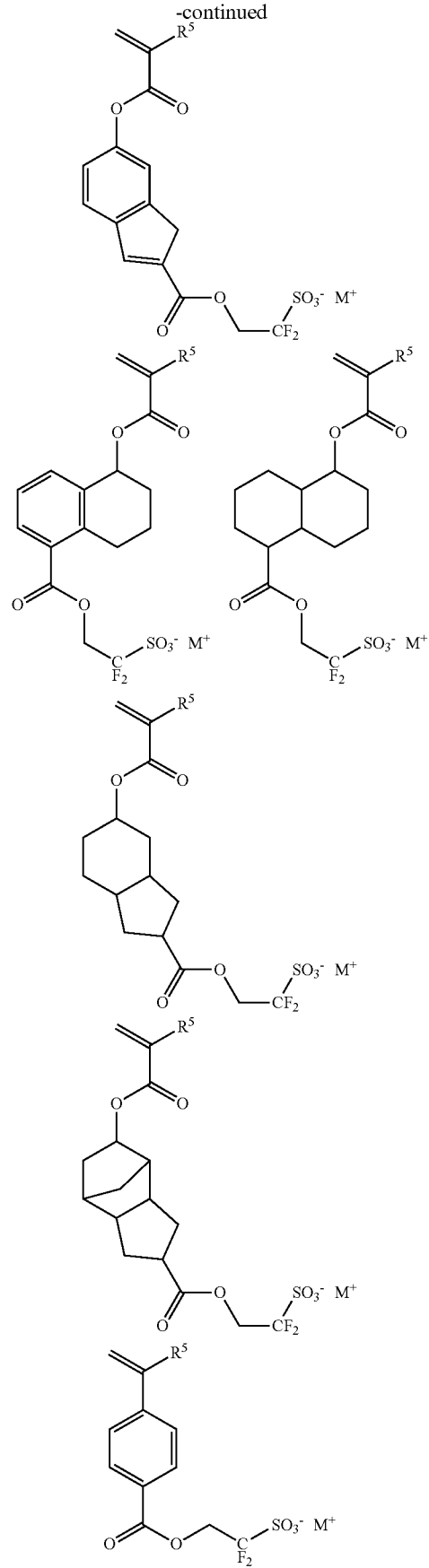

-continued
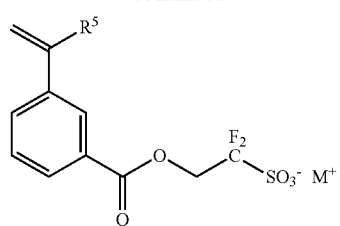
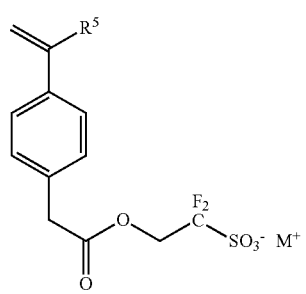
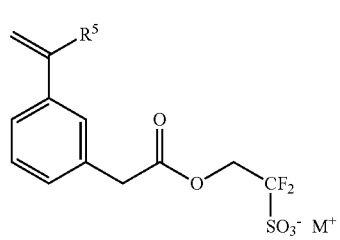
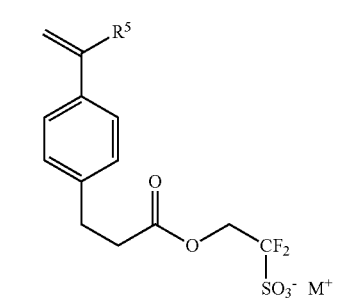
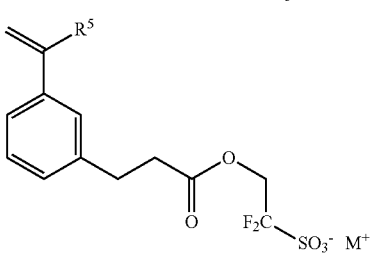
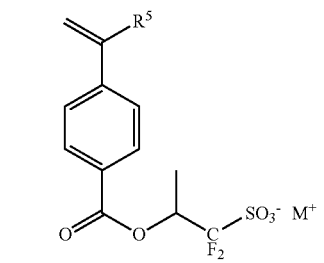
-continued
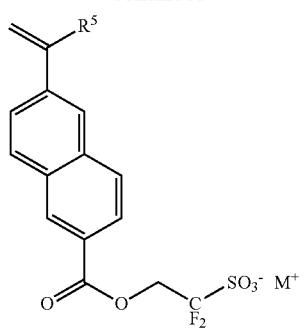
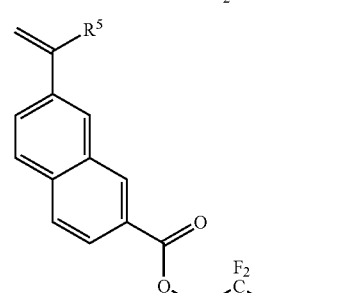
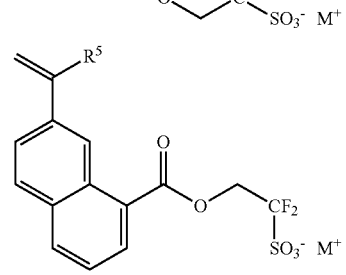
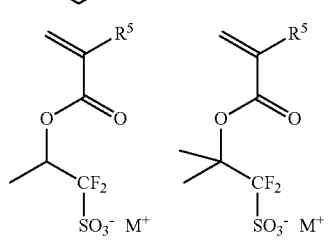
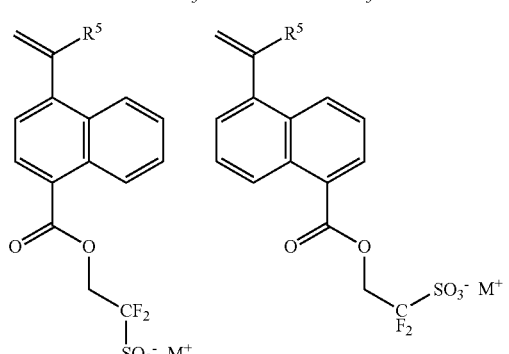
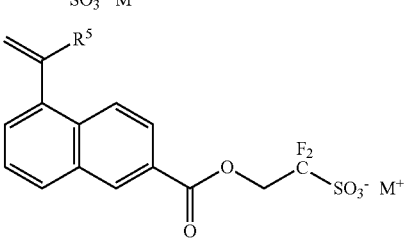

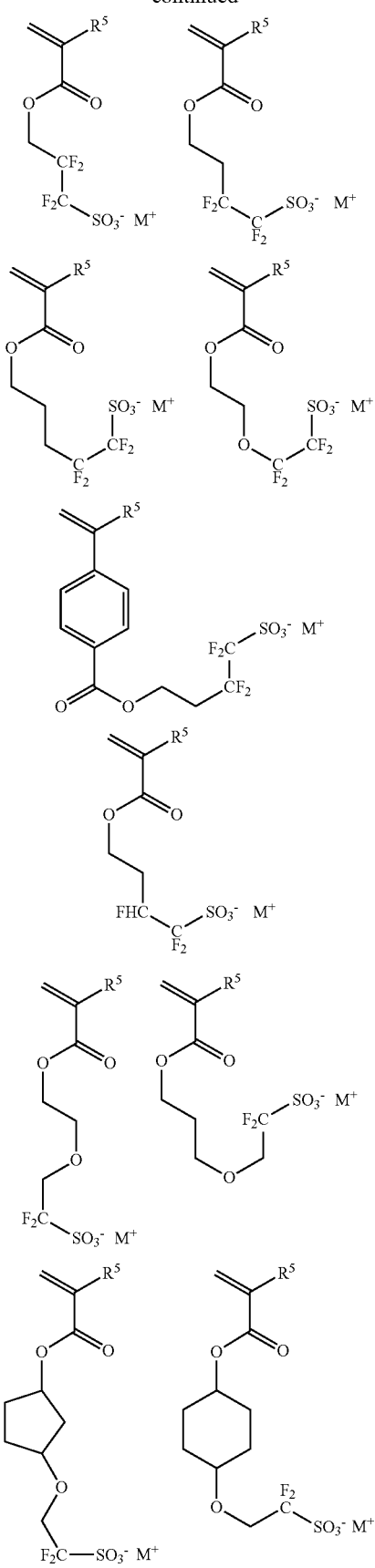
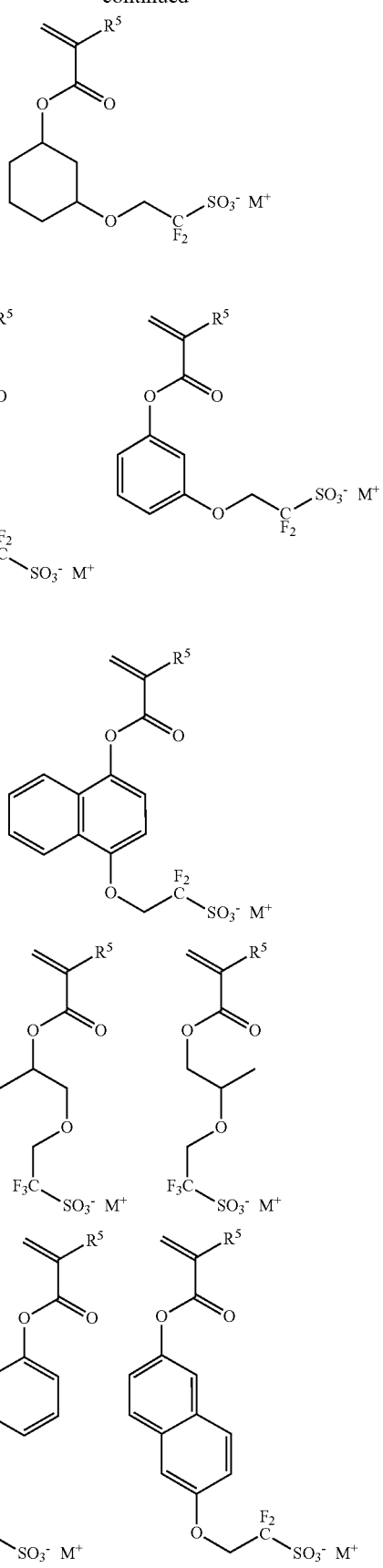

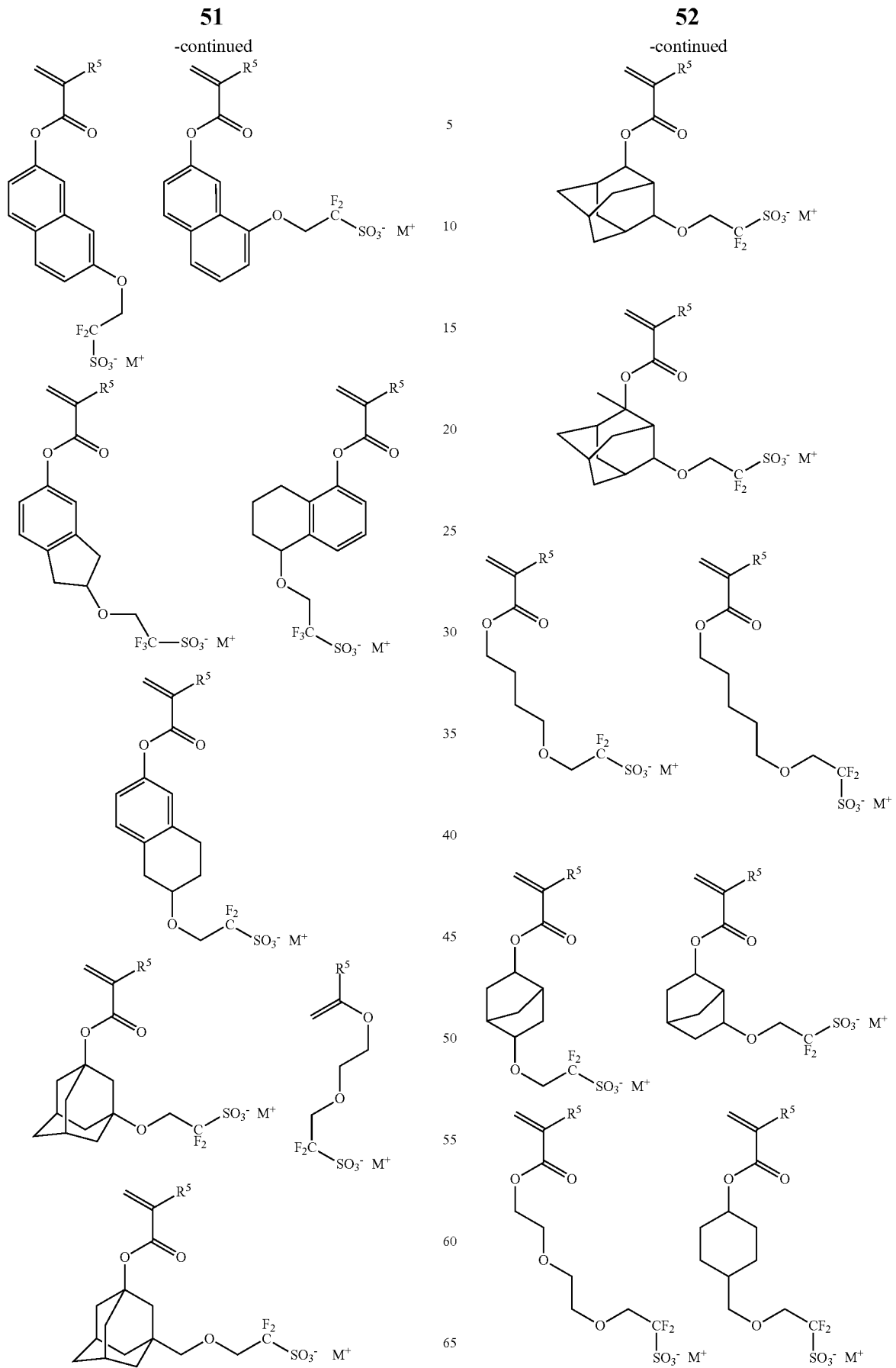

-continued
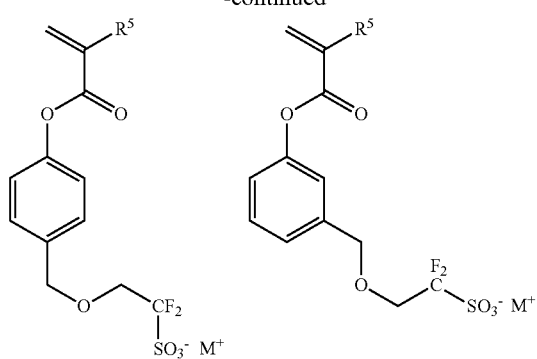
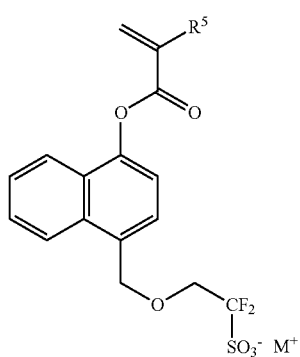
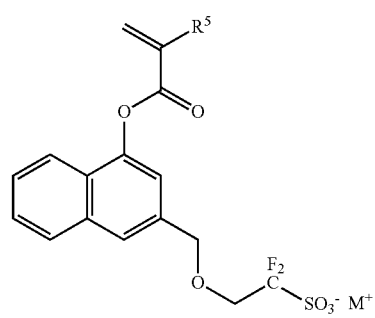
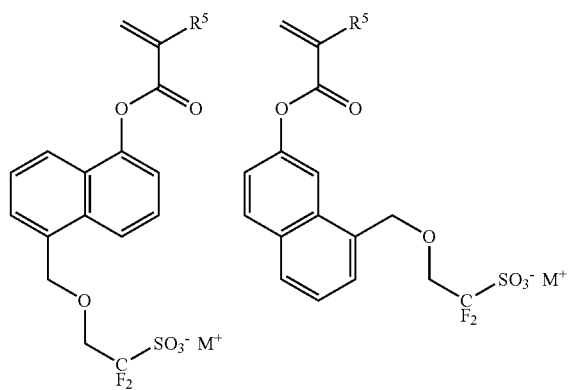
-continued
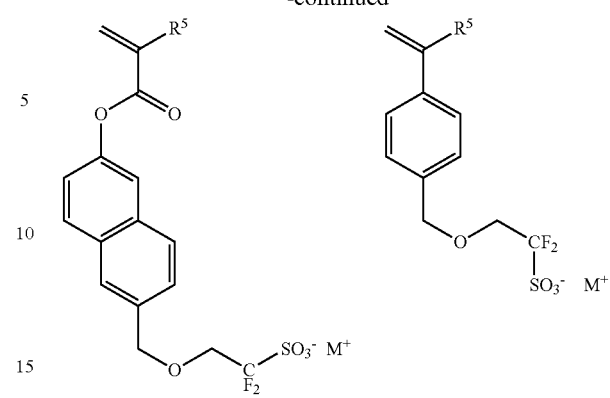
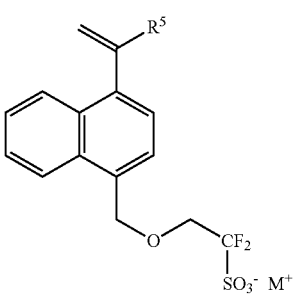
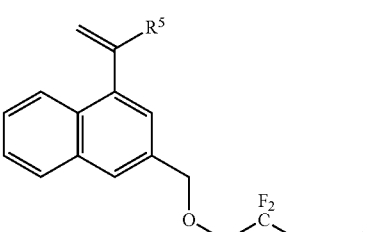
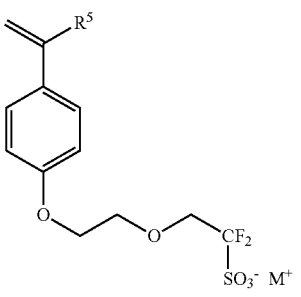

-continued
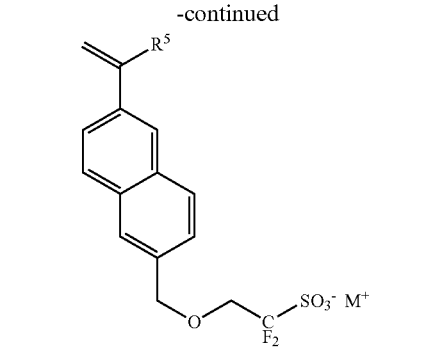
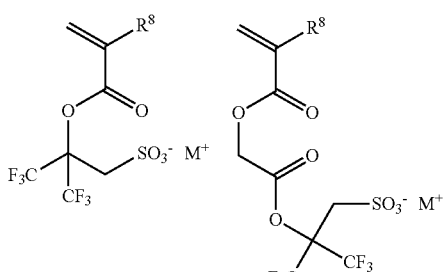
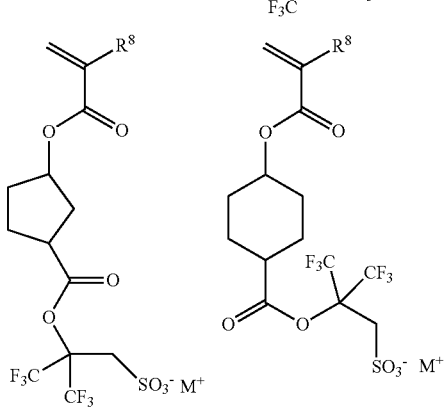
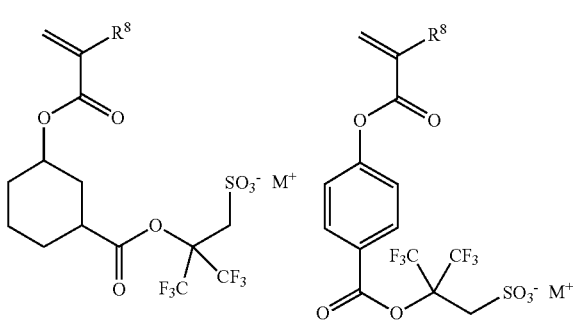
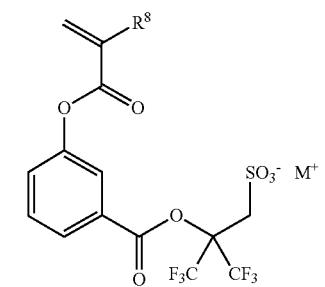
-continued
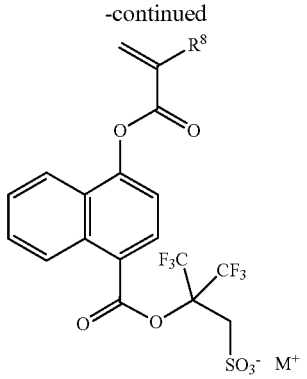
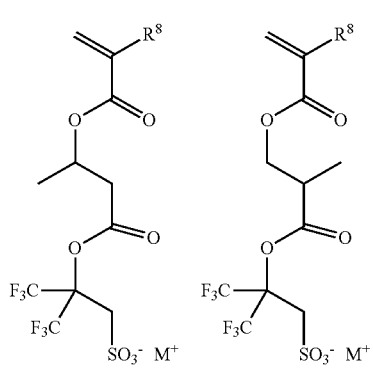
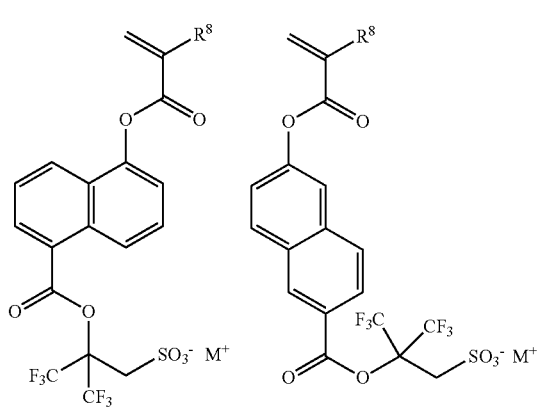
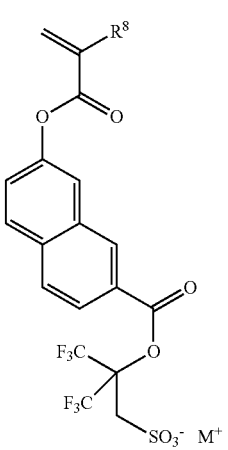

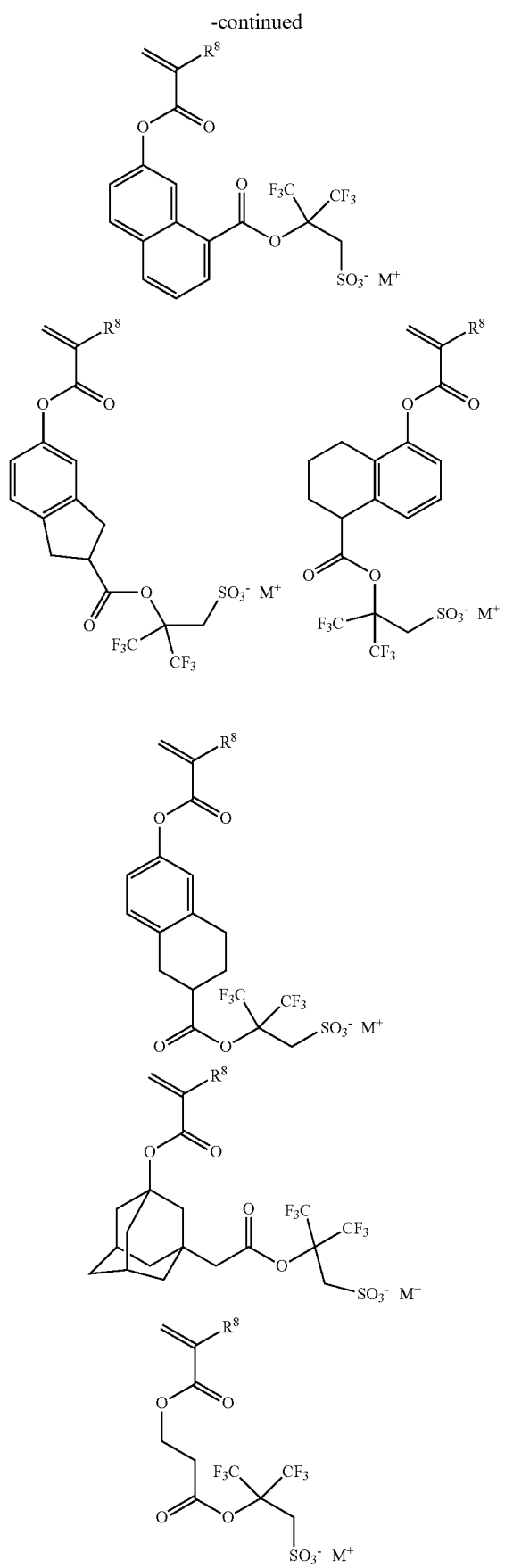
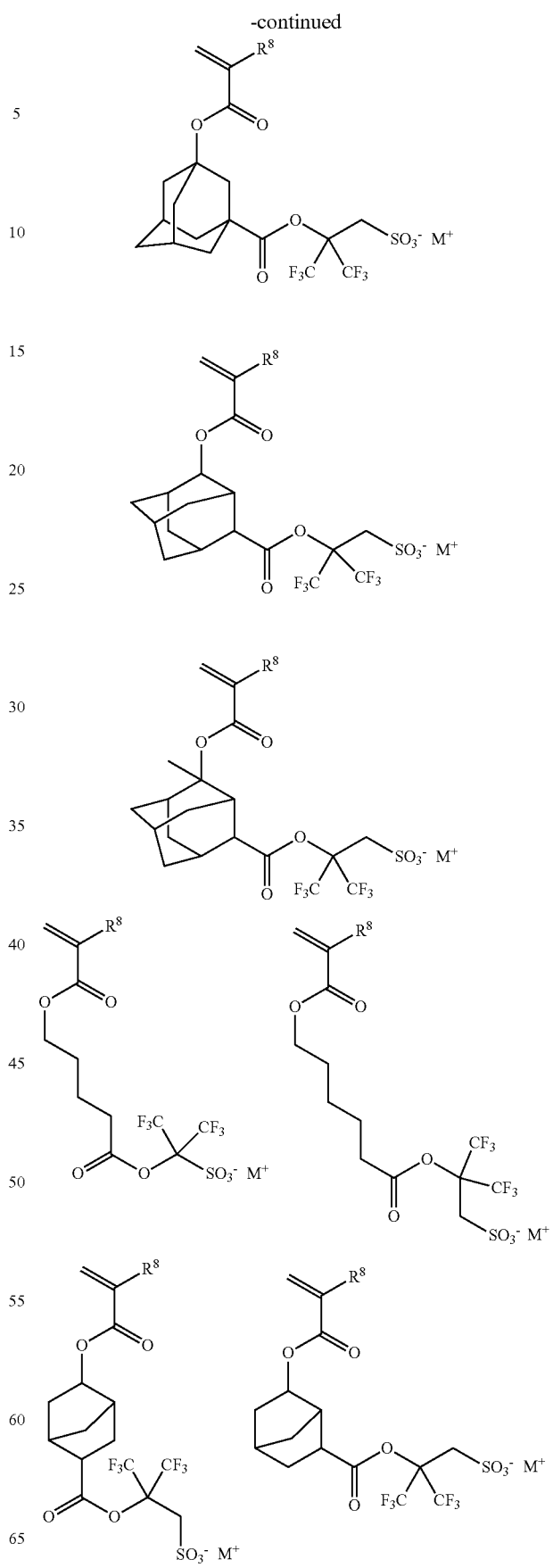

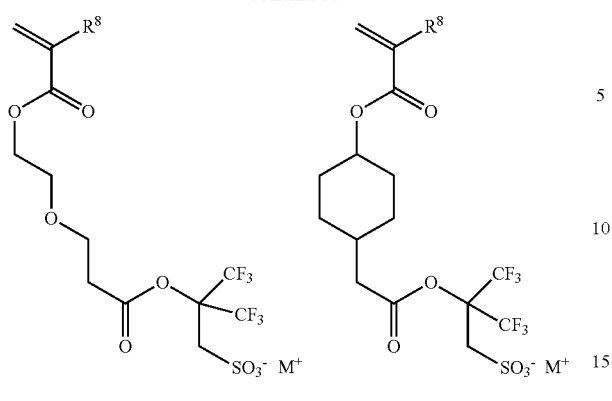
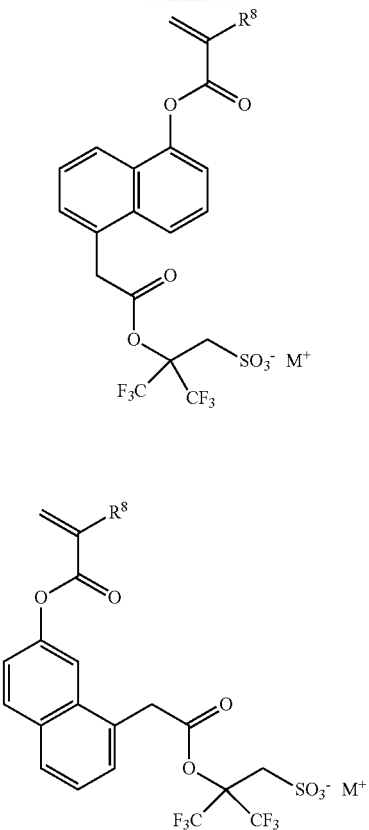
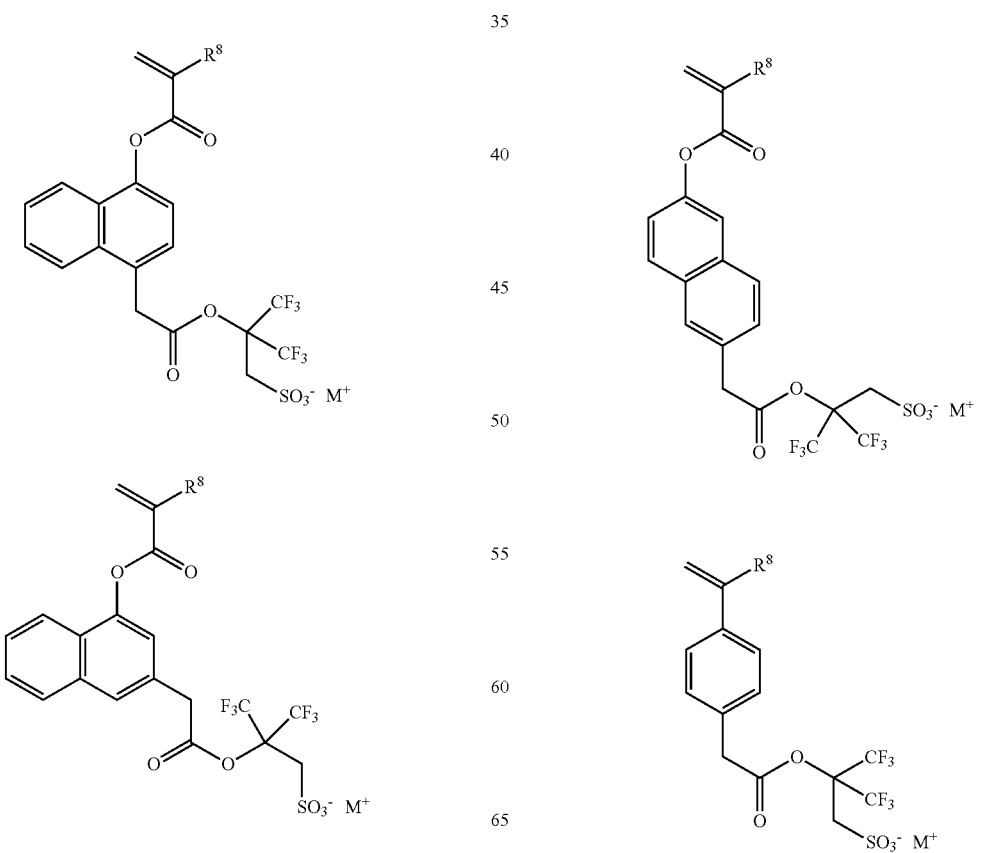

61
-continued
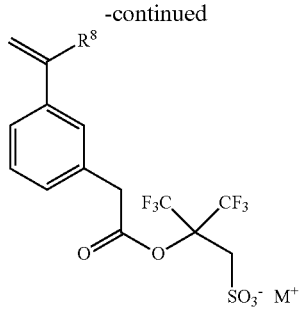
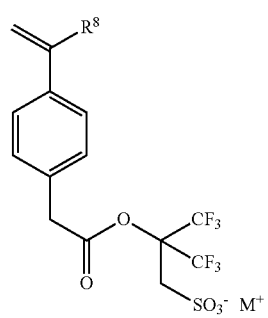
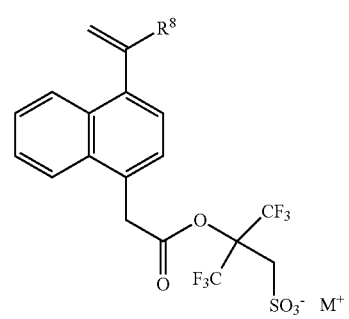
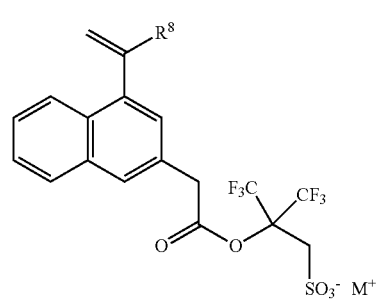
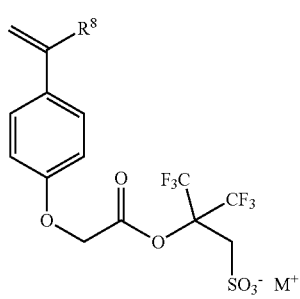
62
-continued
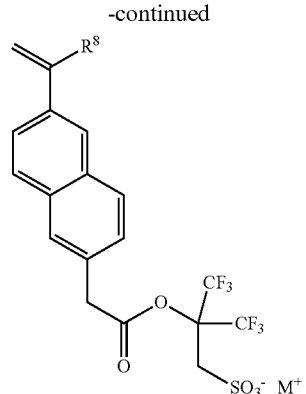
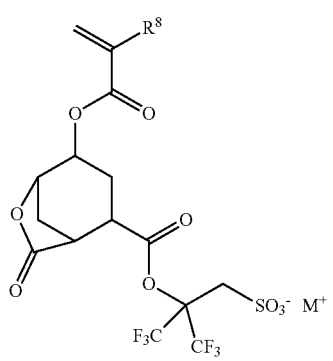
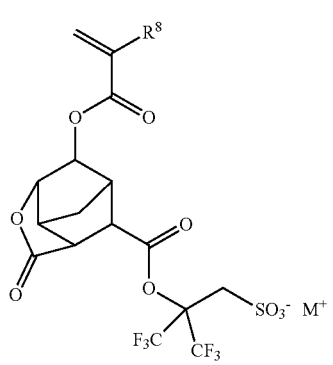
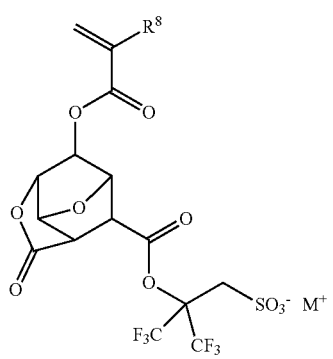

-continued
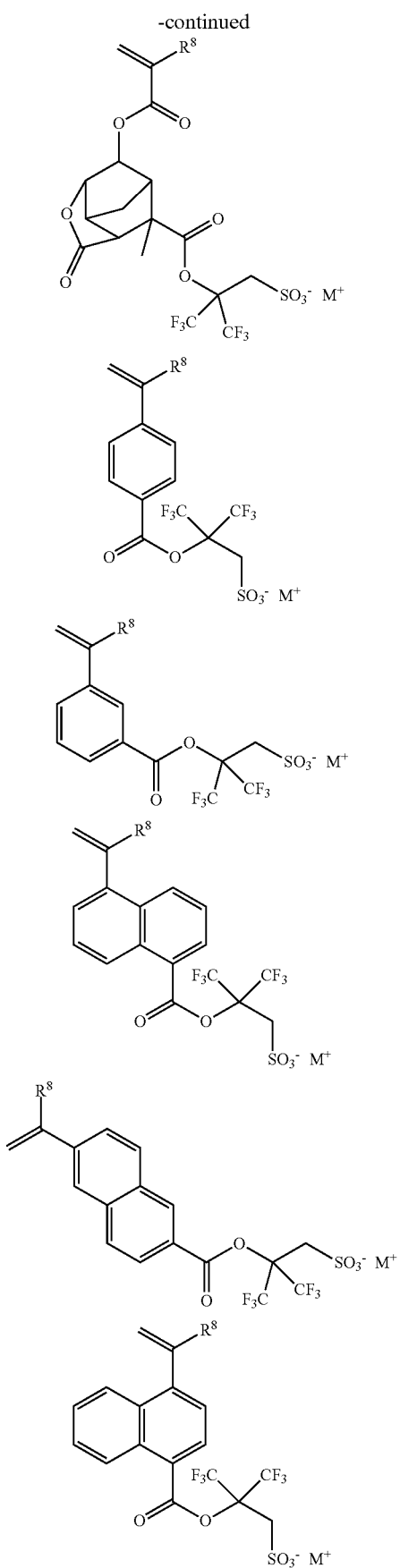
-continued
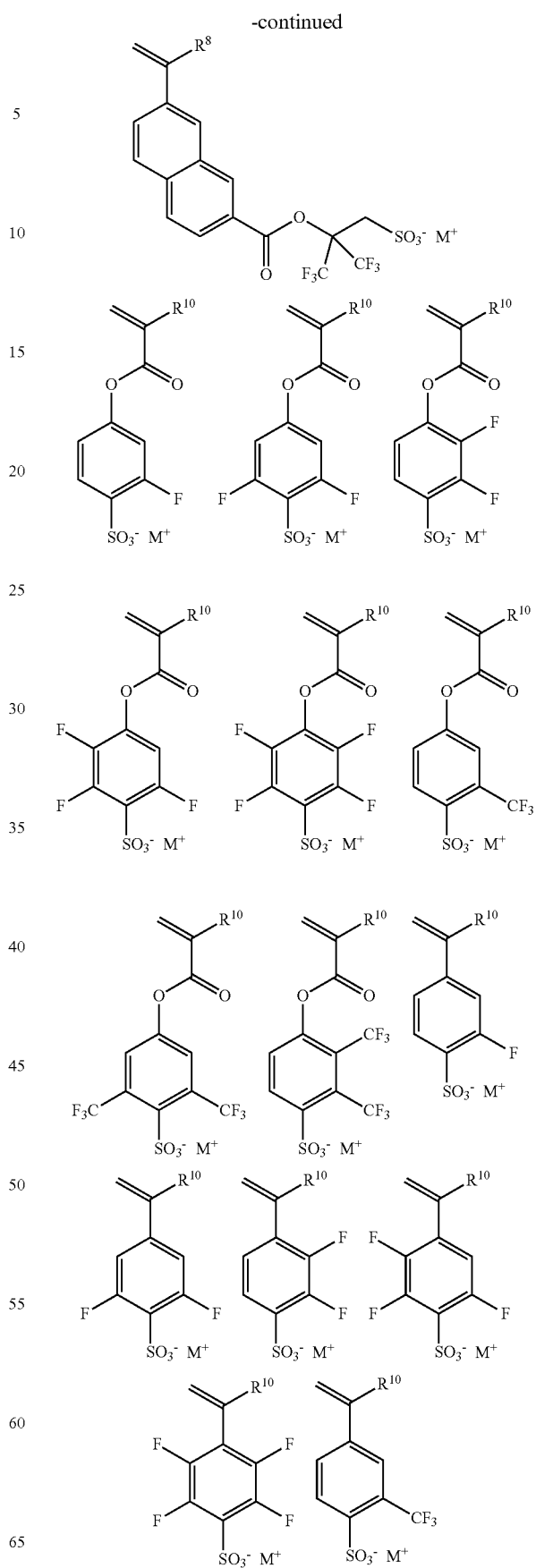

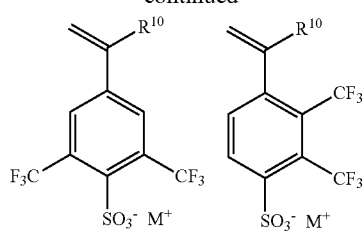
Specific examples of sulfonimide salt monomer to give the repeating unit-a6 of the above general formula include the following.
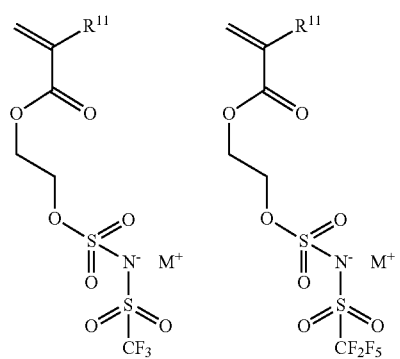
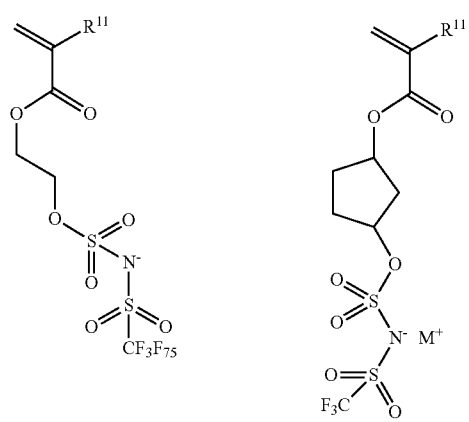
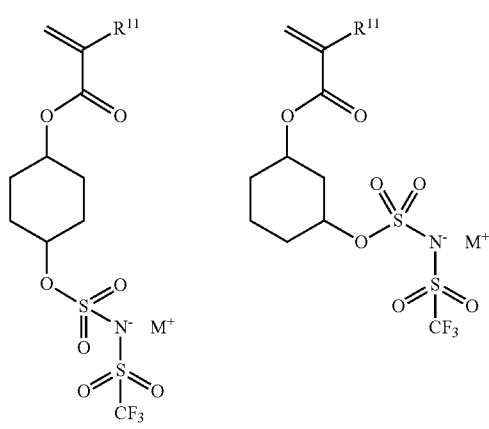
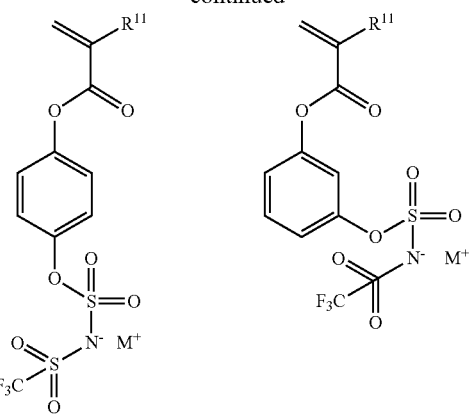
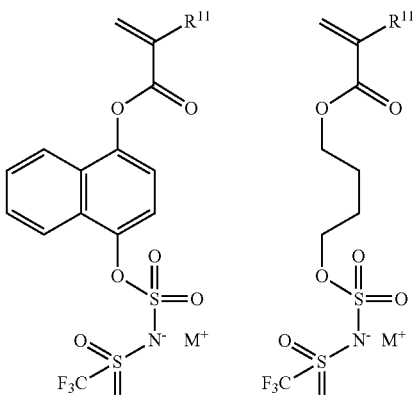
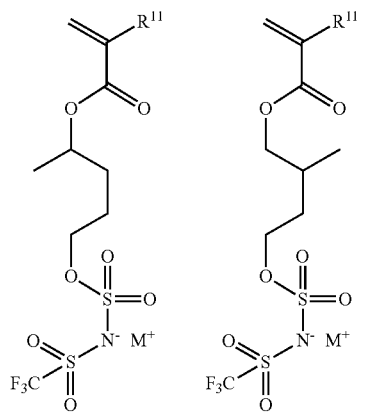
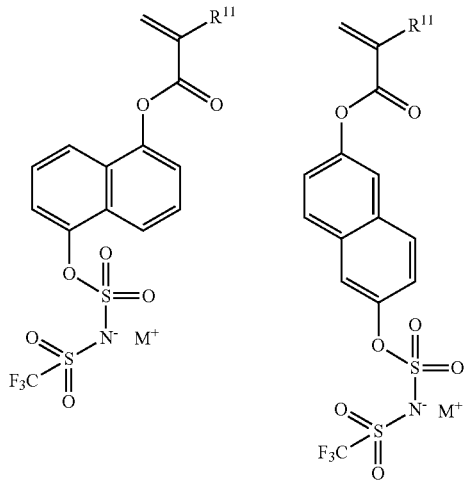

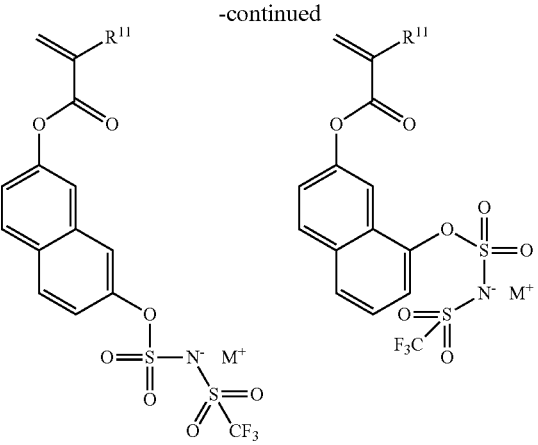
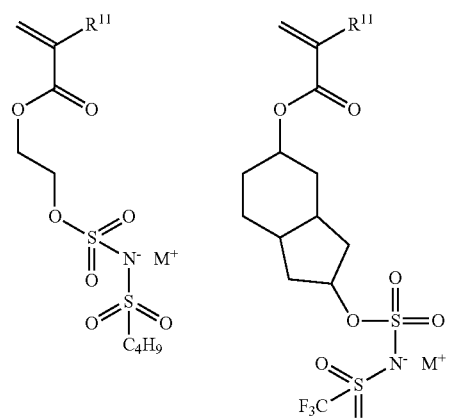
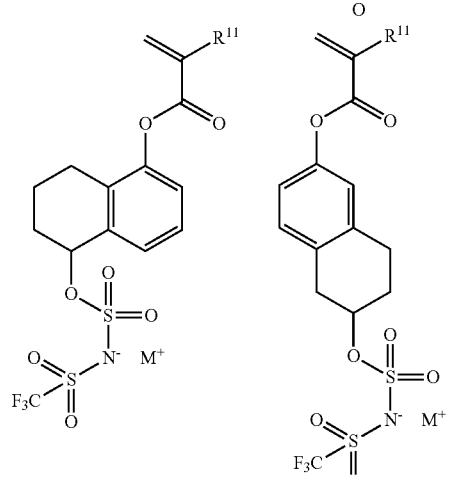
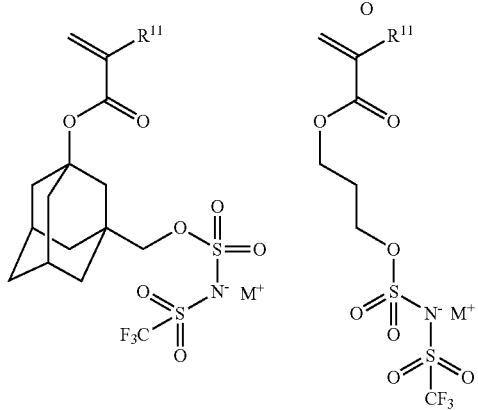
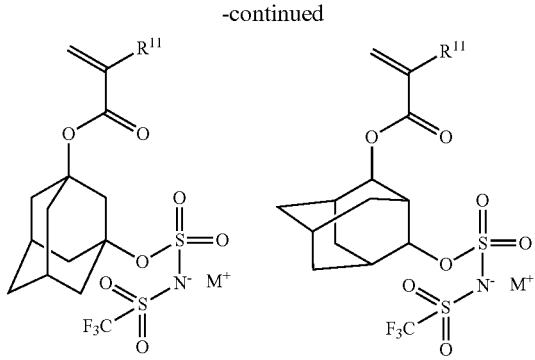
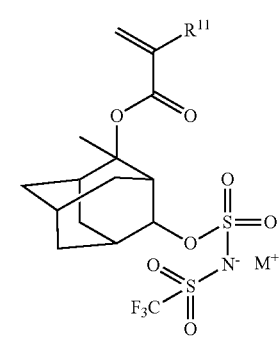
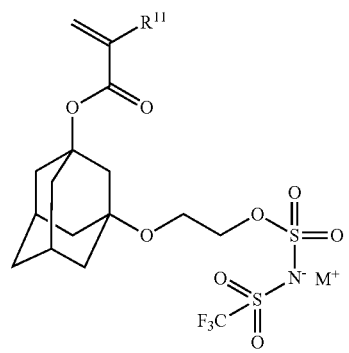
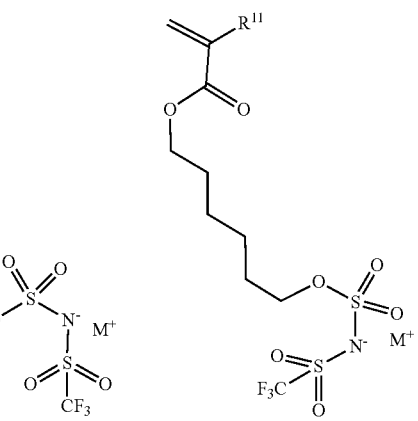

-continued
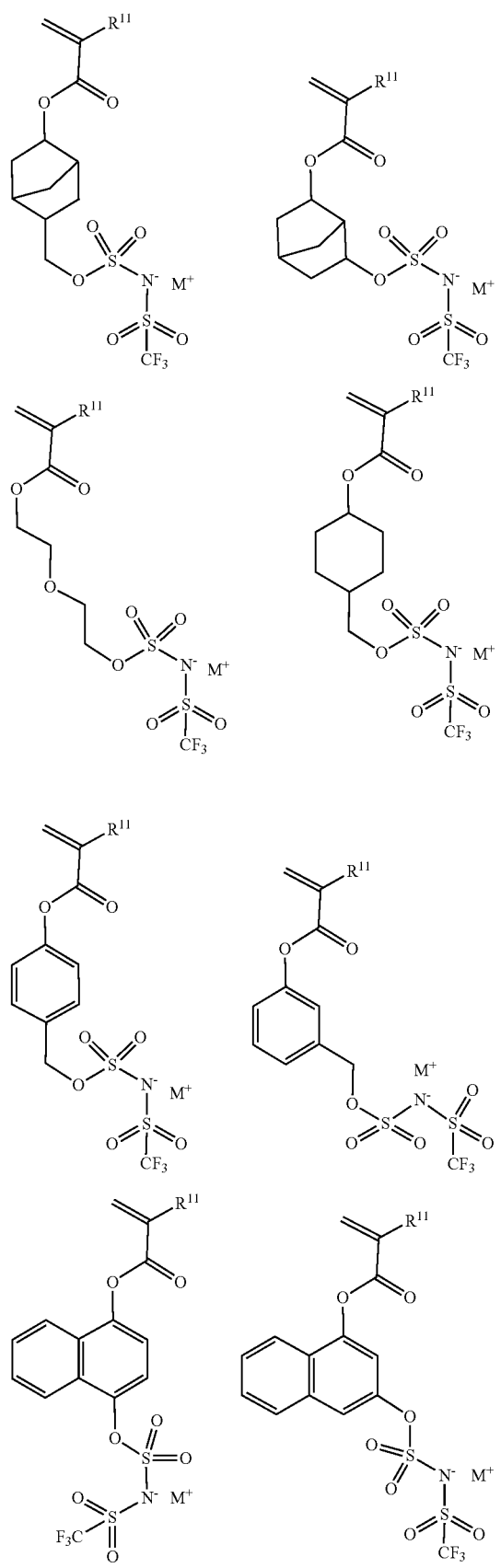
-continued
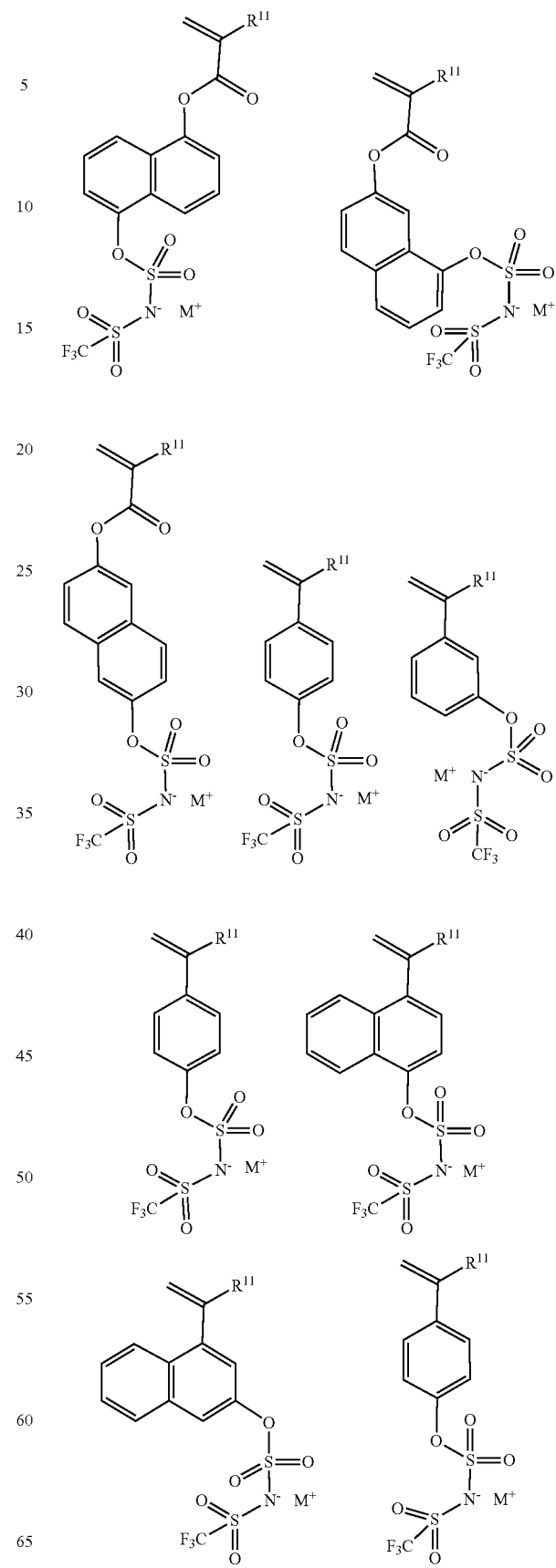

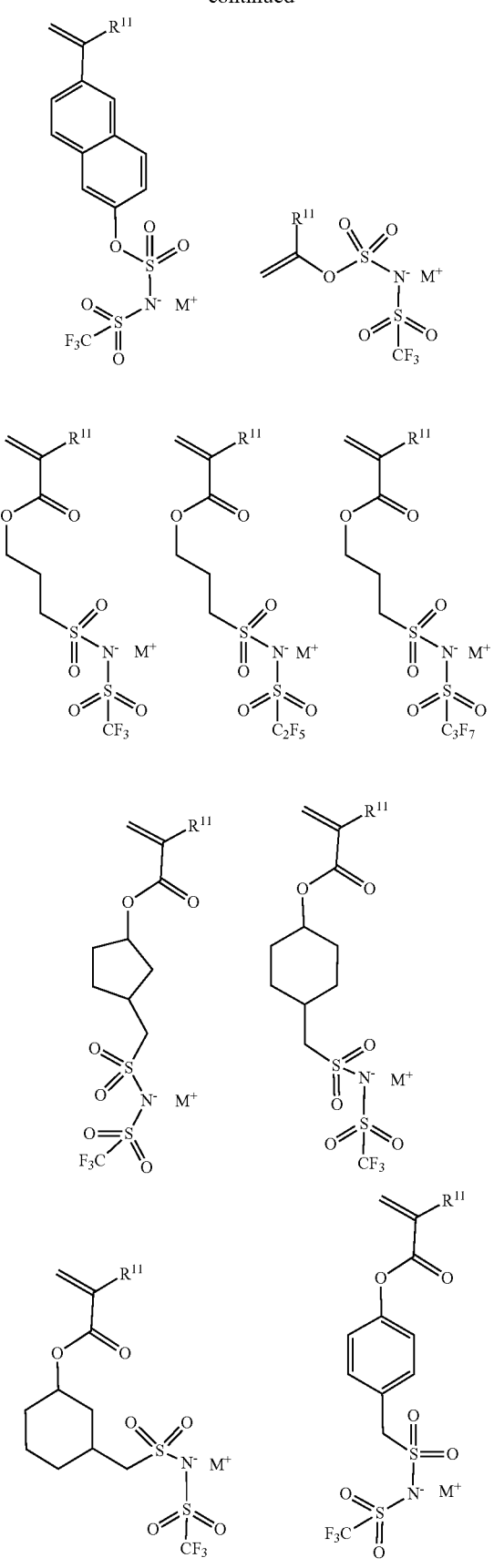
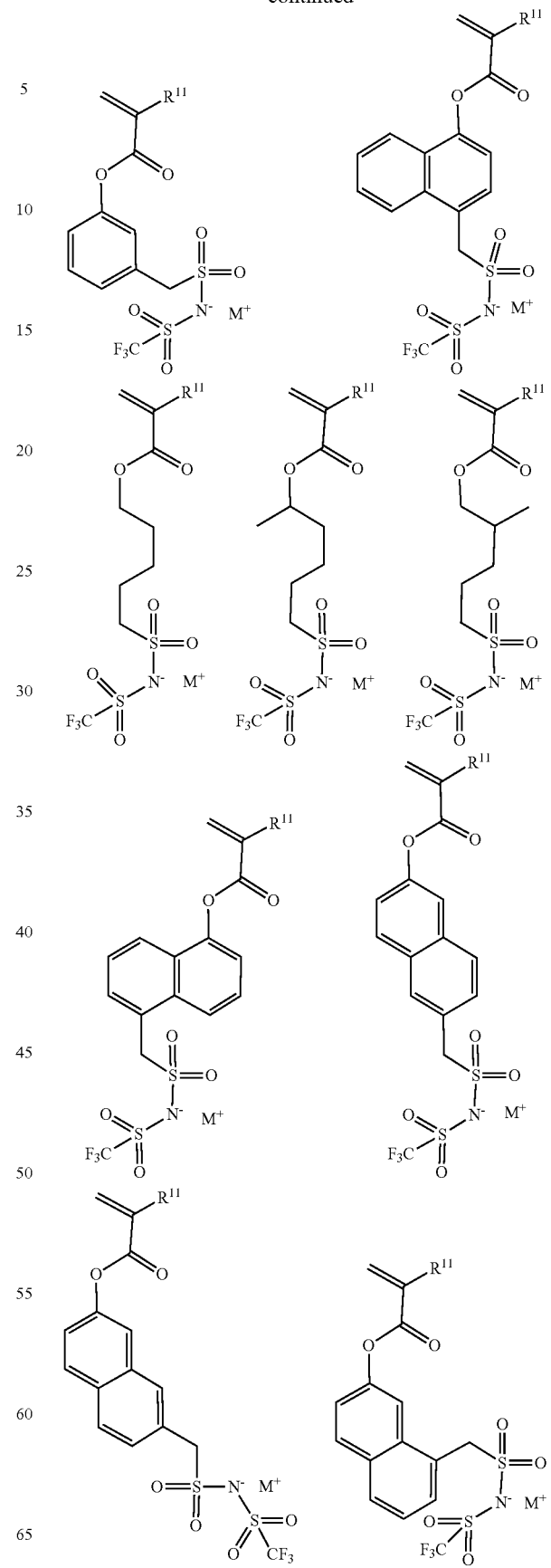

73
-continued
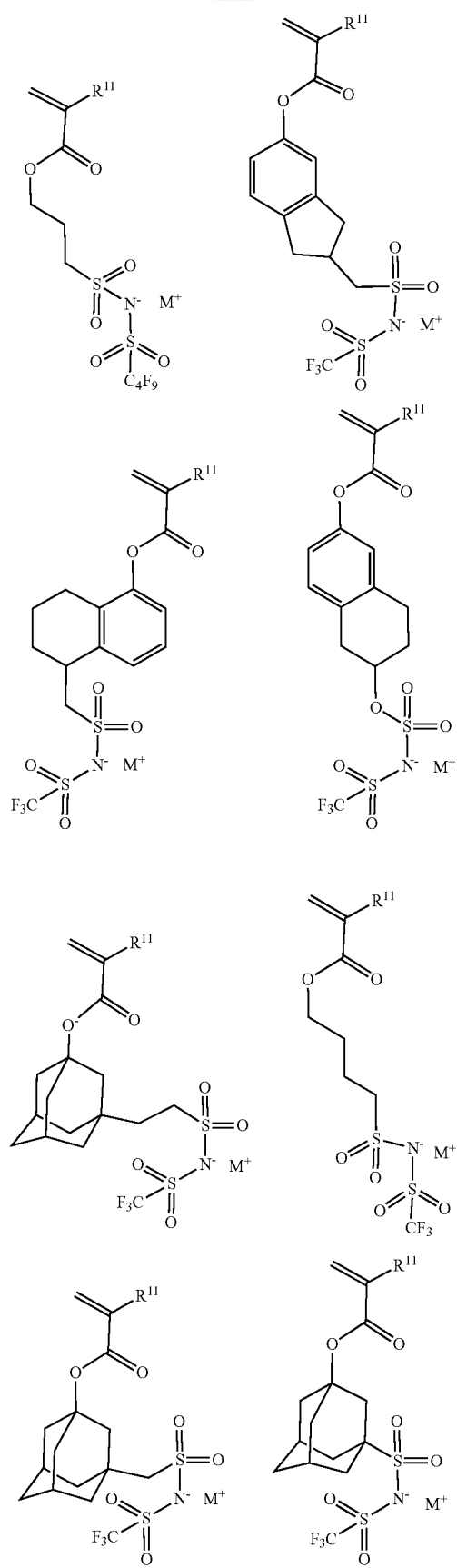
74
-continued
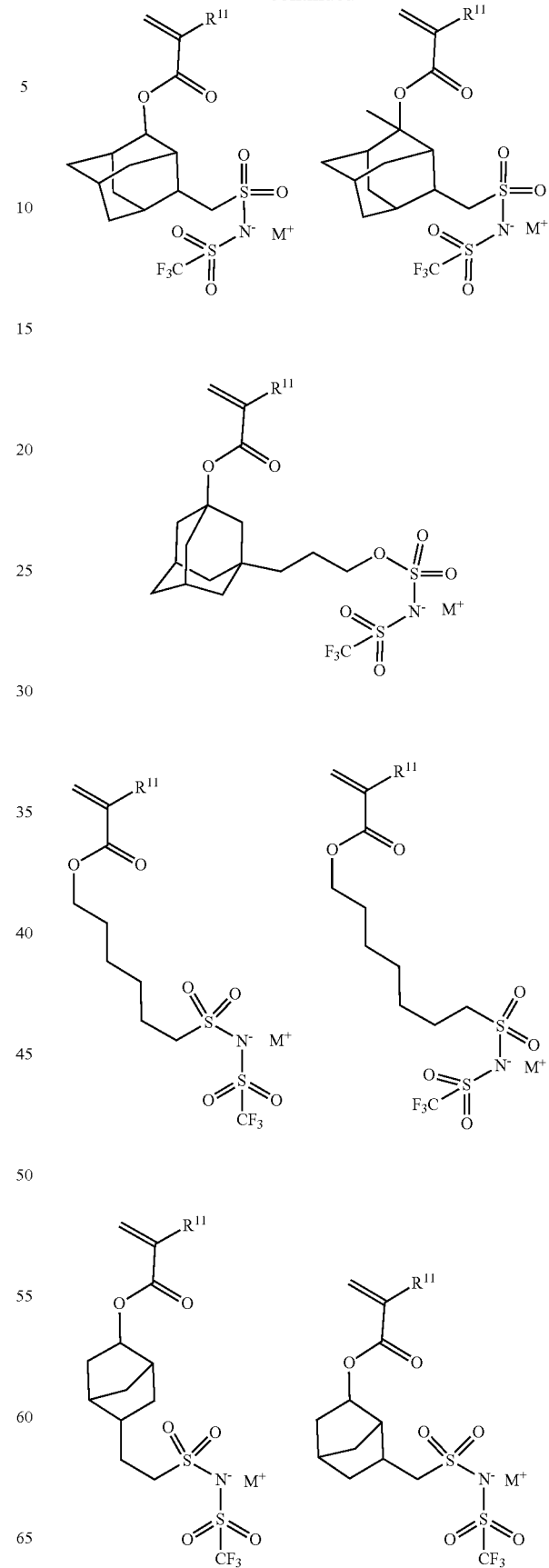

75
-continued
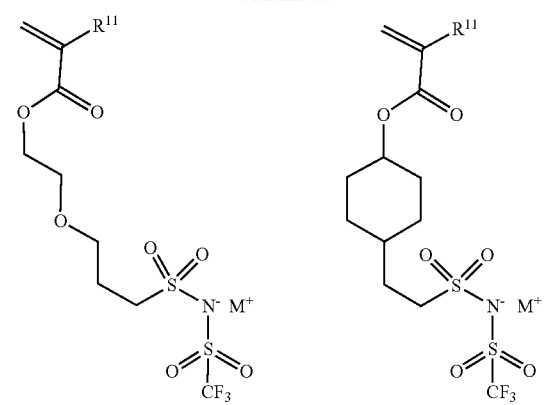
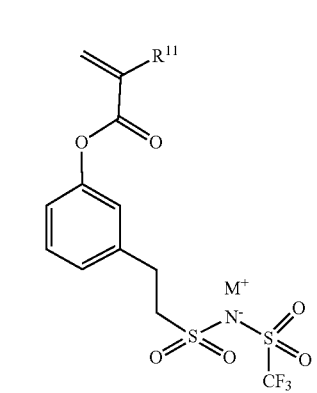
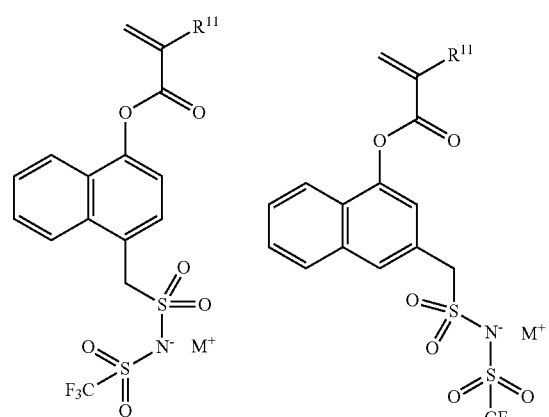
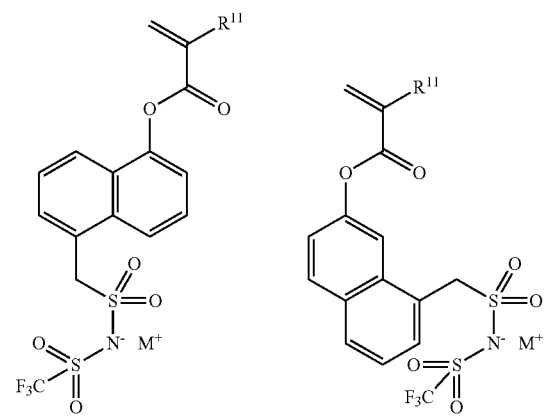
76
-continued
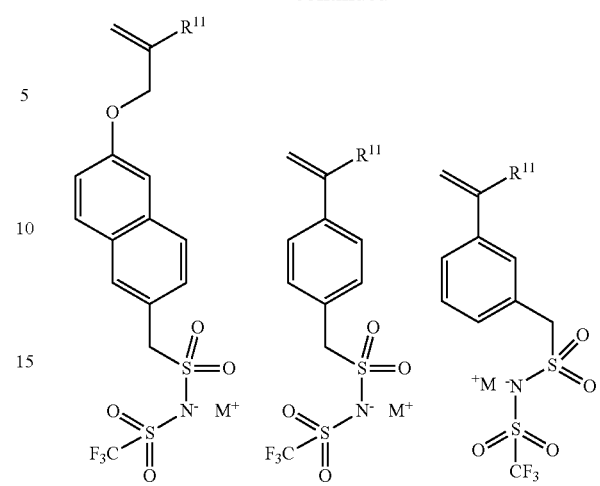
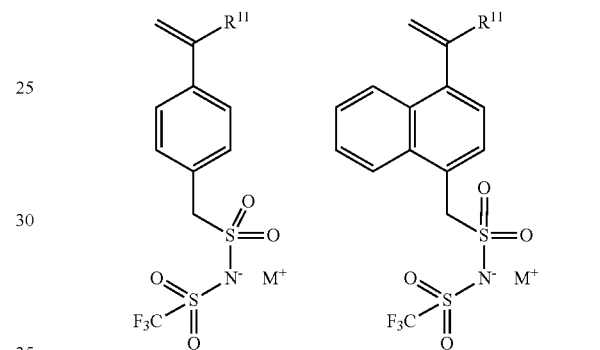
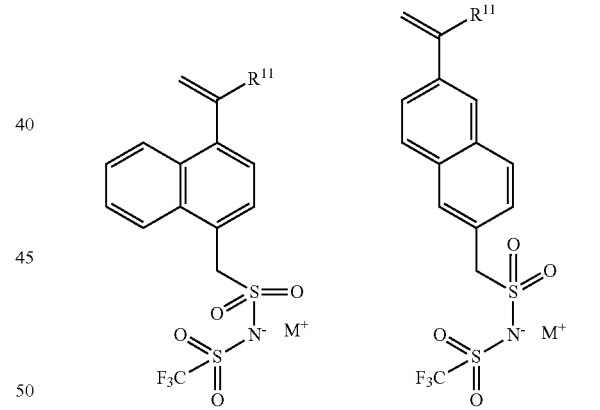
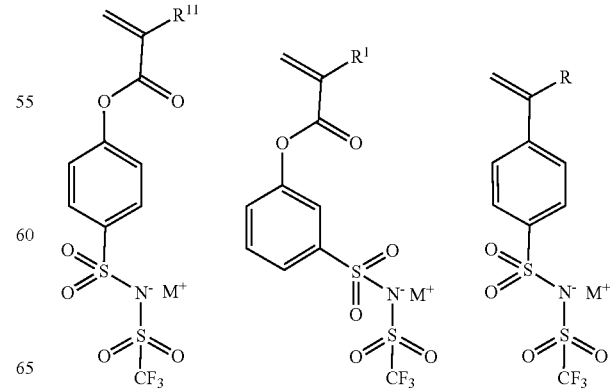

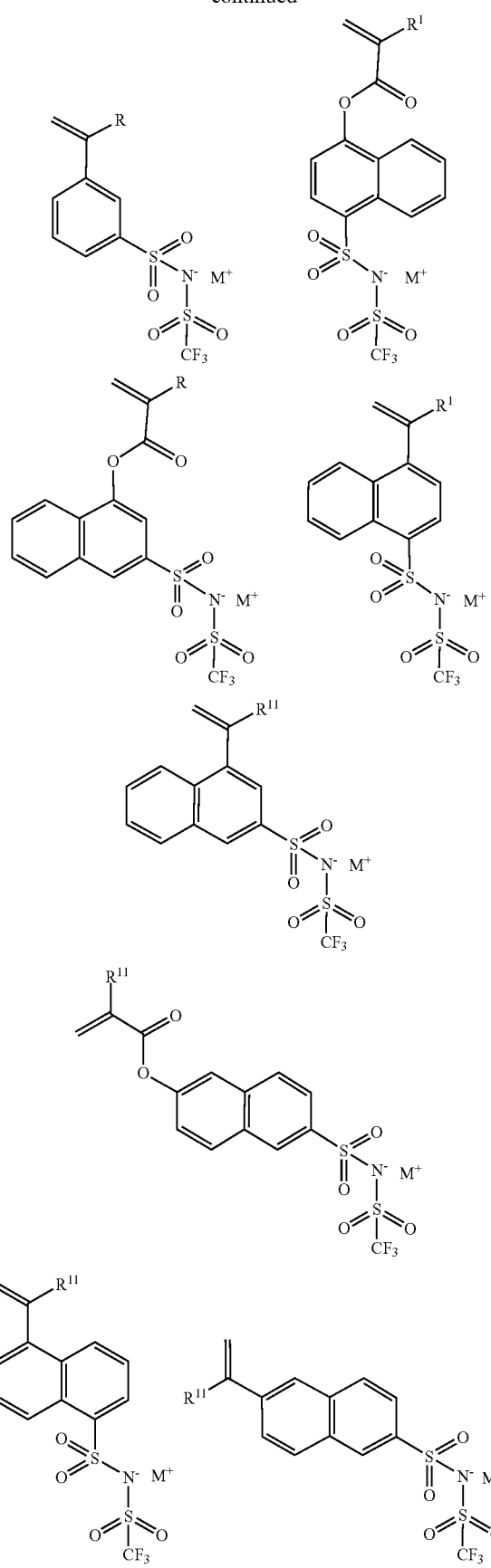
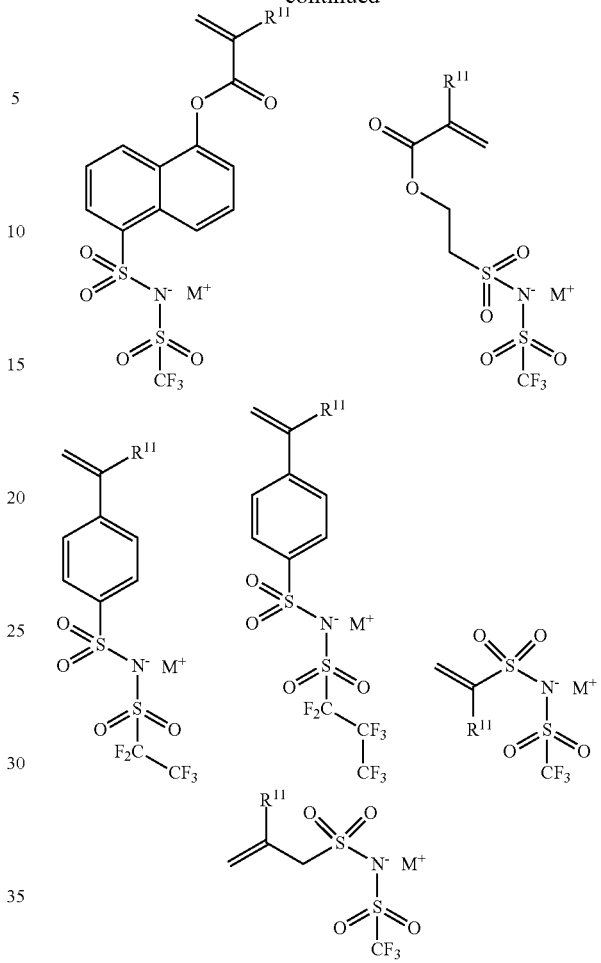
Specific examples of N-carbonylsulfonamide salt monomer to give the repeating unit-a7 of the above general formula include the following.
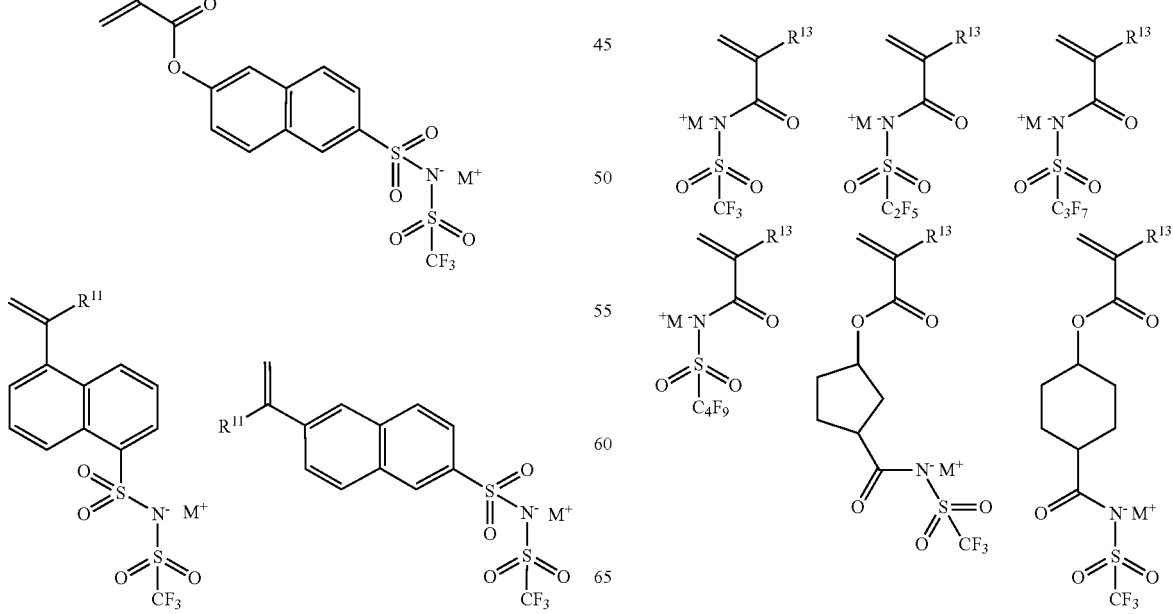

-continued
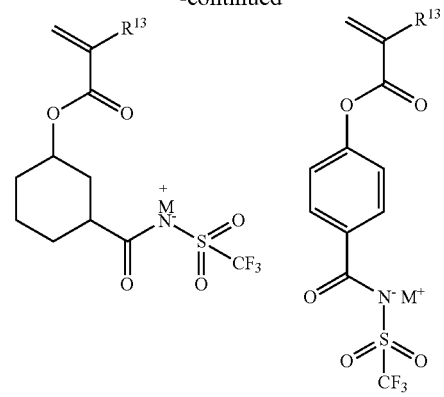
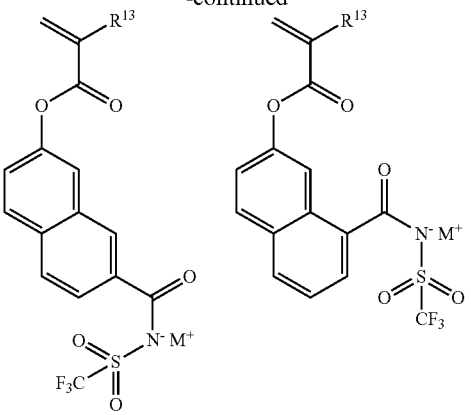
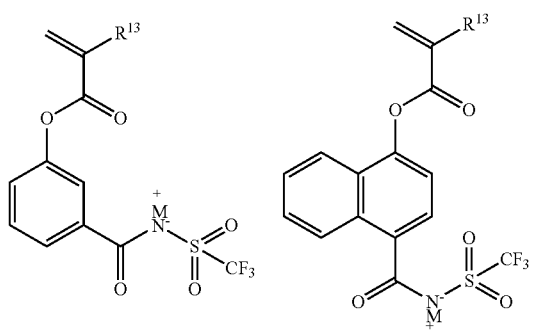
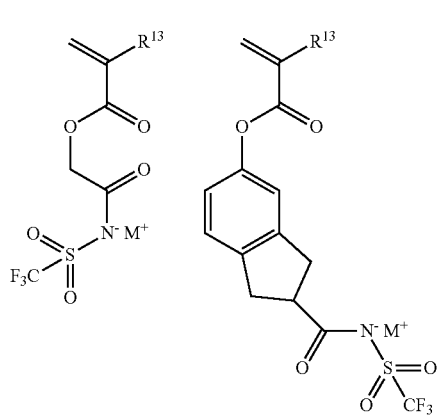
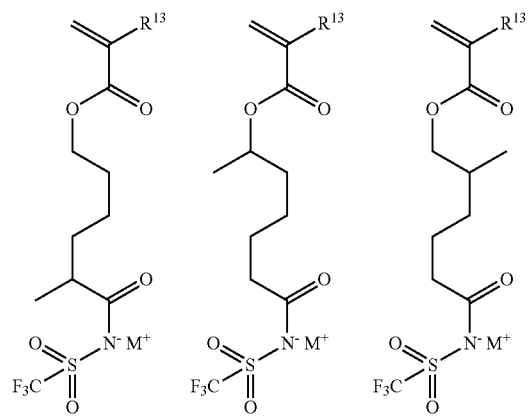
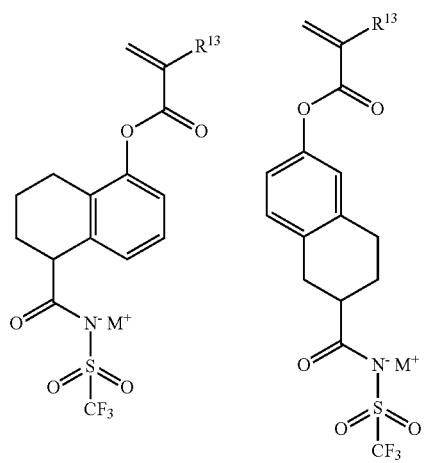
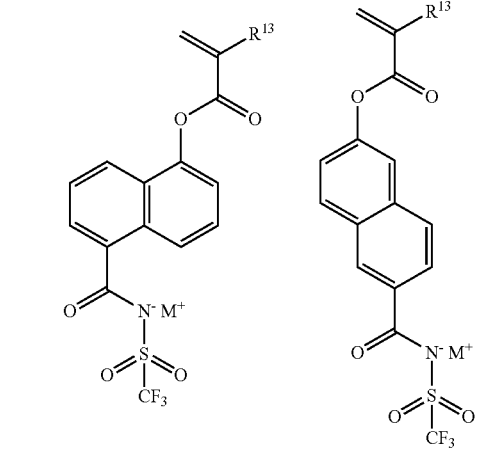
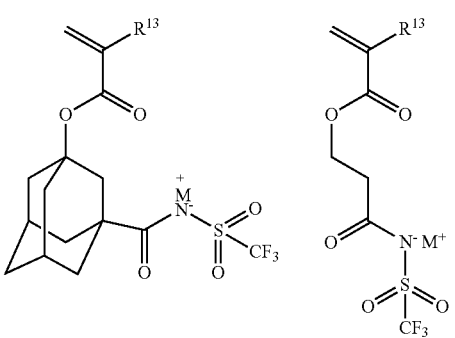

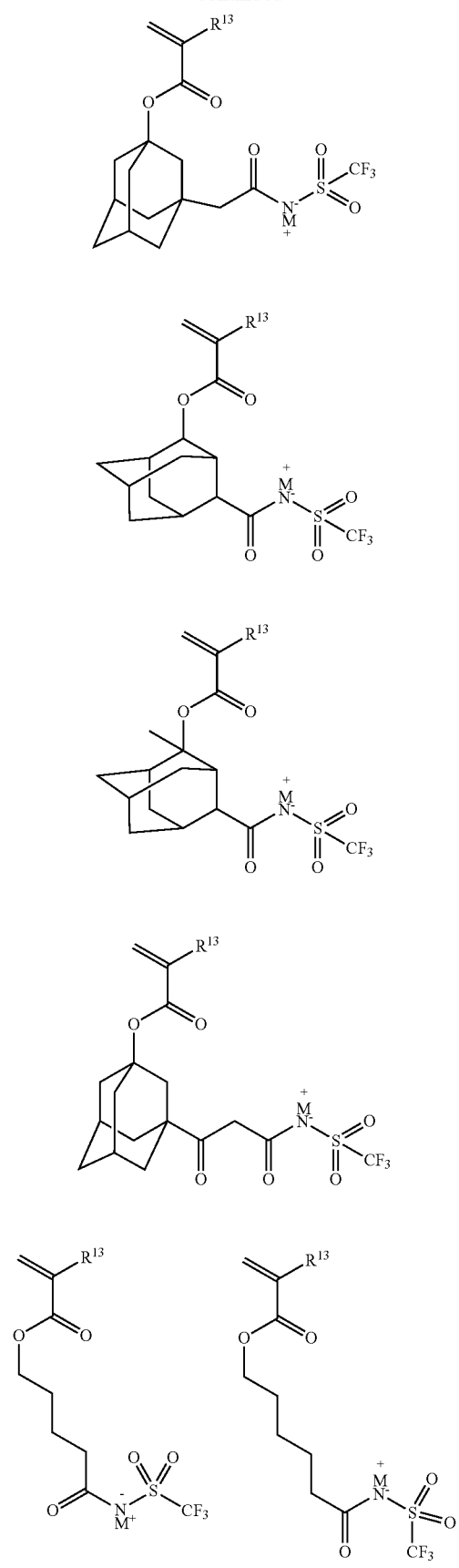
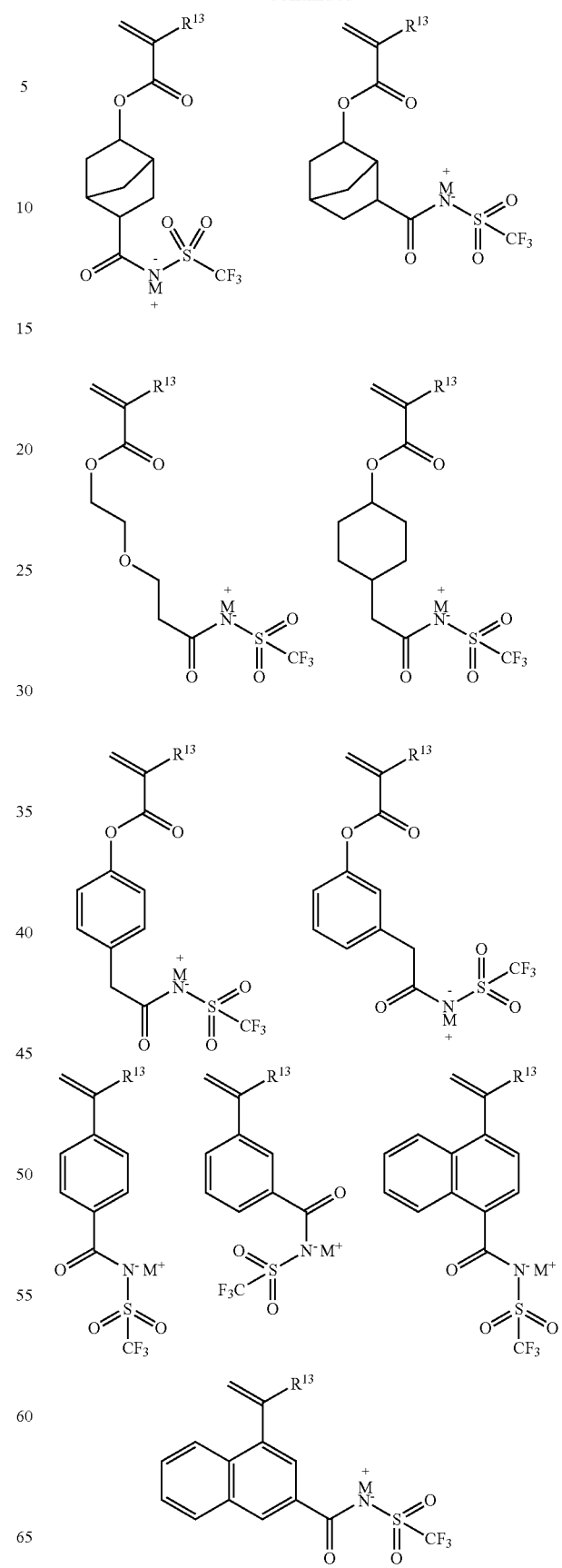

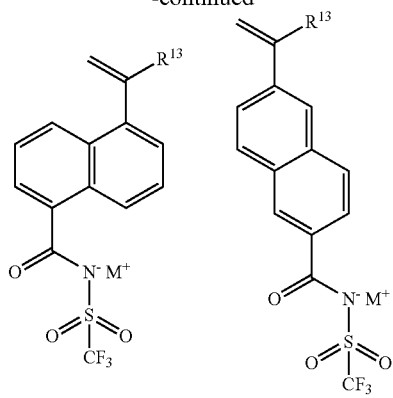

The component (A) preferably contains an ammonium ion (ammonium cation) shown by the following general formula (3) as $M^+$ in the repeating unit-a,

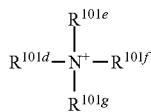

(3)

where $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, and optionally have one or more selected from an ether group, a carbonyl group, an ester group, a hydroxy group, an amino group, a nitro group, a sulfonyl group, a sulfinyl group, a halogen atom, and a sulfur atom; $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$ and $R^{101f}$ represent an alkylene group having 3 to 10 carbon atoms, or to form a heteroaromatic ring having the nitrogen atom in the formula within the ring.

Specific examples of the ammonium ion shown by the general formula (3) include the following.

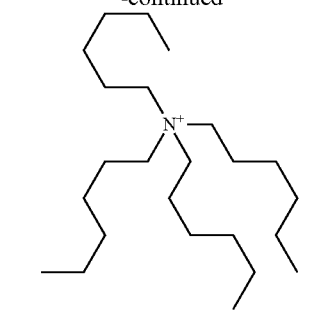

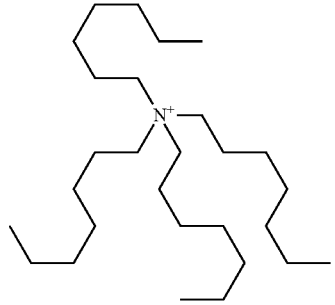

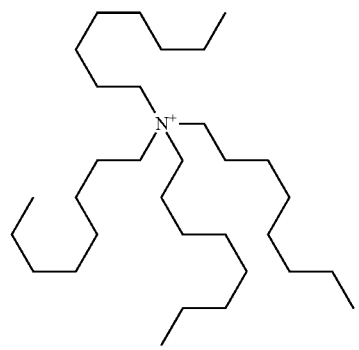

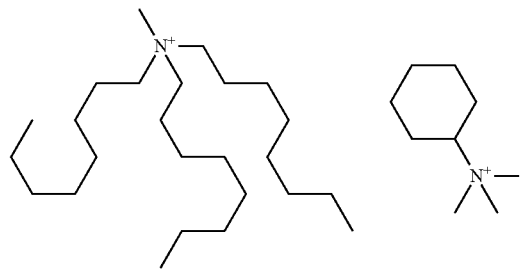

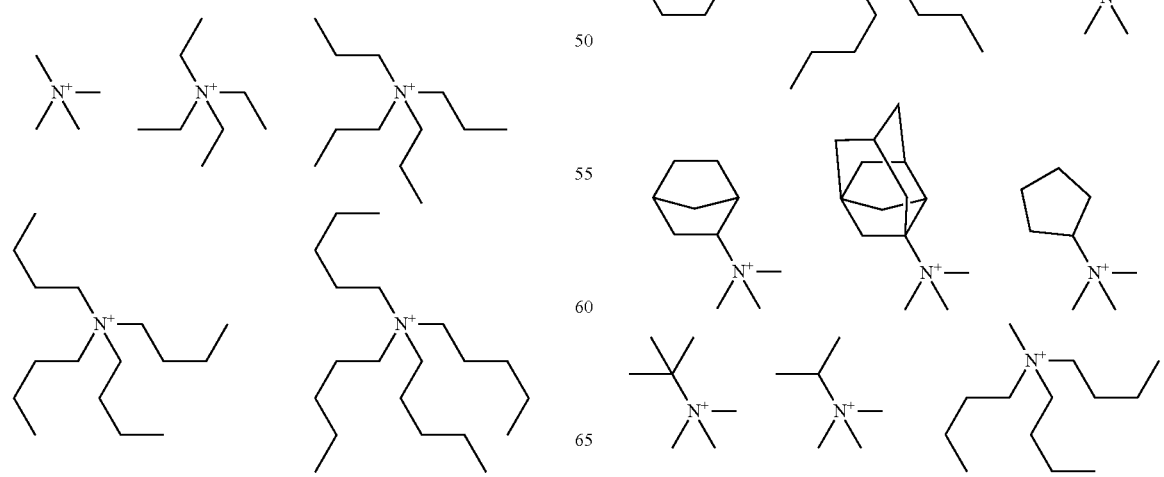

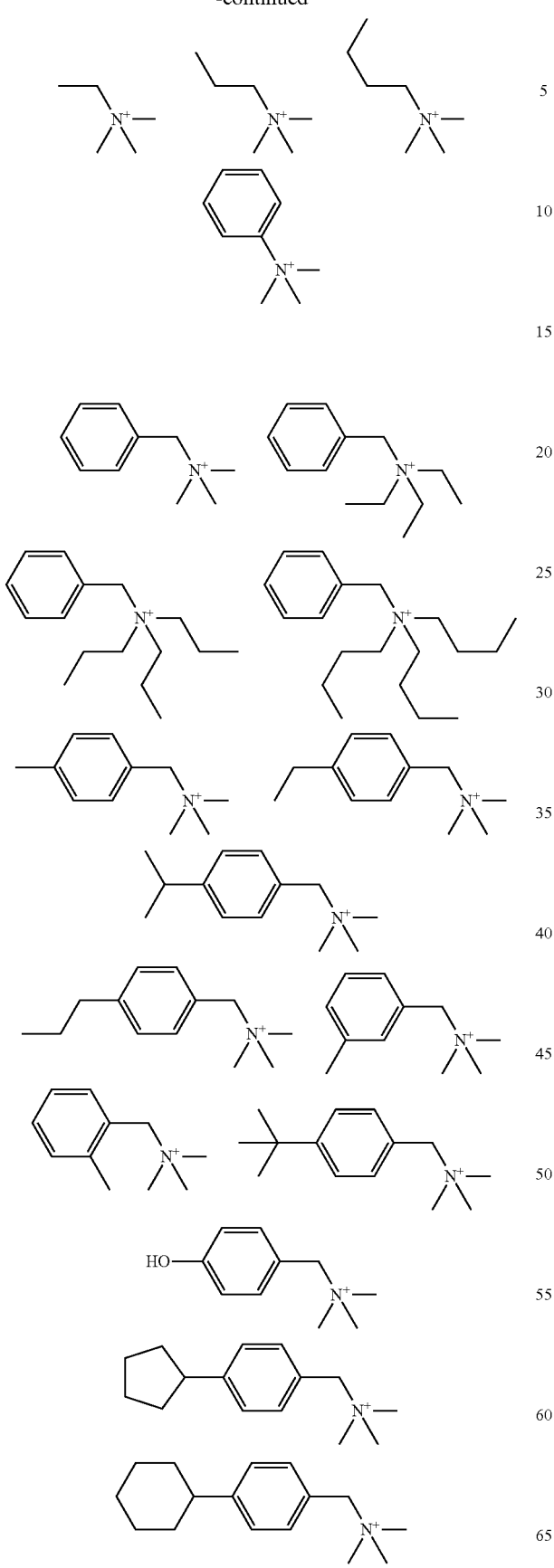
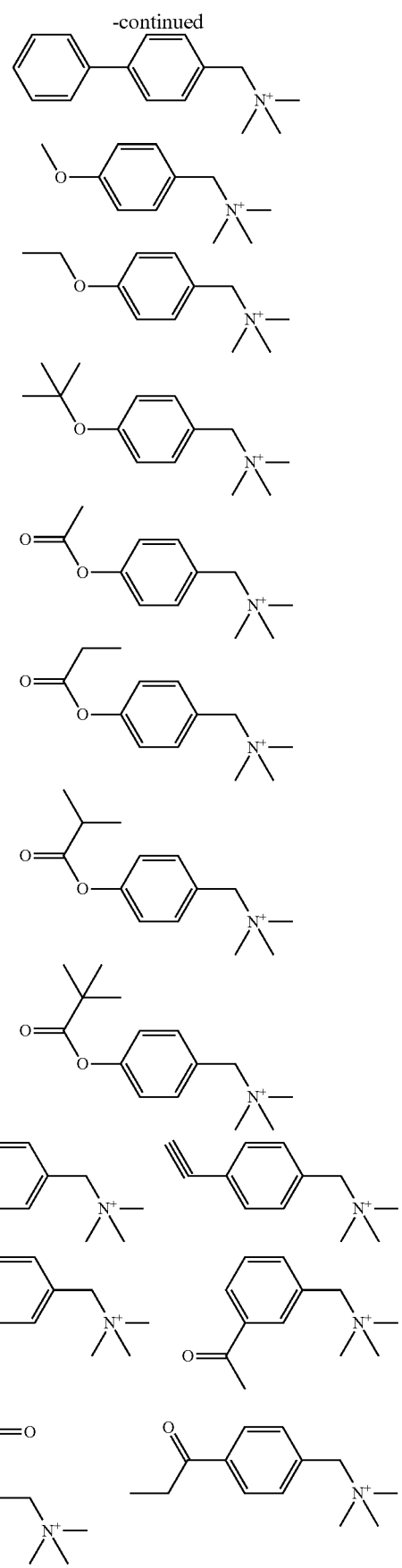

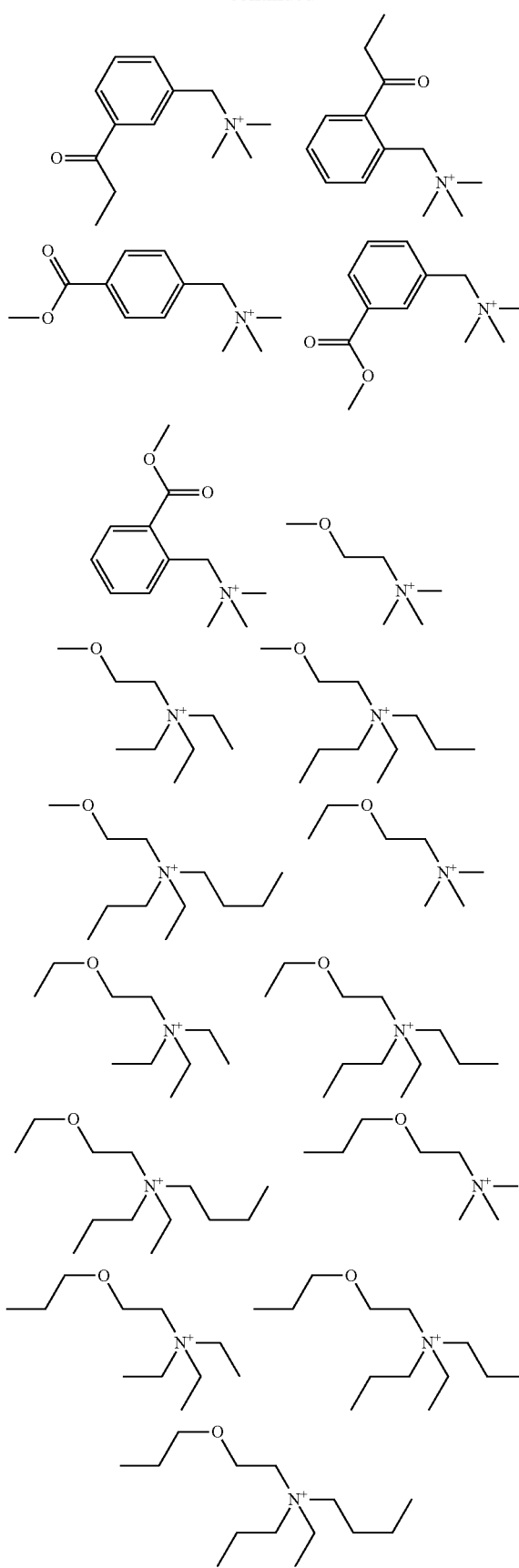
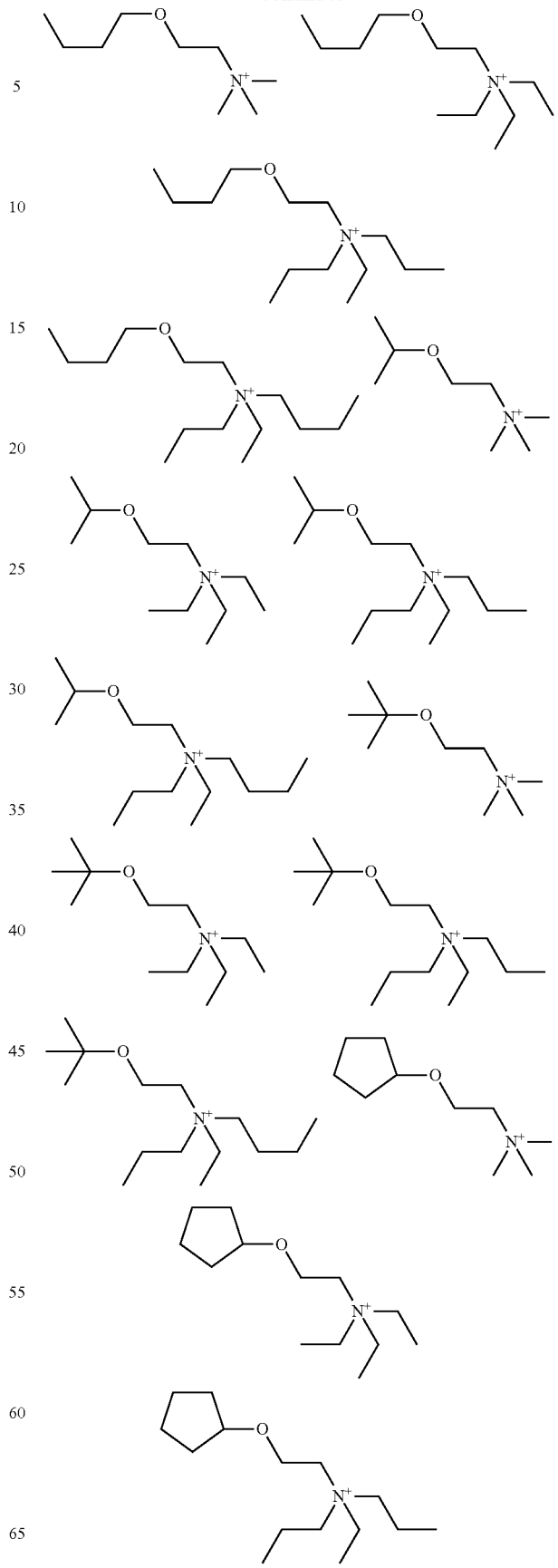

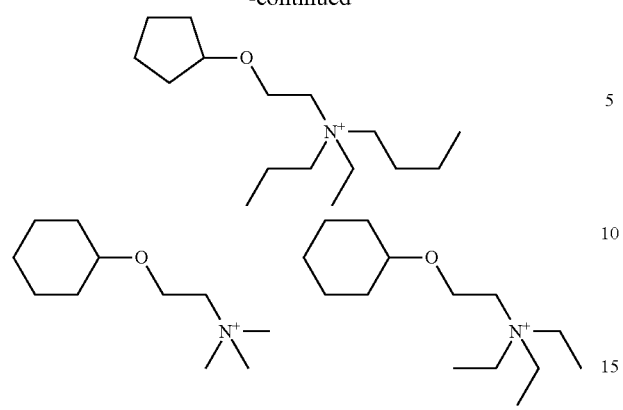
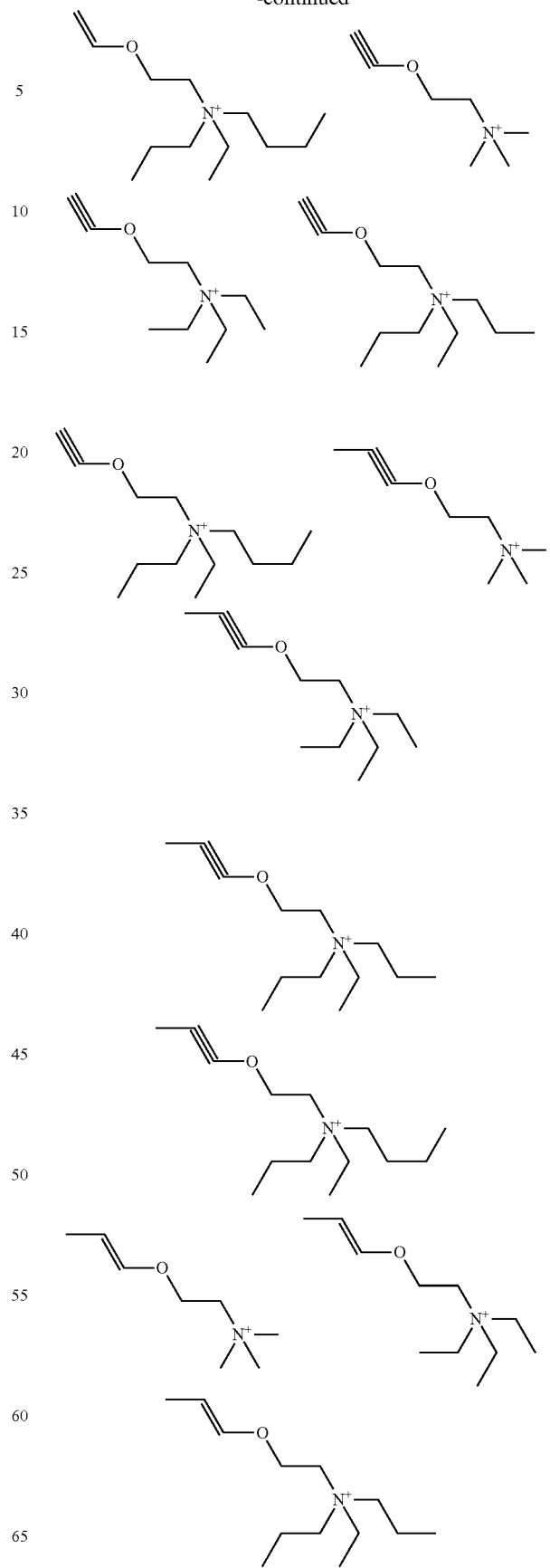

91
-continued
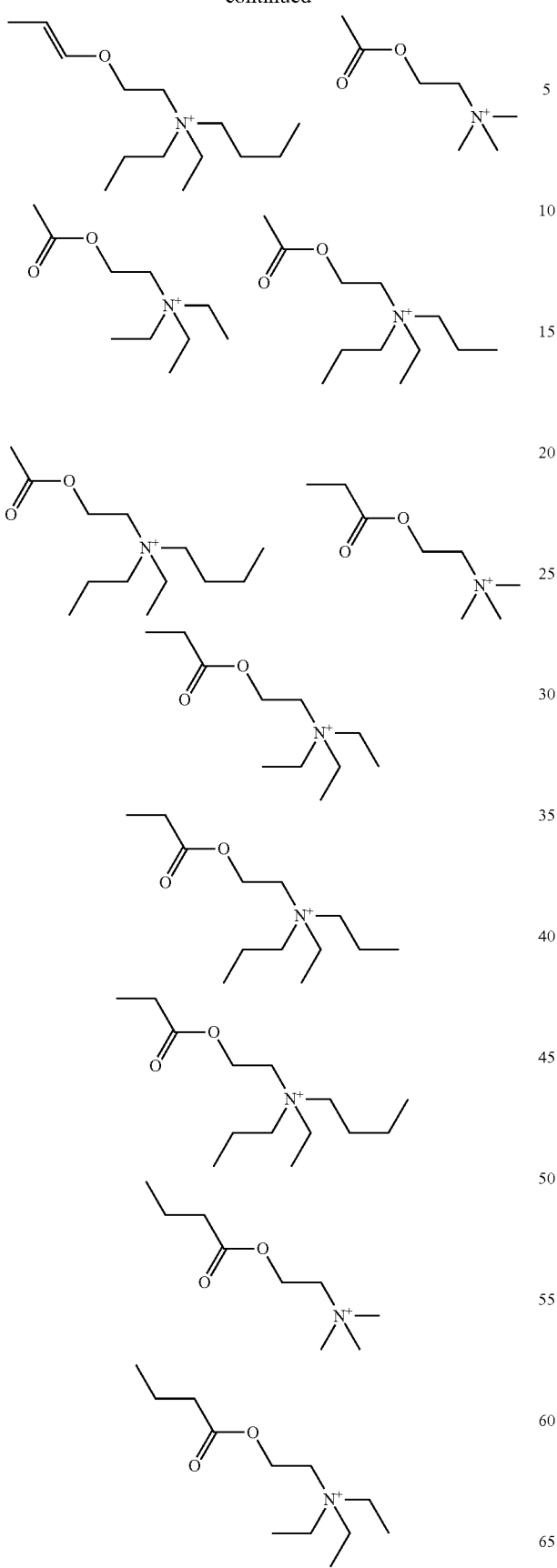
92
-continued
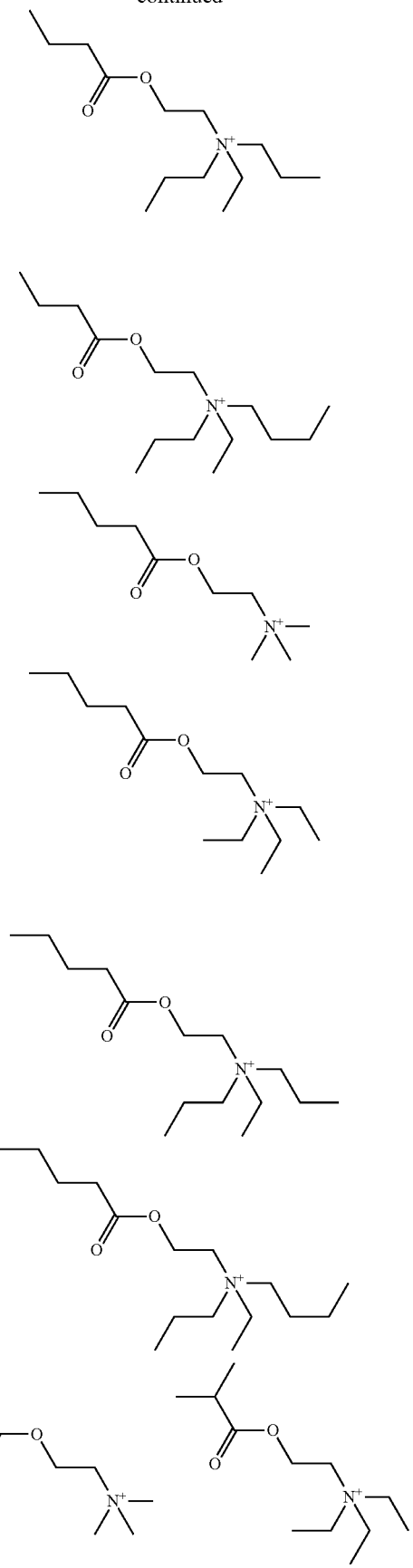

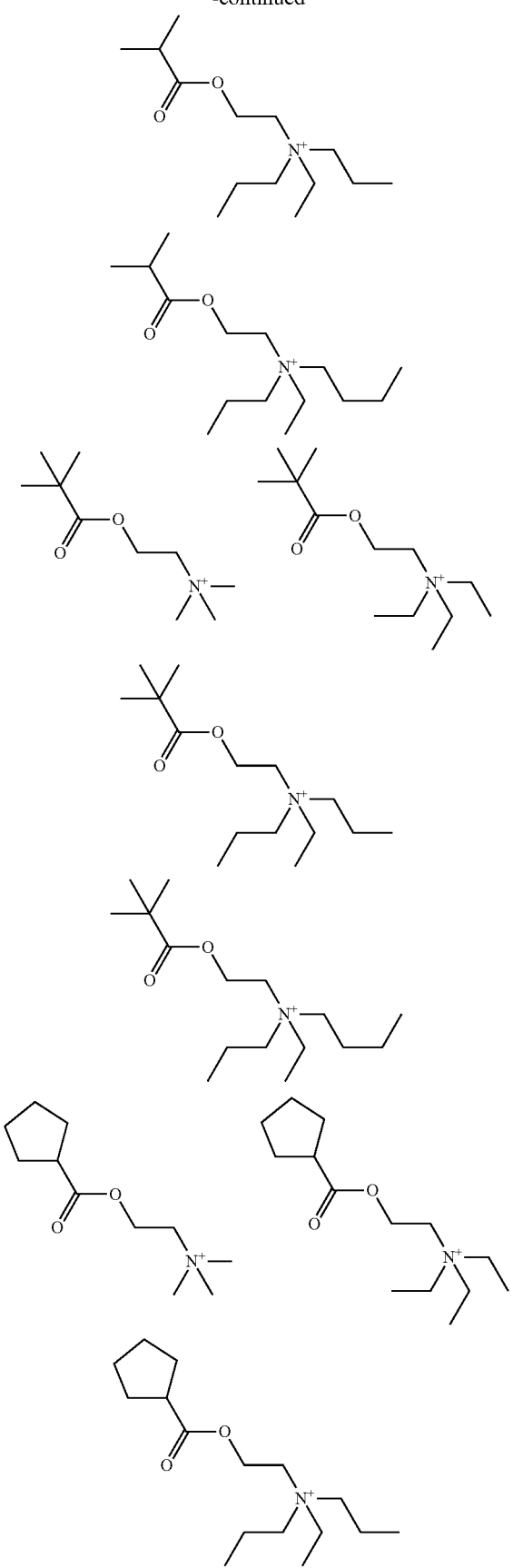
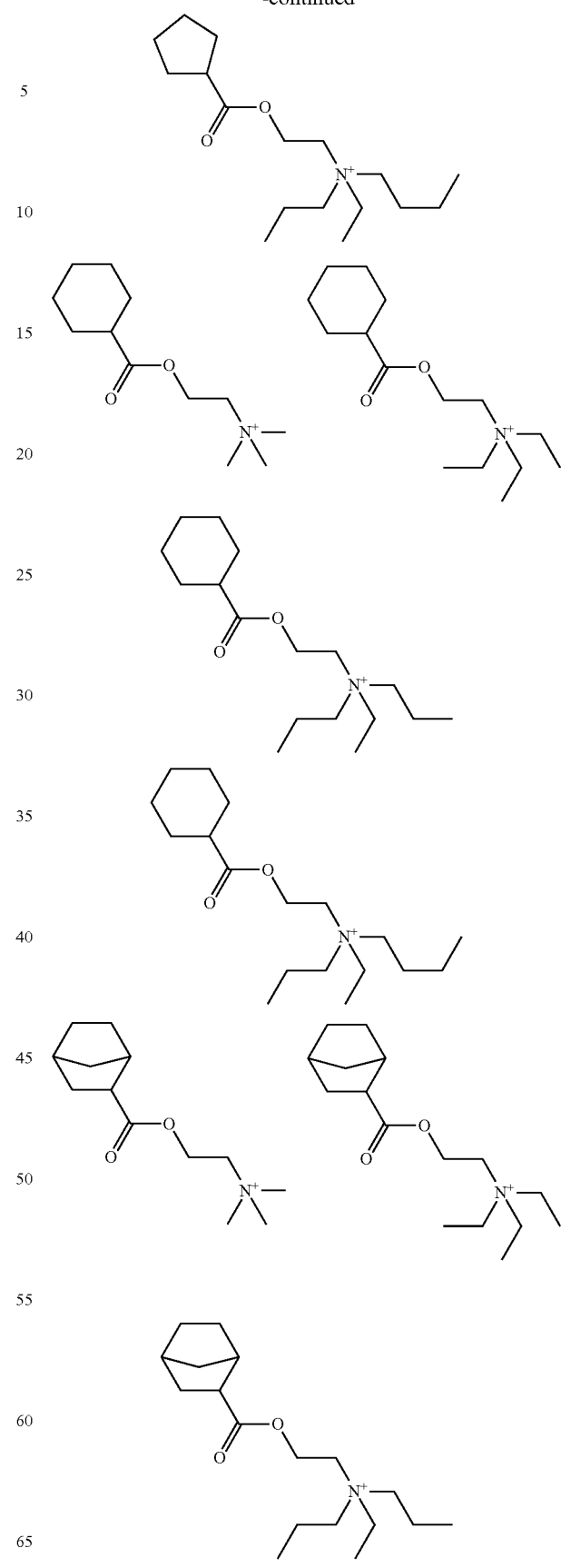

95
-continued
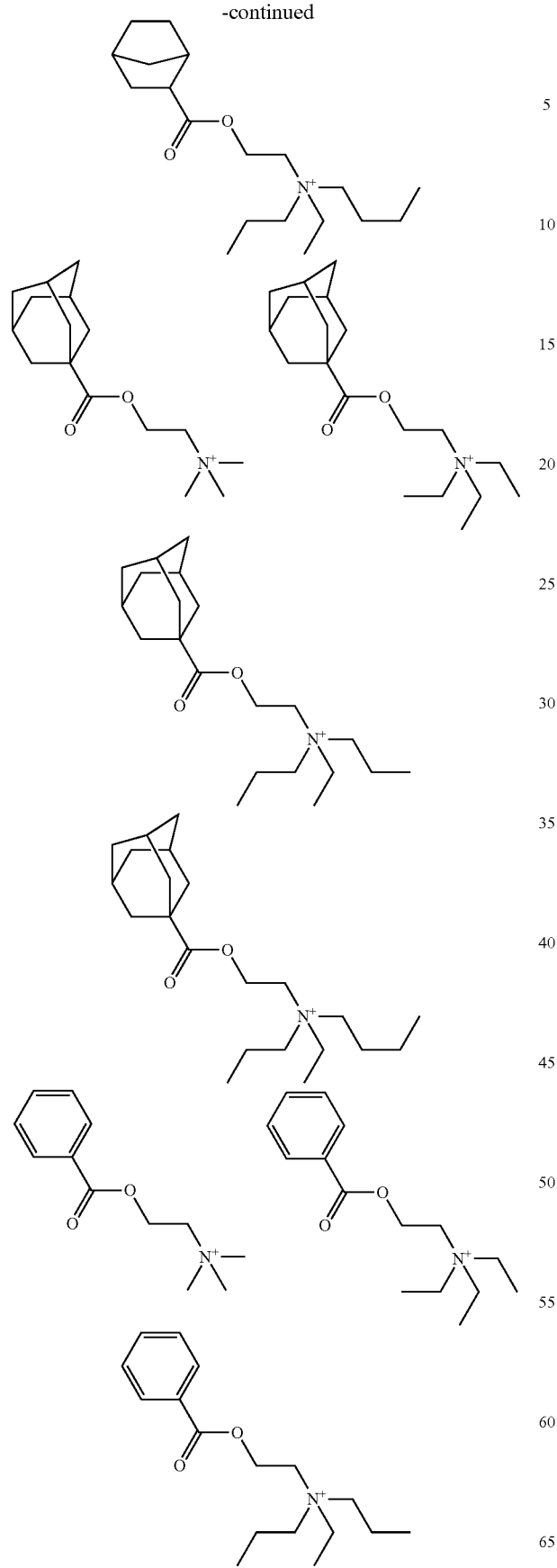
96
-continued
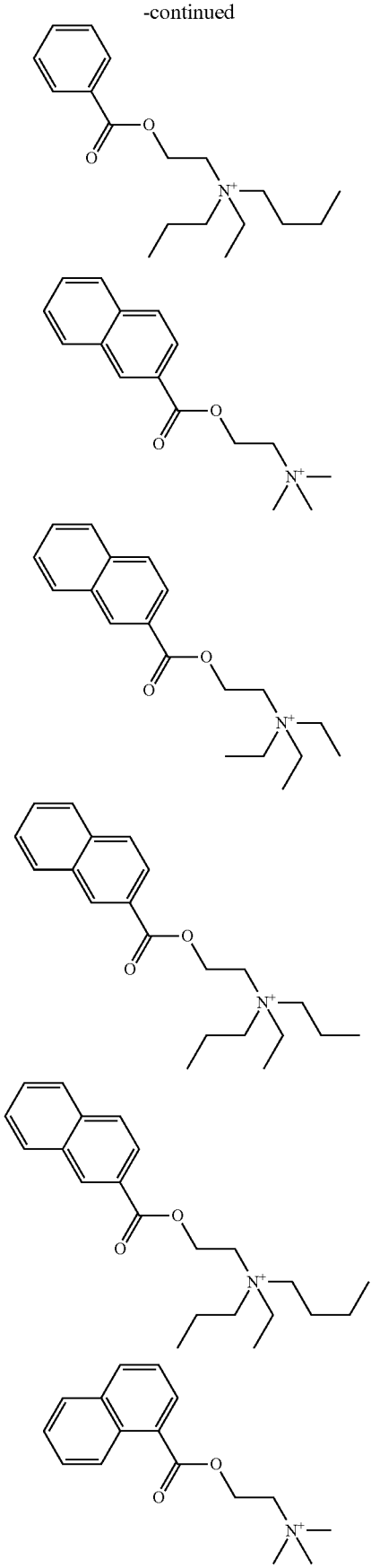

97
-continued
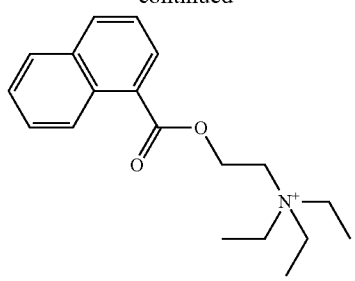
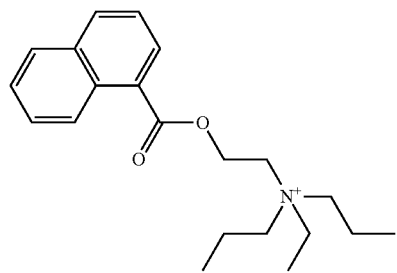
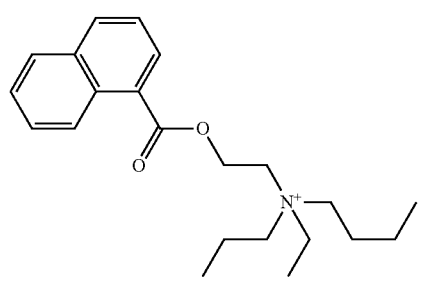
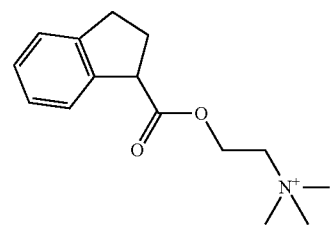
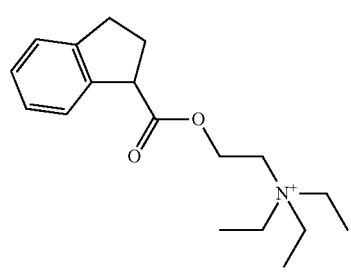
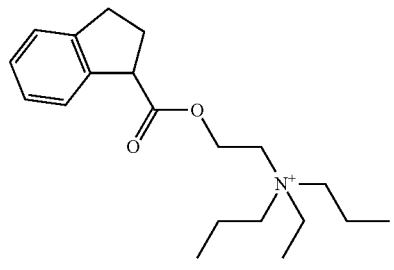
98
-continued
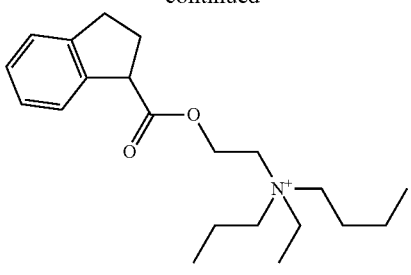
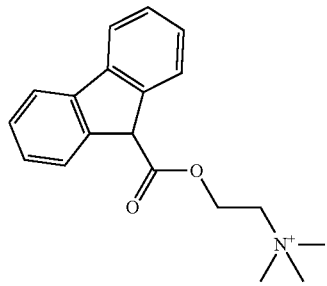
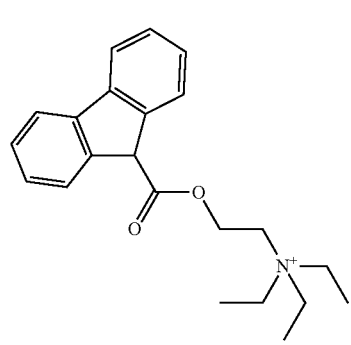
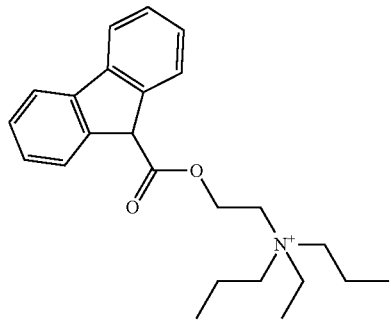
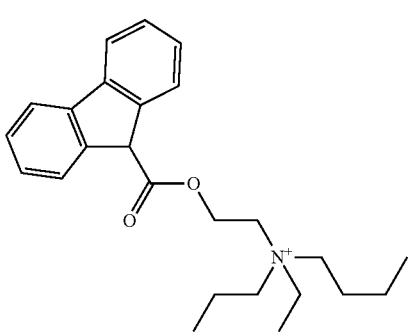

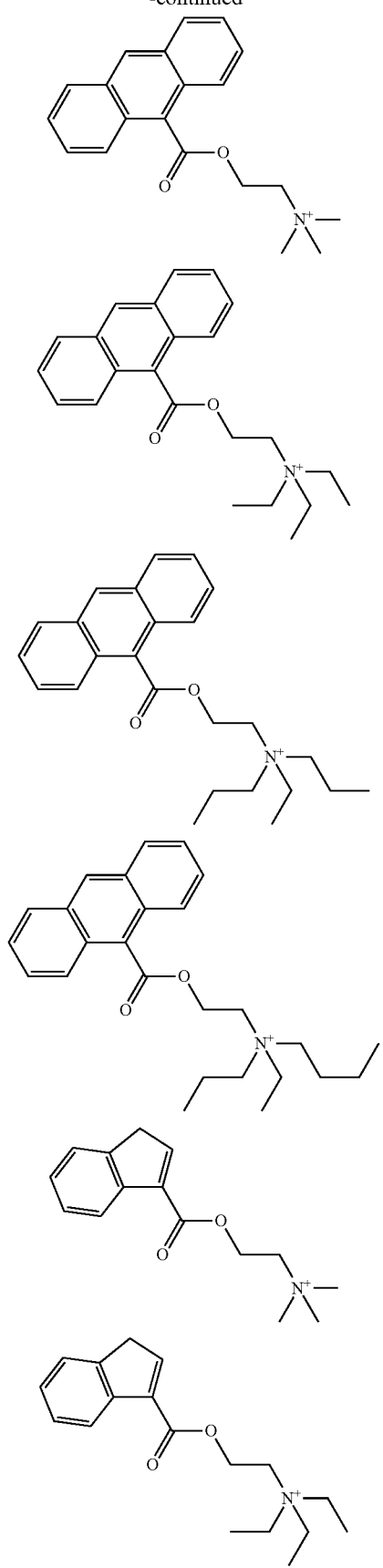

101
-continued
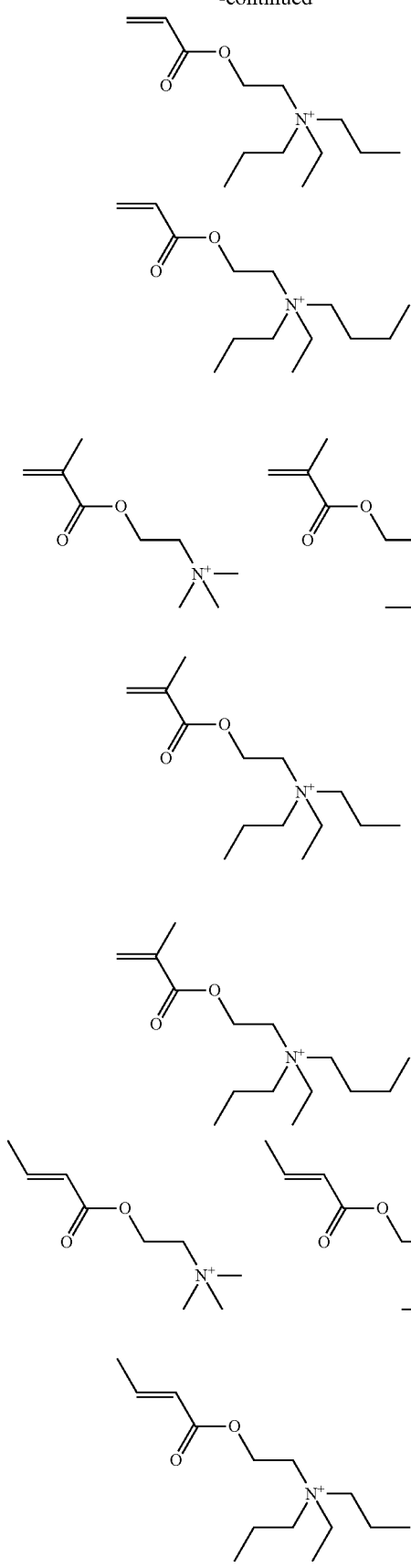
102
-continued
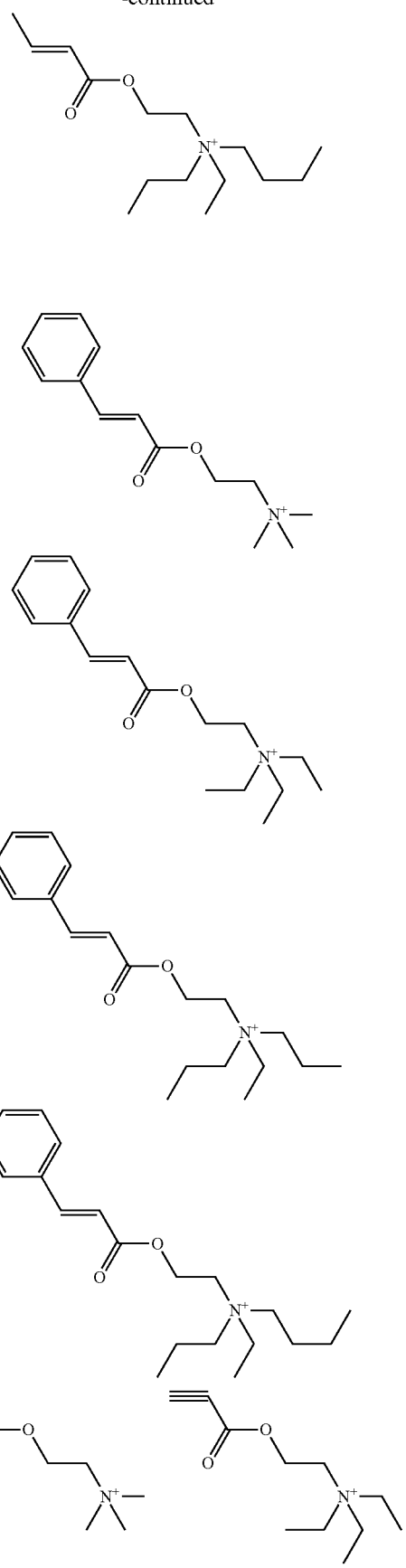

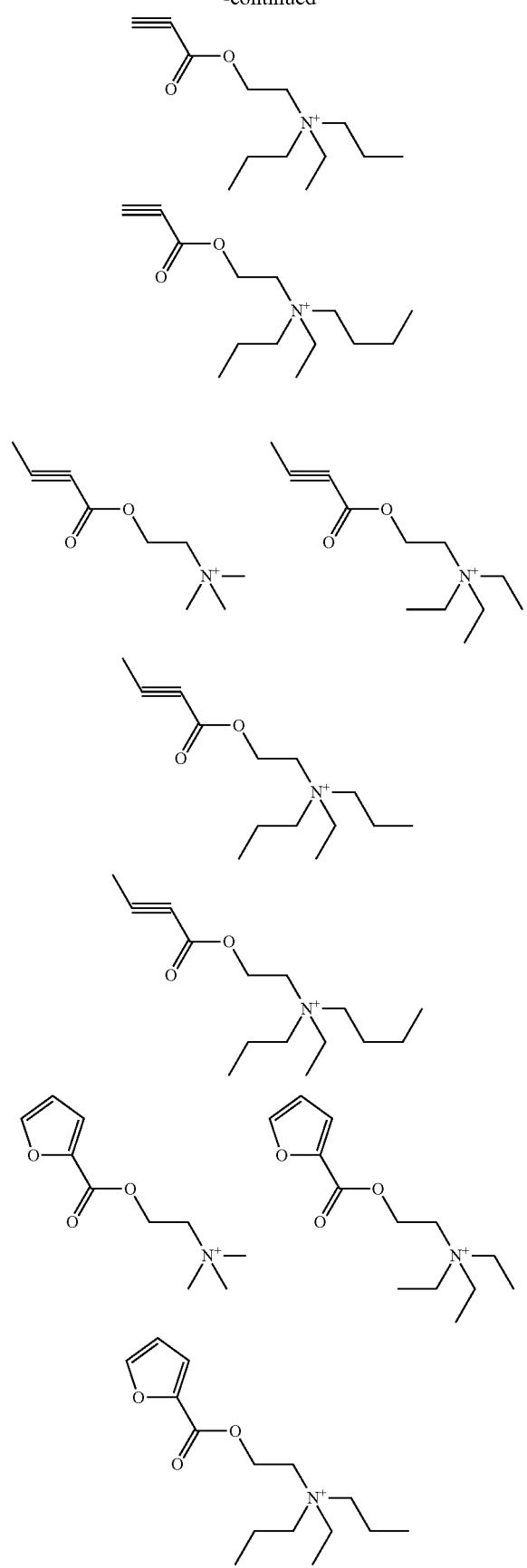
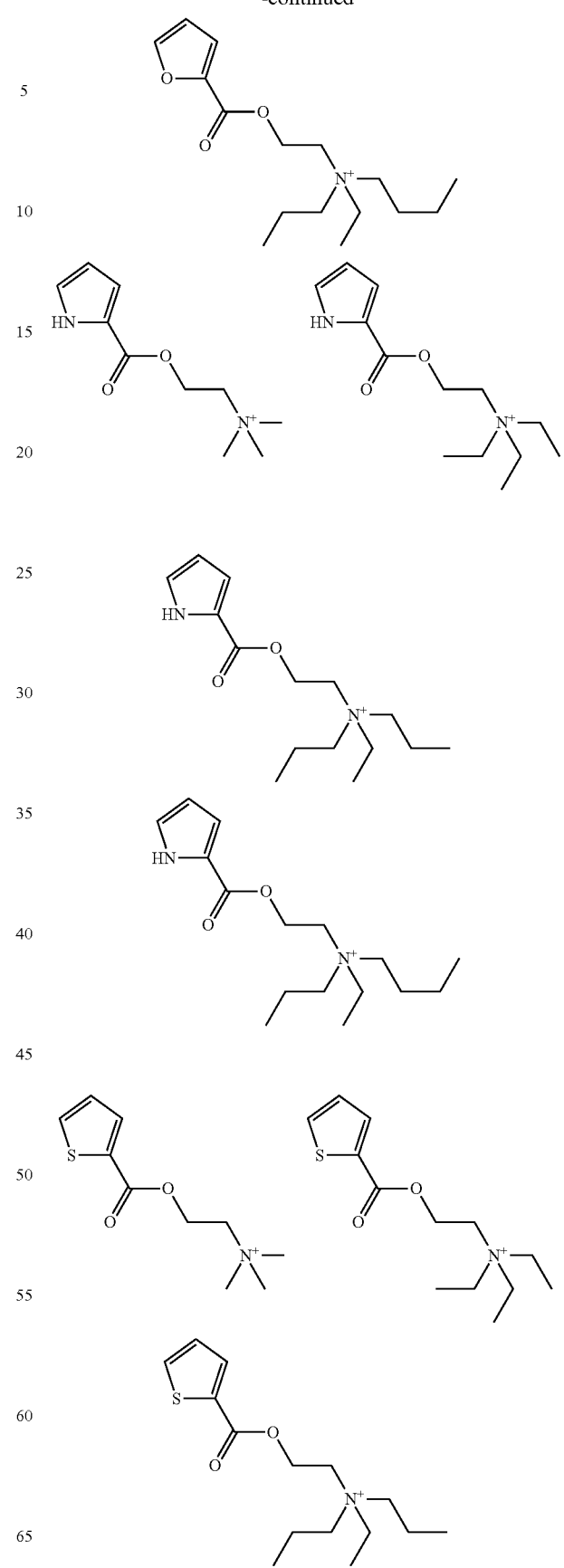

105
-continued
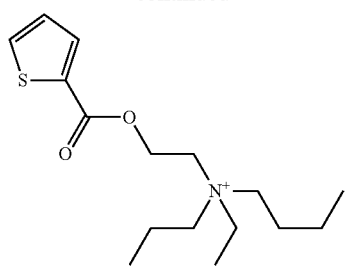
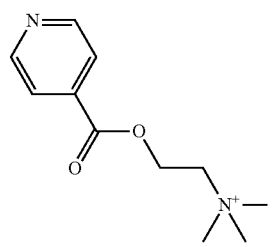
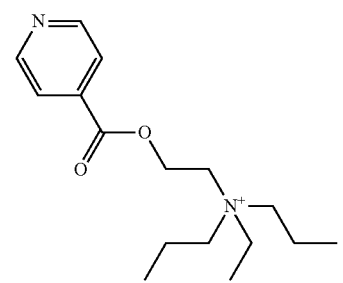
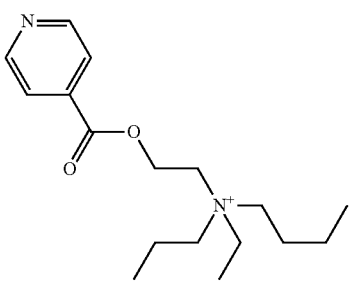
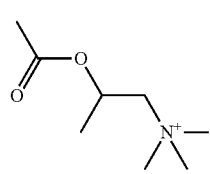
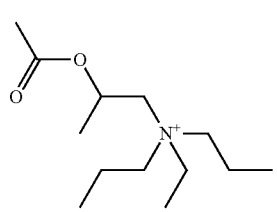
106
-continued
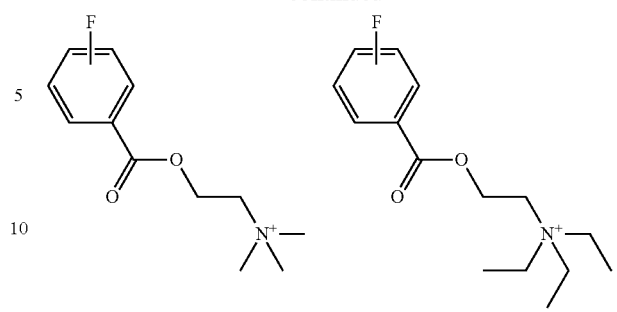
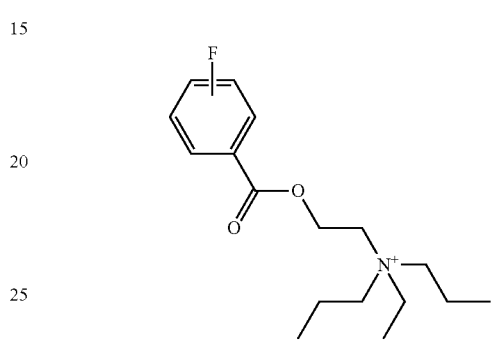
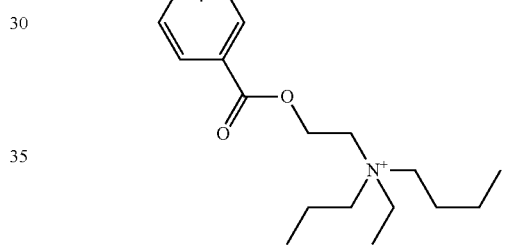
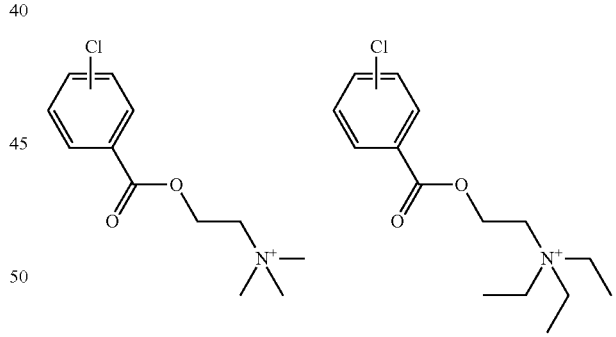
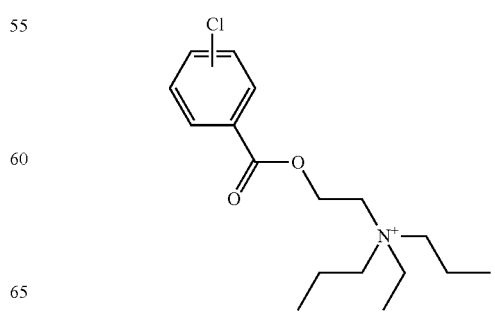

107
-continued
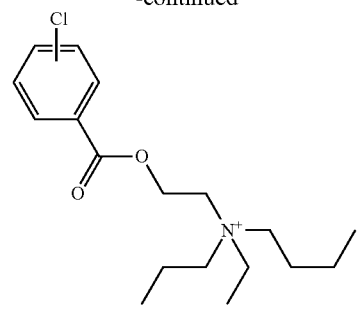
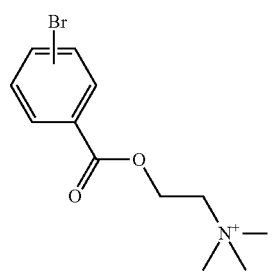 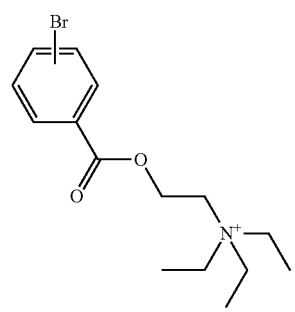
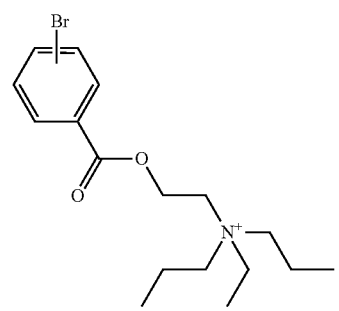
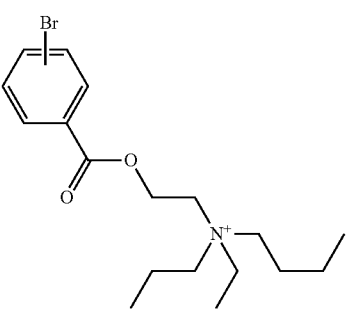
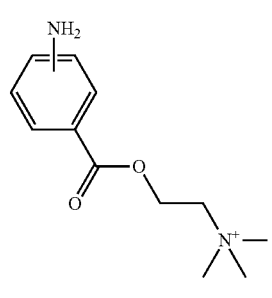 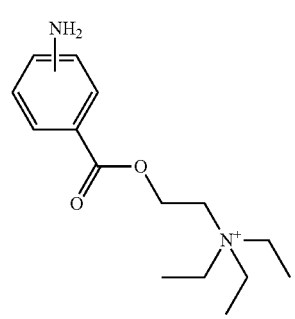
108
-continued
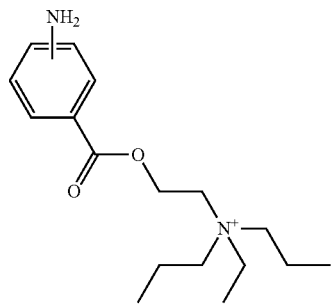
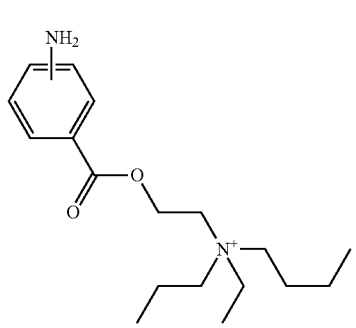
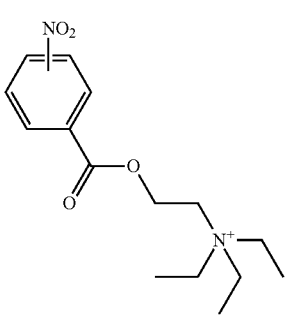
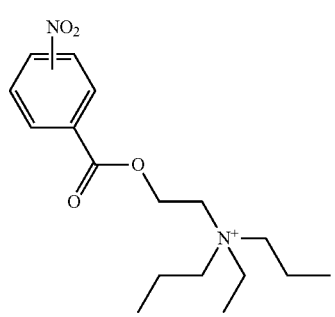
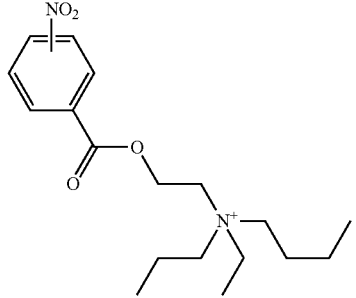

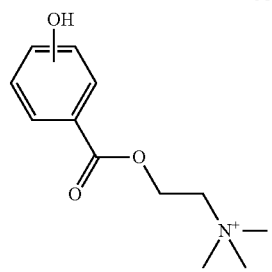
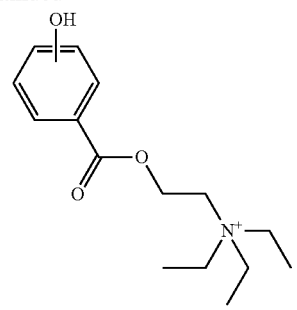
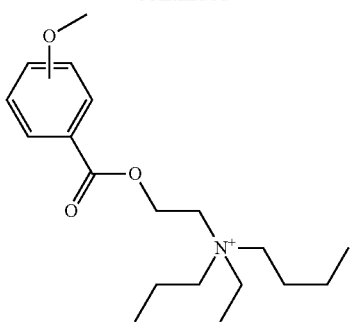
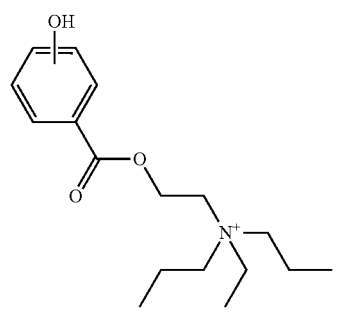
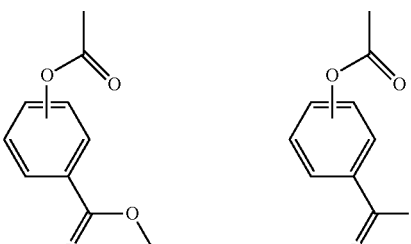
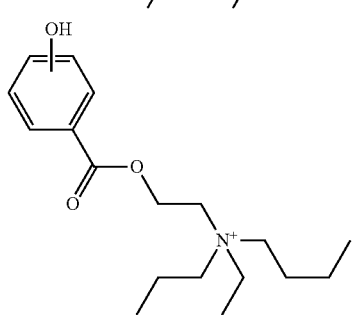
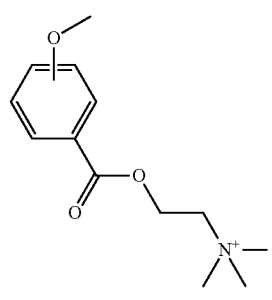
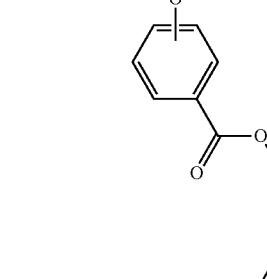
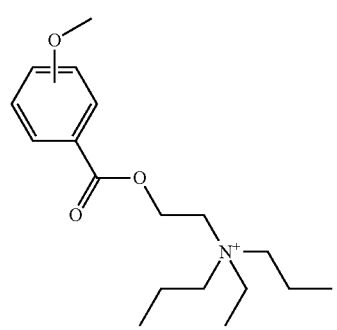
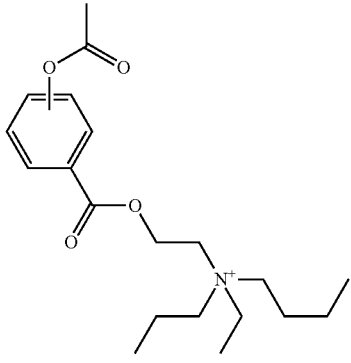

111
-continued
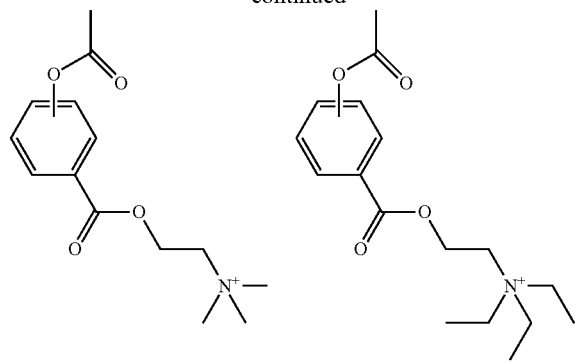
112
-continued
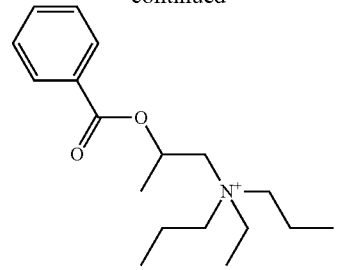
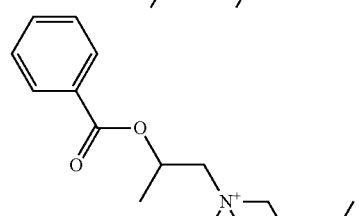
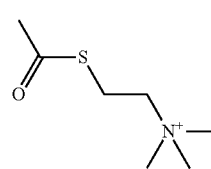
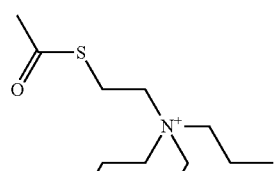 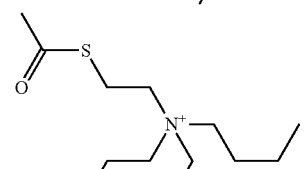
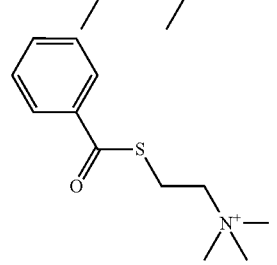
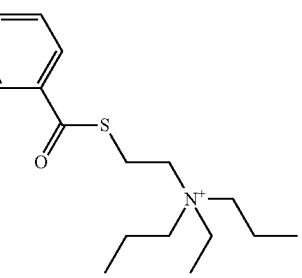
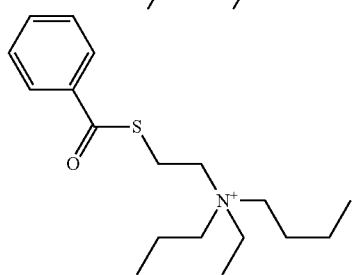

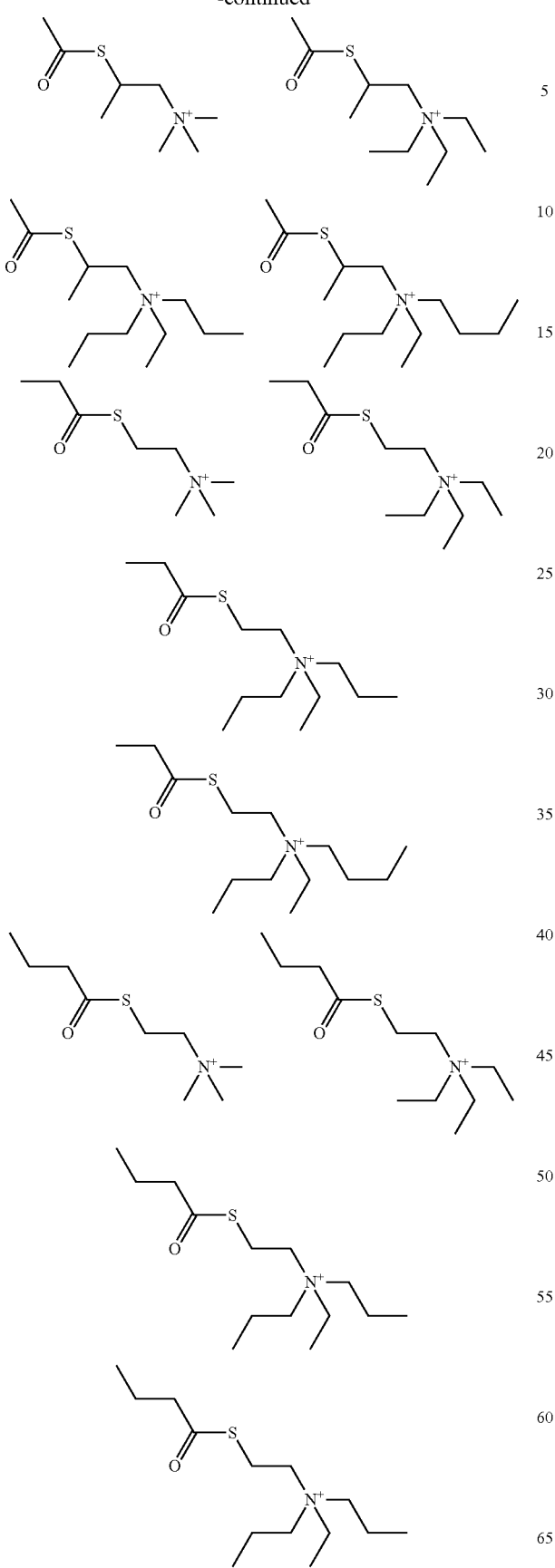
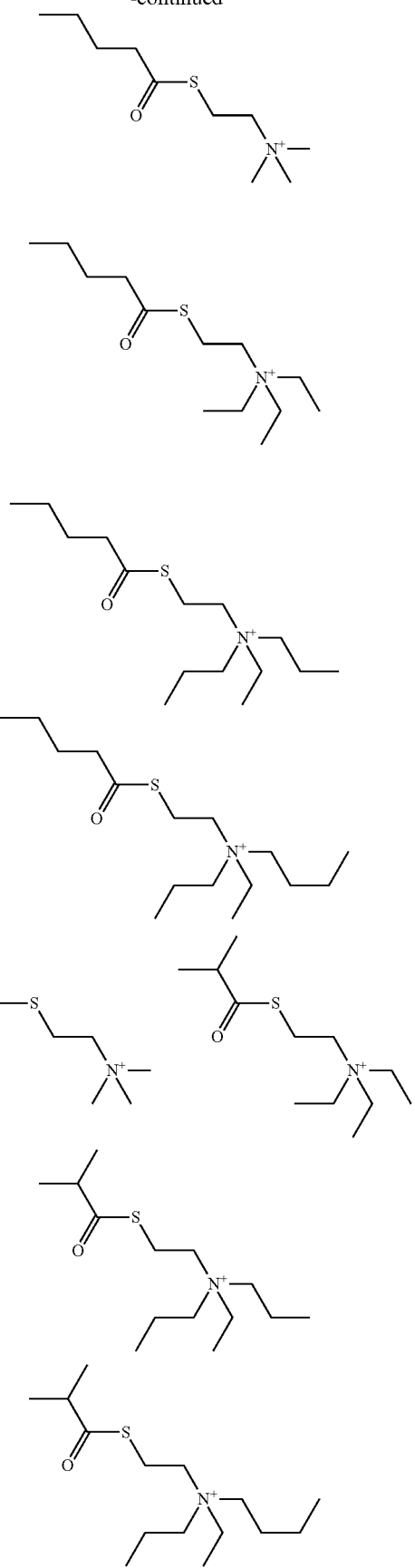

115
-continued
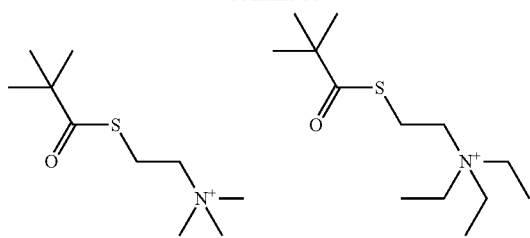
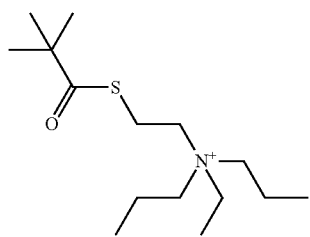
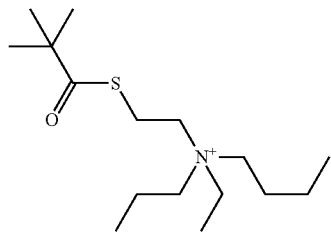
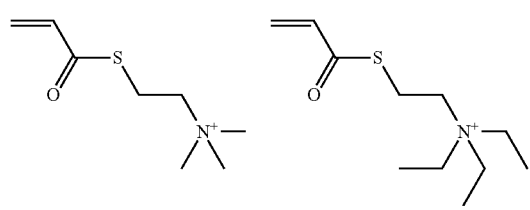
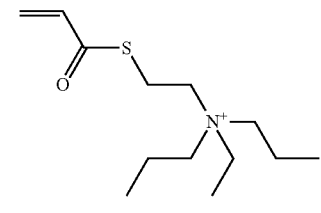
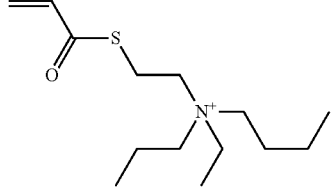
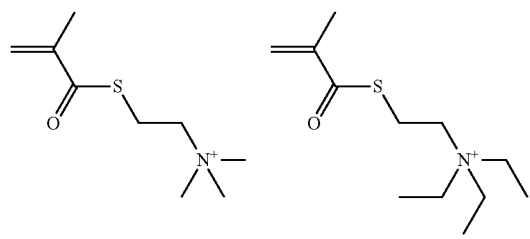
116
-continued
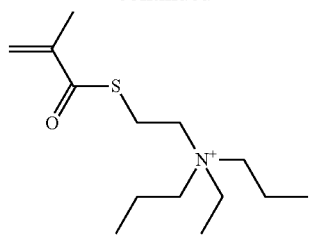
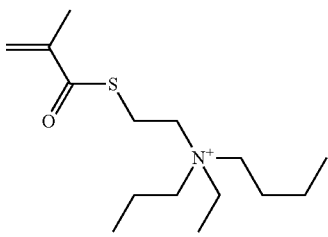
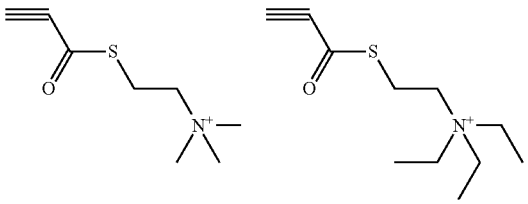
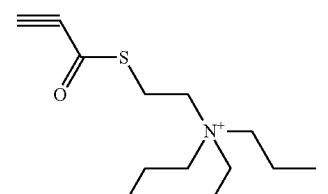
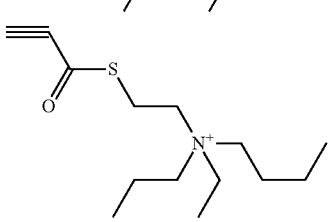
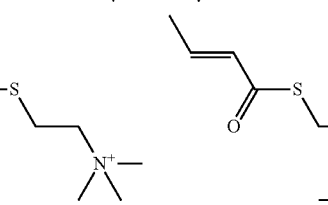
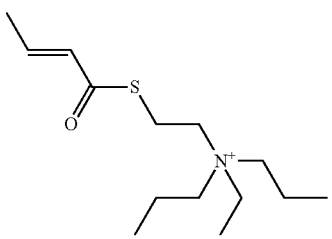

-continued
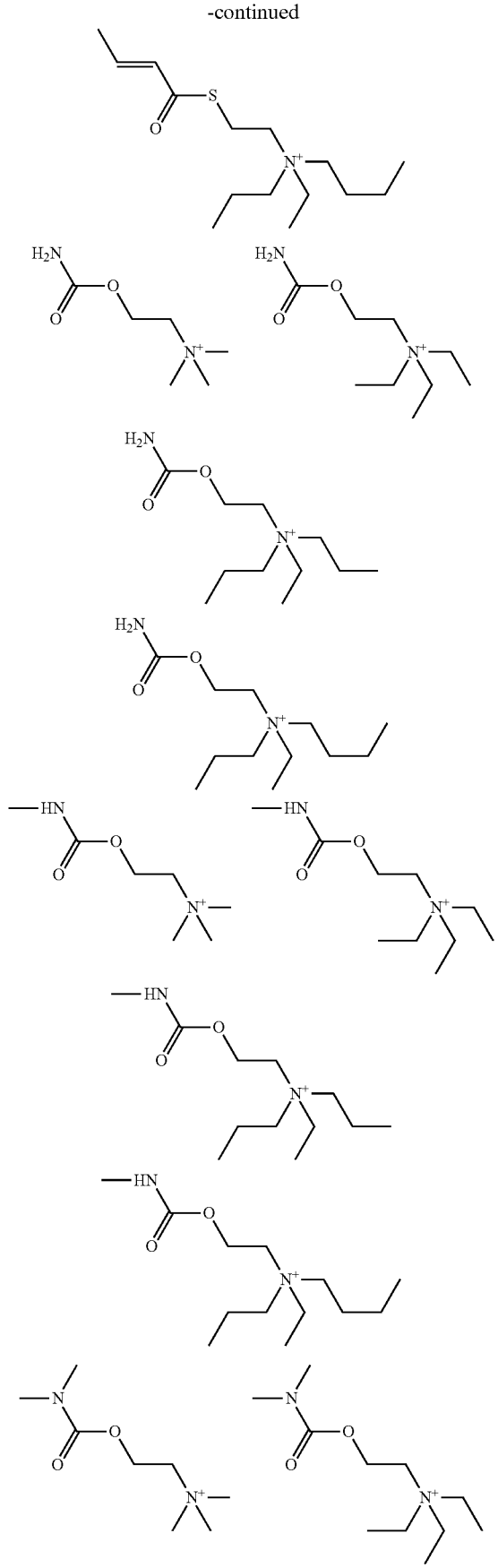
-continued
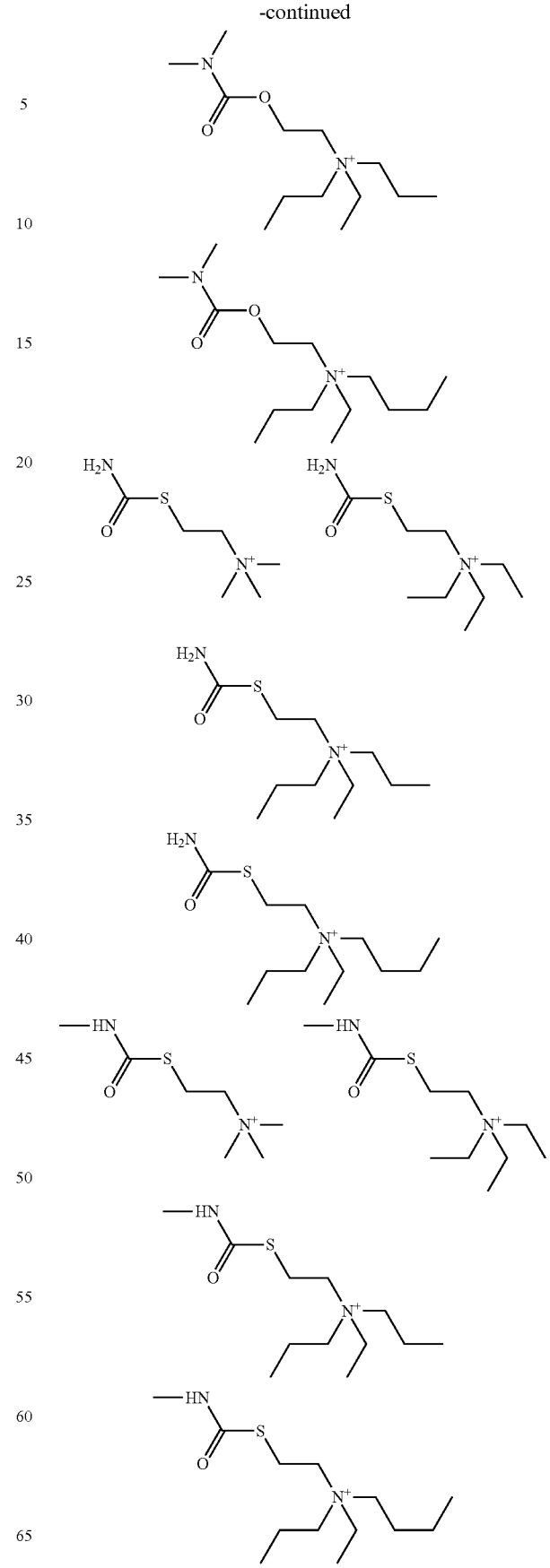

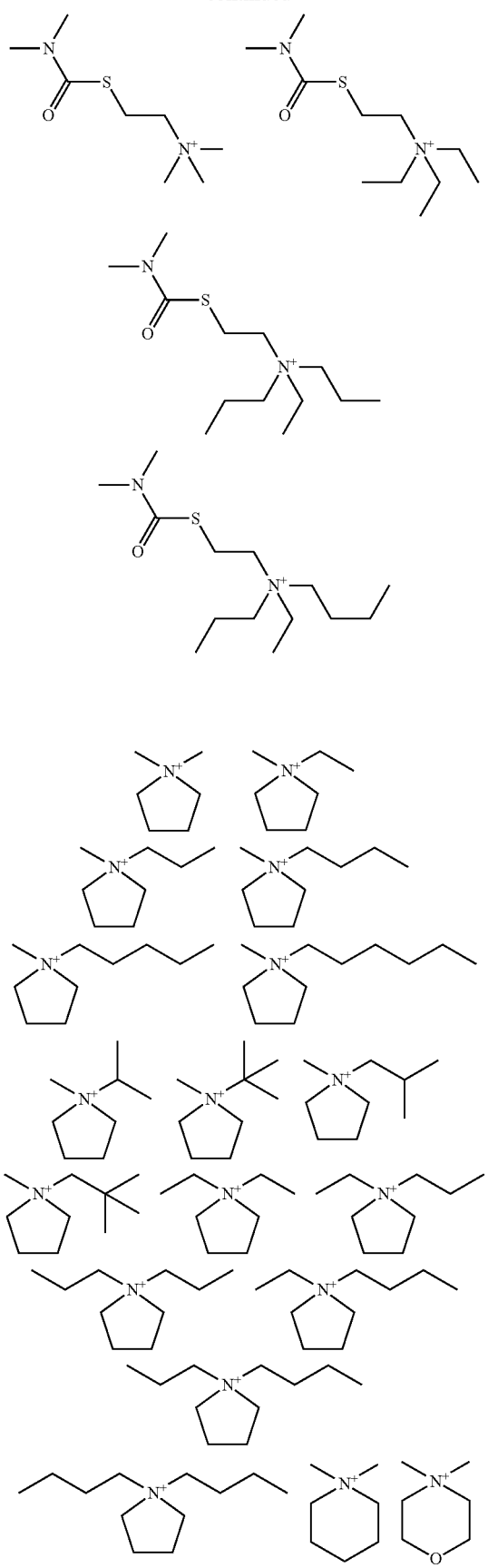
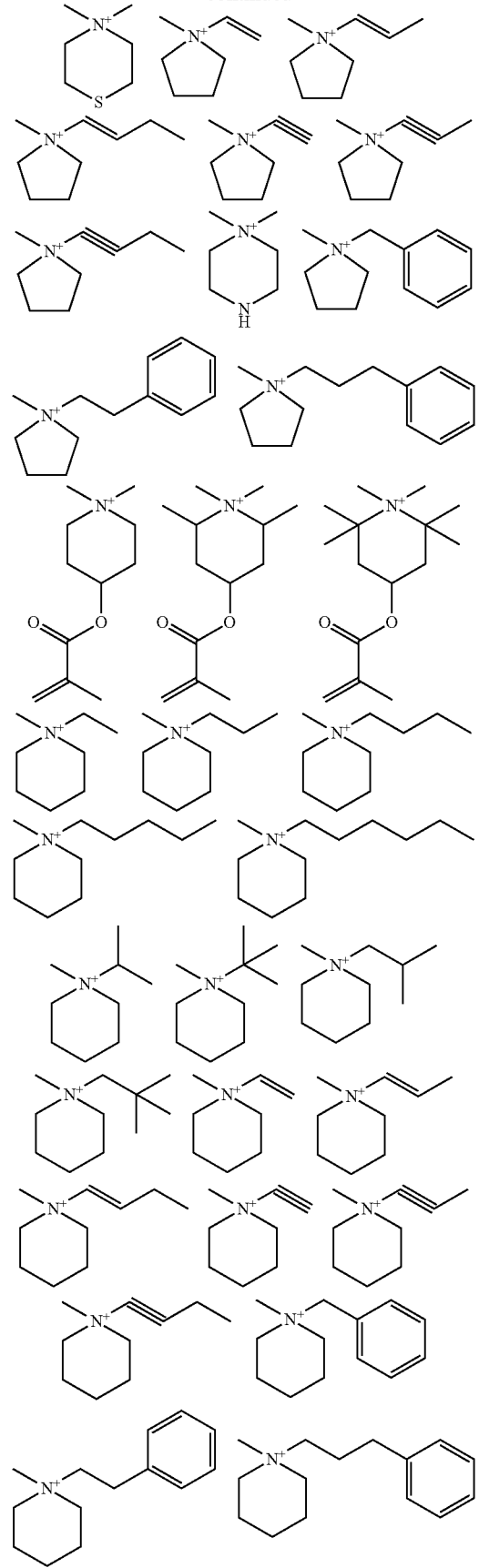

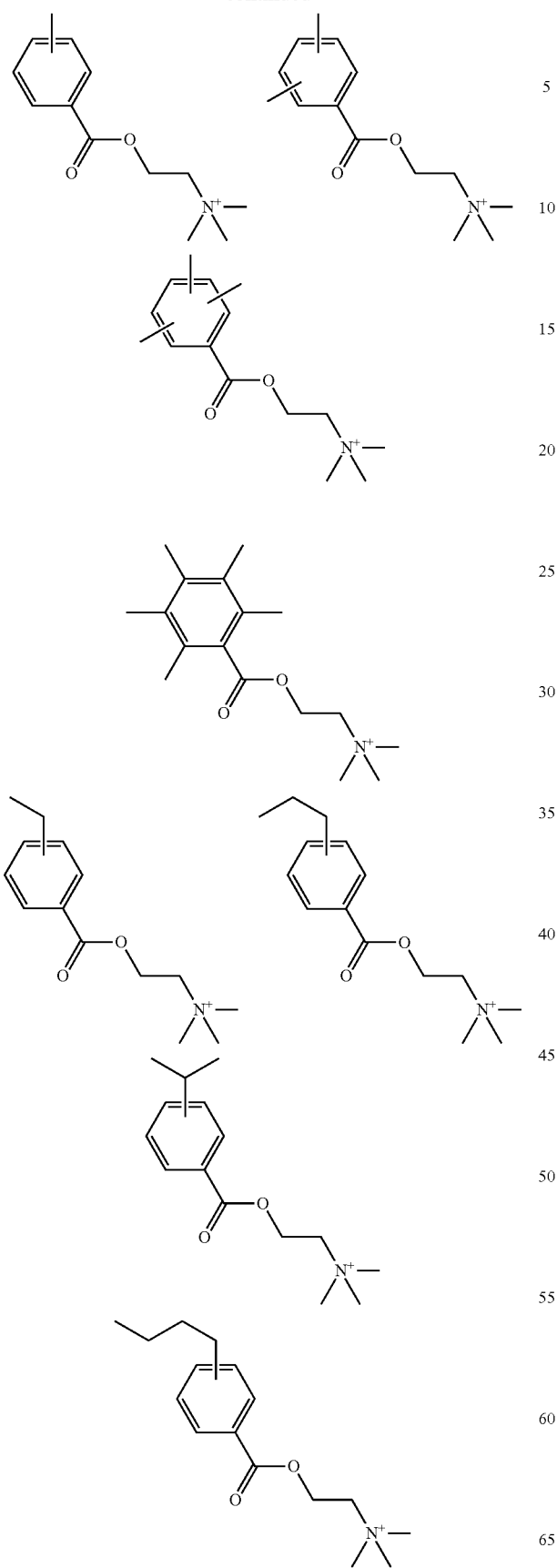
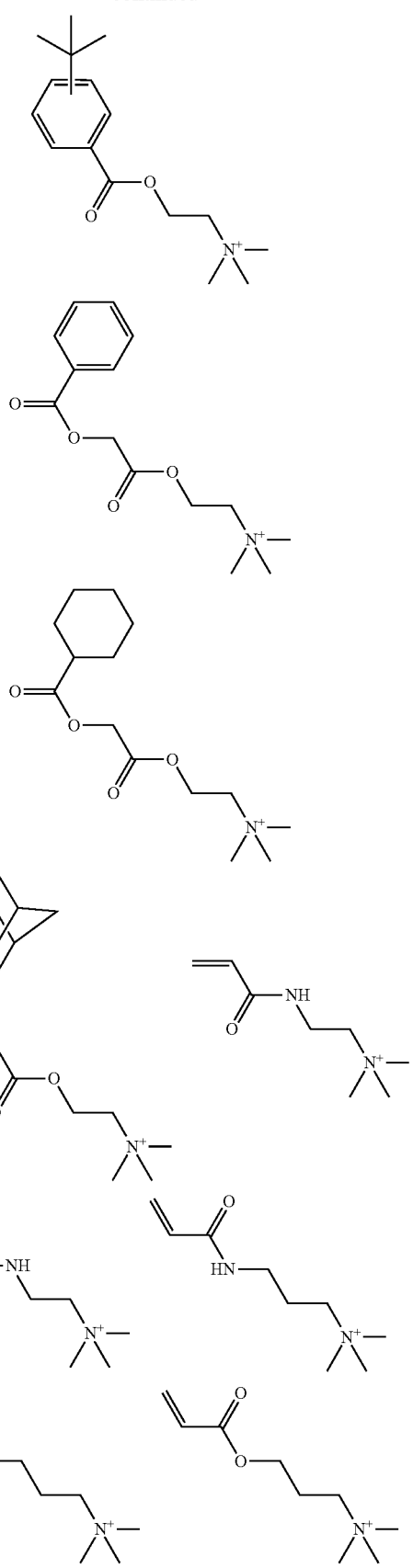

123
-continued
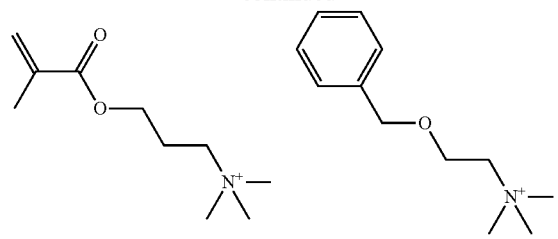
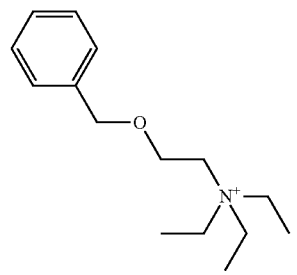
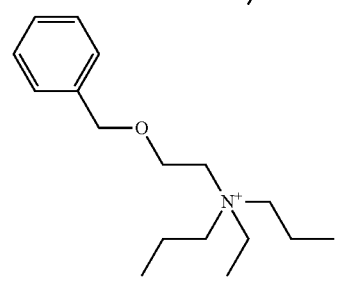
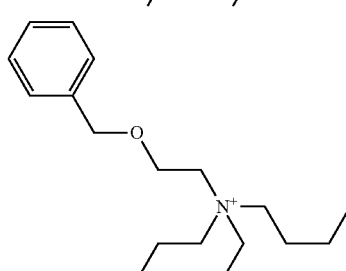
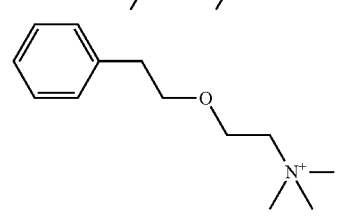
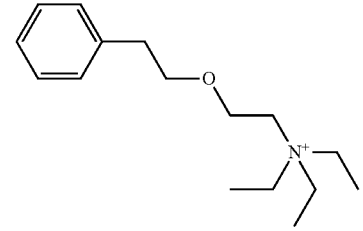
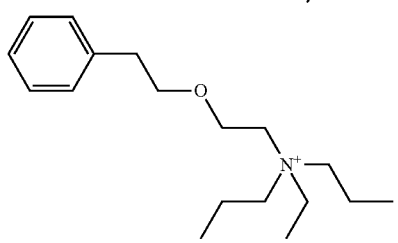
124
-continued
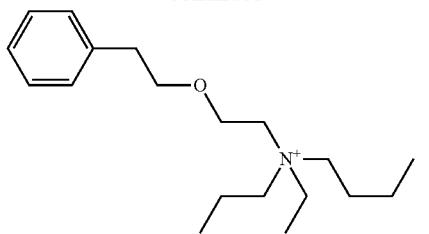
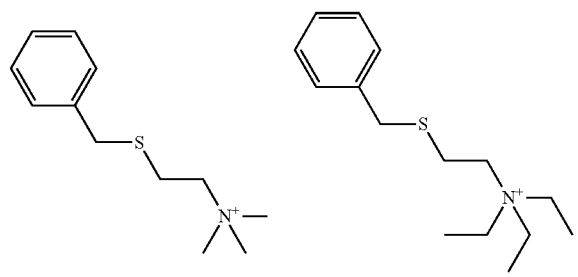
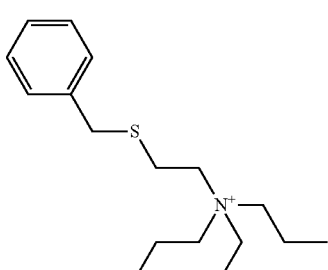
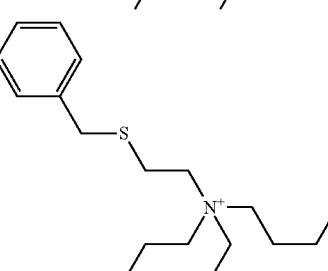
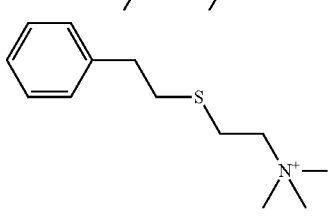
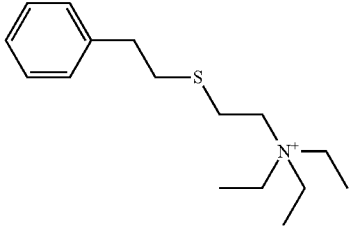
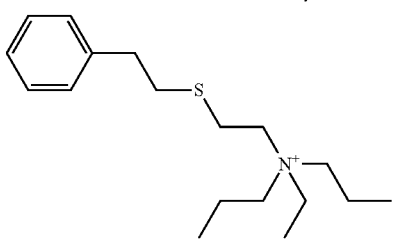

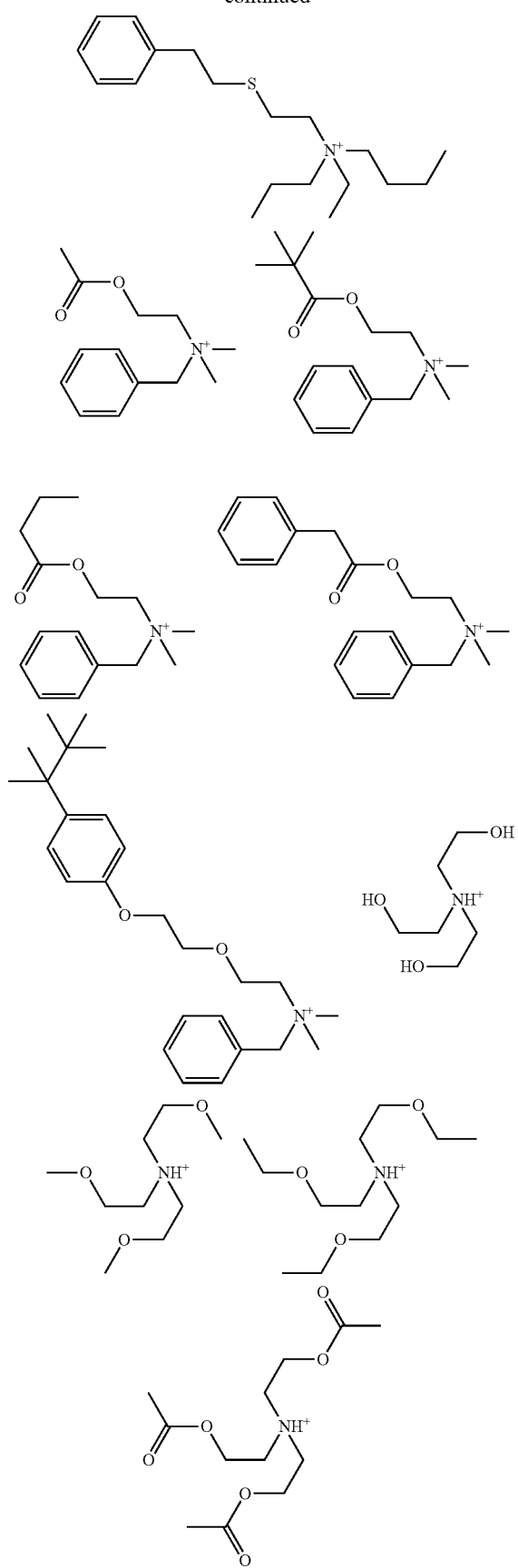
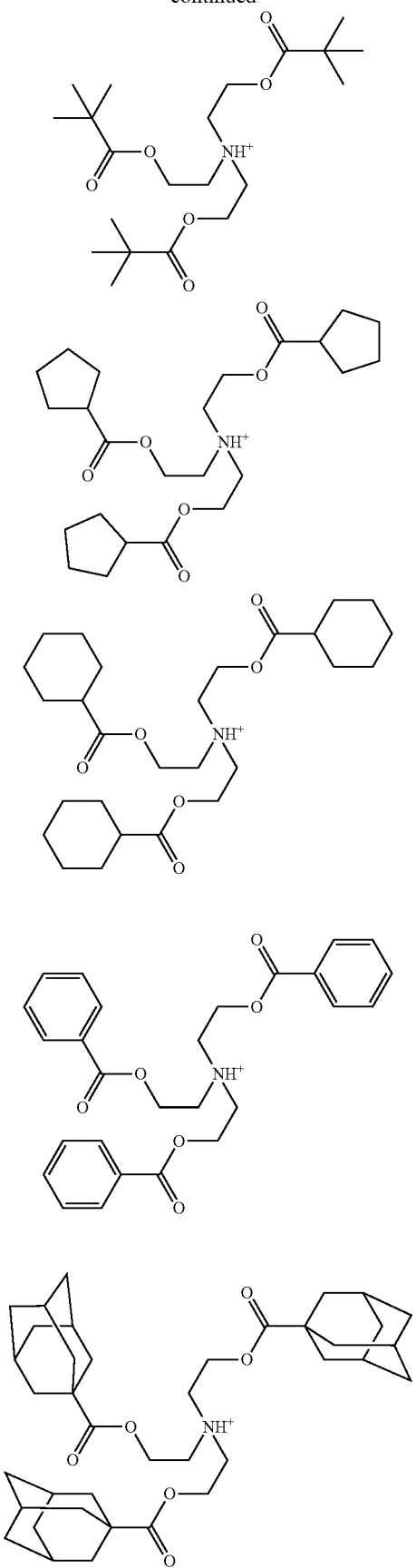

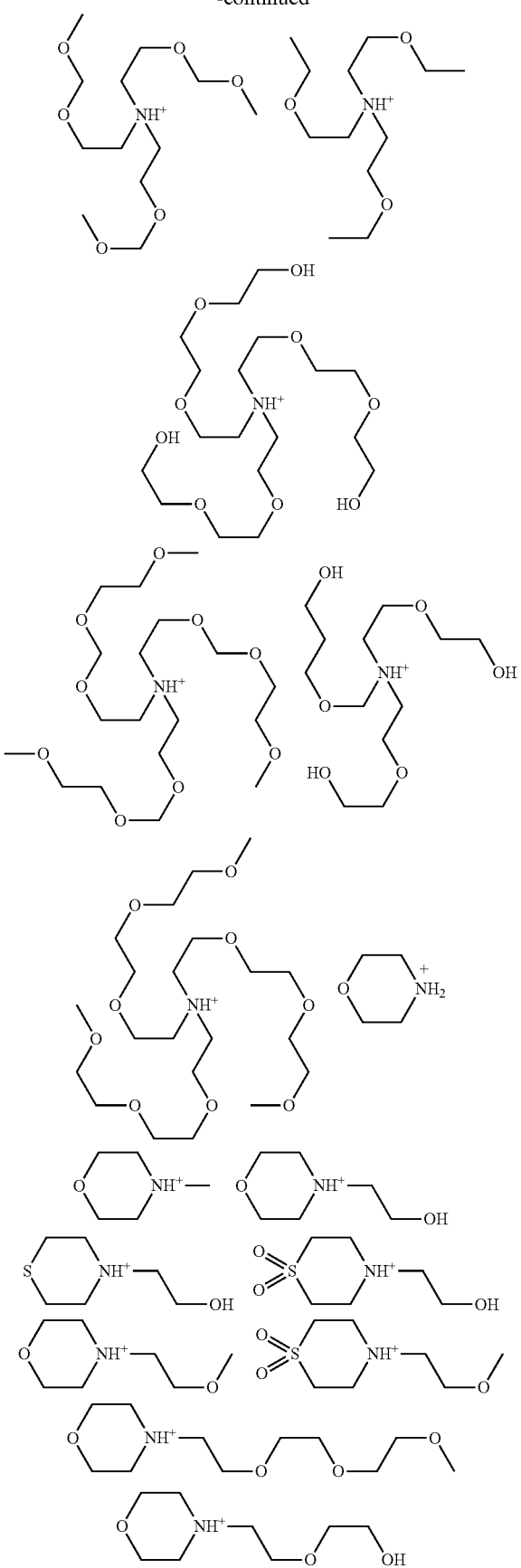
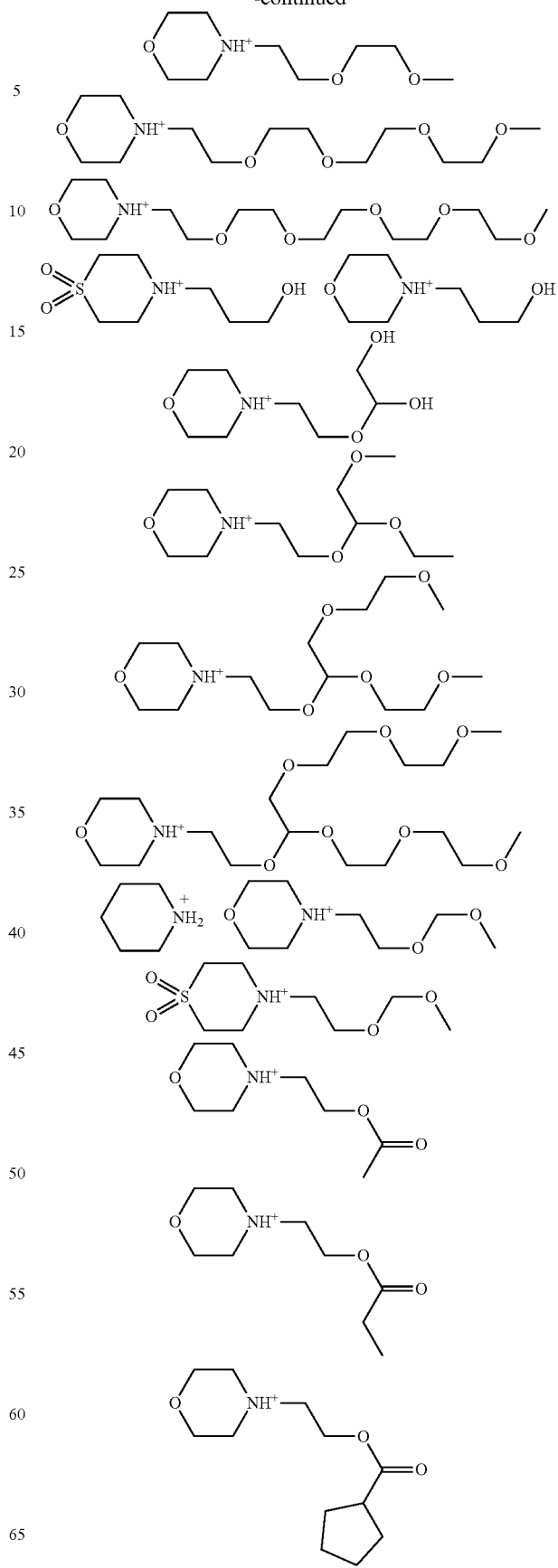

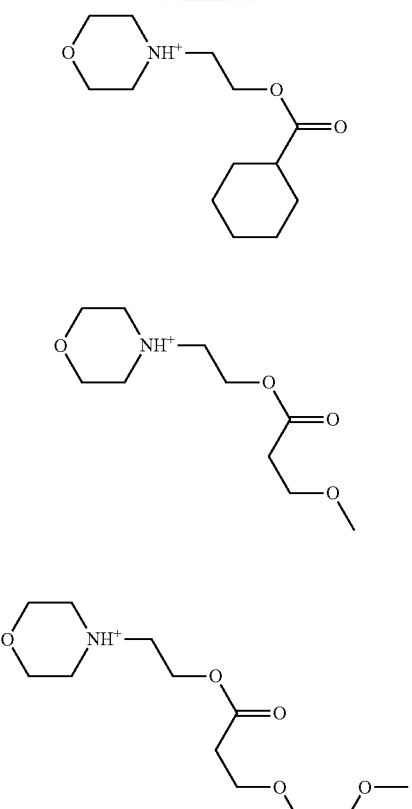

The ammonium ion shown by the general formula (3) is particularly preferably a tertiary or quaternary ammonium ion.

(Repeating Unit-b)

The component (A) of the inventive bio-electrode composition can contain a repeating unit-b having silicon in addition to the repeating unit(s) selected from the repeating units-a1 to -a7. Specific examples of a monomer to give the repeating unit-b include the following.

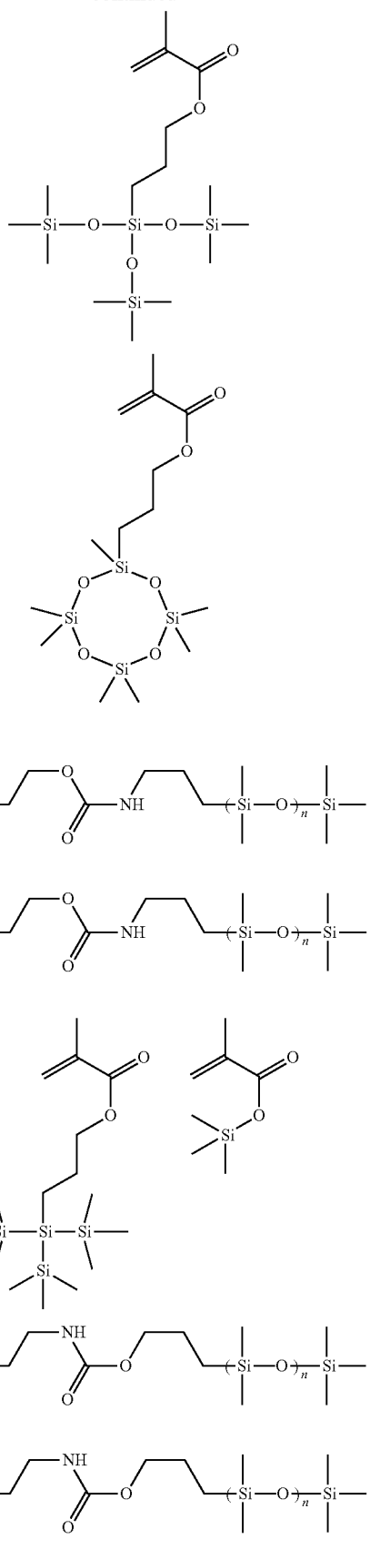

-continued
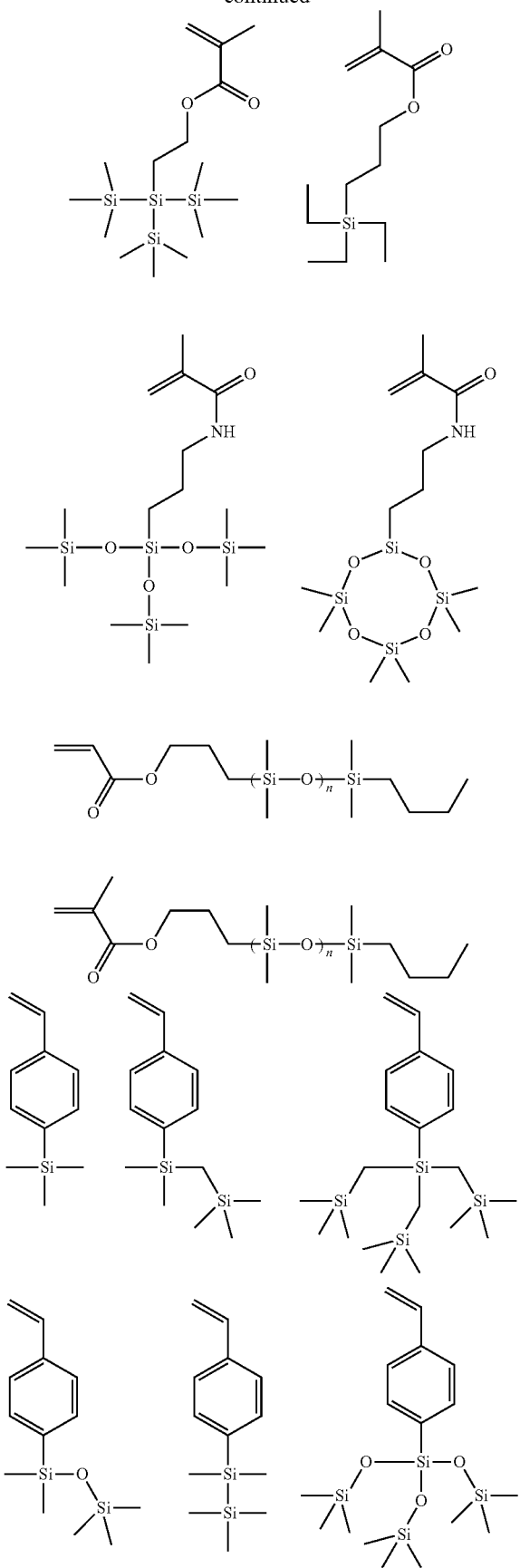
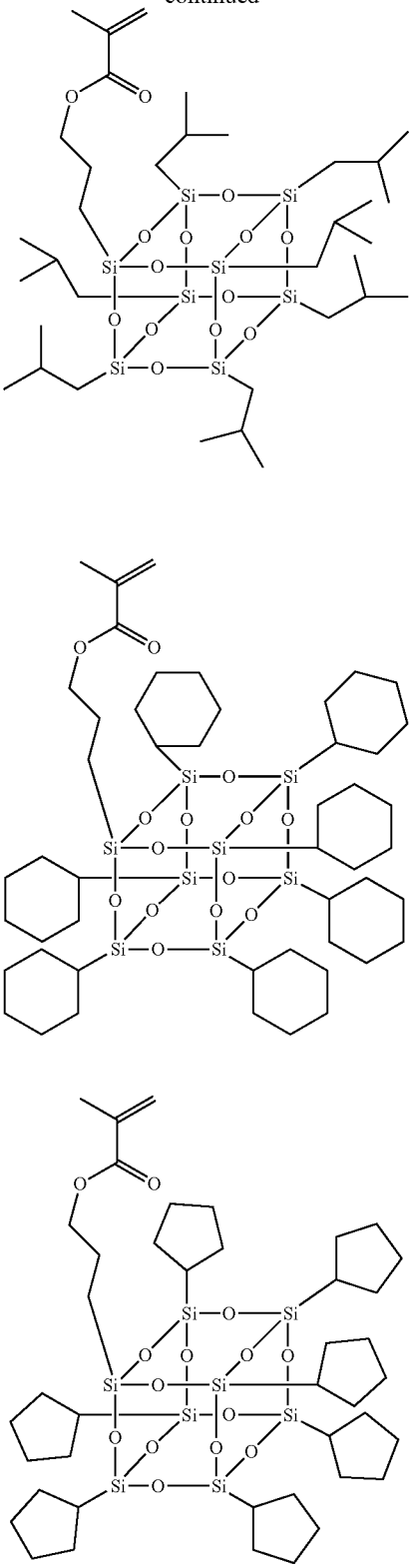
(Repeating Unit-c)
In the component (A) of the inventive bio-electrode composition, a repeating unit-c having a glyme chain can be copolymerized in addition to the repeating units-a1 to -a7 and -b in order to improve the electric conductivity.

Specific examples of a monomer to give the repeating unit-c having a glyme chain include the following.
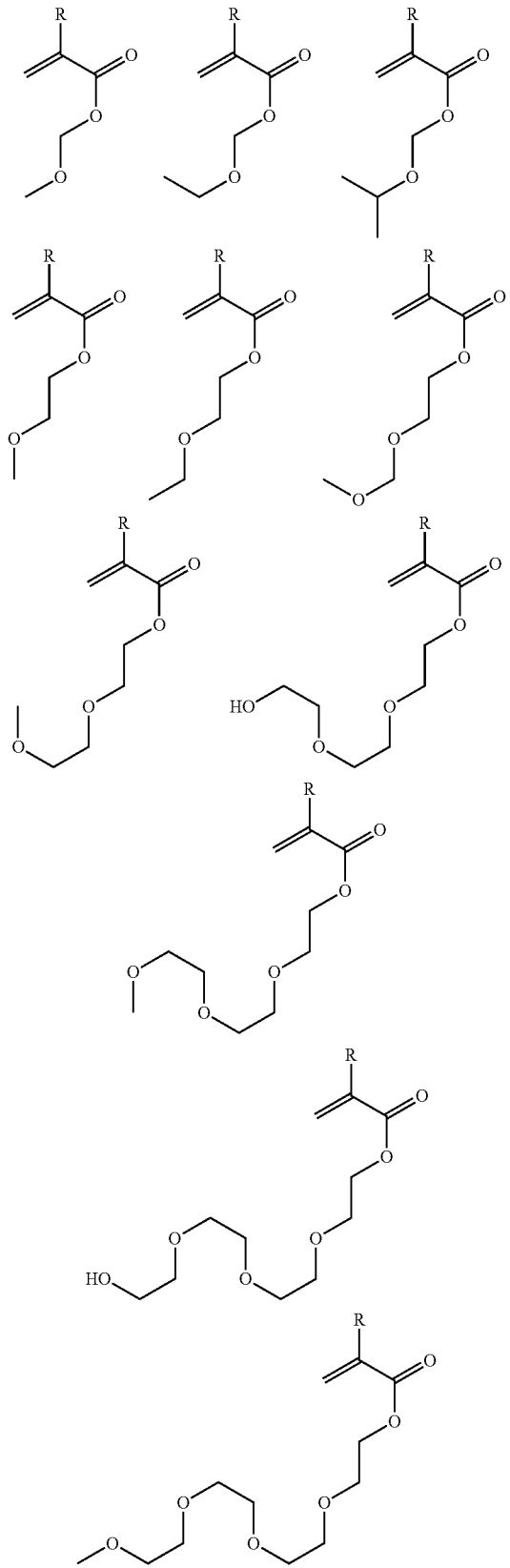
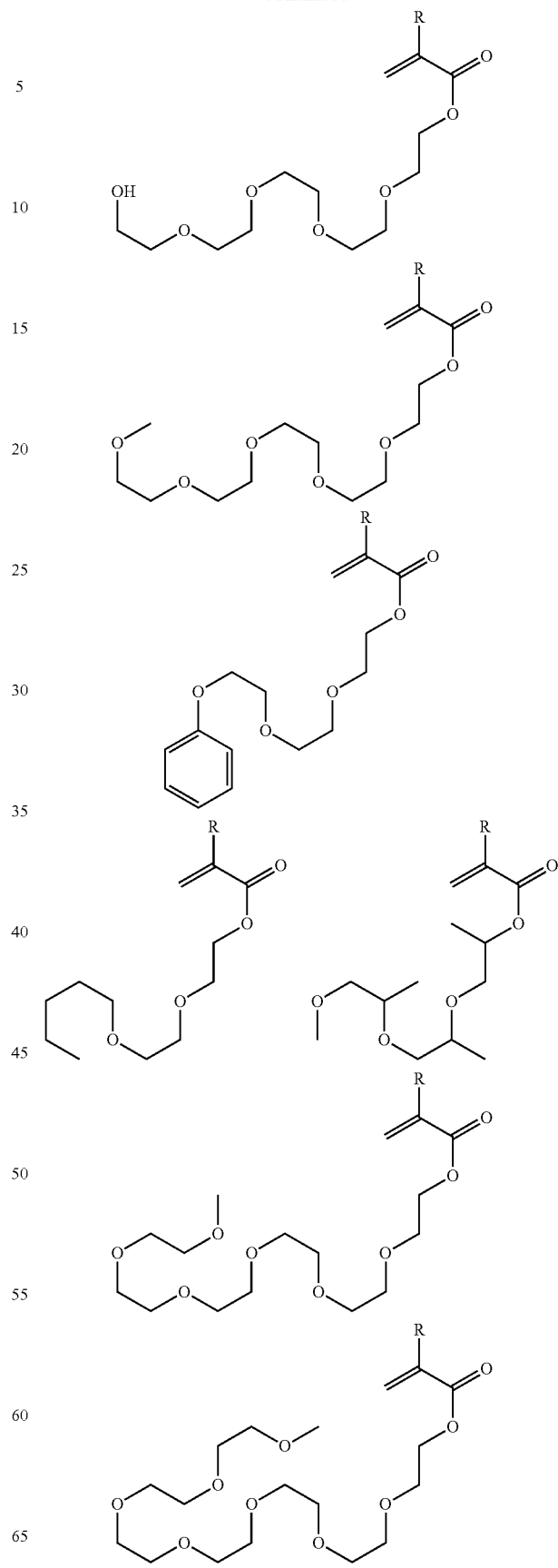

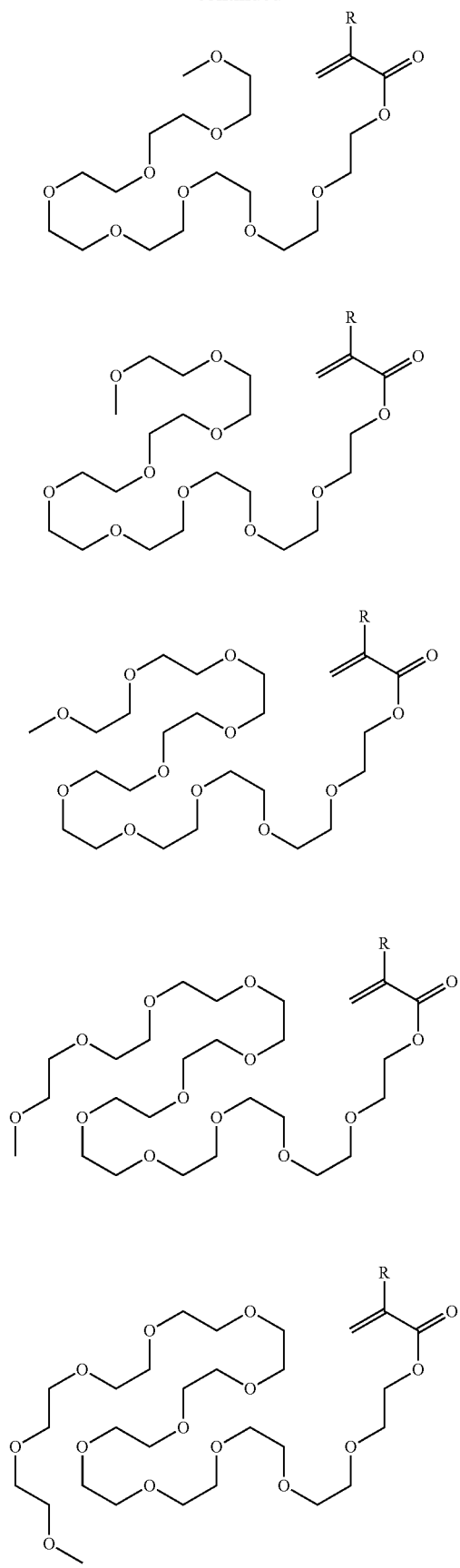
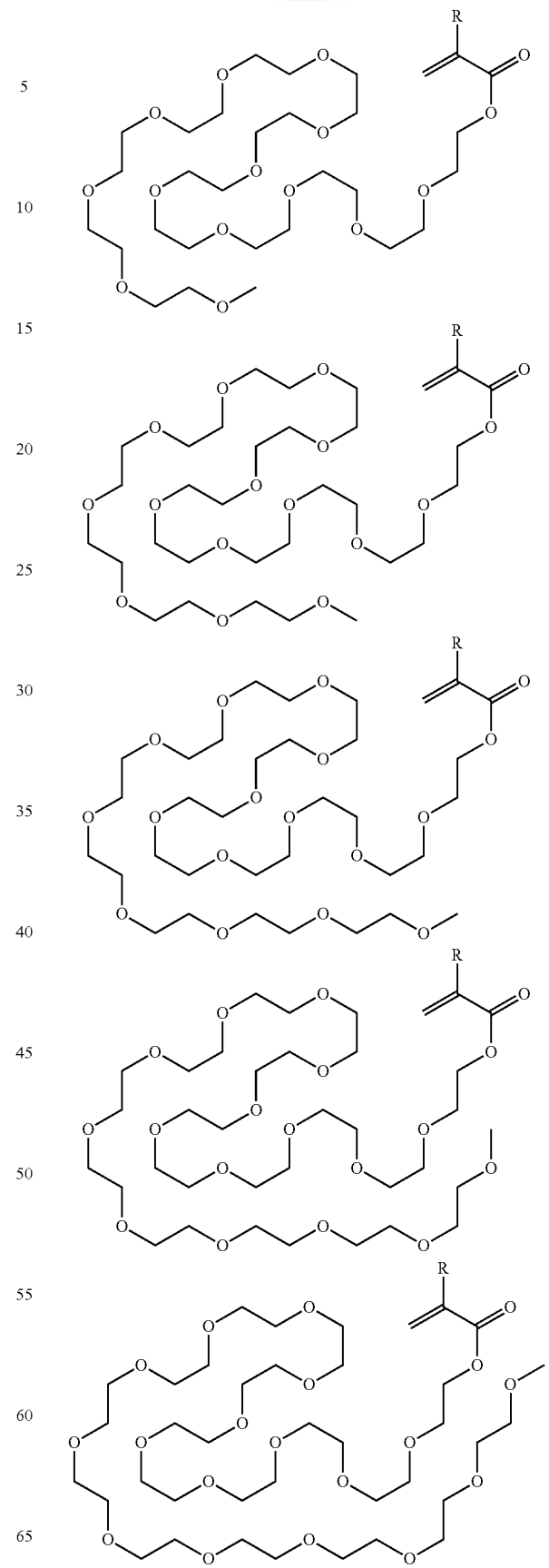

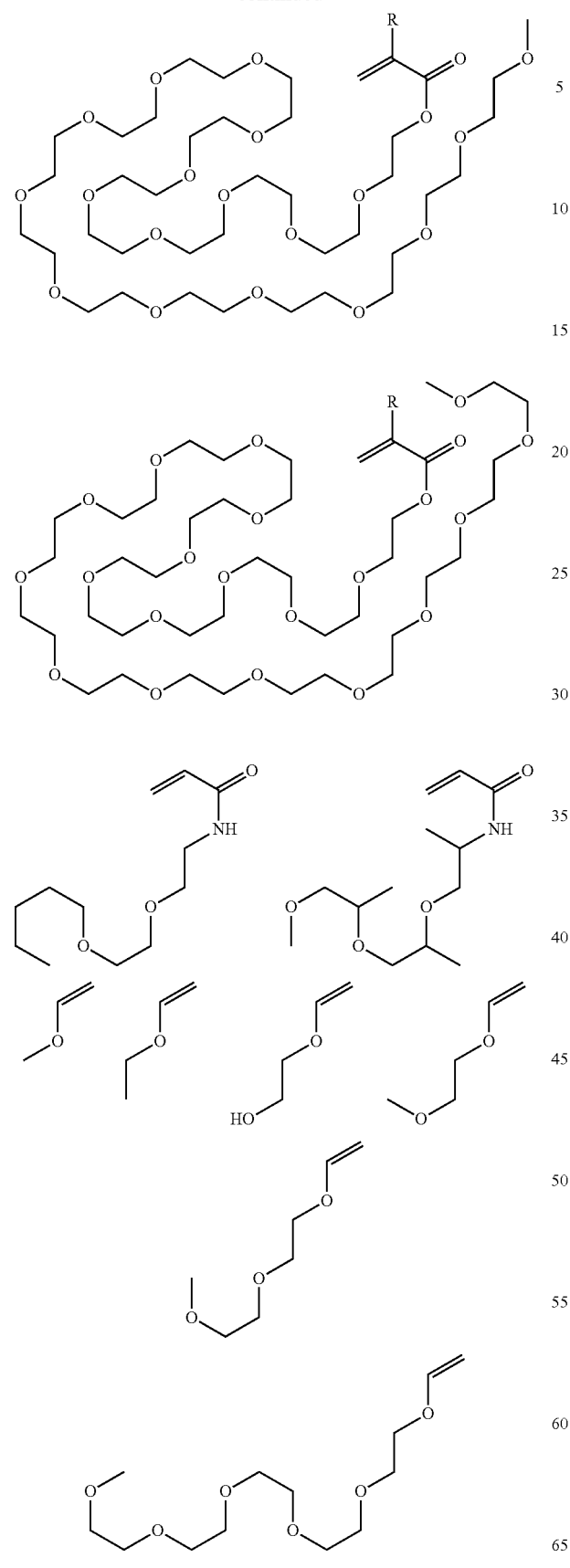

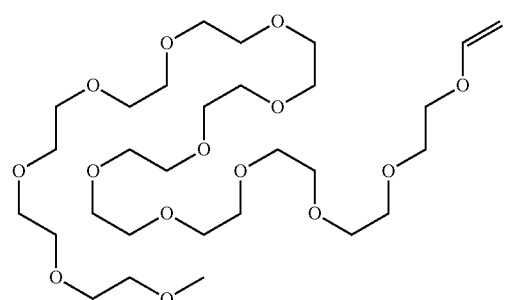
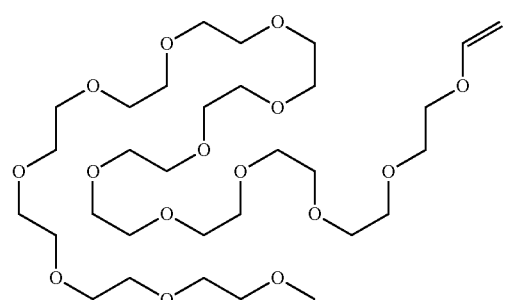
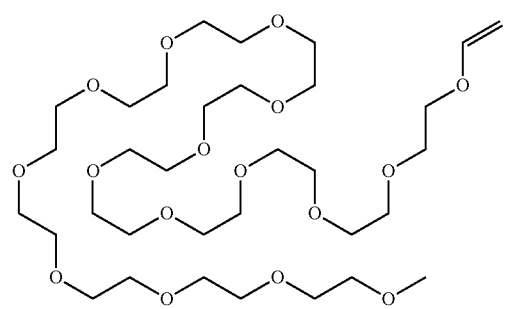
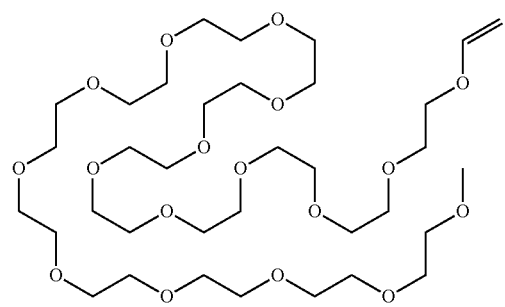
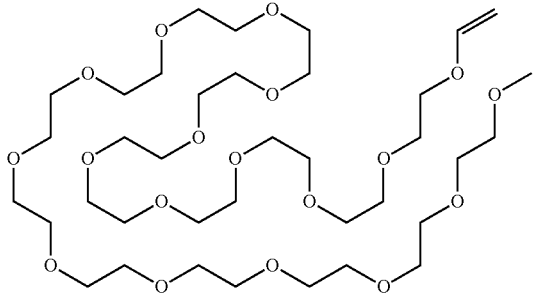
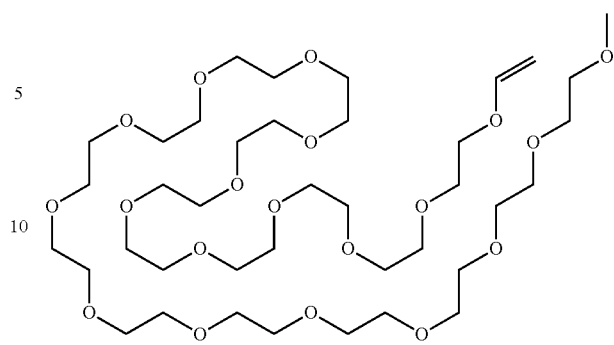
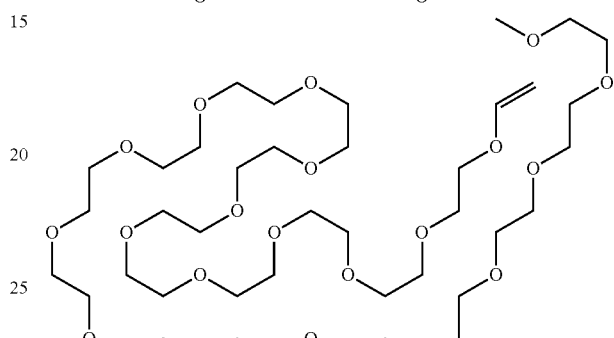
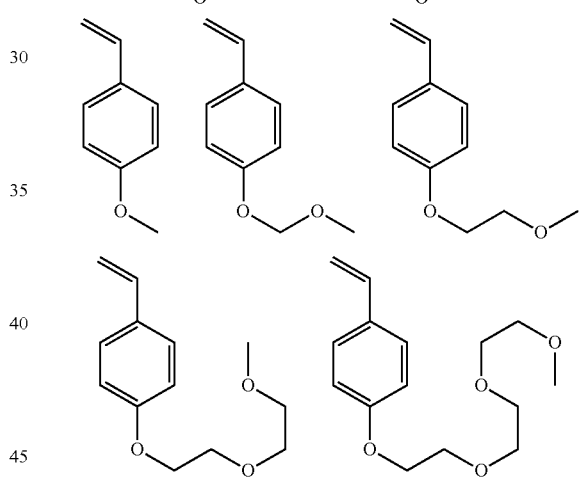
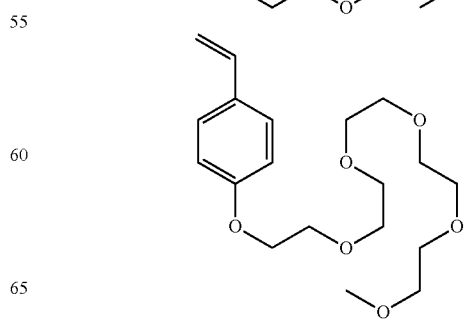

-continued
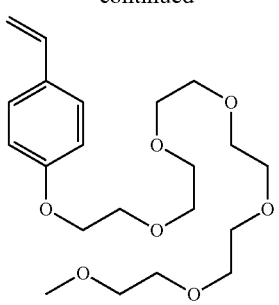
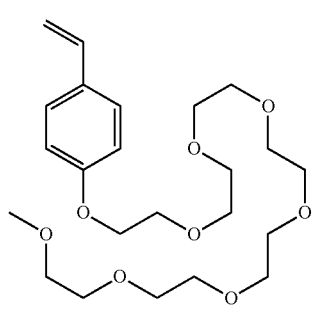
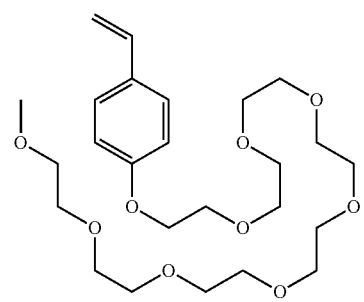
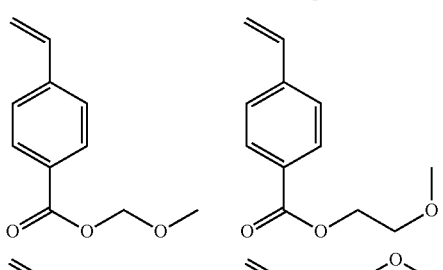
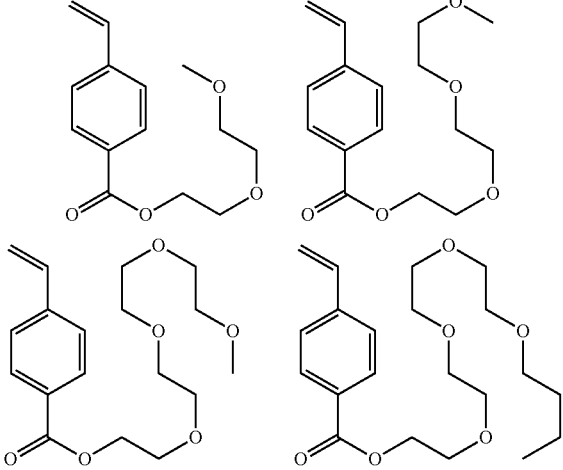
-continued
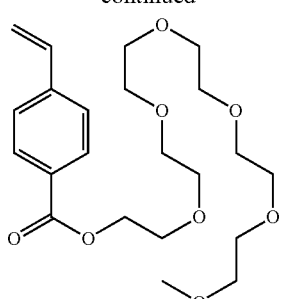
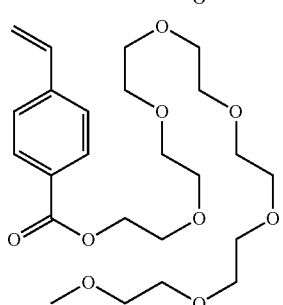
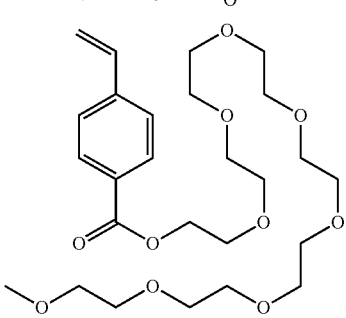
(Repeating Unit-d)
The polymer compound in the inventive bio-electrode composition can contain a repeating unit-d to give adhesion properties.
Specific examples of a monomer to give the repeating unit-d include the following.
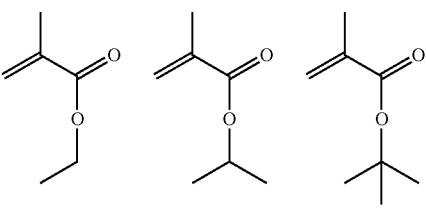
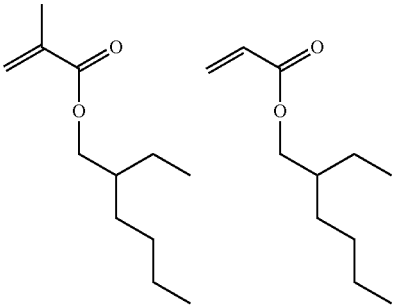

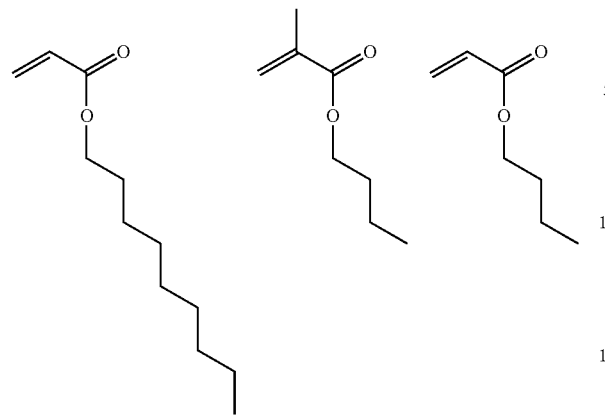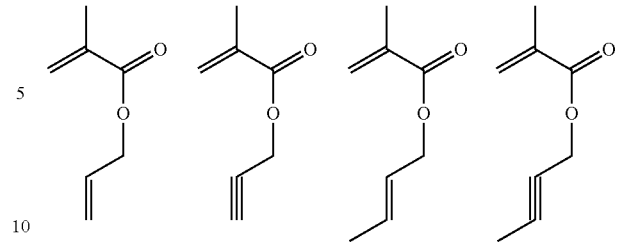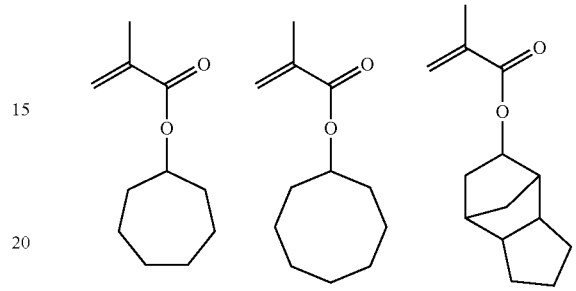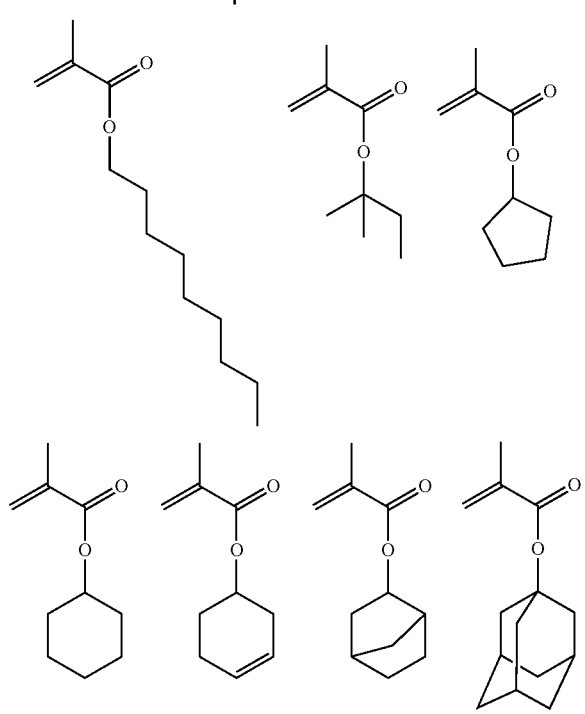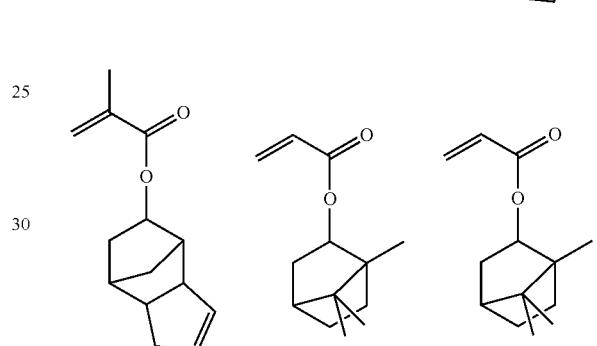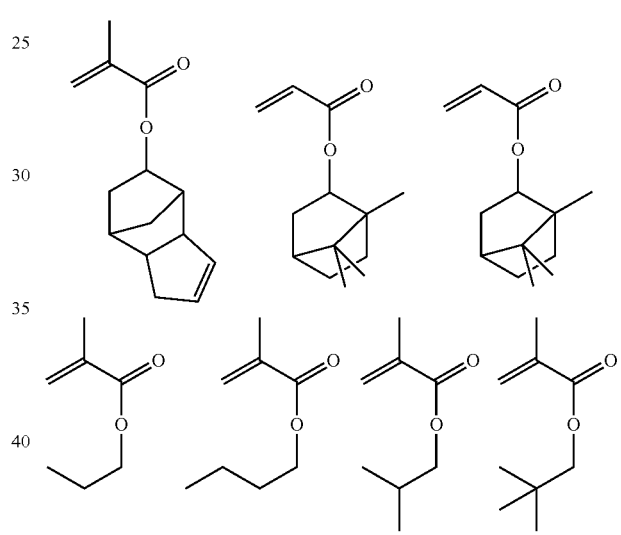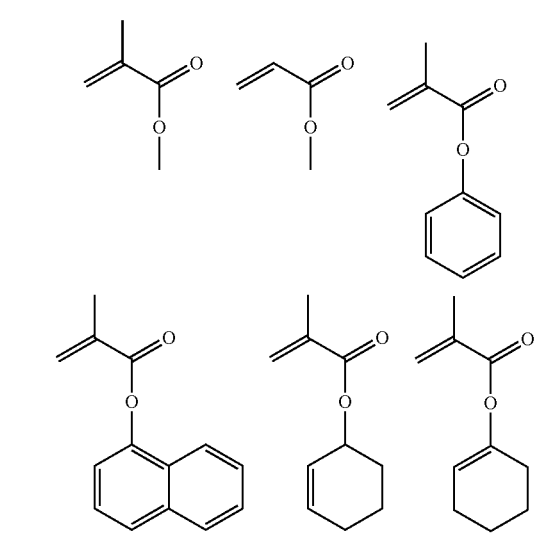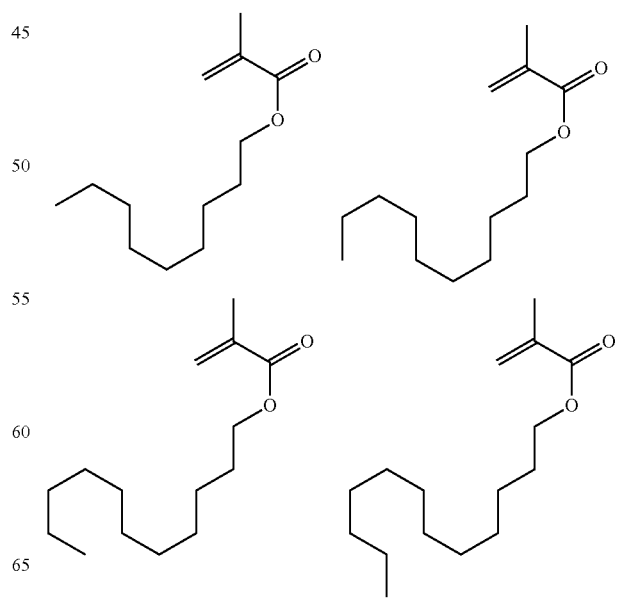

145
-continued
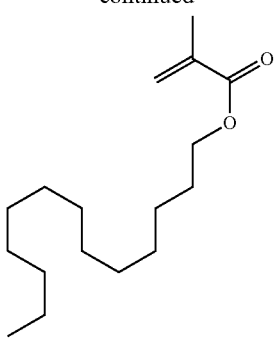
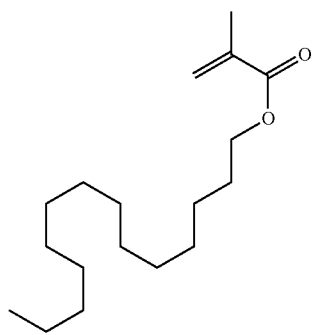
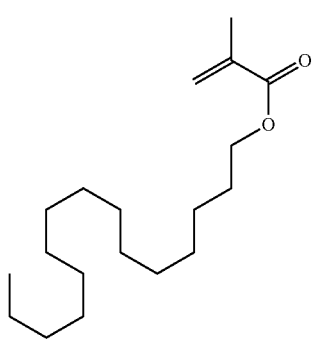
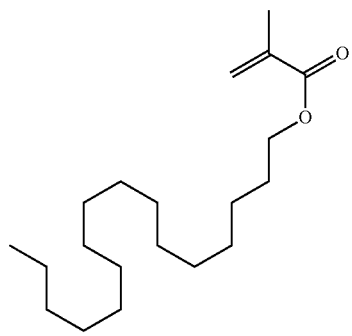
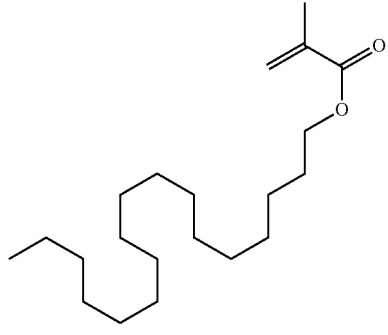
146
-continued
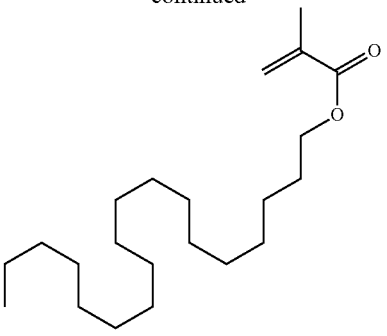
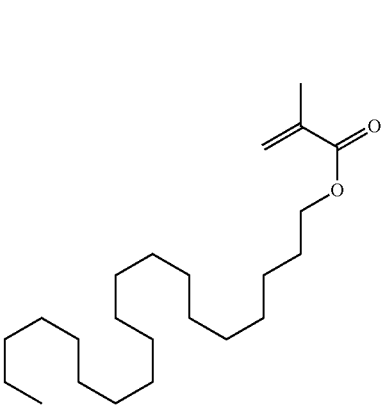
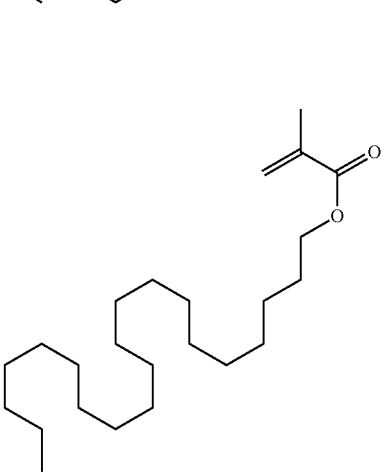
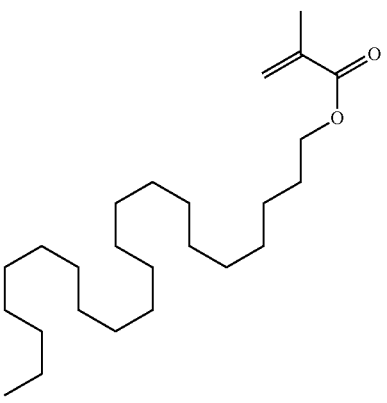

147
-continued
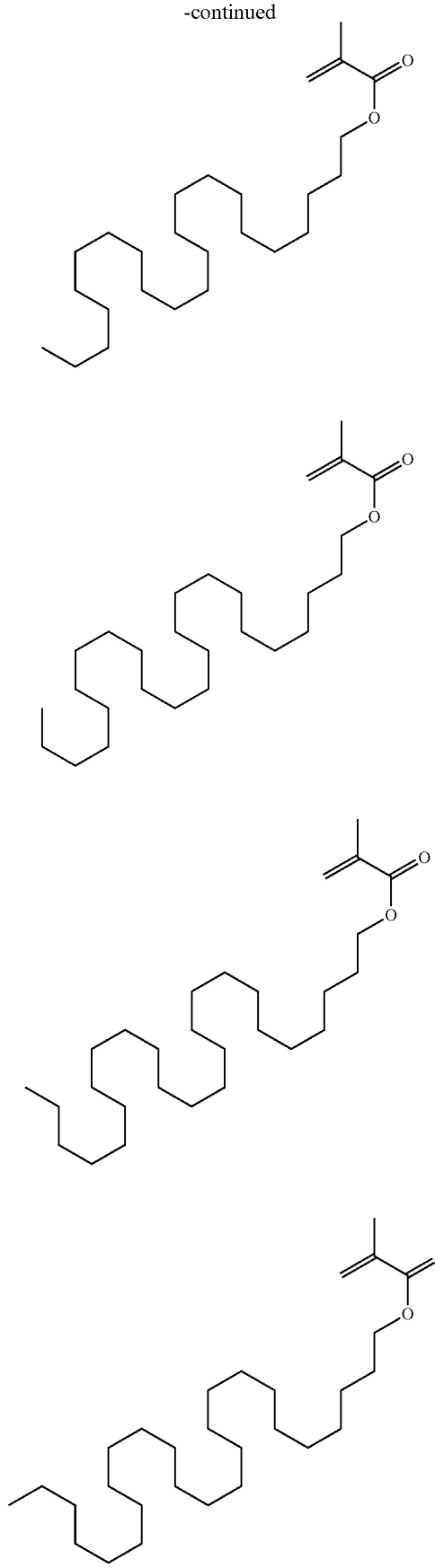
148
-continued
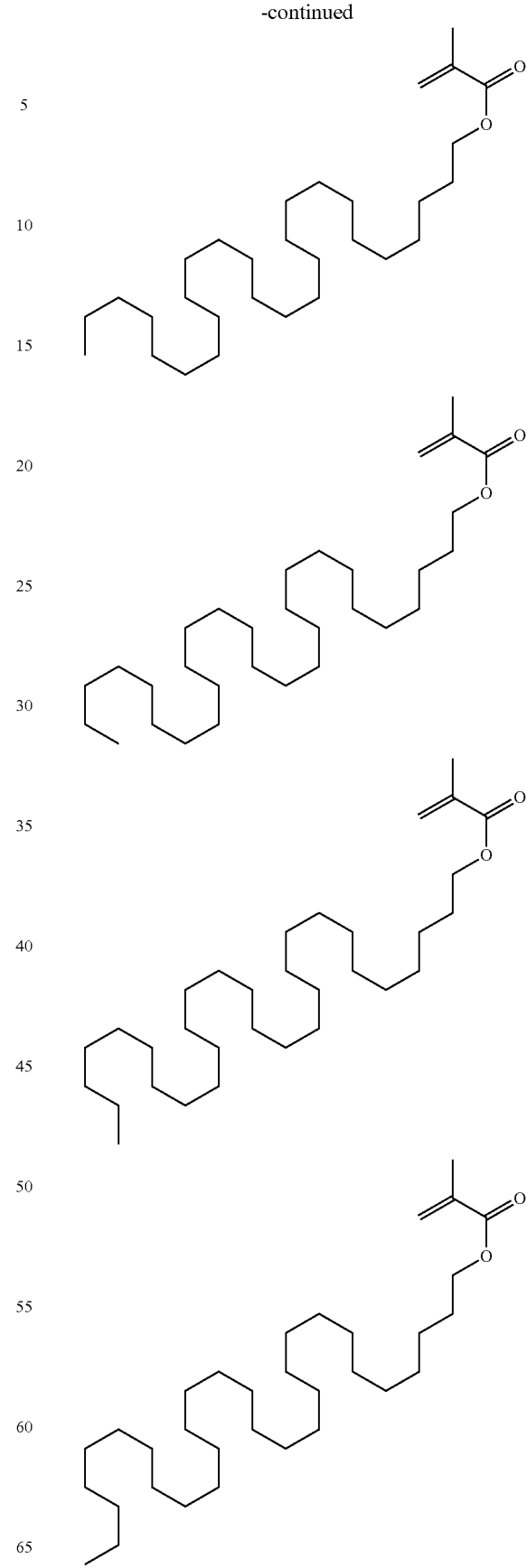

149
-continued
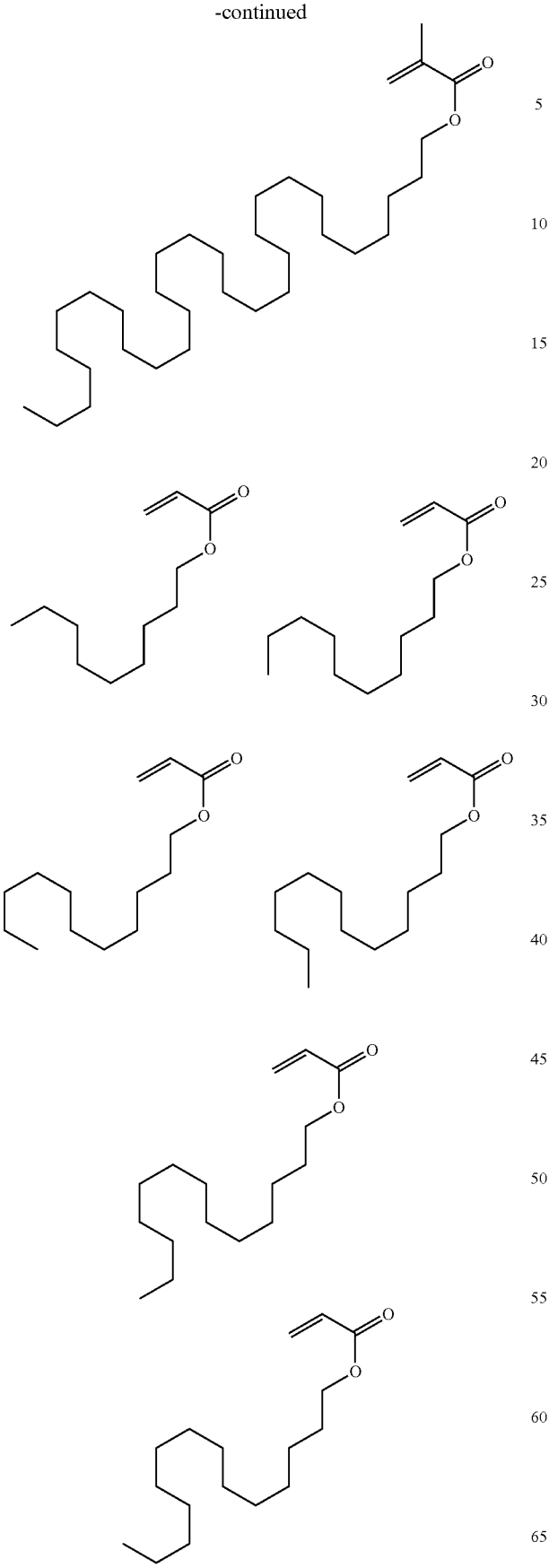
150
-continued
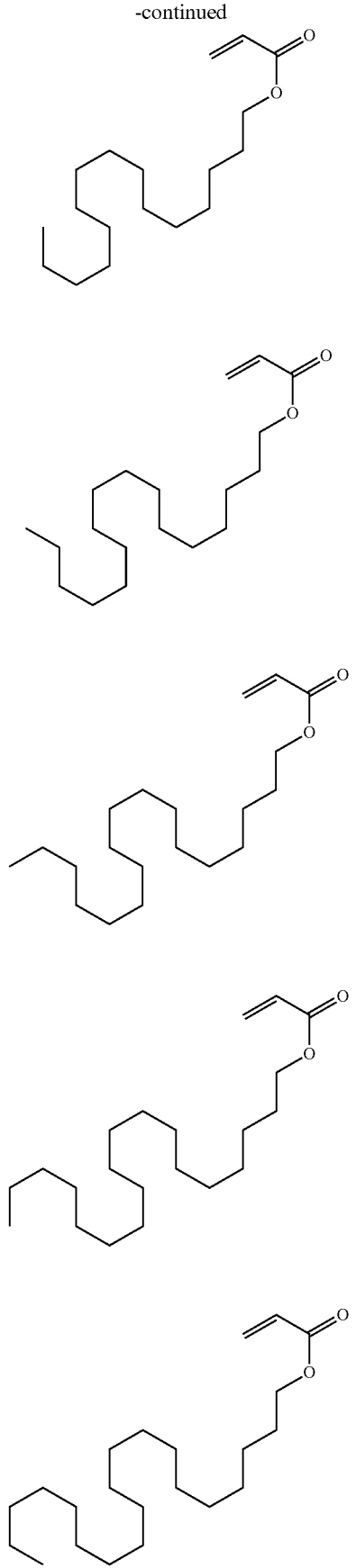

151
-continued
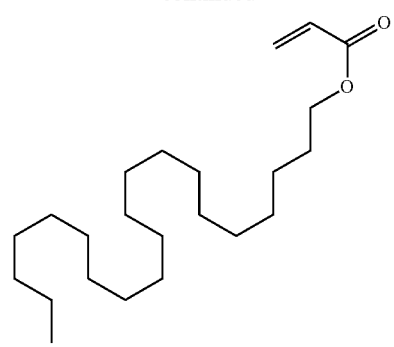
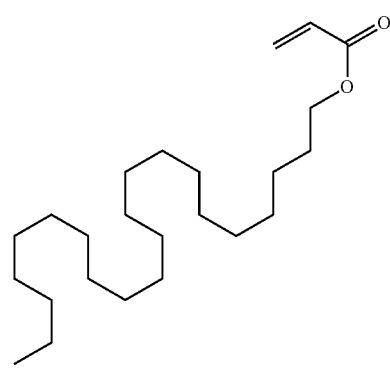
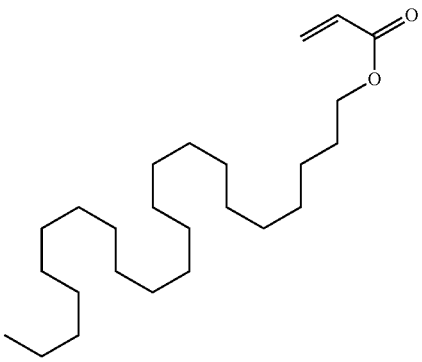
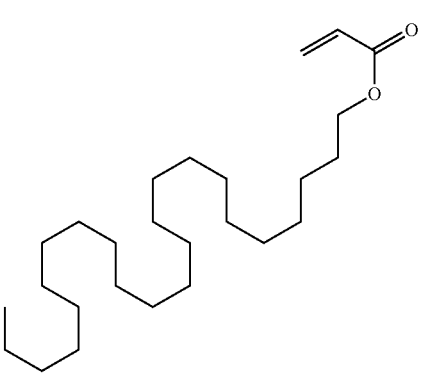
152
-continued
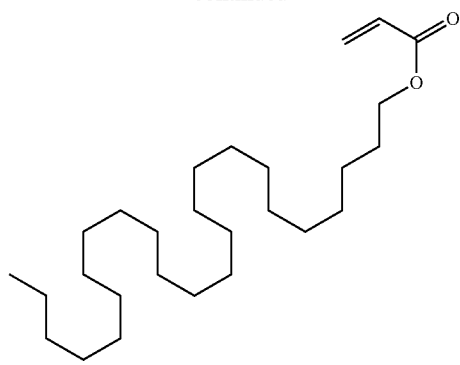
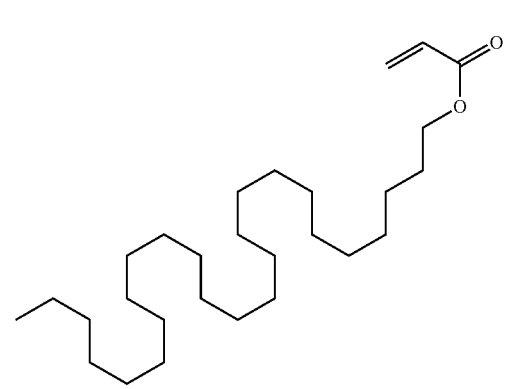
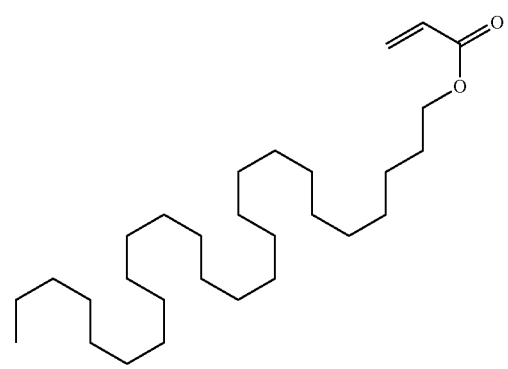
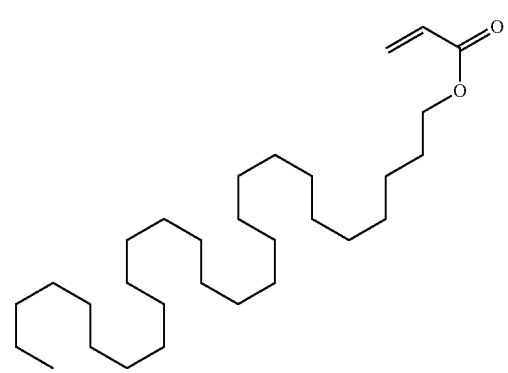

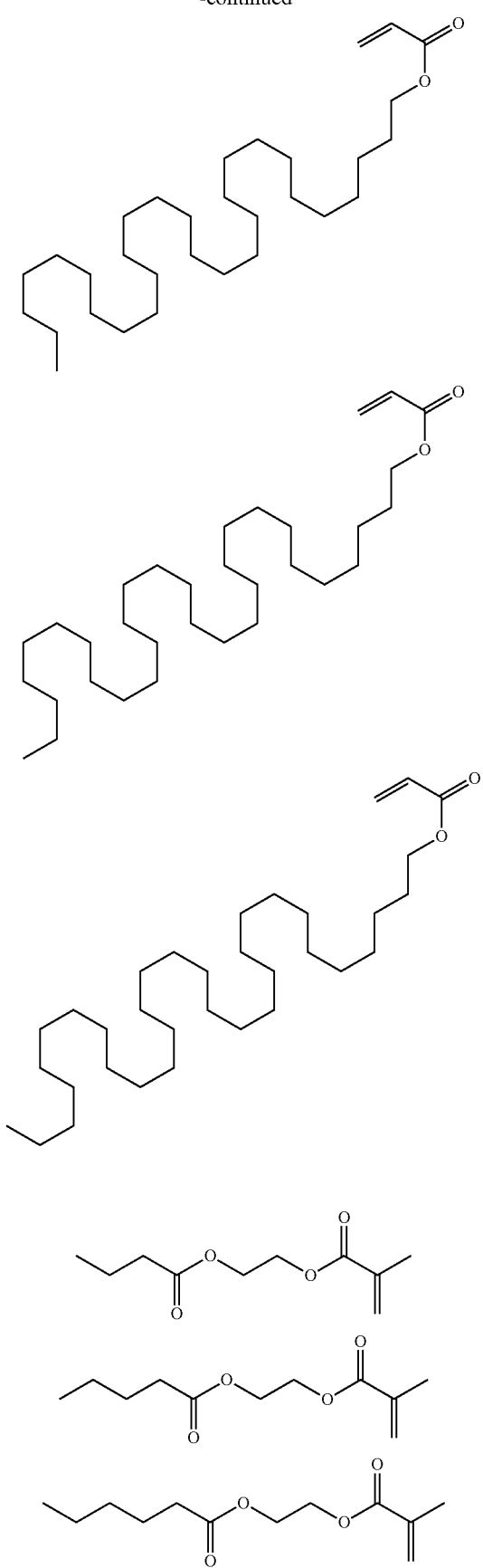
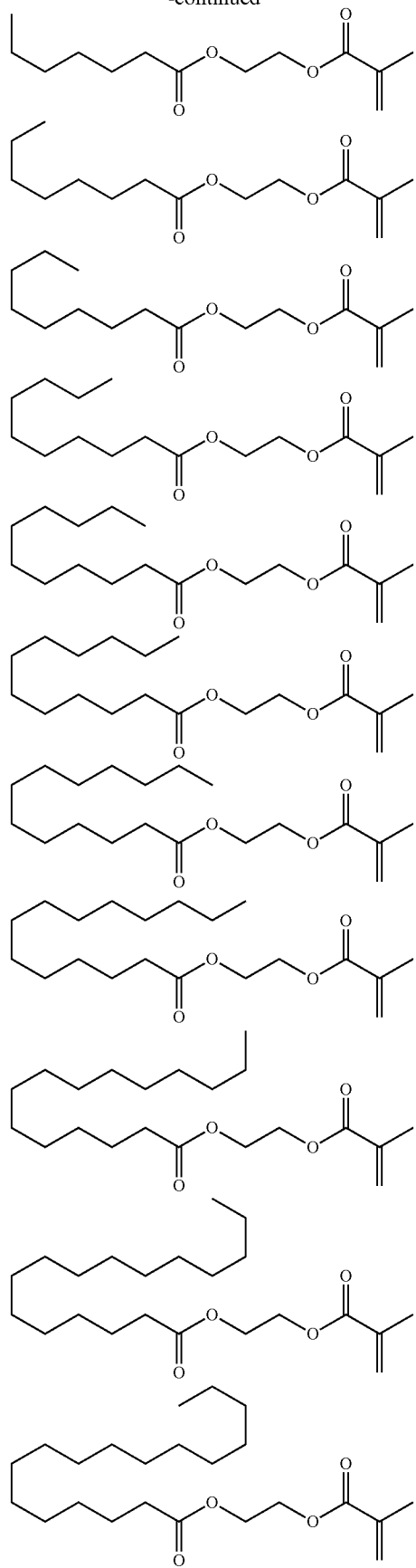

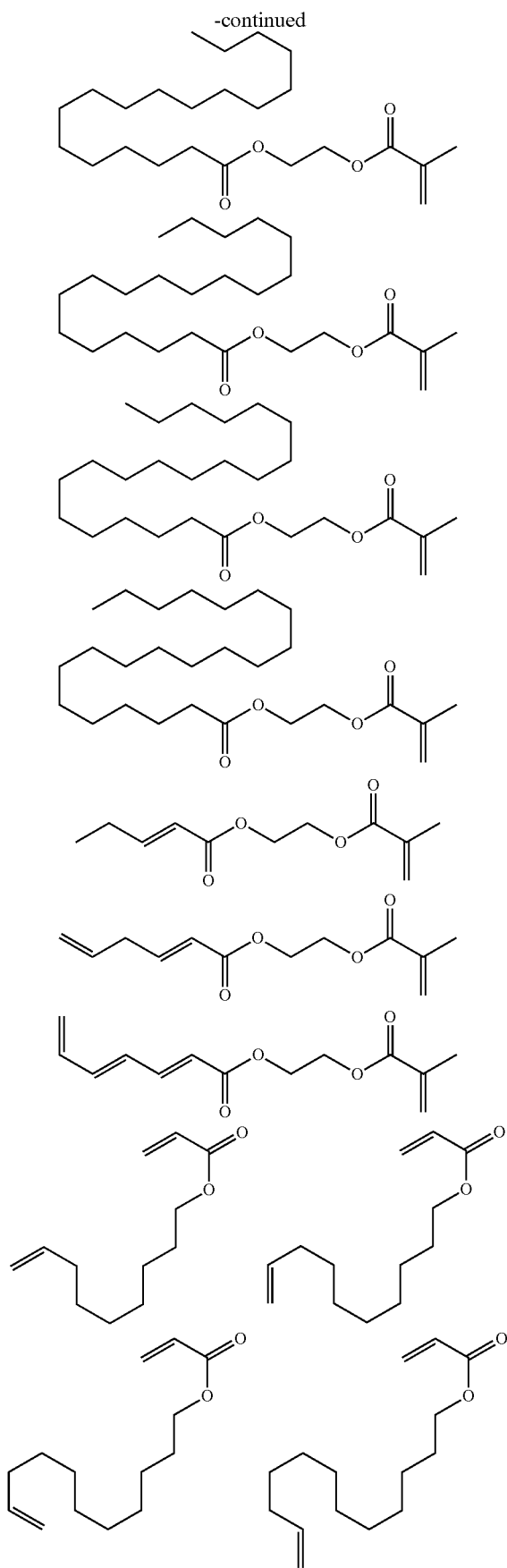

157
-continued
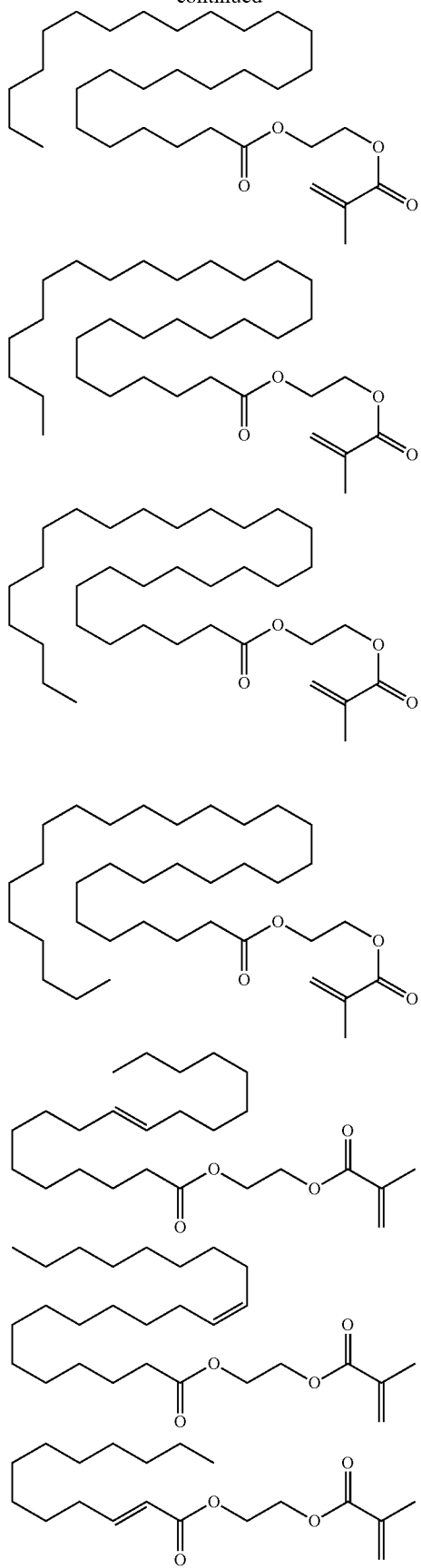
158
-continued
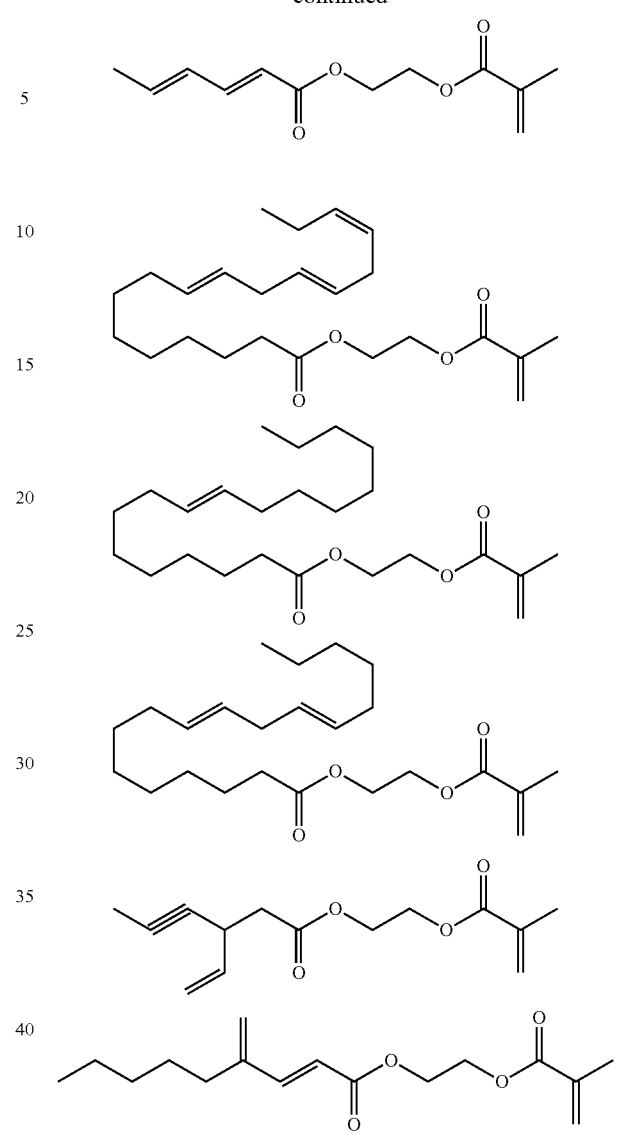
(Repeating Unit-e)
Additionally, it is also possible to copolymerize a crosslinkable repeating unit-e. Examples of the crosslinkable repeating unit include repeating units having an oxirane ring or an oxetane ring.
Specific examples of monomers to give the repeating unit-e having an oxirane ring or an oxetane ring include the following.
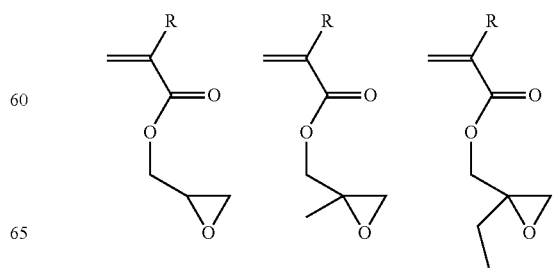

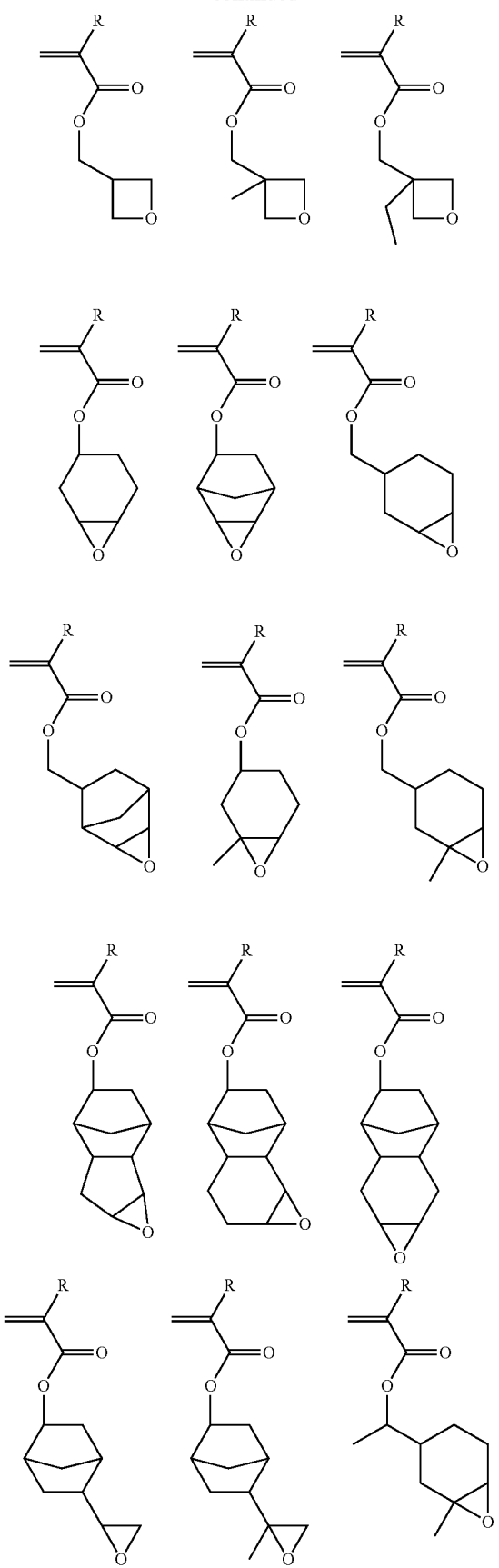
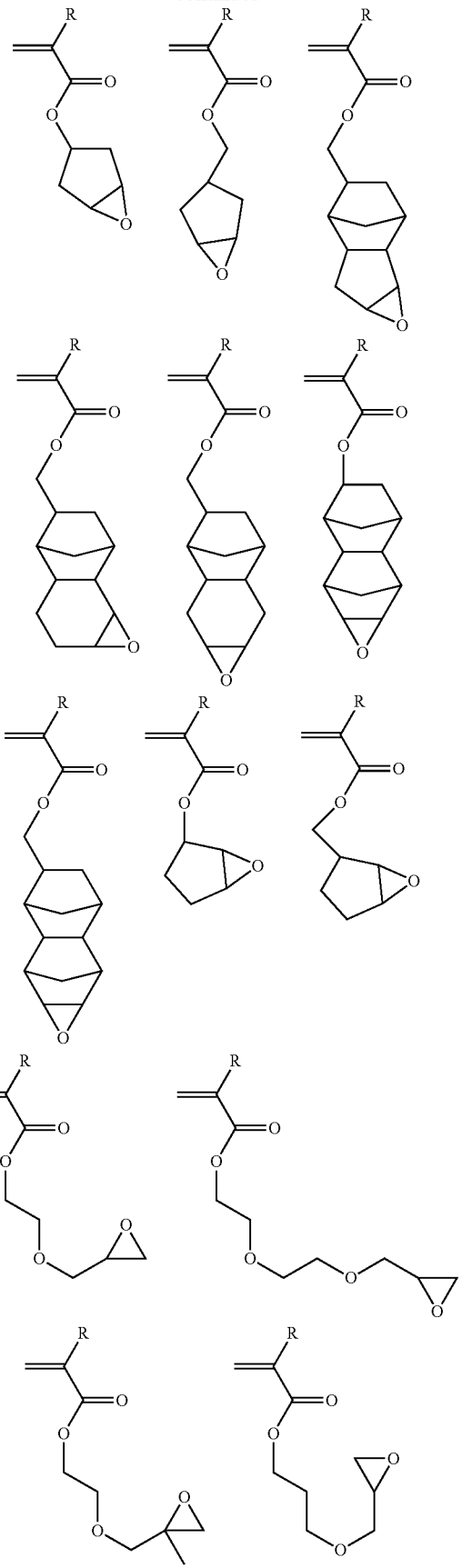

161
-continued
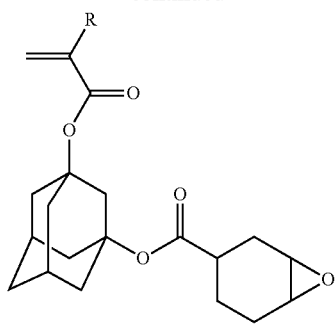
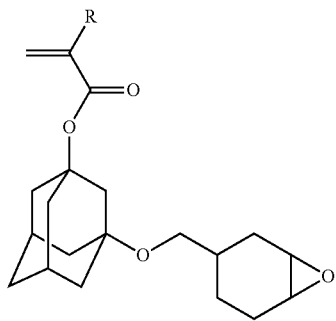
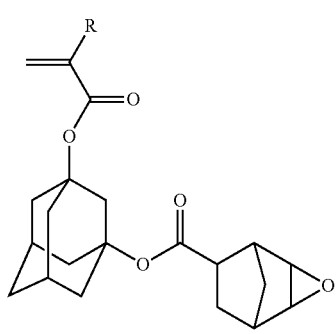
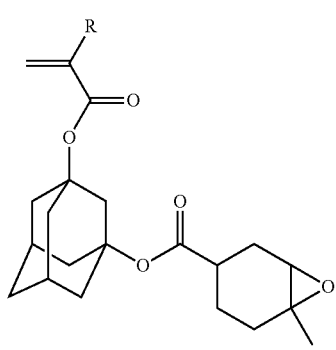
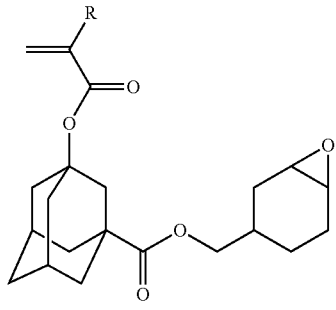
162
-continued
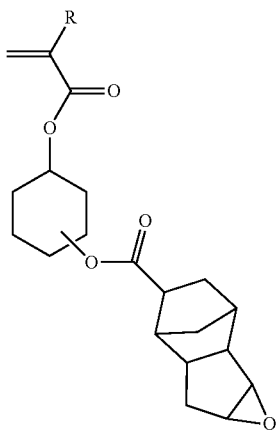
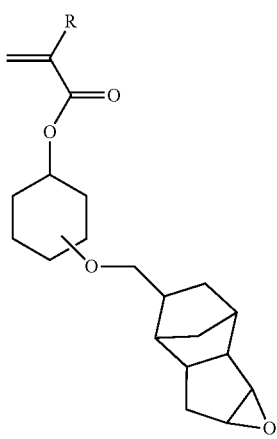
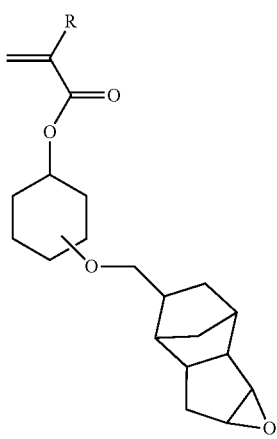

-continued

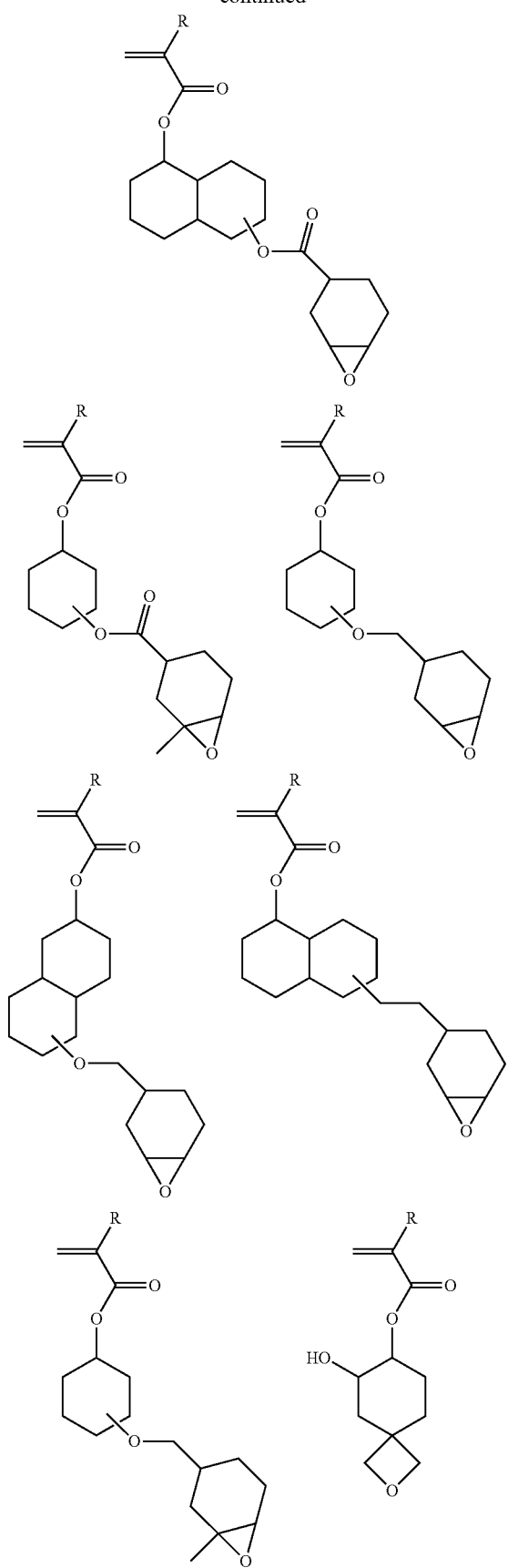

-continued

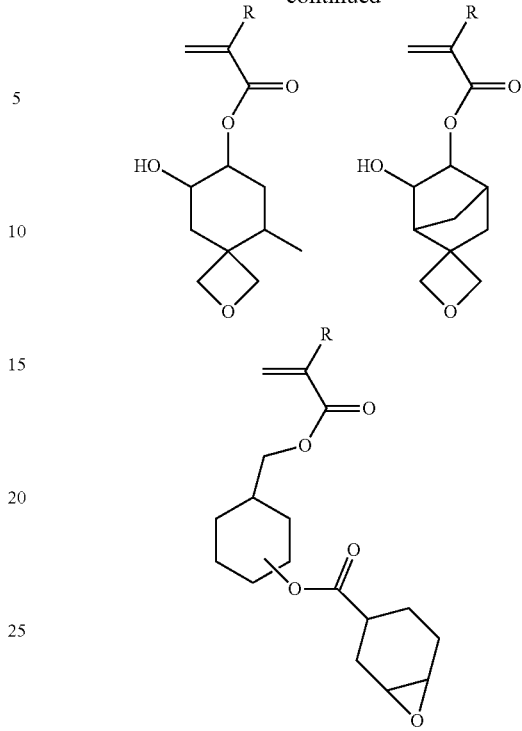

In these formulae, R represents a methyl group or a hydrogen atom.

As one of the method for synthesizing the polymer compound of the component (A) (ionic material), a copolymer compound can be obtained, for example, by a method in which desired monomer(s) among the monomers to give the repeating unit-a (a1 to a7) and the optional repeating units-b, -c, -d, and -e undergo heat polymerization in an organic solvent to which a radical polymerization initiator is added.

Examples of the organic solvent used in the polymerization include toluene, benzene, tetrahydrofuran, diethyl ether, dioxane, and the like. Examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, lauroyl peroxide, and the like. The heating temperature is preferably 50 to 80° C., and the reaction time is preferably 2 to 100 hours, more preferably 5 to 20 hours.

The ratios of the repeating units-a1 to -a7, -b, -c, -d, and -e may be $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, $0 \leq a1+a2+a3+a4+a5+a6+a7 \leq 1.0$, $0 \leq b \leq 1.0$, $0 \leq c \leq 1.0$, $0 \leq d \leq 1.0$, and $0 \leq e \leq 0.5$; preferably $0 \leq a1 \leq 0.9$, $0 \leq a2 \leq 0.9$, $0 \leq a3 \leq 0.9$, $0 \leq a4 \leq 0.9$, $0 \leq a5 \leq 0.9$, $0 \leq a6 \leq 0.9$, $0 \leq a7 \leq 0.9$, $0.01 \leq a1+a2+a3+a4+a5+a6+a7 \leq 0.9$, $0.05 \leq b \leq 0.9$, $0 \leq c \leq 0.8$, $0 \leq d \leq 0.6$, and $0 \leq e \leq 0.4$; more preferably $0 \leq a1 \leq 0.8$, $0 a2 \leq 0.8$, $0 \leq a3 \leq 0.8$, $0 \leq a4 \leq 0.8$, $0 \leq a5 \leq 0.8$, $0 \leq a6 \leq 0.8$, $0 \leq a7 \leq 0.8$, $0.02 \leq a1+a2+a3+a4+a5+a6+a7 \leq 0.8$, $0.07 \leq b \leq 0.8$, $0 \leq c \leq 0.7$, $0 \leq d \leq 0.5$, and $0 \leq e \leq 0.3$.

Incidentally, for example, a1+a2+a3+a4+a5+a6+a7+b+c+d+e=1 means that the total amount of the repeating units-a1, -a2, -a3, -a4, -a5, -a6, -a7, -b, -c, -d, and -e is 100 mol % on the basis of the total amount of the whole repeating units in a polymer compound containing the repeating units-a1, -a2, -a3, -a4, -a5, -a6, -a7, -b, -c, -d, and -e; and a1+a2+a3+a4+a5+a6+a7+b+c+d+e≤1 means that the total amount of the repeating units-a1, -a2, -a3, -a4, -a5, -a6, -a7, -b, -c, -d, and -e is less than 100 mol % on the basis of the total amount of the whole repeating units, and that another repeating unit(s) are contained in addition to the repeating units-a1, -a2, -a3, -a4, -a5, -a6, -a7, -b, -c, -d, and -e.

Regarding the molecular weight of the component (A), the weight average molecular weight is preferably 500 or more, more preferably 1,000 or more and 1,000,000 or less, further preferably 2,000 or more and 500,000 or less. Regarding the ionic monomer (residual monomer) that is not incorporated into the component (A) after polymerization, if the amount is small, the residual monomer can be prevented from permeating to skin in a biocompatibility test to cause allergy. Accordingly, it is preferable to decrease the amount of residual monomer(s). The amount of residual monomer(s) is preferably 10 parts by mass or less on the basis of 100 parts by mass of the whole component (A). The component (A) may be used singly or in admixture of two or more kinds which differ in molecular weight, dispersity, constitutive polymerizable monomer, and so forth.

[(B) Lithium Titanate Powder]

The inventive bio-electrode composition contains a lithium titanate powder as the component (B). The component (B) has a function to enhance ion reception sensitivity. This lithium titanate is not particularly limited, as long as it is a lithium-titanium composite oxide. Examples thereof include $Li_{1+x}Ti_{2-x}O_4$-type lithium titanium spinel with a space group Fd3m and $0 \le x \le \frac{1}{3}$, and any lithium-titanium mixed oxide shown by a general formula $Li_xTi_yO$ (0<x, y<1). Specific examples include $Li_2TiO_3$, $LiTiO_2$, $Li_4Ti_5O_{12}$ with a spinel structure, and the like. Ones having a spinel structure are preferable. It is also possible to use carbon-incorporated lithium titanate particles. The particle diameter of the powder is preferably smaller than 100 μm, more preferably 1 μm or less. Finer particles have a larger surface area, so that the bio-electrode can receive a larger amount of ions and has higher sensitivity.

In the inventive bio-electrode composition, the amount of the component (B) blended is preferably 0.1 to 300 parts by mass, more preferably 1 to 200 parts by mass, on the basis of 100 parts by mass of the component (A). The component (B) may be used singly or in admixture of two or more kinds.

[(C) Resin]

The present inventors have found that the use of (A) the ionic material (salt) mixed with adhesive (resin), such as a silicone type, an acrylic type, and a urethane type, makes it possible to obtain a bio-electrode capable of continuous adhesion to skin to obtain electric signals that are stable for a long time. More specifically, the resin (C), which is blended as necessary into the inventive bio-electrode composition, is a component for preventing elution of (A) the ionic material (salt) by being compatibilized with the salt, for holding the constituent components such as the lithium titanate powder, and for achieving adhesion. When the ionic material (A) has adhesion, the resin (C) is inessential. It is to be noted that the resin may be any resin other than the component (A), and is preferably either or both of a thermosetting resin and a photo-curable resin, particularly preferably one or more resins selected from silicone base, acrylic base, and urethane base resins.

The adherent (adhesive) silicone base resin include an addition-curable (addition reaction-curable) type and a radical curable (radical crosslinking reaction-curable) type. As the addition-curable type, it is possible to use one that contains diorganosiloxane having an alkenyl group(s), an MQ resin having $R_3SiO_{0.5}$ and $SiO_2$ units, organohydrogenpolysiloxane having a plurality of SiH groups, a platinum catalyst, an addition reaction inhibitor, and organic solvent, for example, described in JP 2015-193803A. As the radical curable type, it is possible to use one that contains diorganopolysiloxane with or without an alkenyl group, an MQ resin having $R_3SiO_{0.5}$ and $SiO_2$ units, organic peroxide, and organic solvent, for example, described in JP 2015-193803A. Herein, R represents a substituted or unsubstituted monovalent hydrocarbon group having 1 to 10 carbon atoms.

It is also possible to use a polysiloxane-resin integrated compound that is formed by condensation reaction of an MQ resin and polysiloxane having silanol at the terminal or the side chain of the polymer. The MQ resin contains many silanols and improves adhesion by addition of it, but does not bind to polysiloxane in molecular level because it is not crosslinkable. The adhesion can be increased by integrating the polysiloxane and the resin as described above.

The silicone resin may contain modified siloxane that has a group selected from an amino group, an oxirane group, an oxetane group, a polyether group, a hydroxy group, a carboxy group, a mercapto group, a methacryl group, an acryl group, a phenol group, a silanol group, a carboxylic anhydride group, an aryl group, an aralkyl group, an amide group, an ester group, and a lactone ring. The addition of the modified siloxane improves dispersibility of the component (A) in the silicone resin. The modified siloxane may be modified at any part such as one terminal, both terminals, or a side chain of the siloxane.

As the adherent acrylic base resin, it is possible to use one having hydrophilic (meth)acrylic ester and hydrophobic long chain (meth)acrylic ester as the repeating units described in JP 2016-011338A, for example. In some cases, it is also possible to copolymerize (meth)acrylic ester having a functional group or (meth)acrylic ester having a siloxane bond.

As the adherent urethane base resin, it is possible to use one having a urethane bond with a polyether bond, a polyester bond, a polycarbonate bond, or a siloxane bond described in JP 2016-065238A, for example.

In the inventive bio-electrode composition, the resin (C) preferably has high compatibility with the component (A) to prevent lowering of the electric conductivity due to elution of the component (A) from the living body contact layer. In the inventive bio-electrode composition, the resin (C) preferably has high adhesion to the electro-conductive base material to prevent peeling of the living body contact layer from the electro-conductive base material. In order to increase the compatibility of the resin with the electro-conductive base material and the salt, the use of a resin with high polarity is effective. Examples of such a resin include resin having one or more moieties selected from an ether bond, an ester bond, an amide bond, an imide bond, a urethane bond, a thiourethane bond, and a thiol group; a polyacrylic resin, a polyamide resin, a polyimide resin, a polyurethane resin, a polythiourethane resin, and the like. On the other hand, the living body contact layer is in contact with a living body, thereby being susceptible to perspiration. Accordingly, in the inventive bio-electrode composition, the resin (C) preferably has high repellency and is hardly hydrolyzed. To make the resin be highly repellent and hardly hydrolyzed, the use of a silicon-containing resin is effective.

The silicon atom-containing polyacrylic resin includes a polymer that has a silicone main chain and a polymer that has a silicon atom(s) on the side chain, each of which can be suitably used. As the polymer that has a silicone main chain, silsesquioxane, siloxane having a (meth)acrylpropyl group, or the like can be used. In this case, an addition of a photoradical generator allows the (meth)acryl moiety to polymerize to cure.

As the silicon atom-containing polyamide resin, it is possible to suitably use polyamide silicone resins described in JP 2011-079946A and U.S. Pat. No. 5,981,680, for example. Such polyamide silicone resins can be synthesized by combining, for example, a silicone or non-silicone compound having amino groups at both terminals and a non-silicone or silicone compound having carboxy groups at both terminals.

It is also possible to use polyamic acid before cyclization thereof, which is obtained by reacting carboxylic anhydride and amine. The carboxy group of the polyamic acid may be crosslinked by using a crosslinking agent such as an epoxy type and an oxetane type. It is also possible to esterify the carboxy group with hydroxyethyl (meth)acrylate to perform photoradical crosslinking of the (meth)acrylate moiety.

As the silicon atom-containing polyimide resin, it is possible to suitably use polyimide silicone resins described in JP 2002-332305A, for example. Although polyimide resins have very high viscosity, the viscosity can be decreased by blending a (meth)acrylic monomer as a solvent and a crosslinking agent.

Examples of the silicon atom-containing polyurethane resin include polyurethane silicone resins. Such polyurethane silicone resins can be crosslinked through urethane bond by blending a compound having isocyanate groups at both terminals and a compound having a hydroxy group(s) at the terminal(s), followed by heating thereof. In this case, a silicon atom(s) (siloxane bond) have to be contained in either or both of the compound having isocyanate groups at both terminals and the compound having a hydroxy group(s) at the terminal(s). Alternatively, polysiloxane and a urethane (meth)acrylate monomer can be blended and photo-crosslinked as described in JP 2005-320418A. It is also possible to photo-crosslink a polymer having both of a siloxane bond(s) and a urethane bond(s), with the terminal having a (meth)acrylate group(s).

The silicon atom-containing polythiourethane resin can be obtained by reaction of a compound having a thiol group(s) and a compound having an isocyanate group(s), provided that either of them has to contain a silicon atom(s). It can also be photo-cured if (meth)acrylate groups are contained at the terminals.

The silicone base resin is improved in compatibility with the foregoing salt by adding modified siloxane that has a group selected from an amino group, an oxirane group, an oxetane group, a polyether group, a hydroxy group, a carboxy group, a mercapto group, a methacryl group, an acryl group, a phenol group, a silanol group, a carboxylic anhydride group, an aryl group, an aralkyl group, an amide group, an ester group, and a lactone ring in addition to the diorganosiloxane having an alkenyl group(s), the MQ resin having $R_3SiO_{0.5}$ and $SiO_2$ units, and the organohydrogenpolysiloxane having a plurality of SiH groups.

In the inventive bio-electrode composition, the amount of the component (C) blended is preferably 0 to 2000 parts by mass, more preferably 10 to 1000 parts by mass, on the basis of 100 parts by mass of the component (A). The component (C) may be used singly or in admixture of two or more kinds.

As will be described later, the living body contact layer is a cured material of the bio-electrode composition. Curing the bio-electrode composition improves the adhesion of the living body contact layer to both of skin and the electroconductive base material. The curing means is not particularly limited, and common means can be used, including crosslinking reaction by either or both of heat and light, an acid catalyst, or a base catalyst, for example. The crosslinking reaction can be performed, for example, by appropriately selecting methods described in "Kakyou han-nou handbook (handbook of crosslinking reaction)", Chapter 2, pages 51-371, Yasuharu Nakamura, Maruzen shuppan (2013).

The diorganosiloxane having an alkenyl group(s) and the organohydrogenpolysiloxane having a plurality of SiH groups can be crosslinked through an addition reaction with a platinum catalyst.

Examples of the platinum catalyst include platinum-based catalysts such as platinic chloride, alcohol solution of platinic chloride, reaction product of platinic chloride and alcohol, reaction product of platinic chloride and an olefin compound, reaction product of platinic chloride and vinyl group-containing siloxane, a platinum-olefin complex, and a complex of platinum and vinyl group-containing siloxane; platinum group metal-based catalysts such as a rhodium complex and a ruthenium complex; and the like. These catalysts may be used after dissolved or dispersed in alcohol solvent, hydrocarbon solvent, or siloxane solvent.

The amount of the platinum catalyst added is preferably in a range of 5 to 2,000 ppm, particularly preferably in a range of 10 to 500 ppm, on the basis of 100 parts by mass of the resin including (A) and (C).

When the addition curable silicone resin is used, an addition reaction inhibitor may be added. This addition reaction inhibitor is added as a quencher to prevent the platinum catalyst from acting in the solution and under a low temperature circumstance after forming the coating film and before heat curing. Specific examples of the addition reaction inhibitor include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, 1,1,3,3-tetramethyl-1,3-divinyldisiloxane, and the like.

The amount of the addition reaction inhibitor added is preferably in a range of 0 to 10 parts by mass, particularly preferably in a range of 0.05 to 3 parts by mass, on the basis of 100 parts by mass of the resin.

Examples of the photo-curing method include a method of adding a photoradical generator to generate radical by light, together with a resin having a (meth)acrylate terminal(s) or an olefin terminal(s), or a crosslinking agent with the terminal(s) being (meth)acrylate, olefin, or a thiol group(s); and a method of adding a photo-acid generator to generate acid by light, together with a resin or a crosslinking agent having an oxirane group(s), an oxetane group(s), or a vinyl ether group(s).

Examples of the photoradical generator include acetophenone, 4,4'-dimethoxybenzyl, benzyl, benzoin, benzophenone, 2-benzoylbenzoic acid, 4,4'-bis(dimethylamino)benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoate, 2-(1,3-benzodioxole-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthene-9-one, diphenyl(2,4,6-trimethylbenzoyl)phosphine oxide (BAPO), 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitrosopropiophenone, and 2-phenyl-2-(p-toluenesulfonyloxy)acetophenone.

The curing can also be performed by adding a radical generator of a heat decomposition type. Examples of the thermal radical generator include 2,2'-azobis(isobutyronitrile), 2,2'-azobis(2,4-dimethylvaleronitrile), 2,2'-azobis(2-methylbutyronitrile), 2,2'-azobis(methylpropionamidine) hydrochloride, 2,2'-azobis[2-(2-imidazolin-2-yl)propane] hydrochloride, 2,2'-azobis(4-methoxy-2,4-dimethylvaleronitrile), 2,2'-azobis(cyclohexane-1-carbonitrile), 1[(1-cyano-1-methylethyl)azo]formamide, 2,2'-azobis[2-methyl-N-(2-hydroxyethyl)propionamide], 2,2'-azobis[N-(2-propenyl)-2-methylpropionamide], 2,2'-azobis(N-butyl-2-methylpropionamide), dimethyl-2,2'-azobis(isobutylate), 4,4'-azobis(4-cyanopentanoic acid), dimethyl-2,2'-azobis(2-methylpropionate), benzoyl peroxide, tert-butyl hydroperoxide, cumene hydroperoxide, di-tert-butyl peroxide, di-tert-amyl peroxide, di-n-butyl peroxide, dicumyl peroxide, and the like.

Examples of the photo-acid generator include sulfonium salt, iodonium salt, sulfonyldiazomethane, N-sulfonyloxyimide, oxime-O-sulfonate type acid generators, and the like. Specific examples of the photo-acid generator include ones described in paragraphs [0122] to [0142] of JP 2008-111103A, and in JP 2009-080474A.

The amount of radical generator or photo-acid generator added is preferably in a range of 0.1 to 50 parts by mass on the basis of 100 parts by mass of the resin.

Among them, particularly preferable resin of the component (C) contains: a silicone resin having an $SiO_2$ unit and an $R_xSiO_{(4-x)/2}$ unit, where R represents a substituted or unsubstituted monovalent hydrocarbon group having 1 to 10 carbon atoms, and "x" is a number in a range of 2.5 to 3.5; diorganosiloxane having an alkenyl group; and organohydrogenpolysiloxane having an SiH group.

[Metal Powder]

The inventive bio-electrode composition can also contain a metal powder selected from gold, silver, platinum, copper, tin, titanium, nickel, aluminum, tungsten, molybdenum, ruthenium, chromium, and indium in order to improve electronic conductivity. The amount of the metal powder added is preferably in a range of 1 to 50 parts by mass on the basis of 100 parts by mass of the resin.

As the kind of the metal powder, gold, silver, and platinum are preferable in view of electric conductivity; and silver, copper, tin, titanium, nickel, aluminum, tungsten, molybdenum, ruthenium, and chromium are preferable in view of cost. In view of biocompatibility, noble metals are preferable. On the whole of these viewpoints, silver is most preferable.

The metal powder may have any shape, such as a spherical shape, a disk shape, a flaky shape, and a needle shape. The addition of flaky powder brings highest electric conductivity and is preferable thereby. The metal powder is preferably a flake having relatively lower density and larger specific surface area with a size of 100 μm or less, a tapped density of 5 $g/cm^3$ or less, and a specific surface area of 0.5 $m^2/g$ or more.

[Carbon Material]

To form a bio-electrode with higher sensitivity, the bio-electrode may need to have not only high ionic conductivity but also high electronic conductivity. In this case, the electronic conductivity is improved effectively by adding carbon in addition to the lithium titanate powder.

For this purpose, a carbon material can be added as an electric conductivity improver. Examples of the carbon material include carbon black, graphite, carbon nanotube, carbon fiber, and the like. The carbon nanotube may be either single layer or multilayer, and the surface may be modified with an organic group(s). The amount of the carbon material added is preferably in a range of 1 to 50 parts by mass on the basis of 100 parts by mass of the resin.

[Tackifier]

The inventive bio-electrode composition may contain a tackifier in order to have adhesion to a living body. Examples of such a tackifier include silicone resin, non-crosslinkable siloxane, non-crosslinkable poly(meth)acrylate, non-crosslinkable polyether, and the like.

[Crosslinking Agent]

The inventive bio-electrode composition may contain an epoxy-type crosslinking agent. This crosslinking agent is a compound having multiple epoxy groups or oxetane groups in one molecule. The amount of the crosslinking agent added is preferably 1 to 30 parts by mass on the basis of 100 parts by mass of the resin.

[Crosslinking Catalyst]

The inventive bio-electrode composition may contain a catalyst for crosslinking an epoxy group or an oxetane group. As this catalyst, ones described in paragraphs 0027 to 0029 of JP 2019-503406A can be used. Specific examples include aliphatic and aromatic tertiary amines such as dimethylaminopropylamine, pyridine, and the like. These function as the catalyst and enable substantial crosslinking. Other examples include boron complexes, particularly a boron complex with monoethanolamine; imidazoles such as 2-ethyl-methylimidazole; guanidines such as tetramethylguanidine; dicyanodiamide; substituted ureas such as toluene diisocyanate urea; and acid anhydrides such as 4-methyl tetrahydroxy phthalic anhydride, 3-methyl tetrahydroxy phthalic anhydride, and methyl norbornene phthalic anhydride. The amount of the catalyst added is preferably 0.01 to 10 parts by mass on the basis of 100 parts by mass of the resin.

[Organic Solvent]

The inventive bio-electrode composition may contain organic solvent. Specific examples of the organic solvent include aromatic hydrocarbon solvent such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene; aliphatic hydrocarbon solvent such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffin; ketone solvent such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvent such as 3-methoxybutanol, 3-methyl-3-methoxybutanol, 1-methoxy-2-propanol, and 1-ethoxy-2-propanol; ether solvent such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, di-sec-pentyl ether, di-tert-amyl ether, di-n-hexyl ether, and anisole; ester solvent such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactone solvent such as γ-butyrolactone; and the like.

The amount of the organic solvent added is preferably in a range of 10 to 50,000 parts by mass on the basis of 100 parts by mass of the resin.

As described above, the inventive bio-electrode composition makes it possible to form a living body contact layer for a bio-electrode that is capable of conducting electric signals from skin efficiently to a device (i.e., excellent in electric conductivity), free from the risk of causing allergies even when the bio-electrode is worn on skin for a long time (i.e., excellent in biocompatibility), light-weight, manufacturable at low cost, and free from large lowering of the electric conductivity even when the bio-electrode is wetted with water or dried. It is possible to improve the electric conductivity still more by adding a carbon material, and to manufacture a bio-electrode with particularly high adhesion and stretchability by combining a resin with adhesion and stretchability. Furthermore, it is possible to improve the stretchability and adhesion to skin by additives and so forth, and to control the stretchability and adhesion by adjusting the composition of the resin and the thickness of the living body contact layer appropriately.

<Bio-Electrode>

The present invention also provides a bio-electrode comprising an electro-conductive base material and a living body contact layer formed on the electro-conductive base material, wherein the living body contact layer is a cured material of the inventive bio-electrode composition described above.

Hereinafter, the inventive bio-electrode will be specifically described by reference to the drawings, but the present invention is not limited thereto.

FIG. 1 is a schematic sectional view showing an example of the inventive bio-electrode. The bio-electrode 1 of FIG. 1 has the electro-conductive base material 2 and the living body contact layer 3 formed on the electro-conductive base material 2. The living body contact layer 3 is a layer in which the ionic polymer (ionic material) 4 and the lithium titanate powder 5a are dispersed in the resin 6. In accordance with needs, the carbon material 5b can be added as an electric conductivity improver in addition to the lithium titanate powder 5a.

When using the bio-electrode 1 of FIG. 1 like this, electric signals are picked from the living body 7 through the ionic polymer 4 and the lithium titanate powder 5a while bringing the living body contact layer 3 (i.e., the layer in which the ionic polymer 4 and the lithium titanate powder 5a are dispersed in the resin 6) into contact with the living body 7, and then conducted to a sensor device etc. (not shown) through the electro-conductive base material 2 as shown in FIG. 2. As described above, the inventive bio-electrode is capable of coping with both electric conductivity and biocompatibility by using the ionic polymer (ionic material) described above and obtaining electric signals from skin stably in high sensitivity because the contact area with skin is kept constant due to the adhesion thereof. Incidentally, 5b in FIGS. 1 and 2 is a carbon material (e.g., carbon nanotube).

Hereinafter, each component composing the inventive bio-electrode will be described more specifically.

[Electro-Conductive Base Material]

The inventive bio-electrode comprises an electro-conductive base material. This electro-conductive base material is usually connected electrically with a sensor device and so on, and conducts electrical signals picked from a living body through the living body contact layer to the sensor device and so on.

As the electro-conductive base material, any electro-conductive material can be used without being limited to particular ones. However, it is preferable to comprise one or more species selected from gold, silver, silver chloride, platinum, aluminum, magnesium, tin, tungsten, iron, copper, nickel, stainless steel, chromium, titanium, and carbon, for example.

The electro-conductive base material may be a hard electro-conductive substrate, an electro-conductive film having flexibility, a cloth with the surface being coated with electro-conductive paste, a cloth into which electro-conductive polymer is kneaded, or the like without being limited to particular substrates. The electro-conductive base material may be flat, uneven, or mesh-form of woven metal wires, which can be appropriately selected in accordance with the use of the bio-electrode, and so forth.

[Living Body Contact Layer]

The inventive bio-electrode comprises a living body contact layer formed on the electro-conductive base material. This living body contact layer is a part to be actually in contact with a living body when using the bio-electrode, and has electric conductivity and adhesion. The living body contact layer is a cured material of the inventive bio-electrode composition described above, that is to say, an adherent resin layer containing (A) the ionic material (salt) and (B) the lithium titanate powder, together with additives such as the resin (C).

The living body contact layer preferably has adhesion in a range of 0.5 N/25 mm or more and 20 N/25 mm or less. The adhesion is commonly measured by the method shown in JIS Z 0237, in which a metal substrate such as a stainless steel (SUS) substrate or a polyethylene terephthalate (PET) substrate can be used as a base material or, alternatively, human skin can be used for measuring. Human skin has lower surface energy compared to metals and various plastics, which is as low as that of Teflon (registered trade mark), and is hard to adhere.

The living body contact layer of the bio-electrode has a thickness of preferably 1 m or more and 5 mm or less, more preferably 2 μm or more and 3 mm or less. As the living body contact layer is thinner, the adhesion lowers, but the flexibility is improved, and the weight decreases to improve the compatibility with skin. The thickness of the living body contact layer can be selected based on the balance of adhesion and texture.

The inventive bio-electrode may be provided with an adherent film separately on the living body contact layer as previous bio-electrodes (e.g., the bio-electrode described in JP 2004-033468A) in order to prevent peeling off of the bio-electrode from a living body during the use. When the adherent film is prepared separately, the adherent film may be formed by using a raw material for the adherent film such as an acrylic type, a urethane type, and a silicone type. Particularly, the silicone type is suitable because of: the high transparency of oxygen, which enables dermal respiration while pasting the same, the high water repellency, which decreases lowering of adhesion due to perspiration, and the low irritation to skin. It is to be noted that the inventive bio-electrode does not necessarily require the adherent film that is prepared separately described above, because peeling off from a living body can be prevented by adding tackifier to the bio-electrode composition or using a resin having good adhesion to a living body as described above.

When the inventive bio-electrode is used as a wearable device, wiring between the bio-electrode and a sensor device, and other components are not limited to particular ones. For example, it is possible to apply the ones described in JP 2004-033468A.

As described above, the inventive bio-electrode is capable of conducting electric signals from skin efficiently to a device (i.e., excellent in electric conductivity), free from the risk of causing allergies even when the bio-electrode is worn on skin for a long time (i.e., excellent in biocompatibility), light-weight, manufacturable at low cost, and free from large lowering of the electric conductivity even when the bio-electrode is wetted with water or dried, because the living body contact layer is formed from a cured material of the inventive bio-electrode composition described above. It is possible to improve the ionic conductivity still more by adding a lithium titanate powder, and to manufacture a bio-electrode with particularly high adhesion and stretchability by combining a resin with adhesion and stretchability. It is also possible to improve the stretchability and adhesion to skin by additives and so forth, and to control the stretchability and adhesion by adjusting the composition of the resin and the thickness of the living body contact layer appropriately. Accordingly, the inventive bio-electrode described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, comprising: applying the inventive bio-electrode composition described above onto the electro-conductive base material; and curing the bio-electrode composition to form the living body contact layer.

Incidentally, the electro-conductive base material, the bio-electrode composition, etc. used for the inventive method for manufacturing a bio-electrode may be the same as those described above.

The method for applying the bio-electrode composition onto the electro-conductive base material is not limited to particular ones; and dip coating, spray coating, spin coating, roll coating, flow coating, doctor coating, screen printing, flexographic printing, gravure printing, stencil printing, ink-jet printing, and so on are suitable methods, for example.

The method for curing the resin can be appropriately selected based on a kind of the resin (C) used for the bio-electrode composition without being limited to particular methods. For example, the bio-electrode composition is preferably cured by either or both of heat and light. The foregoing bio-electrode composition can also be cured by adding a catalyst to generate acid or base to the bio-electrode composition, which causes a crosslinking reaction.

In case of heating, the temperature is not particularly limited and may be appropriately selected based on a kind of the resin (C) used for the bio-electrode composition, but is preferably about 50 to 250° C., for example.

When the heating and light irradiation are combined, it is possible to perform the heating and the light irradiation simultaneously, to perform the heating after the light irradiation, or to perform the light irradiation after the heating. It is also possible to perform air-drying to evaporate solvent before heating the coating film.

As described above, the inventive method for manufacturing a bio-electrode makes it possible to manufacture the inventive bio-electrode easily and at low cost, with the bio-electrode being excellent in electric conductivity and biocompatibility, light-weight, and free from large lowering of the electric conductivity even when the bio-electrode is wetted with water or dried.

EXAMPLE

Hereinafter, the present invention will be specifically described by giving Examples and Comparative Examples, but the present invention is not limited thereto. Incidentally, "Me" represents a methyl group, and "Vi" represents a vinyl group in the below.

Ionic polymers 1 to 12, which were blended to bio-electrode composition solutions as an ionic material (electro-conductive material), were synthesized as follows. Each 30 mass % monomer solution in PGMEA was introduced into a reaction vessel and mixed. The reaction vessel was cooled to −70° C. under a nitrogen atmosphere, and subjected to vacuum degassing and nitrogen blowing, which were repeated for three times. After raising the temperature to room temperature, azobisisobutyronitrile (AIBN) was added thereto as a polymerization initiator in an amount of 0.01 mole per 1 mole of the whole monomers, this was warmed to a temperature of 60° C. and then allowed to react for 15 hours. The composition of obtained polymer was identified by $^1$H-NMR after drying the solvent. The molecular weight (Mw) and the dispersity (Mw/Mn) of the obtained polymer were determined by gel permeation chromatography (GPC) using tetrahydrofuran (THF) as a solvent. Thus synthesized Ionic polymers 1 to 12 are shown below.

Ionic polymer 1

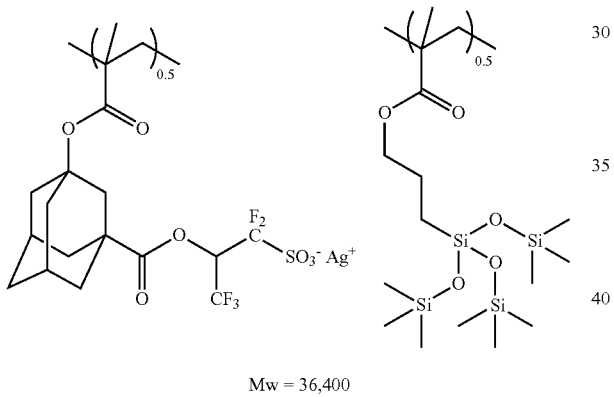

Mw = 36,400
Mw/Mn = 2.11

Ionic polymer 2

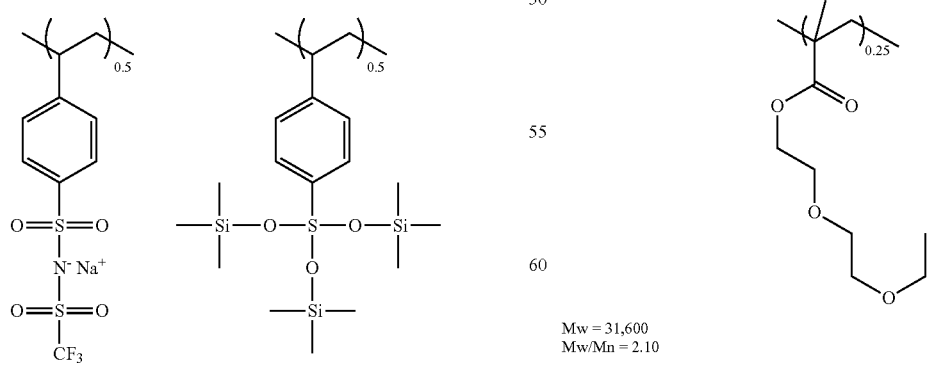

Mw = 24,800
Mw/Mn = 1.99

Ionic polymer 3

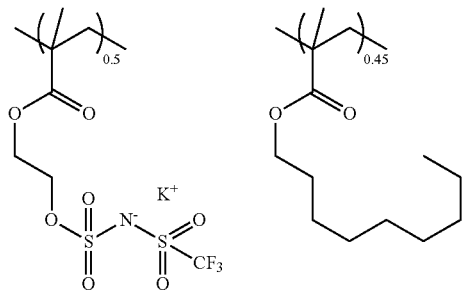

Mw = 150,600
Mw/Mn = 1.85

The repeating number in the formula shows the average value.

Ionic polymer 4

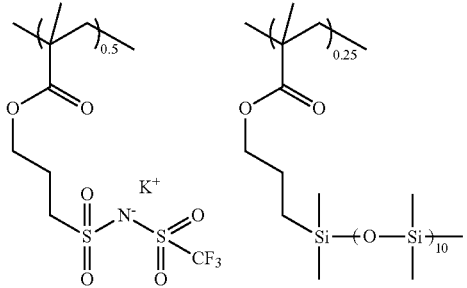

Mw = 31,600
Mw/Mn = 2.10

The repeating number in the formula shows the average value.

Ionic polymer 5
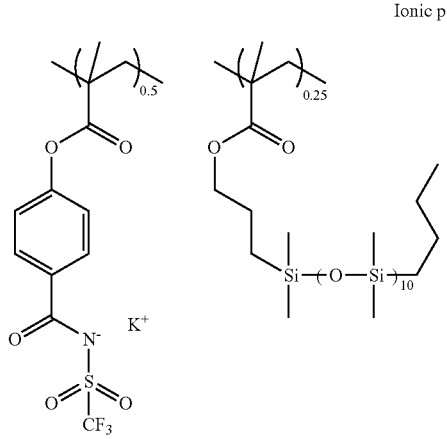
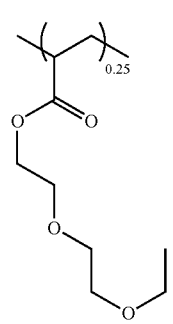
Mw = 55,100
Mw/Mn = 2.02
The repeating number in the formula shows the average value.
Ionic polymer 6
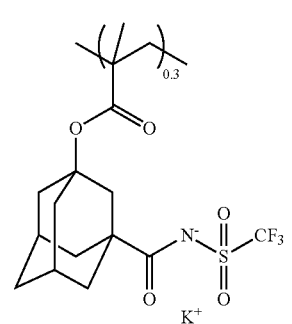
-continued
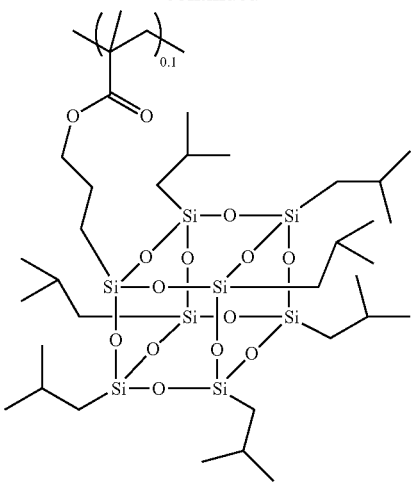
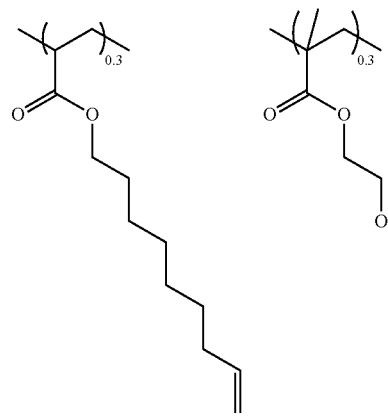
Mw = 26,100
Mw/Mn = 1.99
Ionic polymer 7
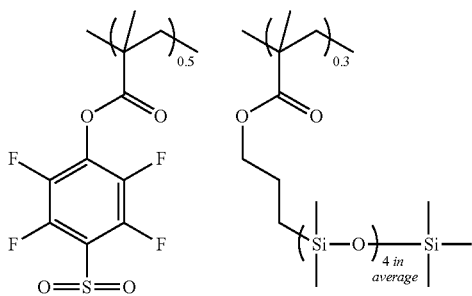
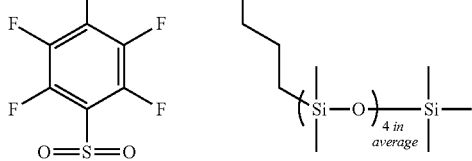
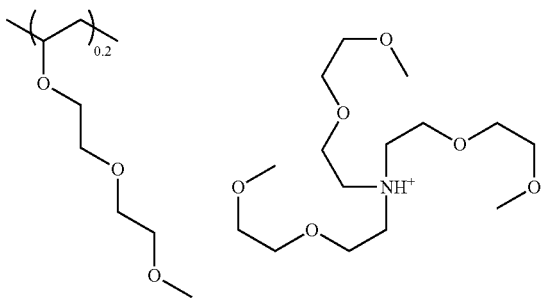
Mw = 87,500
Mw/Mn = 2.01

The repeating number in the formula shows the average value.
Ionic polymer 8
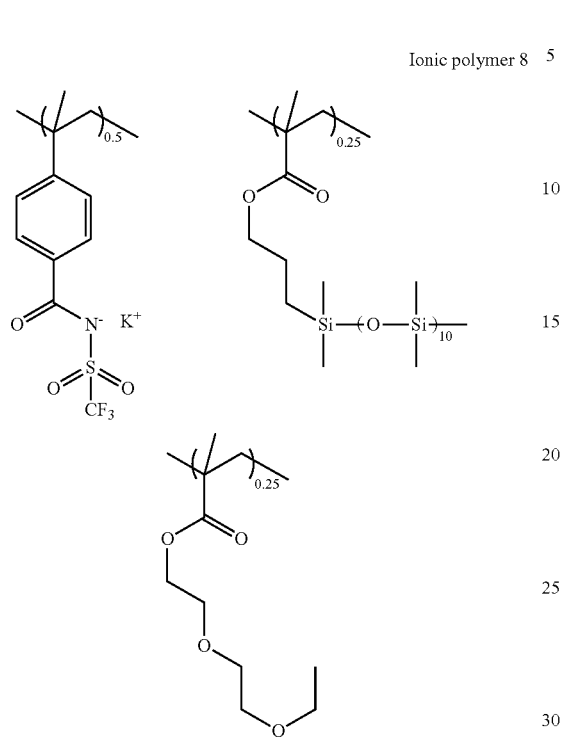
Mw = 43,600
Mw/Mn = 1.91
The repeating number in the formula shows the average value.
Ionic polymer 9
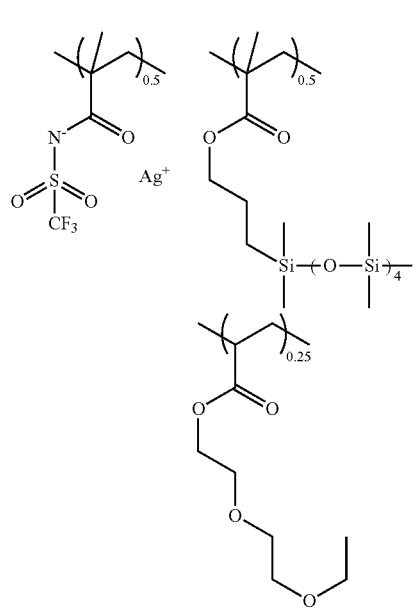
Mw = 97,100
Mw/Mn = 2.20
The repeating number in the formula shows the average value.
Ionic polymer 10
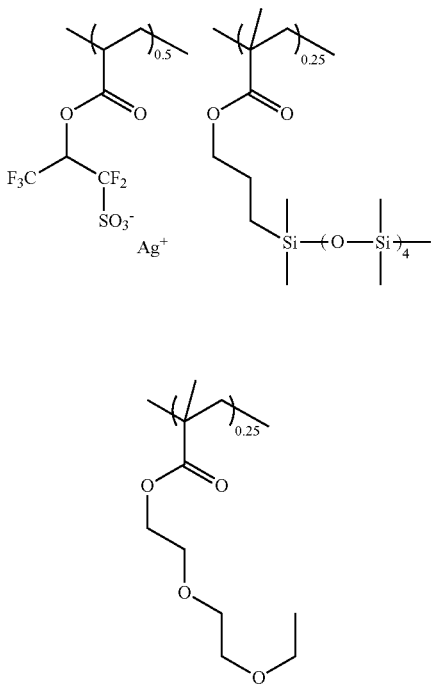
Mw = 98,300
Mw/Mn = 2.05
The repeating number in the formula shows the average value.
Ionic polymer 11
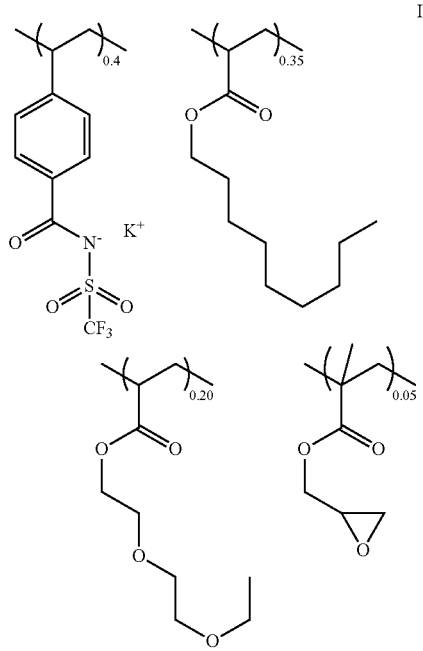
Mw = 32,800
Mw/Mn = 1.98

Ionic polymer 12

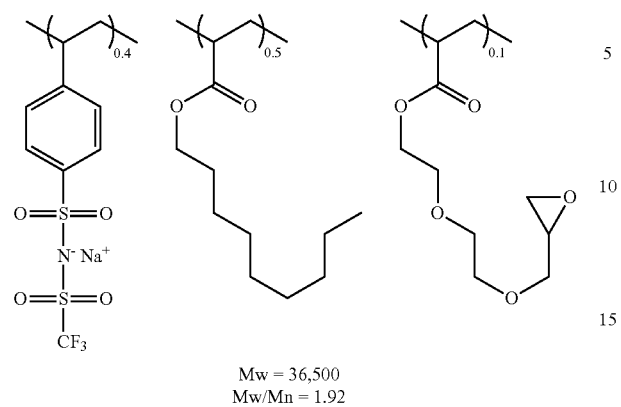

Mw = 36,500
Mw/Mn = 1.92

Comparative salts 1 to 4, which were blended as an ionic material to bio-electrode composition solutions of Comparative Examples, and Comparative ionic polymers 1 and 2 are shown below.

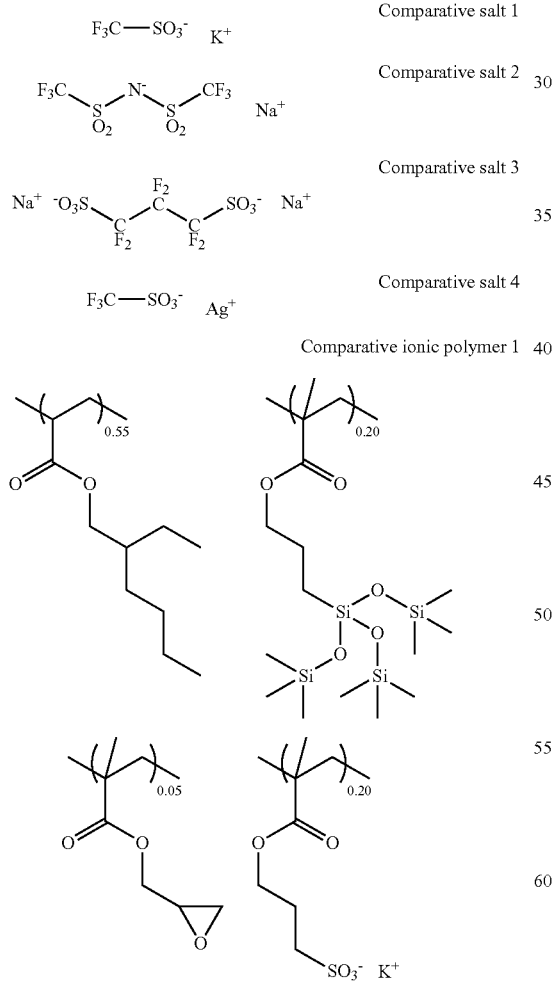

Mw = 44,900
Mw/Mn = 2.59

Comparative ionic polymer 2

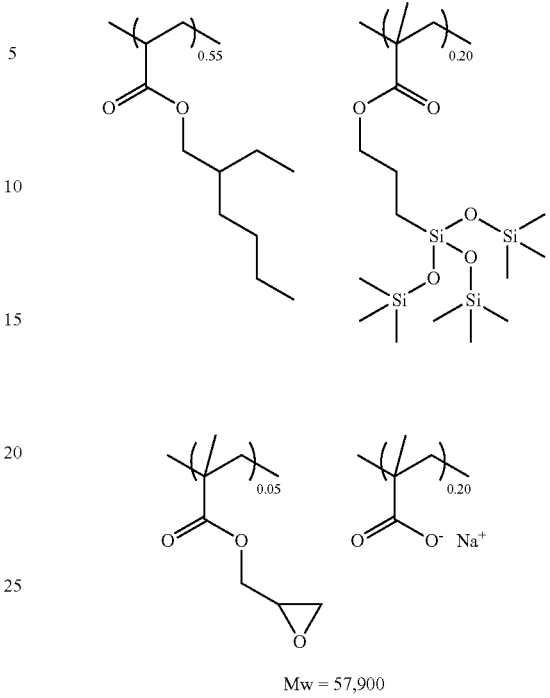

Mw = 57,900
Mw/Mn = 1.89

Siloxane compounds 1 to 4, which were blended to the bio-electrode composition solutions as a silicone base resin, are shown below.

(Siloxane Compound 1)

Siloxane compound 1 was vinyl group-containing polydimethylsiloxane having an alkenyl group-content of 0.007 mol/100 g in which the terminals of molecular chain were blocked with $SiMe_2Vi$ groups, with the 30% toluene solution having a viscosity of 27,000 mPa·s.

(Siloxane Compound 2)

Siloxane compound 2 was a 60% toluene solution of polysiloxane of MQ resin composed of an $Me_3SiO_{0.5}$ unit and an $SiO_2$ unit ($Me_3SiO_{0.5}$ unit/$SiO_2$ unit=0.8).

(Siloxane Compound 3)

Siloxane compound 3 was polydimethylsiloxane-bonded MQ resin obtained by heating a solution (composed of 40 parts by mass of vinyl group-containing polydimethylsiloxane having an alkenyl group-content of 0.007 mol/100 g in which the terminals of molecular chain were blocked with OH groups, with the 30% toluene solution having a viscosity of 42,000 mPa·s; 100 parts by mass of 60% toluene solution of polysiloxane of MQ resin composed of an $Me_3SiO_{0.5}$ unit and an $SiO_2$ unit ($Me_3SiO_{0.5}$ unit/$SiO_2$ unit=0.8); and 26.7 parts by mass of toluene) with refluxing for 4 hours, followed by cooling.

(Siloxane Compound 4)

As methylhydrogensilicone oil, KF-99 manufactured by Shin-Etsu Chemical Co., Ltd. was used.

As a silicone base resin, KF-353 manufactured by Shin-Etsu Chemical Co., Ltd. was used, which is polyether type silicone oil with the side chain being modified with polyether.

Acrylic polymer blended as an acrylic base resin to the bio-electrode composition solution is shown below.

Acrylic polymer 1

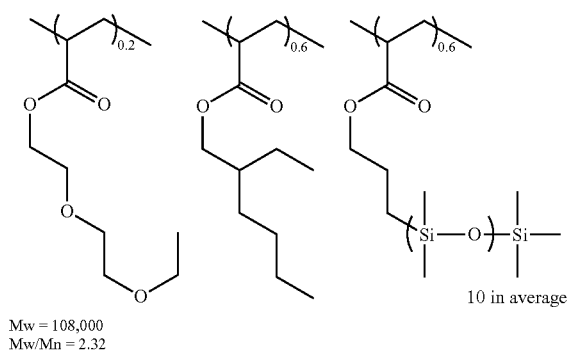

Acrylic polymer 1

Mw = 108,000
Mw/Mn = 2.32

The repeating number in the formula shows the average value.

Silicone-urethane acrylates 1 and 2, which were blended to the bio-electrode composition solutions as a silicone base, acrylic base, or urethane base resin, are shown below.

The repeating number in the formula shows the average value.

Organic solvents, which were blended to the bio-electrode composition solutions, are shown below.
PGMEA: propylene glycol-1-monomethyl ether-2-acetate
PGME: propylene glycol-1-monomethyl ether
PGEE: propylene glycol-1-monoethyl ether The following are a lithium titanate powder, a radical generator, a platinum catalyst, and electric conductivity improvers (carbon black and carbon nanotube) blended to the bio-electrode composition solutions as additives.
Lithium titanate powder ($L_4Ti_5O_{12}$), spinel: manufactured by Sigma-Aldrich Co. LLC., with the size of 200 nm or less
Radical generator: V-601 manufactured by FUJI FILM Wako Pure Chemical Corporation
Platinum catalyst: CAT-PL-50T manufactured by Shin-Etsu Chemical Co., Ltd.
Carbon black: DENKA BLACK HS-100 manufactured by Denka Co., Ltd.
Multilayer carbon nanotube: manufactured by Sigma-Aldrich Co. LLC., with the diameter of 110 to 170 nm and the length of 5 to 9 μm Examples 1 to 16, Comparative Examples 1 to 8

On the basis of the compositions shown in Tables 1 and 2, the ionic material (salt), the resin, the organic solvent, and

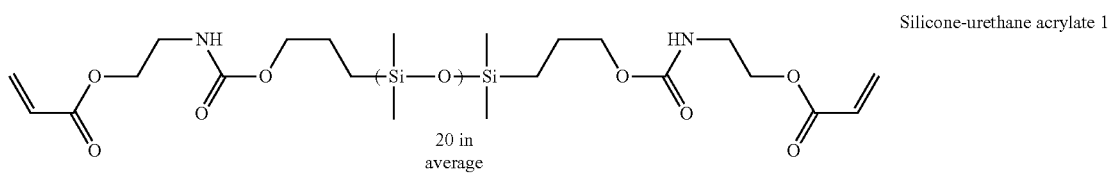

Silicone-urethane acrylate 1

Silicone-urethane acrylate 2 the additive (radical generator, platinum catalyst, electric conductivity improver) were blended to prepare each bio-electrode composition solution (Bio-electrode solutions 1 to 16, Comparative bio-electrode solutions 1 to 8).

TABLE 1

| Bio-electrode solution | Ionic material (parts by mass) | Resins (parts by mass) | Organic solvent (parts by mass) | Additives (parts by mass) |
|---|---|---|---|---|
| Bio-electrode solution 1 | Ionic polymer 1(20) | Siloxane compound 1(40) Siloxane compound 2(100) Siloxane compound 4(3) | toluene(30) | CAT-PL-50T(1.5) Lithium titanate powder(10) |
| Bio-electrode solution 2 | Ionic polymer 2(20) | Siloxane compound 3(126) Siloxane compound 4(3) | heptane(30) PGMEA(14) | CAT-PL-50T(0.7) Lithium titanate powder(10) |
| Bio-electrode solution 3 | Ionic polymer 3(22.5) | Siloxane compound 1(40) Siloxane compound 2(100) Siloxane compound 4(3) | toluene(30) PGMEA(14) | CAT-PL-50T(0.7) Lithium titanate powder(10) |
| Bio-electrode solution 4 | Ionic polymer 4(20) | Siloxane compound 1(40) Siloxane compound 2(100) Siloxane compound 4(3) | toluene(30) PGMEA(14) | CAT-PL-50T(0.7) Lithium titanate powder(12) |
| Bio-electrode solution 5 | Ionic polymer 5(20) | Siloxane compound 3(126) Siloxane compound 4(3) | toluene(44) | CAT-PL-50T(1.0) Lithium titanate powder(10) Carbon black(5) |
| Bio-electrode solution 6 | Ionic polymer 6(20) | Siloxane compound 3(126) Siloxane compound 4(3) KF-353(26) | toluene(30) 2-heptanone (14) | CAT-PL-50T(2.0) Lithium titanate powder(5) Carbon black(5) |
| Bio-electrode solution 7 | Ionic polymer 7(25) | Siloxane compound 3(126) Siloxane compound 4(3) | toluene(30) PGME(14) | CAT-PL-50T(1.0) Lithium titanate powder(5) Carbon black(5) |
| Bio-electrode solution 8 | Ionic polymer 8(24) | Siloxane compound 3(126) Siloxane compound 4(3) | toluene(30) PGME(14) | CAT-PL-50T(1.5) Lithium titanate powder(5) Carbon black(5) |
| Bio-electrode solution 9 | Ionic polymer 8(24) | Siloxane compound 3(126) Siloxane compound 4(3) | toluene(30) PGME(14) | CAT-PL-50T(1.5) Lithium titanate powder(5) Multilayer carbon nanotube(3) |
| Bio-electrode solution 10 | Ionic polymer 1(20) | Acrylic polymer 1(60) Silicone-urethane acrylate 1(20) | PGMEA(100) | Radical generator V-601(4) Lithium titanate powder(10) |
| Bio-electrode solution 11 | Ionic polymer 1(20) | Acrylic polymer 1(55) Silicone-urethane acrylate 1(25) | PGMEA(100) | Radical generator V-601(4) Lithium titanate powder(15) |
| Bio-electrode solution 12 | Ionic polymer 1(20) | Acrylic polymer 1(60) Silicone-urethane acrylate 2(20) | PGMEA(100) | Radical generator V-601(4) Lithium titanate powder(15) |
| Bio-electrode solution 13 | Ionic polymer 9(25) | Siloxane compound 3(126) Siloxane compound 4(3) | toluene(30) PGEE(14) | CAT-PL-50T(0.7) Lithium titanate powder(12) |
| Bio-electrode solution 14 | Ionic polymer 10(25) | Siloxane compound 3(126) Siloxane compound 4(3) | toluene(30) PGEE(14) | CAT-PL-50T(0.7) Lithium titanate powder(12) |
| Bio-electrode solution 15 | Ionic polymer 11(100) | — | PGEE(100) | Lithium titanate powder(20) 2-ethylmethylimidazole(2.0) |
| Bio-electrode solution 16 | Ionic polymer 12(100) | — | PGEE(100) | Lithium titanate powder(20) 2-ethylmethylimidazole(2.0) |

TABLE 2

| Bio-electrode solution | Ionic material (parts by mass) | Resins (parts by mass) | Organic solvent (parts by mass) | Additives (parts by mass) |
|---|---|---|---|---|
| Comparative bio-electrode solution 1 | Comparative salt 1(4.7) | Siloxane compound 3(126) Siloxane compound 4(3) | toluene(30) PGME(14) | CAT-PL-50T(1.5) Lithium titanate powder(5) Carbon black(5) |
| Comparative bio-electrode solution 2 | Comparative salt 2(8.2) | Siloxane compound 3(126) Siloxane compound 4(3) | toluene(30) PGME(14) | CAT-PL-50T(1.5) Lithium titanate powder(5) Carbon black(5) |

TABLE 2-continued

| Bio-electrode solution | Ionic material (parts by mass) | Resins (parts by mass) | Organic solvent (parts by mass) | Additives (parts by mass) |
|---|---|---|---|---|
| Comparative bio-electrode solution 3 | Comparative salt 3(8.4) | Siloxane compound 3(126) Siloxane compound 4(3) | toluene(30) PGME(14) | CAT-PL-50T(1.5) Lithium titanate powder(5) Carbon black(5) |
| Comparative bio-electrode solution 4 | Comparative salt 4(8.4) | Siloxane compound 3(126) Siloxane compound 4(3) | toluene(30) PGME(14) | CAT-PL-50T(1.5) Lithium titanate powder(5) Carbon black(5) |
| Comparative bio-electrode solution 5 | — | Siloxane compound 3(126) Siloxane compound 4(3) | toluene(30) PGME(14) | CAT-PL-50T(1.5) Lithium titanate powder(5) Carbon black(5) |
| Comparative bio-electrode solution 6 | Ionic polymer 1(100) | Siloxane compound 3(126) Siloxane compound 4(3) | toluene(30) PGME(14) | CAT-PL-50T(1.5) |
| Comparative bio-electrode solution 7 | Comparative ionic polymer 1(20) | Siloxane compound 3(126) Siloxane compound 4(3) | toluene(30) PGME(14) | CAT-PL-50T(1.0) Lithium titanate powder(5) Carbon black(5) |
| Comparative bio-electrode solution 8 | Comparative ionic polymer 2(20) | Siloxane compound 3(126) Siloxane compound 4(3) | toluene(30) PGME(14) | CAT-PL-50T(1.0) Lithium titanate powder(5) Carbon black(5) |

(Evaluation of Electric Conductivity)

Figure 4:
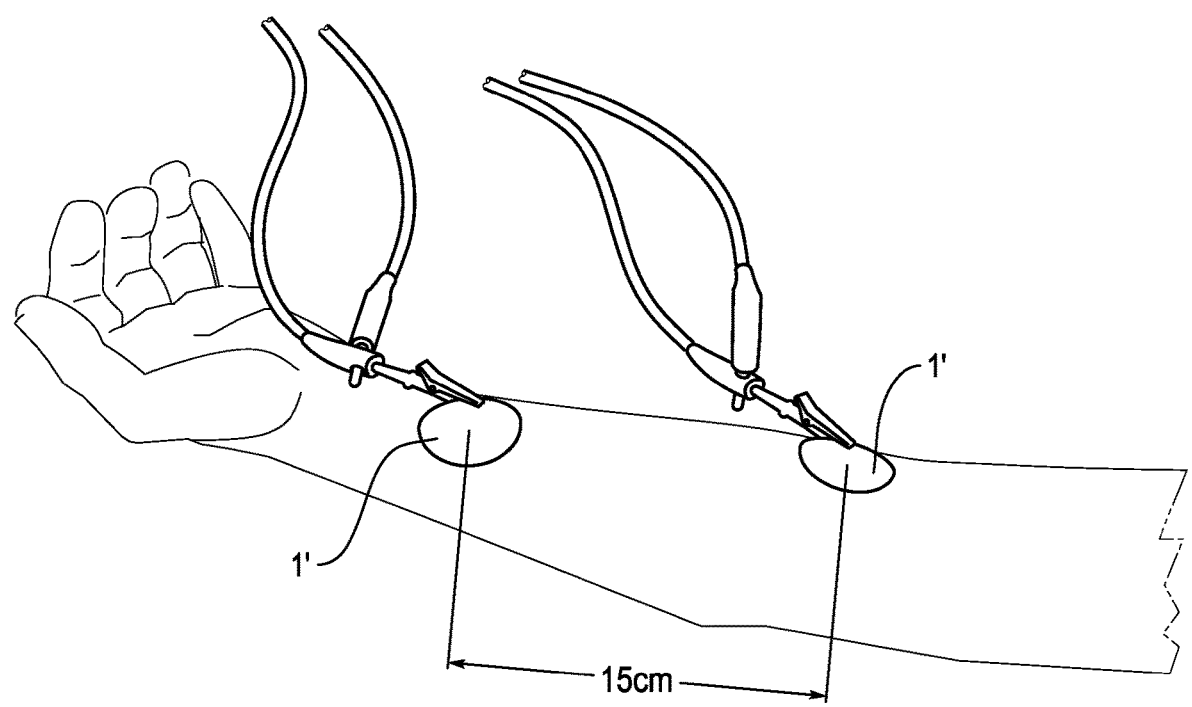
FIG. 4 is a photograph of a scene of measuring impedance on the surface of skin by using the bio-electrode produced in Examples of the present invention.

Each bio-electrode composition solution (adhesive solution) was applied onto an aluminum disk having a diameter of 3 cm and a thickness of 0.2 mm by using an applicator. The resultant was air-dried at room temperature for 6 hours and then cured by baking at 120° C. for 30 minutes under a nitrogen atmosphere using an oven, thereby producing four pieces of bio-electrodes for each bio-electrode composition solution. As shown in FIGS. 3A and 3B, each bio-electrode thus obtained had the living body contact layer 3 at one side and the aluminum disk 8 as an electro-conductive base material at the other side. Then, the copper wiring 9 was pasted on the surface of the aluminum disk 8 with self-adhesive tape at the side that had not been coated with the living body contact layer to form a lead-out electrode, which was connected to an impedance measurement apparatus as shown in FIG. 3B. Two pieces of the bio-electrodes 1' were pasted on a human arm at a distance of 15 cm from each other such that the side of each living body contact layer was in contact with the skin of the human arm as shown in FIG. 4. The initial impedance was measured while altering the frequency by using an AC impedance measurement apparatus SI1260 manufactured by Solartron. Then, the remained two pieces of the bio-electrodes were immersed in pure water for 1 hour, and used for measuring the impedance on skin by the same method described above after drying the water. Each impedance at the frequency of 1,000 Hz is shown in Table 3.

(Measurement of Thickness of Living Body Contact Layer)

On each bio-electrode produced in the evaluation test of electric conductivity described above, the thickness of the living body contact layer was measured by using a micrometer. The results are shown in Table 3.

TABLE 3

| Example | Adhesive solution (to be in contact with body) | Thickness of resin (μm) | Initial impedance (Ω) | Impedance (Ω) after water immersion |
|---|---|---|---|---|
| Example 1 | Adhesive solution 1 | 260 | $3.8E^4$ | $4.1E^4$ |
| Example 2 | Adhesive solution 2 | 320 | $3.8E^4$ | $3.4E^4$ |
| Example 3 | Adhesive solution 3 | 280 | $2.1E^4$ | $2.3E^4$ |
| Example 4 | Adhesive solution 4 | 310 | $4.1E^4$ | $4.2E^4$ |
| Example 5 | Adhesive solution 5 | 320 | $3.1E^4$ | $3.2E^4$ |
| Example 6 | Adhesive solution 6 | 290 | $4.7E^4$ | $4.1E^4$ |
| Example 7 | Adhesive solution 7 | 270 | $4.9E^4$ | $3.9E^4$ |
| Example 8 | Adhesive solution 8 | 280 | $3.5E^4$ | $3.1E^4$ |
| Example 9 | Adhesive solution 9 | 320 | $2.2E^4$ | $2.8E^4$ |
| Example 10 | Adhesive solution 10 | 330 | $2.5E^4$ | $2.9E^4$ |
| Example 11 | Adhesive solution 11 | 370 | $3.1E^4$ | $3.3E^4$ |
| Example 12 | Adhesive solution 12 | 290 | $5.1E^4$ | $5.3E^4$ |
| Example 13 | Adhesive solution 13 | 290 | $4.0E^4$ | $4.3E^4$ |
| Example 14 | Adhesive solution 14 | 310 | $4.0E^4$ | $4.5E^4$ |
| Example 15 | Adhesive solution 15 | 210 | $5.0E^4$ | $5.3E^4$ |
| Example 16 | Adhesive solution 16 | 220 | $4.8E^4$ | $4.5E^4$ |
| Comparative Example 1 | Comparative adhesive solution 1 | 320 | $4.2E^4$ | $5.3E^5$ |
| Comparative Example 2 | Comparative adhesive solution 2 | 330 | $5.0E^4$ | $9.3E^5$ |
| Comparative Example 3 | Comparative adhesive solution 3 | 320 | $4.1E^4$ | $7.2E^5$ |
| Comparative Example 4 | Comparative adhesive solution 4 | 360 | $1.9E^5$ | $1.9E^5$ |
| Comparative Example 5 | Comparative adhesive solution 5 | 350 | $8.9E^7$ | $8.8E^7$ |
| Comparative Example 6 | Comparative adhesive solution 6 | 270 | $1.9E^6$ | $1.8E^6$ |
| Comparative Example 7 | Comparative adhesive solution 7 | 330 | $7.9E^6$ | $8.8E^6$ |
| Comparative Example 8 | Comparative adhesive solution 8 | 330 | $8.1E^6$ | $9.8E^6$ |

As shown in Table 3, in Examples 1 to 16, the living body contact layer of which was formed by using the inventive bio-electrode composition containing the salt (ionic material) with a particular structure and the lithium titanate powder blended with or without the resins, the initial impedance was low, and no large change in impedance occurred after the bio-electrodes were immersed to water and dried. That is, Examples 1 to 16 each gave a bio-electrode that had high initial electric conductivity and did not cause large lowering of the electric conductivity even when the bio-electrode was wetted with water or dried. These bio-electrodes of Examples 1 to 16 were light-weight, excellent in biocompatibility, and manufacturable at low cost, and had favorable adhesion like the bio-electrodes of Comparative Examples 1 to 4, in which conventional salt and resin were blended.

In Examples 15 and 16, each living body contact layer was formed using the bio-electrode composition containing the salt but no resin, but excellent bio-electrodes were obtained in this case, too. This suggests that the resin (C) is not necessarily essential in the present invention. In addition, the lithium titanate ($Li_4Ti_5O_{12}$) having spinel structure used in Examples has low electronic conductivity ($10^{-13}$ $Scm^{-1}$) but can increase ionic conductivity. This is presumably the reason that the resulting bio-electrodes had high initial electric conductivity and this electric conductivity was not lowered greatly even when the bio-electrodes were wetted with water or dried. It should be noted that electroconductive lithium titanate (for example, $Li_2[Li_{1/3}Ti_{5/3}]O_4$ etc.) can also be employed.

On the other hand, in Comparative Examples 1 to 3, the living body contact layer of which was formed by using a bio-electrode composition containing conventional salt and resin, the initial impedance was low, but large increase in the impedance occurred by an order of magnitude after water immersion and drying. That is, each of Comparative Examples 1 to 3 only gave a bio-electrode that had high initial electric conductivity but this electric conductivity was greatly lowered when the bio-electrode was wetted with water or dried. Meanwhile, in Comparative Example 4, no large increase in the impedance by an order of magnitude occurred after the bio-electrode was immersed to water and dried, but the initial impedance was high.

In Comparative Example 5, in which the living body contact layer was formed by using a bio-electrode composition containing resins but no salt (ionic material), no large increase in the impedance by an order of magnitude occurred after the bio-electrode was immersed to water and dried because it did not contain the inventive salt, but the initial impedance was high. That is, Comparative Example 5 only gave a bio-electrode with low initial electric conductivity.

In the cases of forming a living body contact layer without a lithium titanate powder (Comparative Example 6) and forming a living body contact layer in which a polymer salt with lower acidity had been added (Comparative Examples 7, 8), each initial impedance was high.

As described above, it was revealed that the bio-electrode, with the living body contact layer formed by using the inventive bio-electrode composition, is excellent in electric conductivity, biocompatibility, adhesion to an electro-conductive base material, and excellent in holding the ionic material to prevent large lowering of the electric conductivity even when the bio-electrode is wetted with water or dried; light-weight; and manufacturable at low cost.

It should be noted that the present invention is not limited to the above-described embodiments. The embodiments are just examples, and any examples that have substantially the same feature and demonstrate the same functions and effects as those in the technical concept disclosed in claims of the present invention are included in the technical scope of the present invention.

The invention claimed is:
1. A bio-electrode composition comprising:
(A) an ionic material; and
(B) a lithium titanate powder, wherein the component (A) is a polymer compound comprising a repeating unit-a having at least one structure selected from the group consisting of the following general formulae (1)-1 to (1)-4,

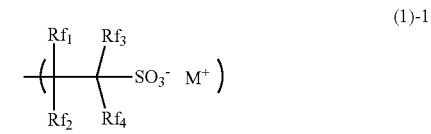

(1)-1

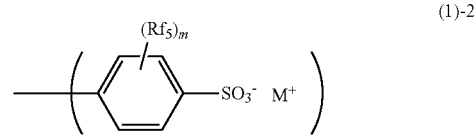

(1)-2

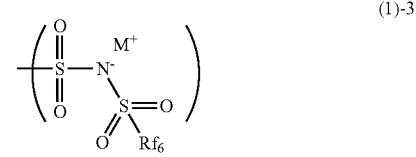

(1)-3

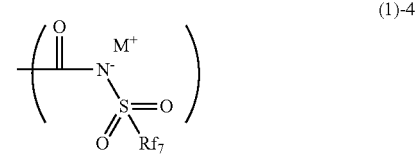

(1)-4 wherein $Rf_1$ and $Rf_2$ each represent a hydrogen atom, a fluorine atom, an oxygen atom, a methyl group, or a trifluoromethyl group, provided that when $Rf_1$ represents an oxygen atom, $Rf_2$ represents the oxygen atom to form a carbonyl group together with a carbon atom bonded therewith; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms and at least one or more fluorine atoms; m represents an integer of 1 to 4; and $M^+$ represents an ion selected from the group consisting of an ammonium ion, a sodium ion, a potassium ion, and a silver ion.

2. The bio-electrode composition according to claim 1, wherein the repeating unit-a is at least one repeating unit selected from the group consisting of repeating units-a1 to -a7 shown by the following general formula (2),

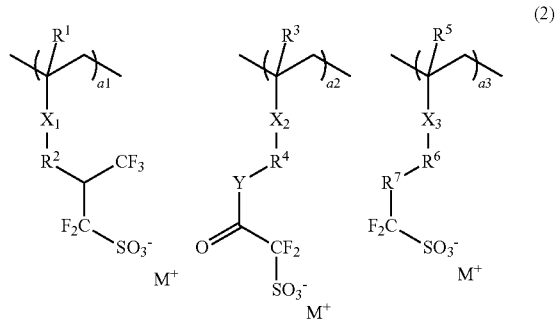

(2)

-continued

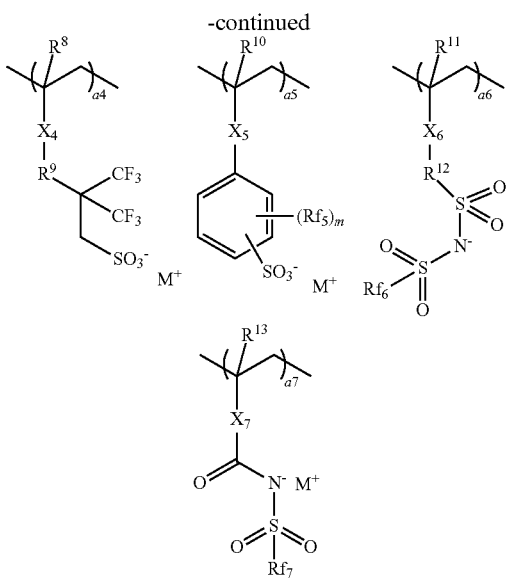

wherein $R^1$, $R^3$, $R^5$, $R^8$, $R^{10}$, $R^{11}$ and $R^{13}$ each independently represent a hydrogen atom or a methyl group; $R^2$, $R^4$, $R^6$, $R^9$, and $R^{12}$ each independently represent any of a single bond, an ester group, and a linear, branched, or cyclic hydrocarbon group having 1 to 13 carbon atoms optionally having either or both of an ether group and an ester group; $R^7$ represents a linear or branched alkylene group having 1 to 4 carbon atoms, and one or two hydrogen atoms in $R^7$ are optionally substituted with a fluorine atom; $X_1$, $X_2$, $X_3$, $X_4$ and $X_6$ each independently represent any of a single bond, a phenylene group, a naphthylene group, an ether group, an ester group, and an amide group; $X_5$ represents any of a single bond, an ether group, and an ester group; $X_7$ represents any of a single bond, an arylene group having 6 to 12 carbon atoms, a —C(=O)—O—$R^{18}$— group, and a —C(=O)—NH—$R^{18}$— group, and $X_7$ optionally has one or more selected from an ether group, a carbonyl group, an ester group, and an amide group; $R^{18}$ represents a single bond, a linear, branched, or cyclic alkylene group having 1 to 12 carbon atoms, or a divalent aromatic hydrocarbon group having 6 to 10 carbon atoms, and the aromatic hydrocarbon group is optionally partially hydrogenated; Y represents an oxygen atom or a —$NR^{19}$— group, and Y and $R^4$ are optionally bonded to each other to form a ring; $R^{19}$ represents a hydrogen atom, or a linear or branched alkyl group having 1 to 4 carbon atoms; "m" represents an integer of 1 to 4; a1, a2, a3, a4, a5, a6 and a7 represent numbers satisfying $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 < a1+a2+a3+a4+a5+a6+a7 \leq 1.0$; and $M^+$ represents an ion selected from an ammonium ion, a sodium ion, a potassium ion, and a silver ion.

3. The bio-electrode composition according to claim 1, wherein the the ion is an ammonium ion shown by the following general formula (3),

wherein $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, and optionally have one or more selected from an ether group, a carbonyl group, an ester group, a hydroxy group, an amino group, a nitro group, a sulfonyl group, a sulfinyl group, a halogen atom, and a sulfur atom; $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula within the ring.

4. The bio-electrode composition according to claim 2, wherein the the ion is an ammonium ion shown by the following general formula (3),

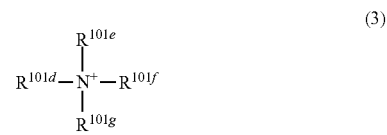

wherein $R^{101d}$, $R^{101e}$, $R^{101f}$, and $R^{101g}$ each represent a hydrogen atom, a linear, branched, or cyclic alkyl group having 1 to 12 carbon atoms, a linear, branched, or cyclic alkenyl group or alkynyl group having 2 to 12 carbon atoms, or an aromatic group having 4 to 20 carbon atoms, and optionally have one or more selected from an ether group, a carbonyl group, an ester group, a hydroxy group, an amino group, a nitro group, a sulfonyl group, a sulfinyl group, a halogen atom, and a sulfur atom; $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula within the ring.

5. The bio-electrode composition according to claim 1, comprising, in addition to the components (A) and (B), a component (C) containing:
   a silicone resin having an $SiO_2$ unit and an $R_xSiO_{(4-x)/2}$ unit, wherein R represents a substituted or unsubstituted monovalent hydrocarbon group having 1 to 10 carbon atoms, and "x" is a number in a range of 2.5 to 3.5;
   diorganosiloxane having an alkenyl group; and
   organohydrogenpolysiloxane having an SiH group.

6. The bio-electrode composition according to claim 1, further comprising an organic solvent.

7. The bio-electrode composition according to claim 1, wherein the component (B) is a powder of lithium titanate having a spinel structure.

8. The bio-electrode composition according to claim 1, comprising a carbon material in addition to the component (B).

9. The bio-electrode composition according to claim 8, wherein the carbon material is either or both of carbon black and carbon nanotube.

10. A bio-electrode comprising an electro-conductive base material and a living body contact layer formed on the electro-conductive base material, wherein the living body contact layer is a cured material of the bio-electrode composition according to claim 1.

11. The bio-electrode according to claim 10, wherein the electro-conductive base material comprises one or more species selected from the group consisting of gold, silver, silver chloride, platinum, aluminum, magnesium, tin, tungsten, iron, copper, nickel, stainless steel, chromium, titanium, and carbon.

12. A method for manufacturing a bio-electrode having an electro-conductive base material and a living body contact layer formed on the electro-conductive base material, comprising:
 applying the bio-electrode composition according to claim 1 onto the electro-conductive base material; and
 curing the bio-electrode composition to form the living body contact layer.

13. The method for manufacturing a bio-electrode according to claim 12, wherein the electro-conductive base material comprises one or more species selected from the group consisting of gold, silver, silver chloride, platinum, aluminum, magnesium, tin, tungsten, iron, copper, nickel, stainless steel, chromium, titanium, and carbon.

\* \* \* \* \*